US012773457B2

(12) United States Patent
Barney et al.

(10) Patent No.: US 12,773,457 B2
(45) **Date of Patent: *Oct. 27, 2026**

(54) IMPLANTABLE DEVICES FOR CELL THERAPY AND RELATED METHODS

(71) Applicant: SIGILON THERAPEUTICS, INC., Cambridge, MA (US)

(72) Inventors: Lauren Emily Barney, Cambridge, MA (US); Michael Beauregard, Boston, MA (US); Guillaume Carmona, Cambridge, MA (US); Francisco Caballero Gonzalez, Brookline, MA (US); Richard Heidebrecht, Somerville, MA (US);

(Continued)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 1085 days.

This patent is subject to a terminal disclaimer.

(21) Appl. No.: 17/280,802

(22) PCT Filed: Sep. 27, 2019

(86) PCT No.: PCT/US2019/053637

§ 371 (c)(1),
(2) Date: Mar. 26, 2021

(87) PCT Pub. No.: WO2020/069429

PCT Pub. Date: Apr. 2, 2020

(65) Prior Publication Data

US 2022/0000789 A1 Jan. 6, 2022

Related U.S. Application Data

(60) Provisional application No. 62/824,768, filed on Mar. 27, 2019, provisional application No. 62/737,835, filed on Sep. 27, 2018.

(51) Int. Cl.
*A61K 47/64* (2017.01)
*A61K 9/50* (2006.01)
(Continued)

(52) U.S. Cl.
CPC ............ *A61K 47/64* (2017.08); *A61K 9/5036* (2013.01); *A61K 35/30* (2013.01); *A61K 38/37* (2013.01); *A61K 48/00* (2013.01); *A61L 27/52* (2013.01)

(58) Field of Classification Search
CPC ........ A61K 35/30; A61K 38/37; A61K 47/61; A61K 47/64; A61K 47/6943; A61K 48/00;
(Continued)

(56) References Cited

U.S. PATENT DOCUMENTS 4,784,950 A 11/1988 Hagen et al.
6,361,771 B1 3/2002 Tao et al.
(Continued)

FOREIGN PATENT DOCUMENTS

CN 104072478 A 10/2014
CN 106795225 A 5/2017
(Continued)

OTHER PUBLICATIONS

Chichagova et al., Cellular regeneration strategies for macular degeneration: past, present and future. Eye 32, 946-971 (2018). https://doi.org/10.1038/s41433-018-0061-z (Year: 2018).*
(Continued)

*Primary Examiner* — Randall L Beane
(74) *Attorney, Agent, or Firm* — Quarles & Brady, LLP

(57) ABSTRACT

Described herein are implantable devices comprising means for mitigating the foreign body response (FBR) and at least one cell-containing compartment which comprises a plurality of cells (e.g., live cells) encapsulated in a polymer
(Continued)

composition comprising a cell-binding substance (CBS), as well as compositions and methods of making and using the same. The cells are capable of expressing a therapeutic agent useful for the treatment of a disease, disorder, or condition described herein.

10 Claims, 50 Drawing Sheets

Specification includes a Sequence Listing.

(72) Inventors: Erika Ellen Johnston, Cambridge, MA (US); Robert James Miller, East Bridgewater, MA (US); Owen O'Connor, Raynham, MA (US); Matthias Alexander Oberli, Cambridge, MA (US); David Peritt, Skokie, IL (US); Jared A. Sewell, Somerville, MA (US); Devyn McKinley Smith, Barrington, RI (US); Omid Veiseh, Bellaire, TX (US); Paul Kevin Wotton, Boston, MA (US); Zoe Yin, Boston, MA (US)

(51) Int. Cl.

| | |
|---|---|
| ***A61K 35/30*** | (2015.01) |
| ***A61K 38/37*** | (2006.01) |
| ***A61K 48/00*** | (2006.01) |
| ***A61L 27/52*** | (2006.01) |

(58) Field of Classification Search

CPC ............... A61K 9/5036; A61L 2300/62; A61L 2300/64; A61L 27/20; A61L 27/3813; A61L 27/52; C07K 14/745; C08L 5/04; C12N 2800/22

See application file for complete search history.

(56) References Cited

U.S. PATENT DOCUMENTS

| | | | | |
|---|---|---|---|---|
| 6,533,819 | B1 | 3/2003 | Urry et al. | |
| 8,741,340 | B2 | 6/2014 | Kusk et al. | |
| 9,121,037 | B2 | 9/2015 | Kusk et al. | |
| 9,422,373 | B2 | 8/2016 | Vegas et al. | |
| 9,555,007 | B2 | 1/2017 | Ma et al. | |
| 9,867,781 | B2 | 1/2018 | Anderson et al. | |
| 9,925,219 | B2 | 3/2018 | Kauper et al. | |
| 10,172,791 | B2 | 1/2019 | Ma et al. | |
| 10,278,922 | B2 | 5/2019 | Anderson et al. | |
| 10,285,949 | B2 | 5/2019 | Vegas et al. | |
| 10,292,936 | B2 | 5/2019 | Vegas et al. | |
| 10,426,735 | B2 | 10/2019 | Vegas et al. | |
| 11,945,786 | B2 * | 4/2024 | Veiseh | C07D 417/06 |
| 12,161,760 | B2 * | 12/2024 | Barney | A61K 35/33 |
| 12,162,994 | B2 * | 12/2024 | Barney | C08J 3/075 |
| 12,306,081 | B2 * | 5/2025 | Beauregard | B01J 2/02 |
| 2005/0180960 | A1 * | 8/2005 | Bjerkvig | C07K 16/2863 435/366 |
| 2008/0076174 | A1 | 3/2008 | Selden et al. | |
| 2008/0193536 | A1 * | 8/2008 | Khademhosseini | A61K 35/545 424/484 |
| 2011/0033504 | A1 * | 2/2011 | Wheatley | A61K 9/70 435/325 |
| 2011/0244550 | A1 * | 10/2011 | Simioni | A61K 38/4846 435/320.1 |
| 2013/0189230 | A1 * | 7/2013 | Shoichet | A61K 47/61 514/781 |
| 2013/0259924 | A1 | 10/2013 | Bancel et al. | |
| 2014/0010861 | A1 | 1/2014 | Bancel et al. | |
| 2014/0271843 | A1 * | 9/2014 | Ma | A61K 9/0024 424/463 |
| 2016/0030359 | A1 * | 2/2016 | Ma | A61K 9/5036 264/10 |
| 2016/0030360 | A1 * | 2/2016 | Vegas | C12N 5/0677 536/3 |
| 2016/0207978 | A1 | 7/2016 | Kelly | |
| 2017/0260516 | A1 | 9/2017 | Tan et al. | |
| 2018/0318612 | A1 | 11/2018 | Tzahor et al. | |
| 2019/0000932 | A1 | 1/2019 | Martini et al. | |
| 2019/0247548 | A1 | 8/2019 | Sant | |
| 2020/0263196 | A1 * | 8/2020 | Carmona | C12N 5/0621 |
| 2021/0060205 | A1 * | 3/2021 | Heidebrecht | C07D 491/10 |
| 2021/0145759 | A1 * | 5/2021 | Barney | A61K 9/5073 |
| 2021/0145889 | A1 * | 5/2021 | Smith | C12N 5/0663 |
| 2023/0123802 | A1 * | 4/2023 | Barney | A61K 35/30 604/522 |
| 2023/0233679 | A1 * | 7/2023 | Bandukwala | A61K 47/6957 424/188.1 |
| 2024/0123040 | A1 * | 4/2024 | Makino | A61K 9/5036 |
| 2025/0017864 | A1 * | 1/2025 | Barney | A61K 9/5036 |
| 2025/0235409 | A1 * | 7/2025 | Barney | A61P 7/02 |

FOREIGN PATENT DOCUMENTS

| | | | | |
|---|---|---|---|---|
| JP | 2004-532234 A | 10/2004 | | |
| JP | 5725475 B2 | 5/2015 | | |
| JP | 2016-516020 A | 6/2016 | | |
| JP | 2016-517879 A | 6/2016 | | |
| JP | 2016-519079 A | 6/2016 | | |
| JP | 2017-524768 A | 8/2017 | | |
| RU | 2423154 C2 | 7/2011 | | |
| RU | 2018101287 A | 7/2019 | | |
| WO | WO-9219195 A1 | * | 11/1992 | A61K 35/12 |
| WO | 2008/021388 A1 | 2/2008 | | |
| WO | 2008/036308 A2 | 3/2008 | | |
| WO | 2010/005533 A2 | 1/2010 | | |
| WO | 2012/112982 A2 | 8/2012 | | |
| WO | 2012/167223 A1 | 12/2012 | | |
| WO | 2014/147386 A1 | 9/2014 | | |
| WO | 2014/153126 A1 | 9/2014 | | |
| WO | 2015/143418 A2 | 9/2015 | | |
| WO | 2016/019391 A1 | 2/2016 | | |
| WO | 2016/187225 A1 | 11/2016 | | |
| WO | 2017/018086 A1 | 2/2017 | | |
| WO | 2017/036533 A1 | 3/2017 | | |
| WO | 2017/075631 A1 | 5/2017 | | |
| WO | WO-2017075630 A1 | * | 5/2017 | A61F 2/0077 |
| WO | 2017/136358 A1 | 8/2017 | | |
| WO | 2018/067615 A1 | 4/2018 | | |
| WO | 2018/197688 A1 | 11/2018 | | |
| WO | 2018/206168 A1 | 11/2018 | | |
| WO | 2019/067766 A1 | 4/2019 | | |
| WO | 2019/195055 A1 | 10/2019 | | |
| WO | 2019/195056 A1 | 10/2019 | | |

OTHER PUBLICATIONS

Bastiaans et al., Factor Xa and thrombin stimulate proinflammatory and profibrotic mediator production by retinal pigment epithelial cells: a role in vitreoretinal disorders?, Graefes Arch Clin Exp Ophthalmol 251, 1723-1733 (2013); https://doi.org/10.1007/s00417-013-2335-2 (Year: 2013).*

Hollborn et al., Activated blood coagulation factor X (FXa) induces angiogenic growth factor expression in human retinal pigment epithelial cells. Invest Ophthalmol Vis Sci. Aug. 31, 2012;53(9):5930-9. doi: 10.1167/iovs.11-9214. PMID: 22871831 (Year: 2012).*

Andersen et al., 3D Cell Culture in Alginate Hydrogels. Microarrays (Basel). Mar. 24, 2015;4(2):133-61. doi: 10.3390/microarrays4020133. PMID: 27600217; PMCID: PMC4996398) (Year: 2015).*

Leena-Stiina Kontturi, Dissertation, Cell encapsulation in hydrogels for long-term protein delivery and tissue engineering applications, University of Helsinki, Finland, 2014, 124 pages (Year: 2014).*

Heidari et al., Alginate as a Cell Culture Substrate for Growth and Differentiation of Human Retinal Pigment Epithelial Cells. Appl

(56) References Cited

OTHER PUBLICATIONS

Biochem Biotechnol 175, 2399-2412 (2015). https://doi.org/10.1007/s12010-014-1431-z (Year: 2015).*
Hunt et al., 3D culture of human pluripotent stem cells in RGD-alginate hydrogel improves retinal tissue development. Acta Biomater. Feb. 2017;49:329-343. doi: 10.1016/j.actbio.2016.11.016. Epub Nov. 5, 2016. PMID: 27826002 (Year: 2016).*
Kong et al., Designing alginate hydrogels to maintain viability of immobilized cells. Biomaterials. Oct. 2003;24(22):4023-9. doi: 10.1016/s0142-9612(03)00295-3. PMID: 12834597 (Year: 2003).*
Wang et al., Injectable hydrogels for ophthalmic applications. J Control Release. Dec. 28, 2017;268:212-224. doi: 10.1016/j.jconrel.2017.10.031. Epub Oct. 20, 2017. PMID: 29061512; PMCID: PMC5722685 (Year: 2017).*
Wikström et al., Alginate-based microencapsulation of retinal pigment epithelial cell line for cell therapy. Biomaterials. Mar. 2008;29(7):869-76. doi: 10.1016/j.biomaterials.2007.10.056. Epub Nov. 28, 2007. PMID: 18045685 (Year: 2007).*
Yang et al., "In situ-forming injectable hydrogels for regenerative medicine." Progress in polymer science 39.12 (2014): 1973-1986 (Year: 2014).*
O'Connell et al., Association behavior of β-casein. Journal of Colloid and Interface Science. vol. 258:33-39 (2003) . 10.1016/S0021-9797(02)00066-8 (Year: 2003).*
Maguire et al., Characterization of particles in solution—a perspective on light scattering and comparative technologies. Sci Technol Adv Mater. Oct. 18, 2018;19(1):732-745. doi: 10.1080/14686996.2018.1517587. PMID: 30369998; PMCID: PMC6201793 (Year: 2018).*
Primavera et al., Laser diffraction and light scattering techniques for the analysis of food matrices. Biomed International—Advances In Food Safety and Health. vol. 6:40-60 (2014) (Year: 2014).*
Insua et al., Preparation and antimicrobial evaluation of polyion complex (PIC) nanoparticles loaded with polymyxin B. Eur Polym J. Feb. 2017;87:478-486 and 4 pages of Supplemental Data. doi: 10.1016/j.eurpolymj.2016.08.023. PMID: 28280277; PMCID: PMC5327956 (Year: 2017).*
Belhaj, "Enhancements in alginate microencapsulation technology & impacts on cell therapy development", Disseration, Jan. 2018 (109 pages).
Weber et al., "Multifunctional pancreatic islet encapsulation barriers achieved via multilayer PEG hydrogels", Cell Transplantation, vol. 16, No. 10, pp. 1049-1057, 2007.
Jeon et al., "Biodegradable, photocrosslinked alginate hydrogels with independently tailorable physical properties and cell adhesivity", Tissue Engineering, vol. 16, No. 9, pp. 2915-2925, 2010.
International Search Report and Written Opinion for Application No. PCT/US2019/053637 mailed Feb. 14, 2020.
International Search Report and Written Opinion for Application No. PCT/US2018/053191 mailed Mar. 5, 2019.
Sieving et al., "Ciliary neurotrophic factor (CNTF) for human retinal degeneration: Phase I trial of CNTF delivered by encapsulated cell intraocular implants" Proceedings of the National Academy of Sciences, 2006, vol. 103, No. 10, pp. 3896-3901.
Shintani et al., "Review and update: Current treatment trends for patients with retinitis pigmentosa" Optometry, 2009, vol. 80, No. 7, pp. 384-401.
Wikstrom et al., "Alginate-based microencapsulation of retinal pigment epithelial cell line for cell therapy" Biomaterials, 2008, vol. 29, pp. 869-876.
Carvalho et al., "'Click Chemistry' synthesis of a library of 1,2,3-triazole-substituted galactose derivatives and their evaluation against Trypanosoma cruzi and its cell surface trans-sialidase," Bioorganic & Medicinal Chemistry, vol. 18, No. 7, pp. 2412-2427, (2010).
Corbel et al., "Identification of potential cellular targets of aloisine A by affinity chromatography," Bioorganic & Medicinal Chemistry, vol. 17, No. 15, pp. 5572-5582, (2009).
Struthers et al., "'Click-to-Chelate': Design and Incorporation of Triazole-containing Metal-chelating Systems into Biomolecules of Diagnostic and Therapeutic Interest," Chemistry—A European Journal, vol. 14, No. 20, pp. 6173-6183, (2008).
International Search Report and Written Opinion for PCT/US2017/055001 mailed Nov. 27, 2017.
Arunrungvichian et al., "Selectivity optimization of substituted 1,2,3-Triazoles as a7 nicotinic acetylcholine receptor agonists" ACS Chemical Neuroscience, vol. 6, No. 8, 2015, pp. 1317-1330.
RN: 1545351-08-3, Database Registry [Online], Retrieved from STN, Feb. 16, 2014.
Panda et al., "A nucleus-imaging probe that selectively stabilizes a minor conformation of c-MYC G-quadruplex and Down-regulates c-MYC Transcription in Human Cancer Cells" Scienctific Reports, 2015, vol. 5, pp. 1-16.
Vegas et al., "Long-term glycemic control using polymer-encapsulated human stem cell-derived beta cells in immune-competent mice" Nature Medicine, 2016, vol. 22, No. 3, pp. 306-311.
Vegas et al., "Combinatorial hydrogel library enables identification of materials that mitigate the foreign body response in primates" Nature Biotechnology, 2016, vol. 34, No. 3, pp. 345-352.
International Search Report and Written Opinion for Application No. PCT/US2019/024385 mailed Aug. 7, 2019.
Bremond et al., "Formation of liquid-core capsules having a thin hydrogel membrane: liquid pearls" Soft Matter, 2010, vol. 6, No. 11, pp. 2484-2488.
Veiseh et al., "Size- and shape-dependent foreign body immune response to materials implanted in rodents and non-human primates" Nature Materials, 2015, vol. 14, pp. 643-652.
Lee et al., "Size and shape of calcium alginate beads produced by extrusion dripping" Chemical Engineering and Technology, 2013, vol. 36, No. 10, pp. 1627-1642.
International Search Report and Written Opinion for Application No. PCT/US2019/020248 mailed Jun. 26, 2019.
International Search Report and Written Opinion for Application No. PCT/US2019/020405 mailed Jul. 15, 2019.
International Search Report and Written Opinion for Application No. PCT/US2019/024371 mailed Aug. 14, 2019.
International Search Report and Written Opinion for Application No. PCT/2020/02585 mailed Aug. 28, 2020.
International Search Report and Written Opinion for Application No. PCT/2020/025511 mailed Aug. 28, 2020.
Llacua et al., "Extracellular matrix molecules and their potential contribution to the function of transplanted pancreatic islets" Diabetologia, Jan. 2018, vol. 61, pp. 1261-1272.
Llacua et al., "Laminin and collagen IV inclusion in immunoisolating microcapsules reduces cytokine-mediated cell death in human pancreatic islets" Journal of Tissue Engineering and Regenerative Medicine, May 2017, 25 pages.
Orive et al., "Engineering a clinically translatable bioartificial pancreas to treat type I diabetes" Trends in Biotechnology, Apr. 2018, 12 pages.
Llacua et al., "Extracellular matrix components supporting human islet function in alginate-based immunoprotective microcapsules for treatment of diabetes" Journal of Biomedical Materials Research Part A, Mar. 2018, 10 pages.
Bochenek et al., "Alginate encapsulation as long-term immune protection of allogeneic pancreatic islet cells transplanted into the omental bursa of macaques" Nature Biomedical Engineering, vol. 2, No. 11, pp. 810-821, Nov. 2018.
Bochenek et al., "Alginate encapsulation as long-term immune protection of allogeneic pancreatic islet cells transplanted into the omental bursa of macaques" Nature Biomedical Engineering, Nov. 2018, vol. 2, No. 11, pp. 810-821.
Carmona et al., "Correcting rare blood disorders using coagulation factors produced in vivo by shielded living therapeutics" Blood, Nov. 2019, vol. 134, 3 pages.
Shibeko et al., "Current trends in blood coagulation studies" Pediatric Hematology/Oncology and Immunopathology, May 2020, vol. 19, No. 3, pp. 144-150.

* cited by examiner

FIG. 24A

Table 7:

| SEQ ID NO. | Protein | Amino Acid Sequence |
|---|---|---|
| 1 | rhFVIII-BDD | MQIELSTCFF LCLLRFCFSA TRRYYLGAVE LSWDYMQSDL GELPVDARFP PRVPKSFPFN TSVVYKKTLF VEFTDHLFNI AKPRPPWMGL LGPTIQAEVY DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE GSLAKEKTQT LHKFILLFAV FDEGKSWHSE TKNSLMQDRD AASARAWPKM HTVNGYVNRS LPGLIGCHRK SVYWHVIGMG TTPEVHSIFL EGHTFLVRNH RQASLEISPI TFLTAQTLLM DLGQFLLFCH ISSHQHDGME AYVKVDSCPE EPQLRMKNNE EAEDYDDDLT DSEMDVVRFD DDNSPSFIQI RSVAKKHPKT WVHYIAAEEE DWDYAPLVLA PDDRSYKSQY LNNGPQRIGR KYKKVRFMAY TDETFKTREA IQHESGILGP LLYGEVGDTL LIIFKNQASR PYNIYPHGIT DVRPLYSRRL PKGVKHLKDF PILPGEIFKY KWTVTVEDGP TKSDPRCLTR YYSSFVNMER DLASGLIGPL LICYKESVDQ RGNQIMSDKR NVILFSVFDE NRSWYLTENI QRFLPNPAGV QLEDPEFQAS NIMHSINGYV FDSLQLSVCL HEVAYWYILS IGAQTDFLSV FFSGYTFKHK MVYEDTLTLF PFSGETVFMS MENPGLWILG CHNSDFRNRG MTALLKVSSC DKNTGDYYED SYEDISAYLL SKNNAIEPRS FSQNPPVLKR HQREITRTTL QSDQEEIDYD DTISVEMKKE DFDIYDEDEN QSPRSFQKKT RHYFIAAVER LWDYGMSSSP HVLRNRAQSG SVPQFKKVVF QEFTDGSFTQ PLYRGELNEH LGLLGPYIRA EVEDNIMVTF RNQASRPYSF YSSLISYEED QRQGAEPRKN FVKPNETKTY FWKVQHHMAP TKDEFDCKAW AYFSDVDLEK DVHSGLIGPL LVCHTNTLNP AHGRQVTVQE FALFFTIFDE TKSWYFTENM ERNCRAPCNI QMEDPTFKEN YRFHAINGYI MDTLPGLVMA QDQRIRWYLL SMGSNENIHS IHFSGHVFTV RKKEEYKMAL YNLYPGVFET VEMLPSKAGI WRVECLIGEH LHAGMSTLFL VYSNKCQTPL GMASGHIRDF QITASGQYGQ WAPKLARLHY SGSINAWSTK EPFSWIKVDL LAPMIIHGIK TQGARQKFSS LYISQFIIMY SLDGKKWQTY RGNSTGTLMV FFGNVDSSGI KHNIFNPPII ARYIRLHPTH YSIRSTLRME LMGCDLNSCS MPLGMESKAI SDAQITASSY FTNMFATWSP SKARLHLQGR SNAWRPQVNN PKEWLQVDFQ KTMKVTGVTT QGVKSLLTSM YVKEFLISSS QDGHQWTLFF QNGKVKVFQG NQDSFTPVVN SLDPPLLTRY LRIHPQSWVH QIALRMEVLG CEAQDLY |
| 3 | rhScFVIII-BDD 1 | MQIELSTCFF LCLLRFCFSA TRRYYLGAVE LSWDYMQSDL GELPVDARFP PRVPKSFPFN TSVVYKKTLF VEFTDHLFNI AKPRPPWMGL LGPTIQAEVY DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE GSLAKEKTQT LHKFILLFAV FDEGKSWHSE TKNSLMQDRD AASARAWPKM HTVNGYVNRS LPGLIGCHRK SVYWHVIGMG TTPEVHSIFL EGHTFLVRNH RQASLEISPI TFLTAQTLLM DLGQFLLFCH ISSHQHDGME AYVKVDSCPE EPQLRMKNNE EAEDYDDDLT DSEMDVVRFD DDNSPSFIQI RSVAKKHPKT WVHYIAAEEE DWDYAPLVLA PDDRSYKSQY LNNGPQRIGR KYKKVRFMAY TDETFKTREA IQHESGILGP LLYGEVGDTL LIIFKNQASR PYNIYPHGIT DVRPLYSRRL PKGVKHLKDF PILPGEIFKY KWTVTVEDGP TKSDPRCLTR YYSSFVNMER DLASGLIGPL LICYKESVDQ RGNQIMSDKR NVILFSVFDE NRSWYLTENI QRFLPNPAGV QLEDPEFQAS NIMHSINGYV FDSLQLSVCL HEVAYWYILS IGAQTDFLSV FFSGYTFKHK MVYEDTLTLF PFSGETVFMS MENPGLWILG CHNSDFRNRG MTALLKVSSC DKNTGDYYED SYEDISAYLL SKNNAIEPRS FSQNPPVLKH HQREITRTTL QSDQEEIDYD DTISVEMKKE |

FIG. 24B

Table 7 (continued)

| | | |
|---|---|---|
| | | DFDIYDEDEN QSPRSFQKKT RHYFIAAVER LWDYGMSSSP HVLRNRAQSG SVPQFKKVVF QEFTDGSFTQ PLYRGELNEH LGLLGPYIRA EVEDNIMVTF RNQASRPYSF YSSLISYEED QRQGAEPRKN FVKPNETKTY FWKVQHHMAP TKDEFDCKAW AYFSDVDLEK DVHSGLIGPL LVCHTNTLNP AHGRQVTVQE FALFFTIFDE TKSWYFTENM ERNCRAPCNI QMEDPTFKEN YRFHAINGYI MDTLPGLVMA QDQRIRWYLL SMGSNENIHS IHFSGHVFTV RKKEEYKMAL YNLYPGVFET VEMLPSKAGI WRVECLIGEH LHAGMSTLFL VYSNKCQTPL GMASGHIRDF QITASGQYGQ WAPKLARLHY SGSINAWSTK EPFSWIKVDL LAPMIIHGIK TQGARQKFSS LYISQFIIMY SLDGKKWQTY RGNSTGTLMV FFGNVDSSGI KHNIFNPPII ARYIRLHPTH YSIRSTLRME LMGCDLNSCS MPLGMESKAI SDAQITASSY FTNMFATWSP SKARLHLQGR SNAWRPQVNN PKEWLQVDFQ KTMKVTGVTT QGVKSLLTSM YVKEFLISSS QDGHQWTLFF QNGKVKVFQG NQDSFTPVVN SLDPPLLTRY LRIHPQSWVH QIALRMEVLG CEAQDLY |
| 4 | **rhScFVIII-BDD 2** | MQIELSTCFF LCLLRFCFSA TRRYYLGAVE LSWDYMQSDL GELPVDARFP PRVPKSFPFN TSVVYKKTLF VEFTDHLFNI AKPRPPWMGL LGPTIQAEVY DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE GSLAKEKTQT LHKFILLFAV FDEGKSWHSE TKNSLMQDRD AASARAWPKM HTVNGYVNRS LPGLIGCHRK SVYWHVIGMG TTPEVHSIFL EGHTFLVRNH RQASLEISPI TFLTAQTLLM DLGQFLLFCH ISSHQHDGME AYVKVDSCPE EPQLRMKNNE EAEDYDDDLT DSEMDVVRFD DDNSPSFIQI RSVAKKHPKT WVHYIAAEEE DWDYAPLVLA PDDRSYKSQY LNNGPQRIGR KYKKVRFMAY TDETFKTREA IQHESGILGP LLYGEVGDTL LIIFKNQASR PYNIYPHGIT DVRPLYSRRL PKGVKHLKDF PILPGEIFKY KWTVTVEDGP TKSDPRCLTR YYSSFVNMER DLASGLIGPL LICYKESVDQ RGNQIMSDKR NVILFSVFDE NRSWYLTENI QRFLPNPAGV QLEDPEFQAS NIMHSINGYV FDSLQLSVCL HEVAYWYILS IGAQTDFLSV FFSGYTFKHK MVYEDTLTLF PFSGETVFMS MENPGLWILG CHNSDFRNRG MTALLKVSSC DKNTGDYYED SYEDISAYLL SKNNAIEPRS FSQNPPVLKA HQAEITRTTL QSDQEEIDYD DTISVEMKKE DFDIYDEDEN QSPRSFQKKT RHYFIAAVER LWDYGMSSSP HVLRNRAQSG SVPQFKKVVF QEFTDGSFTQ PLYRGELNEH LGLLGPYIRA EVEDNIMVTF RNQASRPYSF YSSLISYEED QRQGAEPRKN FVKPNETKTY FWKVQHHMAP TKDEFDCKAW AYFSDVDLEK DVHSGLIGPL LVCHTNTLNP AHGRQVTVQE FALFFTIFDE TKSWYFTENM ERNCRAPCNI QMEDPTFKEN YRFHAINGYI MDTLPGLVMA QDQRIRWYLL SMGSNENIHS IHFSGHVFTV RKKEEYKMAL YNLYPGVFET VEMLPSKAGI WRVECLIGEH LHAGMSTLFL VYSNKCQTPL GMASGHIRDF QITASGQYGQ WAPKLARLHY SGSINAWSTK EPFSWIKVDL LAPMIIHGIK TQGARQKFSS LYISQFIIMY SLDGKKWQTY RGNSTGTLMV FFGNVDSSGI KHNIFNPPII ARYIRLHPTH YSIRSTLRME LMGCDLNSCS MPLGMESKAI SDAQITASSY FTNMFATWSP SKARLHLQGR SNAWRPQVNN PKEWLQVDFQ KTMKVTGVTT QGVKSLLTSM YVKEFLISSS QDGHQWTLFF QNGKVKVFQG NQDSFTPVVN SLDPPLLTRY LRIHPQSWVH QIALRMEVLG CEAQDLY |
| 5 | **rhScFVIII-BDD 3 (ΔF)** | MQIELSTCFF LCLLRFCFSA TRRYYLGAVE LSWDYMQSDL GELPVDARFP PRVPKSFPFN TSVVYKKTLF VEFTDHLFNI AKPRPPWMGL LGPTIQAEVY DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE GSLAKEKTQT LHKFILLFAV FDEGKSWHSE TKNSLMQDRD AASARAWPKM HTVNGYVNRS LPGLIGCHRK SVYWHVIGMG TTPEVHSIFL EGHTFLVRNH RQASLEISPI TFLTAQTLLM DLGQFLLFCH ISSHQHDGME AYVKVDSCPE |

FIG. 24C

Table 7 (continued)

| | | |
|---|---|---|
| | | EPQLRMKNNE EAEDYDDDLT DSEMDVVRFD DDNSPSFIQI RSVAKKHPKT<br>WVHYIAAEEE DWDYAPLVLA PDDRSYKSQY LNNGPQRIGR KYKKVRFMAY<br>TDETFKTREA IQHESGILGP LLYGEVGDTL LIIFKNQASR PYNIYPHGIT<br>DVRPLYSRRL PKGVKHLKDF PILPGEIFKY KWTVTVEDGP TKSDPRCLTR<br>YYSSFVNMER DLASGLIGPL LICYKESVDQ RGNQIMSDKR NVILFSVFDE<br>NRSWYLTENI QRFLPNPAGV QLEDPEFQAS NIMHSINGYV FDSLQLSVCL<br>HEVAYWYILS IGAQTDFLSV FFSGYTFKHK MVYEDTLTLF PFSGETVFMS<br>MENPGLWILG CHNSDFRNRG MTALLKVSSC DKNTGDYYED SYEDISAYLL<br>SKNNAIEPRS FSQNPPVLKE ITRTTLQSDQ EEIDYDDTIS VEMKKEDFDI<br>YDEDENQSPR SFQKKTRHYF IAAVERLWDY GMSSSPHVLR NRAQSGSVPQ<br>FKKVVFQEFT DGSFTQPLYR GELNEHLGLL GPYIRAEVED NIMVTFRNQA<br>SRPYSFYSSL ISYEEDQRQG AEPRKNFVKP NETKTYFWKV QHHMAPTKDE<br>FDCKAWAYFS DVDLEKDVHS GLIGPLLVCH TNTLNPAHGR QVTVQEFALF<br>FTIFDETKSW YFTENMERNC RAPCNIQMED PTFKENYRFH AINGYIMDTL<br>PGLVMAQDQR IRWYLLSMGS NENIHSIHFS GHVFTVRKKE EYKMALYNLY<br>PGVFETVEML PSKAGIWRVE CLIGEHLHAG MSTLFLVYSN KCQTPLGMAS<br>GHIRDFQITA SGQYGQWAPK LARLHYSGSI NAWSTKEPFS WIKVDLLAPM<br>IIHGIKTQGA RQKFSSLYIS QFIIMYSLDG KKWQTYRGNS TGTLMVFFGN<br>VDSSGIKHNI FNPPIIARYI RLHPTHYSIR STLRMELMGC DLNSCSMPLG<br>MESKAISDAQ ITASSYFTNM FATWSPSKAR LHLQGRSNAW RPQVNNPKEW<br>LQVDFQKTMK VTGVTTQGVK SLLTSMYVKE FLISSSQDGH QWTLFFQNGK<br>VKVFQGNQDS FTPVVNSLDP PLLTRYLRIH PQSWVHQIAL RMEVLGCEAQ<br>DLY |
| 6 | **rhScFVIII-BDD 4** | MQIELSTCFF LCLLRFCFSA TRRYYLGAVE LSWDYMQSDL GELPVDARFP<br>PRVPKSFPFN TSVVYKKTLF VEFTDHLFNI AKPRPPWMGL LGPTIQAEVY<br>DTVVITLKNM ASHPVSLHAV GVSYWKASEG AEYDDQTSQR EKEDDKVFPG<br>GSHTYVWQVL KENGPMASDP LCLTYSYLSH VDLVKDLNSG LIGALLVCRE<br>GSLAKEKTQT LHKFILLFAV FDEGKSWHSE TKNSLMQDRD AASARAWPKM<br>HTVNGYVNRS LPGLIGCHRK SVYWHVIGMG TTPEVHSIFL EGHTFLVRNH<br>RQASLEISPI TFLTAQTLLM DLGQFLLFCH ISSHQHDGME AYVKVDSCPE<br>EPQLRMKNNE EAEDYDDDLT DSEMDVVRFD DDNSPSFIQI RSVAKKHPKT<br>WVHYIAAEEE DWDYAPLVLA PDDRSYKSQY LNNGPQRIGR KYKKVRFMAY<br>TDETFKTREA IQHESGILGP LLYGEVGDTL LIIFKNQASR PYNIYPHGIT<br>DVRPLYSRRL PKGVKHLKDF PILPGEIFKY KWTVTVEDGP TKSDPRCLTR<br>YYSSFVNMER DLASGLIGPL LICYKESVDQ RGNQIMSDKR NVILFSVFDE<br>NRSWYLTENI QRFLPNPAGV QLEDPEFQAS NIMHSINGYV FDSLQLSVCL<br>HEVAYWYILS IGAQTDFLSV FFSGYTFKHK MVYEDTLTLF PFSGETVFMS<br>MENPGLWILG CHNSDFRNRG MTALLKVSSC DKNTGDYYED SYEDISAYLL<br>SKNNAIEPRS FSQNPPVLKR EITRTTLQSD QEEIDYDDTI SVEMKKEDFD<br>IYDEDENQSP RSFQKKTRHY FIAAVERLWD YGMSSSPHVL RNRAQSGSVP<br>QFKKVVFQEF TDGSFTQPLY RGELNEHLGL LGPYIRAEVE DNIMVTFRNQ<br>ASRPYSFYSS LISYEEDQRQ GAEPRKNFVK PNETKTYFWK VQHHMAPTKD<br>EFDCKAWAYF SDVDLEKDVH SGLIGPLLVC HTNTLNPAHG RQVTVQEFAL<br>FFTIFDETKS WYFTENMERN CRAPCNIQME DPTFKENYRF HAINGYIMDT<br>LPGLVMAQDQ RIRWYLLSMG SNENIHSIHF SGHVFTVRKK EEYKMALYNL<br>YPGVFETVEM LPSKAGIWRV ECLIGEHLHA GMSTLFLVYS NKCQTPLGMA<br>SGHIRDFQIT ASGQYGQWAP KLARLHYSGS INAWSTKEPF SWIKVDLLAP<br>MIIHGIKTQG ARQKFSSLYI SQFIIMYSLD GKKWQTYRGN STGTLMVFFG<br>NVDSSGIKHN IFNPPIIARY IRLHPTHYSI RSTLRMELMG CDLNSCSMPL<br>GMESKAISDA QITASSYFTN MFATWSPSKA RLHLQGRSNA WRPQVNNPKE<br>WLQVDFQKTM KVTGVTTQGV KSLLTSMYVK EFLISSSQDG HQWTLFFQNG |

FIG. 24D

Table 7 (continued)

| | | |
|---|---|---|
| | | KVKVFQGNQD SFTPVVNSLD PPLLTRYLRI HPQSWVHQIA LRMEVLGCEA QDLY |
| 7 | **rhFVIII-BDD addback** | MQIELSTCFF LCLLRFCFSA TRRYYLGAVE LSWDYMQSDL GELPVDARFP PRVPKSFPFN TSVVYKKTLF VEFTDHLFNI AKPRPPWMGL LGPTIQAEVY DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE GSLAKEKTQT LHKFILLFAV FDEGKSWHSE TKNSLMQDRD AASARAWPKM HTVNGYVNRS LPGLIGCHRK SVYWHVIGMG TTPEVHSIFL EGHTFLVRNH RQASLEISPI TFLTAQTLLM DLGQFLLFCH ISSHQHDGME AYVKVDSCPE EPQLRMKNNE EAEDYDDDLT DSEMDVVRFD DDNSPSFIQI RSVAKKHPKT WVHYIAAEEE DWDYAPLVLA PDDRSYKSQY LNNGPQRIGR KYKKVRFMAY TDETFKTREA IQHESGILGP LLYGEVGDTL LIIFKNQASR PYNIYPHGIT DVRPLYSRRL PKGVKHLKDF PILPGEIFKY KWTVTVEDGP TKSDPRCLTR YYSSFVNMER DLASGLIGPL LICYKESVDQ RGNQIMSDKR NVILFSVFDE NRSWYLTENI QRFLPNPAGV QLEDPEFQAS NIMHSINGYV FDSLQLSVCL HEVAYWYILS IGAQTDFLSV FFSGYTFKHK MVYEDTLTLF PFSGETVFMS MENPGLWILG CHNSDFRNRG MTALLKVSSC DKNTGDYYED SYEDISAYLL SKNNAIEPRS FSQNATNVSN NSNTSNDSNV SPPVLKRHQR EITRTTLQSD QEEIDYDDTI SVEMKKEDFD IYDEDENQSP RSFQKKTRHY FIAAVERLWD YGMSSSPHVL RNRAQSGSVP QFKKVVFQEF TDGSFTQPLY RGELNEHLGL LGPYIRAEVE DNIMVTFRNQ ASRPYSFYSS LISYEEDQRQ GAEPRKNFVK PNETKTYFWK VQHHMAPTKD EFDCKAWAYF SDVDLEKDVH SGLIGPLLVC HTNTLNPAHG RQVTVQEFAL FFTIFDETKS WYFTENMERN CRAPCNIQME DPTFKENYRF HAINGYIMDT LPGLVMAQDQ RIRWYLLSMG SNENIHSIHF SGHVFTVRKK EEYKMALYNL YPGVFETVEM LPSKAGIWRV ECLIGEHLHA GMSTLFLVYS NKCQTPLGMA SGHIRDFQIT ASGQYGQWAP KLARLHYSGS INAWSTKEPF SWIKVDLLAP MIIHGIKTQG ARQKFSSLYI SQFIIMYSLD GKKWQTYRGN STGTLMVFFG NVDSSGIKHN IFNPPIIARY IRLHPTHYSI RSTLRMELMG CDLNSCSMPL GMESKAISDA QITASSYFTN MFATWSPSKA RLHLQGRSNA WRPQVNNPKE WLQVDFQKTM KVTGVTTQGV KSLLTSMYVK EFLISSSQDG HQWTLFFQNG KVKVFQGNQD SFTPVVNSLD PPLLTRYLRI HPQSWVHQIA LRMEVLGCEA QDLY |

Table 8: FVIII Coding sequences expressed in ARPE-19 cells

| SEQ ID NO: | Sequence Name | Nucleotide Sequence |
|---|---|---|
| 8 | rhFVIII-BDD | ATGCAAATAG AGCTCTCCAC CTGCTTCTTT CTGTGCCTTT TGCGATTCTG 50<br>CTTTAGTGCC ACCAGAAGAT ACTACCTGGG TGCAGTGGAA CTGTCATGGG 100<br>ACTATATGCA AAGTGATCTC GGTGAGCTGC CTGTGGACGC AAGATTTCCT 150<br>CCTAGAGTGC CAAAATCTTT TCCATTCAAC ACCTCAGTCG TGTACAAAAA 200<br>GACTCTGTTT GTAGAATTCA CGGATCACCT TTTCAACATC GCTAAGCCAA 250<br>GGCCACCCTG GATGGGTCTG CTAGGTCCTA CCATCCAGGC TGAGGTTTAT 300<br>GATACAGTGG TCATTACACT TAAGAACATG GCTTCCCATC CTGTCAGTCT 350<br>TCATGCTGTT GGTGTATCCT ACTGGAAAGC TTCTGAGGGA GCTGAATATG 400<br>ATGATCAGAC CAGTCAAAGG GAGAAAGAAG ATGATAAAGT CTTCCCTGGT 450<br>GGAAGCCATA CATATGTCTG GCAGGTCCTG AAAGAGAATG GTCCAATGGC 500<br>CTCTGACCCA CTGTGCCTTA CCTACTCATA TCTTTCTCAT GTGGACCTGG 550<br>TAAAAGACTT GAATTCAGGC CTCATTGGAG CCCTACTAGT ATGTAGAGAA 600<br>GGGAGTCTGG CCAAGGAAAA GACACAGACC TTGCACAAAT TTATACTACT 650<br>TTTTGCTGTA TTTGATGAAG GGAAAAGTTG GCACTCAGAA ACAAAGAACT 700<br>CCTTGATGCA GGATAGGGAT GCTGCATCTG CTCGGGCCTG GCCTAAAATG 750 |

FIG. 24E

Table 8 (continued)

| | | |
|---|---|---|
| | | CACACAGTCA ATGGTTATGT AAACAGGTCT CTGCCAGGTC TGATTGGATG 800 |
| | | CCACAGGAAA TCAGTCTATT GGCATGTGAT TGGAATGGGC ACCACTCCTG 850 |
| | | AAGTGCACTC AATATTCCTC GAAGGTCACA CATTTCTTGT GAGGAACCAT 900 |
| | | CGCCAGGCGT CCTTGGAAAT CTCGCCAATA ACTTTCCTTA CTGCTCAAAC 950 |
| | | ACTCTTGATG GACCTTGGAC AGTTTCTACT GTTTTGTCAT ATCTCTTCCC 1000 |
| | | ACCAACATGA TGGCATGGAA GCTTATGTCA AAGTAGACAG CTGTCCAGAG 1050 |
| | | GAACCCCAAC TACGAATGAA AAATAATGAA GAAGCGGAAG ACTATGATGA 1100 |
| | | TGATCTTACT GATTCTGAAA TGGATGTGGT CAGGTTTGAT GATGACAACT 1150 |
| | | CTCCTTCCTT TATCCAAATT CGCTCAGTTG CCAAGAAGCA TCCTAAAACT 1200 |
| | | TGGGTACATT ACATTGCTGC TGAAGAGGAG GACTGGGACT ATGCTCCCTT 1250 |
| | | AGTCCTCGCC CCCGATGACA GAAGTTATAA AAGTCAATAT TTGAACAATG 1300 |
| | | GCCCTCAGCG GATTGGTAGG AAGTACAAAA AAGTCCGATT TATGGCATAC 1350 |
| | | ACAGATGAAA CCTTTAAGAC TCGTGAAGCT ATTCAGCATG AATCAGGAAT 1400 |
| | | CTTGGGACCT TTACTTTATG GGGAAGTTGG AGACACACTG TTGATTATAT 1450 |
| | | TTAAGAATCA AGCAAGCAGA CCATATAACA TCTACCCTCA CGGAATCACT 1500 |
| | | GATGTCCGTC CTTTGTATTC AAGGAGATTA CCAAAAGGTG TAAAACATTT 1550 |
| | | GAAGGATTTT CCAATTCTGC CAGGAGAAAT ATTCAAATAT AAATGGACAG 1600 |
| | | TGACTGTAGA AGATGGGCCA ACTAAATCAG ATCCTCGGTG CCTGACCCGC 1650 |
| | | TATTACTCTA GTTTCGTTAA TATGGAGAGA GATCTAGCTT CAGGACTCAT 1700 |
| | | TGGCCCTCTC CTCATCTGCT ACAAAGAATC TGTAGATCAA AGAGGAAACC 1750 |
| | | AGATAATGTC AGACAAGAGG AATGTCATCC TGTTTTCTGT ATTTGATGAG 1800 |
| | | AACCGAAGCT GGTACCTCAC AGAGAATATA CAACGCTTTC TCCCCAATCC 1850 |
| | | AGCTGGAGTG CAGCTTGAGG ATCCAGAGTT CCAAGCCTCC AACATCATGC 1900 |
| | | ACAGCATCAA TGGCTATGTT TTTGATAGTT TGCAGTTGTC AGTTTGTTTG 1950 |
| | | CATGAGGTGG CATACTGGTA CATTCTAAGC ATTGGAGCAC AGACTGACTT 2000 |
| | | CCTTTCTGTC TTCTTCTCTG GATATACCTT CAAACACAAA ATGGTCTATG 2050 |
| | | AAGACACACT CACCCTATTC CCATTCTCAG GAGAAACTGT CTTCATGTCG 2100 |
| | | ATGGAAAACC CAGGTCTATG GATTCTGGGG TGCCACAACT CAGACTTTCG 2150 |
| | | GAACAGAGGC ATGACCGCCT TACTGAAGGT TTCTAGTTGT GACAAGAACA 2200 |
| | | CTGGTGATTA TTACGAGGAC AGTTATGAAG ATATTTCAGC ATACTTGCTG 2250 |
| | | AGTAAAAACA ATGCCATTGA ACCAAGAAGC TTCTCCCAAA ACCCACCAGT 2300 |
| | | CTTGAAACGC CATCAACGGG AAATAACTCG TACTACTCTT CAGTCAGATC 2350 |
| | | AAGAGGAAAT TGACTATGAT GATACCATAT CAGTTGAAAT GAAGAAGGAA 2400 |
| | | GATTTTGACA TTTATGATGA GGATGAAAAT CAGAGCCCCC GCAGCTTTCA 2450 |
| | | AAAGAAAACA CGACACTATT TTATTGCTGC AGTGGAGAGG CTCTGGGATT 2500 |
| | | ATGGGATGAG TAGCTCCCCA CATGTTCTAA GAAACAGGGC TCAGAGTGGC 2550 |
| | | AGTGTCCCTC AGTTCAAGAA AGTTGTTTTC CAGGAATTTA CTGATGGCTC 2600 |
| | | CTTTACTCAG CCCTTATACC GTGGAGAACT AAATGAACAT TTGGGACTCC 2650 |
| | | TGGGGCCATA TATAAGAGCA GAAGTTGAAG ATAATATCAT GGTAACTTTC 2700 |
| | | AGAAATCAGG CCTCTCGTCC CTATTCCTTC TATTCTAGCC TTATTTCTTA 2750 |
| | | TGAGGAAGAT CAGAGGCAAG GAGCAGAACC TAGAAAAAAC TTTGTCAAGC 2800 |
| | | CTAATGAAAC CAAAACTTAC TTTTGGAAAG TGCAACATCA TATGGCACCC 2850 |
| | | ACTAAAGATG AGTTTGACTG CAAAGCCTGG GCTTATTTCT CTGATGTTGA 2900 |
| | | CCTGGAAAAA GATGTGCACT CAGGCCTGAT TGGACCCCTT CTGGTCTGCC 2950 |
| | | ACACTAACAC ACTGAACCCT GCTCATGGGA GACAAGTGAC AGTACAGGAA 3000 |
| | | TTTGCTCTGT TTTTCACCAT CTTTGATGAG ACCAAAAGCT GGTACTTCAC 3050 |
| | | TGAAAATATG GAAAGAAACT GCAGGGCTCC CTGCAATATC CAGATGGAAG 3100 |
| | | ATCCCACTTT TAAAGAGAAT TATCGCTTCC ATGCAATCAA TGGCTACATA 3150 |
| | | ATGGATACAC TACCTGGCTT AGTAATGGCT CAGGATCAAA GGATTCGATG 3200 |
| | | GTATCTGCTC AGCATGGGCA GCAATGAAAA CATCCATTCT ATTCATTTCA 3250 |
| | | GTGGACATGT GTTCACTGTA CGAAAAAAAG AGGAGTATAA AATGGCACTG 3300 |
| | | TACAATCTCT ATCCAGGTGT TTTTGAGACA GTGGAAATGT TACCATCCAA 3350 |
| | | AGCTGGAATT TGGCGGGTGG AATGCCTTAT TGGCGAGCAT CTACATGCTG 3400 |
| | | GGATGAGCAC ACTTTTTCTG GTGTACAGCA ATAAGTGTCA GACTCCCCTG 3450 |
| | | GGAATGGCTT CTGGACACAT TAGAGATTTT CAGATTACAG CTTCAGGACA 3500 |
| | | ATATGGACAG TGGGCCCCAA AGCTGGCCAG ACTTCATTAT TCCGGATCAA 3550 |
| | | TCAATGCCTG GAGCACCAAG GAGCCCTTTT CTTGGATCAA GGTGGATCTG 3600 |

FIG. 24F

Table 8 (continued)

| | | |
|---|---|---|
| | | TTGGCACCAA TGATTATTCA CGGCATCAAG ACCCAGGGTG CCCGTCAGAA 3650<br>GTTCTCCAGC CTCTACATCT CTCAGTTTAT CATCATGTAT AGTCTTGATG 3700<br>GGAAGAAGTG GCAGACTTAT CGAGGAAATT CCACTGGAAC CTTAATGGTC 3750<br>TTCTTTGGCA ATGTGGATTC ATCTGGGATA AAACACAATA TTTTTAACCC 3800<br>TCCAATTATT GCTCGATACA TCCGTTTGCA CCCAACTCAT TATAGCATTC 3850<br>GCAGCACTCT TCGCATGGAG TTGATGGGCT GTGATTTAAA TAGTTGCAGC 3900<br>ATGCCATTGG GAATGGAGAG TAAAGCAATA TCAGATGCAC AGATTACTGC 3950<br>TTCATCCTAC TTTACCAATA TGTTTGCCAC CTGGTCTCCT TCAAAAGCTC 4000<br>GACTTCACCT CCAAGGGAGG AGTAATGCCT GGAGACCTCA GGTGAATAAT 4050<br>CCAAAAGAGT GGCTGCAAGT GGACTTCCAG AAGACAATGA AAGTCACAGG 4100<br>AGTAACTACT CAGGGAGTAA AATCTCTGCT TACCAGCATG TATGTGAAGG 4150<br>AGTTCCTCAT CTCCAGCAGT CAAGATGGCC ATCAGTGGAC TCTCTTTTTT 4200<br>CAGAATGGCA AAGTAAAGGT TTTTCAGGGA AATCAAGACT CCTTCACACC 4250<br>TGTGGTGAAC TCTCTAGACC CACCGTTACT GACTCGCTAC CTTCGAATTC 4300<br>ACCCCCAGAG TTGGGTGCAC CAGATTGCCC TGAGGATGGA GGTTCTGGGC 4350<br>TGCGAGGCAC AGGACCTCTA CTGA 4374 |
| **9** | rhFVIII-<br>BDD<br>Sc1 | ATGCAAATAG AGCTCTCCAC CTGCTTCTTT CTGTGCCTTT TGCGATTCTG<br>CTTTAGTGCC ACCAGAAGAT ACTACCTGGG TGCAGTGGAA CTGTCATGGG<br>ACTATATGCA AAGTGATCTC GGTGAGCTGC CTGTGGACGC AAGATTTCCT<br>CCTAGAGTGC CAAAATCTTT TCCATTCAAC ACCTCAGTCG TGTACAAAAA<br>GACTCTGTTT GTAGAATTCA CGGATCACCT TTTCAACATC GCTAAGCCAA<br>GGCCACCCTG GATGGGTCTG CTAGGTCCTA CCATCCAGGC TGAGGTTTAT<br>GATACAGTGG TCATTACACT TAAGAACATG GCTTCCCATC CTGTCAGTCT<br>TCATGCTGTT GGTGTATCCT ACTGGAAAGC TTCTGAGGGA GCTGAATATG<br>ATGATCAGAC CAGTCAAAGG GAGAAAGAAG ATGATAAAGT CTTCCCTGGT<br>GGAAGCCATA CATATGTCTG GCAGGTCCTG AAAGAGAATG GTCCAATGGC<br>CTCTGACCCA CTGTGCCTTA CCTACTCATA TCTTTCTCAT GTGGACCTGG<br>TAAAAGACTT GAATTCAGGC CTCATTGGAG CCCTACTAGT ATGTAGAGAA<br>GGGAGTCTGG CCAAGGAAAA GACACAGACC TTGCACAAAT TTATACTACT<br>TTTTGCTGTA TTTGATGAAG GGAAAAGTTG GCACTCAGAA ACAAAGAACT<br>CCTTGATGCA GGATAGGGAT GCTGCATCTG CTCGGGCCTG GCCTAAAATG<br>CACACAGTCA ATGGTTATGT AAACAGGTCT CTGCCAGGTC TGATTGGATG<br>CCACAGGAAA TCAGTCTATT GGCATGTGAT TGGAATGGGC ACCACTCCTG<br>AAGTGCACTC AATATTCCTC GAAGGTCACA CATTTCTTGT GAGGAACCAT<br>CGCCAGGCGT CCTTGGAAAT CTCGCCAATA ACTTTCCTTA CTGCTCAAAC<br>ACTCTTGATG GACCTTGGAC AGTTTCTACT GTTTTGTCAT ATCTCTTCCC<br>ACCAACATGA TGGCATGGAA GCTTATGTCA AAGTAGACAG CTGTCCAGAG<br>GAACCCCAAC TACGAATGAA AAATAATGAA GAAGCGGAAG ACTATGATGA<br>TGATCTTACT GATTCTGAAA TGGATGTGGT CAGGTTTGAT GATGACAACT<br>CTCCTTCCTT TATCCAAATT CGCTCAGTTG CCAAGAAGCA TCCTAAAACT<br>TGGGTACATT ACATTGCTGC TGAAGAGGAG GACTGGGACT ATGCTCCCTT<br>AGTCCTCGCC CCCGATGACA GAAGTTATAA AAGTCAATAT TTGAACAATG<br>GCCCTCAGCG GATTGGTAGG AAGTACAAAA AAGTCCGATT TATGGCATAC<br>ACAGATGAAA CCTTTAAGAC TCGTGAAGCT ATTCAGCATG AATCAGGAAT<br>CTTGGGACCT TTACTTTATG GGGAAGTTGG AGACACACTG TTGATTATAT<br>TTAAGAATCA AGCAAGCAGA CCATATAACA TCTACCCTCA CGGAATCACT<br>GATGTCCGTC CTTTGTATTC AAGGAGATTA CCAAAAGGTG TAAAACATTT<br>GAAGGATTTT CCAATTCTGC CAGGAGAAAT ATTCAAATAT AAATGGACAG<br>TGACTGTAGA AGATGGGCCA ACTAAATCAG ATCCTCGGTG CCTGACCCGC<br>TATTACTCTA GTTTCGTTAA TATGGAGAGA GATCTAGCTT CAGGACTCAT<br>TGGCCCTCTC CTCATCTGCT ACAAAGAATC TGTAGATCAA AGAGGAAACC<br>AGATAATGTC AGACAAGAGG AATGTCATCC TGTTTTCTGT ATTTGATGAG<br>AACCGAAGCT GGTACCTCAC AGAGAATATA CAACGCTTTC TCCCCAATCC<br>AGCTGGAGTG CAGCTTGAGG ATCCAGAGTT CCAAGCCTCC AACATCATGC<br>ACAGCATCAA TGGCTATGTT TTTGATAGTT TGCAGTTGTC AGTTTGTTTG<br>CATGAGGTGG CATACTGGTA CATTCTAAGC ATTGGAGCAC AGACTGACTT<br>CCTTTCTGTC TTCTTCTCTG GATATACCTT CAAACACAAA ATGGTCTATG |

FIG. 24G

Table 8 (continued)

| | | |
|---|---|---|
| | | AAGACACACT CACCCTATTC CCATTCTCAG GAGAAACTGT CTTCATGTCG<br>ATGGAAAACC CAGGTCTATG GATTCTGGGG TGCCACAACT CAGACTTTCG<br>GAACAGAGGC ATGACCGCCT TACTGAAGGT TTCTAGTTGT GACAAGAACA<br>CTGGTGATTA TTACGAGGAC AGTTATGAAG ATATTTCAGC ATACTTGCTG<br>AGTAAAAACA ATGCCATTGA ACCAAGAAGC TTCTCCCAAA ACCCACCAGT<br>CTTGAAACAC CATCAACGGG AAATAACTCG TACTACTCTT CAGTCAGATC<br>AAGAGGAAAT TGACTATGAT GATACCATAT CAGTTGAAAT GAAGAAGGAA<br>GATTTTGACA TTTATGATGA GGATGAAAAT CAGAGCCCCC GCAGCTTTCA<br>AAAGAAAACA CGACACTATT TTATTGCTGC AGTGGAGAGG CTCTGGGATT<br>ATGGGATGAG TAGCTCCCCA CATGTTCTAA GAAACAGGGC TCAGAGTGGC<br>AGTGTCCCTC AGTTCAAGAA AGTTGTTTTC CAGGAATTTA CTGATGGCTC<br>CTTTACTCAG CCCTTATACC GTGGAGAACT AAATGAACAT TTGGGACTCC<br>TGGGGCCATA TATAAGAGCA GAAGTTGAAG ATAATATCAT GGTAACTTTC<br>AGAAATCAGG CCTCTCGTCC CTATTCCTTC TATTCTAGCC TTATTTCTTA<br>TGAGGAAGAT CAGAGGCAAG GAGCAGAACC TAGAAAAAAC TTTGTCAAGC<br>CTAATGAAAC CAAAACTTAC TTTTGGAAAG TGCAACATCA TATGGCACCC<br>ACTAAAGATG AGTTTGACTG CAAAGCCTGG GCTTATTTCT CTGATGTTGA<br>CCTGGAAAAA GATGTGCACT CAGGCCTGAT TGGACCCCTT CTGGTCTGCC<br>ACACTAACAC ACTGAACCCT GCTCATGGGA GACAAGTGAC AGTACAGGAA<br>TTTGCTCTGT TTTTCACCAT CTTTGATGAG ACCAAAAGCT GGTACTTCAC<br>TGAAAATATG GAAAGAAACT GCAGGGCTCC CTGCAATATC CAGATGGAAG<br>ATCCCACTTT TAAAGAGAAT TATCGCTTCC ATGCAATCAA TGGCTACATA<br>ATGGATACAC TACCTGGCTT AGTAATGGCT CAGGATCAAA GGATTCGATG<br>GTATCTGCTC AGCATGGGCA GCAATGAAAA CATCCATTCT ATTCATTTCA<br>GTGGACATGT GTTCACTGTA CGAAAAAAAG AGGAGTATAA AATGGCACTG<br>TACAATCTCT ATCCAGGTGT TTTTGAGACA GTGGAAATGT TACCATCCAA<br>AGCTGGAATT TGGCGGGTGG AATGCCTTAT TGGCGAGCAT CTACATGCTG<br>GGATGAGCAC ACTTTTTCTG GTGTACAGCA ATAAGTGTCA GACTCCCCTG<br>GGAATGGCTT CTGGACACAT TAGAGATTTT CAGATTACAG CTTCAGGACA<br>ATATGGACAG TGGGCCCCAA AGCTGGCCAG ACTTCATTAT TCCGGATCAA<br>TCAATGCCTG GAGCACCAAG GAGCCCTTTT CTTGGATCAA GGTGGATCTG<br>TTGGCACCAA TGATTATTCA CGGCATCAAG ACCCAGGGTG CCCGTCAGAA<br>GTTCTCCAGC CTCTACATCT CTCAGTTTAT CATCATGTAT AGTCTTGATG<br>GGAAGAAGTG GCAGACTTAT CGAGGAAATT CCACTGGAAC CTTAATGGTC<br>TTCTTTGGCA ATGTGGATTC ATCTGGGATA AAACACAATA TTTTTAACCC<br>TCCAATTATT GCTCGATACA TCCGTTTGCA CCCAACTCAT TATAGCATTC<br>GCAGCACTCT TCGCATGGAG TTGATGGGCT GTGATTTAAA TAGTTGCAGC<br>ATGCCATTGG GAATGGAGAG TAAAGCAATA TCAGATGCAC AGATTACTGC<br>TTCATCCTAC TTTACCAATA TGTTTGCCAC CTGGTCTCCT TCAAAAGCTC<br>GACTTCACCT CCAAGGGAGG AGTAATGCCT GGAGACCTCA GGTGAATAAT<br>CCAAAAGAGT GGCTGCAAGT GGACTTCCAG AAGACAATGA AAGTCACAGG<br>AGTAACTACT CAGGGAGTAA AATCTCTGCT TACCAGCATG TATGTGAAGG<br>AGTTCCTCAT CTCCAGCAGT CAAGATGGCC ATCAGTGGAC TCTCTTTTTT<br>CAGAATGGCA AAGTAAAGGT TTTTCAGGGA AATCAAGACT CCTTCACACC<br>TGTGGTGAAC TCTCTAGACC CACCGTTACT GACTCGCTAC CTTCGAATTC<br>ACCCCCAGAG TTGGGTGCAC CAGATTGCCC TGAGGATGGA GGTTCTGGGC<br>TGCGAGGCAC AGGACCTCTA CTGA |
| **10** | rhFVIII-<br>BDD<br>Sc2 | ATGCAAATAG AGCTCTCCAC CTGCTTCTTT CTGTGCCTTT TGCGATTCTG 50<br>CTTTAGTGCC ACCAGAAGAT ACTACCTGGG TGCAGTGGAA CTGTCATGGG 100<br>ACTATATGCA AAGTGATCTC GGTGAGCTGC CTGTGGACGC AAGATTTCCT 150<br>CCTAGAGTGC CAAAATCTTT TCCATTCAAC ACCTCAGTCG TGTACAAAAA 200<br>GACTCTGTTT GTAGAATTCA CGGATCACCT TTTCAACATC GCTAAGCCAA 250<br>GGCCACCCTG GATGGGTCTG CTAGGTCCTA CCATCCAGGC TGAGGTTTAT 300<br>GATACAGTGG TCATTACACT TAAGAACATG GCTTCCCATC CTGTCAGTCT 350<br>TCATGCTGTT GGTGTATCCT ACTGGAAAGC TTCTGAGGGA GCTGAATATG 400<br>ATGATCAGAC CAGTCAAAGG GAGAAAGAAG ATGATAAAGT CTTCCCTGGT 450<br>GGAAGCCATA CATATGTCTG GCAGGTCCTG AAAGAGAATG GTCCAATGGC 500 |

FIG. 24H

Table 8 (continued)

| | | |
|---|---|---|
| | | CTCTGACCCA CTGTGCCTTA CCTACTCATA TCTTTCTCAT GTGGACCTGG 550 |
| | | TAAAAGACTT GAATTCAGGC CTCATTGGAG CCCTACTAGT ATGTAGAGAA 600 |
| | | GGGAGTCTGG CCAAGGAAAA GACACAGACC TTGCACAAAT TTATACTACT 650 |
| | | TTTTGCTGTA TTTGATGAAG GGAAAAGTTG GCACTCAGAA ACAAAGAACT 700 |
| | | CCTTGATGCA GGATAGGGAT GCTGCATCTG CTCGGGCCTG GCCTAAAATG 750 |
| | | CACACAGTCA ATGGTTATGT AAACAGGTCT CTGCCAGGTC TGATTGGATG 800 |
| | | CCACAGGAAA TCAGTCTATT GGCATGTGAT TGGAATGGGC ACCACTCCTG 850 |
| | | AAGTGCACTC AATATTCCTC GAAGGTCACA CATTTCTTGT GAGGAACCAT 900 |
| | | CGCCAGGCGT CCTTGGAAAT CTCGCCAATA ACTTTCCTTA CTGCTCAAAC 950 |
| | | ACTCTTGATG GACCTTGGAC AGTTTCTACT GTTTTGTCAT ATCTCTTCCC 1000 |
| | | ACCAACATGA TGGCATGGAA GCTTATGTCA AAGTAGACAG CTGTCCAGAG 1050 |
| | | GAACCCCAAC TACGAATGAA AAATAATGAA GAAGCGGAAG ACTATGATGA 1100 |
| | | TGATCTTACT GATTCTGAAA TGGATGTGGT CAGGTTTGAT GATGACAACT 1150 |
| | | CTCCTTCCTT TATCCAAATT CGCTCAGTTG CCAAGAAGCA TCCTAAAACT 1200 |
| | | TGGGTACATT ACATTGCTGC TGAAGAGGAG GACTGGGACT ATGCTCCCTT 1250 |
| | | AGTCCTCGCC CCCGATGACA GAAGTTATAA AAGTCAATAT TTGAACAATG 1300 |
| | | GCCCTCAGCG GATTGGTAGG AAGTACAAAA AAGTCCGATT TATGGCATAC 1350 |
| | | ACAGATGAAA CCTTTAAGAC TCGTGAAGCT ATTCAGCATG AATCAGGAAT 1400 |
| | | CTTGGGACCT TTACTTTATG GGGAAGTTGG AGACACACTG TTGATTATAT 1450 |
| | | TTAAGAATCA AGCAAGCAGA CCATATAACA TCTACCCTCA CGGAATCACT 1500 |
| | | GATGTCCGTC CTTTGTATTC AAGGAGATTA CCAAAAGGTG TAAAACATTT 1550 |
| | | GAAGGATTTT CCAATTCTGC CAGGAGAAAT ATTCAAATAT AAATGGACAG 1600 |
| | | TGACTGTAGA AGATGGGCCA ACTAAATCAG ATCCTCGGTG CCTGACCCGC 1650 |
| | | TATTACTCTA GTTTCGTTAA TATGGAGAGA GATCTAGCTT CAGGACTCAT 1700 |
| | | TGGCCCTCTC CTCATCTGCT ACAAAGAATC TGTAGATCAA AGAGGAAACC 1750 |
| | | AGATAATGTC AGACAAGAGG AATGTCATCC TGTTTTCTGT ATTTGATGAG 1800 |
| | | AACCGAAGCT GGTACCTCAC AGAGAATATA CAACGCTTTC TCCCCAATCC 1850 |
| | | AGCTGGAGTG CAGCTTGAGG ATCCAGAGTT CCAAGCCTCC AACATCATGC 1900 |
| | | ACAGCATCAA TGGCTATGTT TTTGATAGTT TGCAGTTGTC AGTTTGTTTG 1950 |
| | | CATGAGGTGG CATACTGGTA CATTCTAAGC ATTGGAGCAC AGACTGACTT 2000 |
| | | CCTTTCTGTC TTCTTCTCTG GATATACCTT CAAACACAAA ATGGTCTATG 2050 |
| | | AAGACACACT CACCCTATTC CCATTCTCAG GAGAAACTGT CTTCATGTCG 2100 |
| | | ATGGAAAACC CAGGTCTATG GATTCTGGGG TGCCACAACT CAGACTTTCG 2150 |
| | | GAACAGAGGC ATGACCGCCT TACTGAAGGT TTCTAGTTGT GACAAGAACA 2200 |
| | | CTGGTGATTA TTACGAGGAC AGTTATGAAG ATATTTCAGC ATACTTGCTG 2250 |
| | | AGTAAAAACA ATGCCATTGA ACCAAGAAGC TTCTCCCAAA ACCCACCAGT 2300 |
| | | CTTGAAAGCC CATCAAGCGG AAATAACTCG TACTACTCTT CAGTCAGATC 2350 |
| | | AAGAGGAAAT TGACTATGAT GATACCATAT CAGTTGAAAT GAAGAAGGAA 2400 |
| | | GATTTTGACA TTTATGATGA GGATGAAAAT CAGAGCCCCC GCAGCTTTCA 2450 |
| | | AAAGAAAACA CGACACTATT TTATTGCTGC AGTGGAGAGG CTCTGGGATT 2500 |
| | | ATGGGATGAG TAGCTCCCCA CATGTTCTAA GAAACAGGGC TCAGAGTGGC 2550 |
| | | AGTGTCCCTC AGTTCAAGAA AGTTGTTTTC CAGGAATTTA CTGATGGCTC 2600 |
| | | CTTTACTCAG CCCTTATACC GTGGAGAACT AAATGAACAT TTGGGACTCC 2650 |
| | | TGGGGCCATA TATAAGAGCA GAAGTTGAAG ATAATATCAT GGTAACTTTC 2700 |
| | | AGAAATCAGG CCTCTCGTCC CTATTCCTTC TATTCTAGCC TTATTTCTTA 2750 |
| | | TGAGGAAGAT CAGAGGCAAG GAGCAGAACC TAGAAAAAAC TTTGTCAAGC 2800 |
| | | CTAATGAAAC CAAAACTTAC TTTTGGAAAG TGCAACATCA TATGGCACCC 2850 |
| | | ACTAAAGATG AGTTTGACTG CAAAGCCTGG GCTTATTTCT CTGATGTTGA 2900 |
| | | CCTGGAAAAA GATGTGCACT CAGGCCTGAT TGGACCCCTT CTGGTCTGCC 2950 |
| | | ACACTAACAC ACTGAACCCT GCTCATGGGA GACAAGTGAC AGTACAGGAA 3000 |
| | | TTTGCTCTGT TTTTCACCAT CTTTGATGAG ACCAAAAGCT GGTACTTCAC 3050 |
| | | TGAAAATATG GAAAGAAACT GCAGGGCTCC CTGCAATATC CAGATGGAAG 3100 |
| | | ATCCCACTTT TAAAGAGAAT TATCGCTTCC ATGCAATCAA TGGCTACATA 3150 |
| | | ATGGATACAC TACCTGGCTT AGTAATGGCT CAGGATCAAA GGATTCGATG 3200 |
| | | GTATCTGCTC AGCATGGGCA GCAATGAAAA CATCCATTCT ATTCATTTCA 3250 |
| | | GTGGACATGT GTTCACTGTA CGAAAAAAAG AGGAGTATAA AATGGCACTG 3300 |
| | | TACAATCTCT ATCCAGGTGT TTTTGAGACA GTGGAAATGT TACCATCCAA 3350 |

FIG. 24I

Table 8 (continued)

| | | |
|---|---|---|
| | | AGCTGGAATT TGGCGGGTGG AATGCCTTAT TGGCGAGCAT CTACATGCTG 3400<br>GGATGAGCAC ACTTTTTCTG GTGTACAGCA ATAAGTGTCA GACTCCCCTG 3450<br>GGAATGGCTT CTGGACACAT TAGAGATTTT CAGATTACAG CTTCAGGACA 3500<br>ATATGGACAG TGGGCCCCAA AGCTGGCCAG ACTTCATTAT TCCGGATCAA 3550<br>TCAATGCCTG GAGCACCAAG GAGCCCTTTT CTTGGATCAA GGTGGATCTG 3600<br>TTGGCACCAA TGATTATTCA CGGCATCAAG ACCCAGGGTG CCCGTCAGAA 3650<br>GTTCTCCAGC CTCTACATCT CTCAGTTTAT CATCATGTAT AGTCTTGATG 3700<br>GGAAGAAGTG GCAGACTTAT CGAGGAAATT CCACTGGAAC CTTAATGGTC 3750<br>TTCTTTGGCA ATGTGGATTC ATCTGGGATA AAACACAATA TTTTTAACCC 3800<br>TCCAATTATT GCTCGATACA TCCGTTTGCA CCCAACTCAT TATAGCATTC 3850<br>GCAGCACTCT TCGCATGGAG TTGATGGGCT GTGATTTAAA TAGTTGCAGC 3900<br>ATGCCATTGG GAATGGAGAG TAAAGCAATA TCAGATGCAC AGATTACTGC 3950<br>TTCATCCTAC TTTACCAATA TGTTTGCCAC CTGGTCTCCT TCAAAAGCTC 4000<br>GACTTCACCT CCAAGGGAGG AGTAATGCCT GGAGACCTCA GGTGAATAAT 4050<br>CCAAAAGAGT GGCTGCAAGT GGACTTCCAG AAGACAATGA AAGTCACAGG 4100<br>AGTAACTACT CAGGGAGTAA AATCTCTGCT TACCAGCATG TATGTGAAGG 4150<br>AGTTCCTCAT CTCCAGCAGT CAAGATGGCC ATCAGTGGAC TCTCTTTTTT 4200<br>CAGAATGGCA AAGTAAAGGT TTTTCAGGGA AATCAAGACT CCTTCACACC 4250<br>TGTGGTGAAC TCTCTAGACC CACCGTTACT GACTCGCTAC CTTCGAATTC 4300<br>ACCCCCAGAG TTGGGTGCAC CAGATTGCCC TGAGGATGGA GGTTCTGGGC 4350<br>TGCGAGGCAC AGGACCTCTA CTGA 4374 |
| **11** | rhFVIII-<br>BDD<br>Sc3 | ATGCAAATAG AGCTCTCCAC CTGCTTCTTT CTGTGCCTTT TGCGATTCTG<br>CTTTAGTGCC ACCAGAAGAT ACTACCTGGG TGCAGTGGAA CTGTCATGGG<br>ACTATATGCA AAGTGATCTC GGTGAGCTGC CTGTGGACGC AAGATTTCCT<br>CCTAGAGTGC CAAAATCTTT TCCATTCAAC ACCTCAGTCG TGTACAAAAA<br>GACTCTGTTT GTAGAATTCA CGGATCACCT TTTCAACATC GCTAAGCCAA<br>GGCCACCCTG GATGGGTCTG CTAGGTCCTA CCATCCAGGC TGAGGTTTAT<br>GATACAGTGG TCATTACACT TAAGAACATG GCTTCCCATC CTGTCAGTCT<br>TCATGCTGTT GGTGTATCCT ACTGGAAAGC TTCTGAGGGA GCTGAATATG<br>ATGATCAGAC CAGTCAAAGG GAGAAAGAAG ATGATAAAGT CTTCCCTGGT<br>GGAAGCCATA CATATGTCTG GCAGGTCCTG AAAGAGAATG GTCCAATGGC<br>CTCTGACCCA CTGTGCCTTA CCTACTCATA TCTTTCTCAT GTGGACCTGG<br>TAAAAGACTT GAATTCAGGC CTCATTGGAG CCCTACTAGT ATGTAGAGAA<br>GGGAGTCTGG CCAAGGAAAA GACACAGACC TTGCACAAAT TTATACTACT<br>TTTTGCTGTA TTTGATGAAG GGAAAAGTTG GCACTCAGAA ACAAAGAACT<br>CCTTGATGCA GGATAGGGAT GCTGCATCTG CTCGGGCCTG GCCTAAAATG<br>CACACAGTCA ATGGTTATGT AAACAGGTCT CTGCCAGGTC TGATTGGATG<br>CCACAGGAAA TCAGTCTATT GGCATGTGAT TGGAATGGGC ACCACTCCTG<br>AAGTGCACTC AATATTCCTC GAAGGTCACA CATTTCTTGT GAGGAACCAT<br>CGCCAGGCGT CCTTGGAAAT CTCGCCAATA ACTTTCCTTA CTGCTCAAAC<br>ACTCTTGATG GACCTTGGAC AGTTTCTACT GTTTTGTCAT ATCTCTTCCC<br>ACCAACATGA TGGCATGGAA GCTTATGTCA AAGTAGACAG CTGTCCAGAG<br>GAACCCCAAC TACGAATGAA AAATAATGAA GAAGCGGAAG ACTATGATGA<br>TGATCTTACT GATTCTGAAA TGGATGTGGT CAGGTTTGAT GATGACAACT<br>CTCCTTCCTT TATCCAAATT CGCTCAGTTG CCAAGAAGCA TCCTAAAACT<br>TGGGTACATT ACATTGCTGC TGAAGAGGAG GACTGGGACT ATGCTCCCTT<br>AGTCCTCGCC CCCGATGACA GAAGTTATAA AAGTCAATAT TTGAACAATG<br>GCCCTCAGCG GATTGGTAGG AAGTACAAAA AAGTCCGATT TATGGCATAC<br>ACAGATGAAA CCTTTAAGAC TCGTGAAGCT ATTCAGCATG AATCAGGAAT<br>CTTGGGACCT TTACTTTATG GGGAAGTTGG AGACACACTG TTGATTATAT<br>TTAAGAATCA AGCAAGCAGA CCATATAACA TCTACCCTCA CGGAATCACT<br>GATGTCCGTC CTTTGTATTC AAGGAGATTA CCAAAAGGTG TAAAACATTT<br>GAAGGATTTT CCAATTCTGC CAGGAGAAAT ATTCAAATAT AAATGGACAG<br>TGACTGTAGA AGATGGGCCA ACTAAATCAG ATCCTCGGTG CCTGACCCGC<br>TATTACTCTA GTTTCGTTAA TATGGAGAGA GATCTAGCTT CAGGACTCAT<br>TGGCCCTCTC CTCATCTGCT ACAAAGAATC TGTAGATCAA AGAGGAAACC<br>AGATAATGTC AGACAAGAGG AATGTCATCC TGTTTTCTGT ATTTGATGAG |

FIG. 24J

Table 8 (continued)

| | | |
|---|---|---|
| | | AACCGAAGCT GGTACCTCAC AGAGAATATA CAACGCTTTC TCCCCAATCC<br>AGCTGGAGTG CAGCTTGAGG ATCCAGAGTT CCAAGCCTCC AACATCATGC<br>ACAGCATCAA TGGCTATGTT TTTGATAGTT TGCAGTTGTC AGTTTGTTTG<br>CATGAGGTGG CATACTGGTA CATTCTAAGC ATTGGAGCAC AGACTGACTT<br>CCTTTCTGTC TTCTTCTCTG GATATACCTT CAAACACAAA ATGGTCTATG<br>AAGACACACT CACCCTATTC CCATTCTCAG GAGAAACTGT CTTCATGTCG<br>ATGGAAAACC CAGGTCTATG GATTCTGGGG TGCCACAACT CAGACTTTCG<br>GAACAGAGGC ATGACCGCCT TACTGAAGGT TTCTAGTTGT GACAAGAACA<br>CTGGTGATTA TTACGAGGAC AGTTATGAAG ATATTTCAGC ATACTTGCTG<br>AGTAAAAACA ATGCCATTGA ACCAAGAAGC TTCTCCCAAA ACCCACCAGT<br>CTTGAAAGAA ATAACTCGTA CTACTCTTCA GTCAGATCAA GAGGAAATTG<br>ACTATGATGA TACCATATCA GTTGAAATGA AGAAGGAAGA TTTTGACATT<br>TATGATGAGG ATGAAAATCA GAGCCCCCGC AGCTTTCAAA AGAAAACACG<br>ACACTATTTT ATTGCTGCAG TGGAGAGGCT CTGGGATTAT GGGATGAGTA<br>GCTCCCCACA TGTTCTAAGA AACAGGGCTC AGAGTGGCAG TGTCCCTCAG<br>TTCAAGAAAG TTGTTTTCCA GGAATTTACT GATGGCTCCT TTACTCAGCC<br>CTTATACCGT GGAGAACTAA ATGAACATTT GGGACTCCTG GGGCCATATA<br>TAAGAGCAGA AGTTGAAGAT AATATCATGG TAACTTTCAG AAATCAGGCC<br>TCTCGTCCCT ATTCCTTCTA TTCTAGCCTT ATTTCTTATG AGGAAGATCA<br>GAGGCAAGGA GCAGAACCTA GAAAAAACTT TGTCAAGCCT AATGAAACCA<br>AAACTTACTT TTGGAAAGTG CAACATCATA TGGCACCCAC TAAAGATGAG<br>TTTGACTGCA AAGCCTGGGC TTATTTCTCT GATGTTGACC TGGAAAAAGA<br>TGTGCACTCA GGCCTGATTG GACCCCTTCT GGTCTGCCAC ACTAACACAC<br>TGAACCCTGC TCATGGGAGA CAAGTGACAG TACAGGAATT TGCTCTGTTT<br>TTCACCATCT TTGATGAGAC CAAAAGCTGG TACTTCACTG AAAATATGGA<br>AAGAAACTGC AGGGCTCCCT GCAATATCCA GATGGAAGAT CCCACTTTTA<br>AAGAGAATTA TCGCTTCCAT GCAATCAATG GCTACATAAT GGATACACTA<br>CCTGGCTTAG TAATGGCTCA GGATCAAAGG ATTCGATGGT ATCTGCTCAG<br>CATGGGCAGC AATGAAAACA TCCATTCTAT TCATTTCAGT GGACATGTGT<br>TCACTGTACG AAAAAAAGAG GAGTATAAAA TGGCACTGTA CAATCTCTAT<br>CCAGGTGTTT TTGAGACAGT GGAAATGTTA CCATCCAAAG CTGGAATTTG<br>GCGGGTGGAA TGCCTTATTG GCGAGCATCT ACATGCTGGG ATGAGCACAC<br>TTTTTCTGGT GTACAGCAAT AAGTGTCAGA CTCCCCTGGG AATGGCTTCT<br>GGACACATTA GAGATTTTCA GATTACAGCT TCAGGACAAT ATGGACAGTG<br>GGCCCCAAAG CTGGCCAGAC TTCATTATTC CGGATCAATC AATGCCTGGA<br>GCACCAAGGA GCCCTTTTCT TGGATCAAGG TGGATCTGTT GGCACCAATG<br>ATTATTCACG GCATCAAGAC CCAGGGTGCC CGTCAGAAGT TCTCCAGCCT<br>CTACATCTCT CAGTTTATCA TCATGTATAG TCTTGATGGG AAGAAGTGGC<br>AGACTTATCG AGGAAATTCC ACTGGAACCT TAATGGTCTT CTTTGGCAAT<br>GTGGATTCAT CTGGGATAAA ACACAATATT TTTAACCCTC CAATTATTGC<br>TCGATACATC CGTTTGCACC CAACTCATTA TAGCATTCGC AGCACTCTTC<br>GCATGGAGTT GATGGGCTGT GATTTAAATA GTTGCAGCAT GCCATTGGGA<br>ATGGAGAGTA AAGCAATATC AGATGCACAG ATTACTGCTT CATCCTACTT<br>TACCAATATG TTTGCCACCT GGTCTCCTTC AAAAGCTCGA CTTCACCTCC<br>AAGGGAGGAG TAATGCCTGG AGACCTCAGG TGAATAATCC AAAAGAGTGG<br>CTGCAAGTGG ACTTCCAGAA GACAATGAAA GTCACAGGAG TAACTACTCA<br>GGGAGTAAAA TCTCTGCTTA CCAGCATGTA TGTGAAGGAG TTCCTCATCT<br>CCAGCAGTCA AGATGGCCAT CAGTGGACTC TCTTTTTTCA GAATGGCAAA<br>GTAAAGGTTT TTCAGGGAAA TCAAGACTCC TTCACACCTG TGGTGAACTC<br>TCTAGACCCA CCGTTACTGA CTCGCTACCT TCGAATTCAC CCCCAGAGTT<br>GGGTGCACCA GATTGCCCTG AGGATGGAGG TTCTGGGCTG CGAGGCACAG<br>GACCTCTACT GA |
| **12** | rhFVIII-<br>BDD<br>Sc4 | ATGCAAATAG AGCTCTCCAC CTGCTTCTTT CTGTGCCTTT TGCGATTCTG<br>CTTTAGTGCC ACCAGAAGAT ACTACCTGGG TGCAGTGGAA CTGTCATGGG<br>ACTATATGCA AAGTGATCTC GGTGAGCTGC CTGTGGACGC AAGATTTCCT<br>CCTAGAGTGC CAAAATCTTT TCCATTCAAC ACCTCAGTCG TGTACAAAAA |

FIG. 24K

Table 8 (continued)

| | | |
|---|---|---|
| | | GACTCTGTTT GTAGAATTCA CGGATCACCT TTTCAACATC GCTAAGCCAA<br>GGCCACCCTG GATGGGTCTG CTAGGTCCTA CCATCCAGGC TGAGGTTTAT<br>GATACAGTGG TCATTACACT TAAGAACATG GCTTCCCATC CTGTCAGTCT<br>TCATGCTGTT GGTGTATCCT ACTGGAAAGC TTCTGAGGGA GCTGAATATG<br>ATGATCAGAC CAGTCAAAGG GAGAAAGAAG ATGATAAAGT CTTCCCTGGT<br>GGAAGCCATA CATATGTCTG GCAGGTCCTG AAAGAGAATG GTCCAATGGC<br>CTCTGACCCA CTGTGCCTTA CCTACTCATA TCTTTCTCAT GTGGACCTGG<br>TAAAAGACTT GAATTCAGGC CTCATTGGAG CCCTACTAGT ATGTAGAGAA<br>GGGAGTCTGG CCAAGGAAAA GACACAGACC TTGCACAAAT TTATACTACT<br>TTTTGCTGTA TTTGATGAAG GGAAAAGTTG GCACTCAGAA ACAAAGAACT<br>CCTTGATGCA GGATAGGGAT GCTGCATCTG CTCGGGCCTG GCCTAAAATG<br>CACACAGTCA ATGGTTATGT AAACAGGTCT CTGCCAGGTC TGATTGGATG<br>CCACAGGAAA TCAGTCTATT GGCATGTGAT TGGAATGGGC ACCACTCCTG<br>AAGTGCACTC AATATTCCTC GAAGGTCACA CATTTCTTGT GAGGAACCAT<br>CGCCAGGCGT CCTTGGAAAT CTCGCCAATA ACTTTCCTTA CTGCTCAAAC<br>ACTCTTGATG GACCTTGGAC AGTTTCTACT GTTTTGTCAT ATCTCTTCCC<br>ACCAACATGA TGGCATGGAA GCTTATGTCA AAGTAGACAG CTGTCCAGAG<br>GAACCCCAAC TACGAATGAA AAATAATGAA GAAGCGGAAG ACTATGATGA<br>TGATCTTACT GATTCTGAAA TGGATGTGGT CAGGTTTGAT GATGACAACT<br>CTCCTTCCTT TATCCAAATT CGCTCAGTTG CCAAGAAGCA TCCTAAAACT<br>TGGGTACATT ACATTGCTGC TGAAGAGGAG GACTGGGACT ATGCTCCCTT<br>AGTCCTCGCC CCCGATGACA GAAGTTATAA AAGTCAATAT TTGAACAATG<br>GCCCTCAGCG GATTGGTAGG AAGTACAAAA AAGTCCGATT TATGGCATAC<br>ACAGATGAAA CCTTTAAGAC TCGTGAAGCT ATTCAGCATG AATCAGGAAT<br>CTTGGGACCT TTACTTTATG GGGAAGTTGG AGACACACTG TTGATTATAT<br>TTAAGAATCA AGCAAGCAGA CCATATAACA TCTACCCTCA CGGAATCACT<br>GATGTCCGTC CTTTGTATTC AAGGAGATTA CCAAAAGGTG TAAAACATTT<br>GAAGGATTTT CCAATTCTGC CAGGAGAAAT ATTCAAATAT AAATGGACAG<br>TGACTGTAGA AGATGGGCCA ACTAAATCAG ATCCTCGGTG CCTGACCCGC<br>TATTACTCTA GTTTCGTTAA TATGGAGAGA GATCTAGCTT CAGGACTCAT<br>TGGCCCTCTC CTCATCTGCT ACAAAGAATC TGTAGATCAA AGAGGAAACC<br>AGATAATGTC AGACAAGAGG AATGTCATCC TGTTTTCTGT ATTTGATGAG<br>AACCGAAGCT GGTACCTCAC AGAGAATATA CAACGCTTTC TCCCCAATCC<br>AGCTGGAGTG CAGCTTGAGG ATCCAGAGTT CCAAGCCTCC AACATCATGC<br>ACAGCATCAA TGGCTATGTT TTTGATAGTT TGCAGTTGTC AGTTTGTTTG<br>CATGAGGTGG CATACTGGTA CATTCTAAGC ATTGGAGCAC AGACTGACTT<br>CCTTTCTGTC TTCTTCTCTG GATATACCTT CAAACACAAA ATGGTCTATG<br>AAGACACACT CACCCTATTC CCATTCTCAG GAGAAACTGT CTTCATGTCG<br>ATGGAAAACC CAGGTCTATG GATTCTGGGG TGCCACAACT CAGACTTTCG<br>GAACAGAGGC ATGACCGCCT TACTGAAGGT TTCTAGTTGT GACAAGAACA<br>CTGGTGATTA TTACGAGGAC AGTTATGAAG ATATTTCAGC ATACTTGCTG<br>AGTAAAAACA ATGCCATTGA ACCAAGAAGC TTCTCCCAAA ACCCACCAGT<br>CTTGAAACGC GAAATAACTC GTACTACTCT TCAGTCAGAT CAAGAGGAAA<br>TTGACTATGA TGATACCATA TCAGTTGAAA TGAAGAAGGA AGATTTTGAC<br>ATTTATGATG AGGATGAAAA TCAGAGCCCC CGCAGCTTTC AAAAGAAAAC<br>ACGACACTAT TTTATTGCTG CAGTGGAGAG GCTCTGGGAT TATGGGATGA<br>GTAGCTCCCC ACATGTTCTA AGAAACAGGG CTCAGAGTGG CAGTGTCCCT<br>CAGTTCAAGA AAGTTGTTTT CCAGGAATTT ACTGATGGCT CCTTTACTCA<br>GCCCTTATAC CGTGGAGAAC TAAATGAACA TTTGGGACTC CTGGGGCCAT<br>ATATAAGAGC AGAAGTTGAA GATAATATCA TGGTAACTTT CAGAAATCAG<br>GCCTCTCGTC CCTATTCCTT CTATTCTAGC CTTATTTCTT ATGAGGAAGA<br>TCAGAGGCAA GGAGCAGAAC CTAGAAAAAA CTTTGTCAAG CCTAATGAAA<br>CCAAAACTTA CTTTTGGAAA GTGCAACATC ATATGGCACC CACTAAAGAT<br>GAGTTTGACT GCAAAGCCTG GGCTTATTTC TCTGATGTTG ACCTGGAAAA<br>AGATGTGCAC TCAGGCCTGA TTGGACCCCT TCTGGTCTGC CACACTAACA<br>CACTGAACCC TGCTCATGGG AGACAAGTGA CAGTACAGGA ATTTGCTCTG<br>TTTTTCACCA TCTTTGATGA GACCAAAAGC TGGTACTTCA CTGAAAATAT |

FIG. 24L

Table 8 (continued)

| | | |
|---|---|---|
| | | GGAAAGAAAC TGCAGGGCTC CCTGCAATAT CCAGATGGAA GATCCCACTT<br>TTAAAGAGAA TTATCGCTTC CATGCAATCA ATGGCTACAT AATGGATACA<br>CTACCTGGCT TAGTAATGGC TCAGGATCAA AGGATTCGAT GGTATCTGCT<br>CAGCATGGGC AGCAATGAAA ACATCCATTC TATTCATTTC AGTGGACATG<br>TGTTCACTGT ACGAAAAAAA GAGGAGTATA AAATGGCACT GTACAATCTC<br>TATCCAGGTG TTTTTGAGAC AGTGGAAATG TTACCATCCA AAGCTGGAAT<br>TTGGCGGGTG GAATGCCTTA TTGGCGAGCA TCTACATGCT GGGATGAGCA<br>CACTTTTTCT GGTGTACAGC AATAAGTGTC AGACTCCCCT GGGAATGGCT<br>TCTGGACACA TTAGAGATTT TCAGATTACA GCTTCAGGAC AATATGGACA<br>GTGGGCCCCA AAGCTGGCCA GACTTCATTA TTCCGGATCA ATCAATGCCT<br>GGAGCACCAA GGAGCCCTTT TCTTGGATCA AGGTGGATCT GTTGGCACCA<br>ATGATTATTC ACGGCATCAA GACCCAGGGT GCCCGTCAGA AGTTCTCCAG<br>CCTCTACATC TCTCAGTTTA TCATCATGTA TAGTCTTGAT GGGAAGAAGT<br>GGCAGACTTA TCGAGGAAAT TCCACTGGAA CCTTAATGGT CTTCTTTGGC<br>AATGTGGATT CATCTGGGAT AAAACACAAT ATTTTTAACC CTCCAATTAT<br>TGCTCGATAC ATCCGTTTGC ACCCAACTCA TTATAGCATT CGCAGCACTC<br>TTCGCATGGA GTTGATGGGC TGTGATTTAA ATAGTTGCAG CATGCCATTG<br>GGAATGGAGA GTAAAGCAAT ATCAGATGCA CAGATTACTG CTTCATCCTA<br>CTTTACCAAT ATGTTTGCCA CCTGGTCTCC TTCAAAAGCT CGACTTCACC<br>TCCAAGGGAG GAGTAATGCC TGGAGACCTC AGGTGAATAA TCCAAAAGAG<br>TGGCTGCAAG TGGACTTCCA GAAGACAATG AAAGTCACAG GAGTAACTAC<br>TCAGGGAGTA AAATCTCTGC TTACCAGCAT GTATGTGAAG GAGTTCCTCA<br>TCTCCAGCAG TCAAGATGGC CATCAGTGGA CTCTCTTTTT TCAGAATGGC<br>AAAGTAAAGG TTTTTCAGGG AAATCAAGAC TCCTTCACAC CTGTGGTGAA<br>CTCTCTAGAC CCACCGTTAC TGACTCGCTA CCTTCGAATT CACCCCCAGA<br>GTTGGGTGCA CCAGATTGCC CTGAGGATGG AGGTTCTGGG CTGCGAGGCA<br>CAGGACCTCT ACTGA |
| 13 | rhFVIII-<br>BDD CO2 | ATGCAGATCG AGCTGTCTAC CTGCTTCTTC CTGTGCCTGC TGCGGTTCTG 50<br>CTTCAGCGCC ACCAGAAGAT ATTACCTGGG CGCCGTGGAA CTGAGCTGGG 100<br>ACTACATGCA GTCTGACCTG GGAGAGCTGC CCGTGGACGC TAGATTTCCT 150<br>CCAAGAGTGC CCAAGAGCTT CCCCTTCAAC ACCTCCGTGG TGTACAAGAA 200<br>AACCCTGTTC GTGGAATTCA CCGACCACCT GTTCAATATC GCCAAGCCTC 250<br>GGCCTCCTTG GATGGGACTG CTGGGACCTA CAATTCAGGC CGAGGTGTAC 300<br>GACACCGTGG TCATCACCCT GAAGAACATG GCCAGCCATC CTGTGTCTCT 350<br>GCACGCCGTG GGAGTGTCTT ACTGGAAGGC TTCTGAGGGC GCCGAGTACG 400<br>ACGATCAGAC AAGCCAGAGA GAGAAAGAGG ACGACAAGGT TTTCCCTGGC 450<br>GGCAGCCACA CCTATGTCTG GCAGGTCCTG AAAGAAAACG GCCCTATGGC 500<br>CTCCGATCCT CTGTGCCTGA CATACAGCTA CCTGAGCCAC GTGGACCTGG 550<br>TCAAGGACCT GAATTCTGGC CTGATCGGAG CCCTGCTCGT GTGTAGAGAA 600<br>GGCAGCCTGG CCAAAGAGAA AACCCAGACA CTGCACAAGT TCATCCTGCT 650<br>GTTCGCCGTG TTCGACGAGG GCAAGAGCTG GCACAGCGAG ACAAAGAACA 700<br>GCCTGATGCA GGACAGGGAT GCCGCCTCTG CTAGAGCTTG GCCTAAGATG 750<br>CACACCGTGA ACGGCTACGT GAACAGAAGC CTGCCTGGAC TGATCGGCTG 800<br>CCACAGAAAG TCCGTGTACT GGCACGTGAT CGGCATGGGC ACAACACCTG 850<br>AGGTGCACAG CATCTTTCTG GAAGGACACA CCTTCCTCGT GCGGAACCAT 900<br>AGACAGGCCA GCCTGGAAAT CAGCCCTATC ACCTTCCTGA CCGCTCAGAC 950<br>CCTGCTGATG GATCTGGGCC AGTTTCTGCT GTTCTGCCAC ATCAGCTCCC 1000<br>ACCAGCACGA TGGCATGGAA GCCTACGTGA AGGTGGACAG CTGCCCCGAA 1050<br>GAACCCCAGC TGCGGATGAA GAACAACGAG GAAGCCGAGG ACTACGACGA 1100<br>CGACCTGACC GACTCTGAGA TGGACGTCGT CAGATTCGAC GACGATAACA 1150<br>GCCCCAGCTT CATCCAGATC AGAAGCGTGG CCAAGAAGCA CCCCAAGACC 1200<br>TGGGTGCACT ATATCGCCGC CGAGGAAGAG GACTGGGATT ACGCTCCTCT 1250<br>GGTGCTGGCC CCTGACGACA GAAGCTACAA GAGCCAGTAC CTGAACAACG 1300<br>GCCCTCAGCG GATCGGCCGG AAGTATAAGA AAGTGCGGTT CATGGCCTAC 1350<br>ACCGACGAGA CATTCAAGAC CAGAGAGGCC ATCCAGCACG AGAGCGGAAT 1400<br>TCTGGGCCCT CTGCTGTATG GCGAAGTGGG CGATACACTG CTGATCATCT 1450<br>TCAAGAACCA GGCCAGCAGA CCCTACAACA TCTACCCTCA CGGCATCACC 1500 |

FIG. 24M

Table 8 (continued)

| | | |
|---|---|---|
| | | GATGTGCGGC CCCTGTATTC TAGAAGGCTG CCCAAGGGCG TGAAGCACCT 1550 |
| | | GAAGGACTTC CCTATCCTGC CTGGCGAGAT CTTCAAGTAC AAGTGGACCG 1600 |
| | | TGACCGTGGA AGATGGCCCC ACCAAGAGCG ACCCTAGATG TCTGACACGG 1650 |
| | | TACTACAGCA GCTTCGTGAA CATGGAACGC GACCTGGCCA GCGGCCTGAT 1700 |
| | | TGGACCTCTG CTGATCTGCT ACAAAGAAAG CGTGGACCAG CGGGGCAACC 1750 |
| | | AGATCATGAG CGACAAGCGG AACGTGATCC TGTTTAGCGT GTTCGATGAG 1800 |
| | | AACCGGTCCT GGTATCTGAC CGAGAACATC CAGCGGTTTC TGCCCAATCC 1850 |
| | | TGCTGGCGTG CAGCTGGAAG ATCCTGAGTT CCAGGCCTCC AACATCATGC 1900 |
| | | ACTCCATCAA TGGCTATGTG TTCGACAGCC TGCAGCTGAG CGTGTGCCTG 1950 |
| | | CACGAAGTGG CCTACTGGTA CATCCTGAGC ATTGGCGCCC AGACCGACTT 2000 |
| | | CCTGTCCGTG TTCTTTAGCG GCTACACCTT CAAGCACAAG ATGGTGTACG 2050 |
| | | AGGATACCCT GACACTGTTC CCATTCAGCG GCGAGACAGT GTTCATGAGC 2100 |
| | | ATGGAAAACC CCGGCCTGTG GATCCTGGGC TGTCACAACA GCGACTTCCG 2150 |
| | | GAACAGAGGC ATGACAGCCC TGCTGAAGGT GTCCAGCTGC GACAAGAACA 2200 |
| | | CCGGCGACTA CTACGAGGAC AGCTATGAGG ACATCAGCGC CTACCTGCTG 2250 |
| | | AGCAAGAACA ATGCCATCGA GCCTCGGAGC TTCAGCCAGA ATCCTCCTGT 2300 |
| | | GCTGAAGCGG CACCAGCGCG AGATCACCAG AACAACCCTG CAGAGCGACC 2350 |
| | | AAGAGGAAAT CGATTACGAC GACACCATCA GCGTCGAGAT GAAGAAAGAA 2400 |
| | | GATTTCGACA TCTACGACGA GGACGAGAAT CAGAGCCCCA GAAGCTTTCA 2450 |
| | | GAAAAAGACC CGGCACTACT TCATTGCCGC CGTCGAGAGA CTGTGGGACT 2500 |
| | | ACGGCATGTC TAGCAGCCCT CACGTGCTGA GAAATAGAGC CCAGAGCGGC 2550 |
| | | AGCGTGCCCC AGTTCAAGAA AGTGGTGTTC CAAGAGTTCA CCGACGGCAG 2600 |
| | | CTTCACCCAG CCACTGTATA GAGGCGAGCT GAACGAGCAT CTGGGCCTGC 2650 |
| | | TGGGCCCTTA TATCAGAGCC GAAGTGGAAG ATAACATCAT GGTCACCTTC 2700 |
| | | CGGAATCAGG CCTCTCGGCC CTACAGCTTC TACAGCTCCC TGATCAGCTA 2750 |
| | | CGAAGAGGAC CAGAGACAGG GCGCTGAGCC CAGAAAGAAC TTCGTGAAGC 2800 |
| | | CCAACGAGAC TAAGACCTAC TTTTGGAAGG TGCAGCACCA CATGGCCCCT 2850 |
| | | ACAAAGGACG AGTTCGACTG CAAGGCCTGG GCCTACTTTT CCGATGTGGA 2900 |
| | | TCTGGAAAAG GACGTGCACA GCGGGCTCAT CGGACCACTG CTTGTGTGCC 2950 |
| | | ACACCAACAC ACTGAACCCC GCTCACGGCA GACAAGTGAC AGTGCAAGAG 3000 |
| | | TTCGCCCTGT TCTTCACCAT CTTCGACGAA ACAAAGAGCT GGTACTTCAC 3050 |
| | | CGAGAATATG GAACGGAACT GCAGAGCCCC TTGCAACATC CAGATGGAAG 3100 |
| | | ATCCCACCTT CAAAGAGAAC TACCGGTTCC ACGCCATCAA CGGCTACATC 3150 |
| | | ATGGACACAC TGCCCGGCCT GGTTATGGCT CAGGATCAGA GAATCCGGTG 3200 |
| | | GTATCTGCTG TCCATGGGCT CCAACGAGAA TATCCACAGC ATCCACTTCA 3250 |
| | | GCGGCCACGT GTTCACCGTG CGGAAAAAAG AAGAGTACAA AATGGCCCTG 3300 |
| | | TACAATCTGT ACCCTGGGGT GTTCGAAACC GTGGAAATGC TGCCTTCCAA 3350 |
| | | GGCCGGCATT TGGAGAGTGG AATGTCTGAT TGGAGAGCAC CTCCACGCCG 3400 |
| | | GAATGAGCAC CCTGTTTCTG GTGTACAGCA ACAAGTGTCA GACCCCTCTC 3450 |
| | | GGCATGGCCT CTGGACACAT CAGAGACTTC CAGATCACCG CCTCTGGCCA 3500 |
| | | GTACGGACAG TGGGCTCCTA AACTGGCTCG GCTGCACTAC AGCGGCAGCA 3550 |
| | | TCAATGCCTG GTCCACCAAA GAGCCCTTCA GCTGGATCAA GGTGGACCTG 3600 |
| | | CTGGCTCCCA TGATCATCCA CGGAATCAAG ACCCAGGGCG CCAGACAGAA 3650 |
| | | GTTCAGCAGC CTGTACATCA GCCAGTTCAT CATCATGTAC AGCCTGGACG 3700 |
| | | GCAAGAAGTG GCAGACCTAC AGAGGCAACA GCACCGGCAC ACTCATGGTG 3750 |
| | | TTCTTCGGCA ACGTGGACTC CAGCGGCATT AAGCACAACA TCTTCAACCC 3800 |
| | | TCCAATCATT GCCCGGTACA TCCGGCTGCA CCCCACACAC TACAGCATCC 3850 |
| | | GGTCTACCCT GAGAATGGAA CTGATGGGCT GCGACCTGAA CAGCTGCAGC 3900 |
| | | ATGCCCCTCG GAATGGAAAG CAAGGCCATC AGCGACGCCC AGATCACAGC 3950 |
| | | CAGCAGCTAC TTCACCAACA TGTTCGCCAC TTGGAGCCCC TCCAAGGCTA 4000 |
| | | GACTGCATCT GCAGGGCAGA AGCAACGCTT GGAGGCCCCA AGTGAACAAC 4050 |
| | | CCCAAAGAGT GGCTGCAGGT CGACTTTCAA AAGACCATGA AAGTGACCGG 4100 |
| | | CGTGACCACA CAGGGCGTCA AGTCTCTGCT GACCTCTATG TACGTGAAAG 4150 |
| | | AGTTCCTGAT CTCCAGCAGC CAGGACGGCC ATCAGTGGAC CCTGTTTTTC 4200 |
| | | CAGAACGGCA AAGTGAAAGT GTTCCAGGGC AATCAGGACA GCTTCACACC 4250 |
| | | CGTGGTCAAC TCCCTGGATC CTCCACTGCT GACCAGATAC CTGCGGATTC 4300 |
| | | ACCCTCAGTC TTGGGTGCAC CAGATCGCTC TGCGGATGGA AGTGCTGGGC 4350 |

FIG. 24N

Table 8 (continued)

| | | |
|---|---|---|
| | | TGTGAAGCTC AGGACCTCTA CTGA 4374 |
| **14** | rhFVIII-BDD CO3 | ATGCAGATCG AGCTGAGCAC CTGCTTCTTC CTGTGCCTGC TGCGCTTCTG 50 |
| | | CTTCAGCGCC ACCCGCCGCT ACTACCTGGG CGCCGTGGAG CTGAGCTGGG 100 |
| | | ACTACATGCA GAGCGACCTG GGCGAGCTGC CCGTGGACGC CCGCTTCCCC 150 |
| | | CCCCGCGTGC CCAAGAGCTT CCCCTTCAAC ACCAGCGTGG TGTACAAGAA 200 |
| | | GACCCTGTTC GTGGAGTTCA CCGACCACCT GTTCAACATC GCCAAGCCCC 250 |
| | | GCCCCCCCTG GATGGGCCTG CTGGGCCCCA CCATCCAGGC CGAGGTGTAC 300 |
| | | GACACCGTGG TGATCACCCT GAAGAACATG GCCAGCCACC CCGTGAGCCT 350 |
| | | GCACGCCGTG GGCGTGAGCT ACTGGAAGGC CAGCGAGGGC GCCGAGTACG 400 |
| | | ACGACCAGAC CAGCCAGCGC GAGAAGGAGG ACGACAAGGT GTTCCCCGGC 450 |
| | | GGCAGCCACA CCTACGTGTG GCAGGTGCTG AAGGAGAACG GCCCCATGGC 500 |
| | | CAGCGACCCC CTGTGCCTGA CCTACAGCTA CCTGAGCCAC GTGGACCTGG 550 |
| | | TGAAGGACCT GAACAGCGGC CTGATCGGCG CCCTGCTGGT GTGCCGCGAG 600 |
| | | GGCAGCCTGG CCAAGGAGAA GACCCAGACC CTGCACAAGT TCATCCTGCT 650 |
| | | GTTCGCCGTG TTCGACGAGG GCAAGAGCTG GCACAGCGAG ACCAAGAACA 700 |
| | | GCCTGATGCA GGACCGCGAC GCCGCCAGCG CCCGCGCCTG GCCCAAGATG 750 |
| | | CACACCGTGA ACGGCTACGT GAACCGCAGC CTGCCCGGCC TGATCGGCTG 800 |
| | | CCACCGCAAG AGCGTGTACT GGCACGTGAT CGGCATGGGC ACCACCCCCG 850 |
| | | AGGTGCACAG CATCTTCCTG GAGGGCCACA CCTTCCTGGT GCGCAACCAC 900 |
| | | CGCCAGGCCA GCCTGGAGAT CAGCCCCATC ACCTTCCTGA CCGCCCAGAC 950 |
| | | CCTGCTGATG GACCTGGGCC AGTTCCTGCT GTTCTGCCAC ATCAGCAGCC 1000 |
| | | ACCAGCACGA CGGCATGGAG GCCTACGTGA AGGTGGACAG CTGCCCCGAG 1050 |
| | | GAGCCCCAGC TGCGCATGAA GAACAACGAG GAGGCCGAGG ACTACGACGA 1100 |
| | | CGACCTGACC GACAGCGAGA TGGACGTGGT GCGCTTCGAC GACGACAACA 1150 |
| | | GCCCCAGCTT CATCCAGATC CGCAGCGTGG CCAAGAAGCA CCCCAAGACC 1200 |
| | | TGGGTGCACT ACATCGCCGC CGAGGAGGAG GACTGGGACT ACGCCCCCCT 1250 |
| | | GGTGCTGGCC CCCGACGACC GCAGCTACAA GAGCCAGTAC CTGAACAACG 1300 |
| | | GCCCCCAGCG CATCGGCCGC AAGTACAAGA AGGTGCGCTT CATGGCCTAC 1350 |
| | | ACCGACGAGA CCTTCAAGAC CCGCGAGGCC ATCCAGCACG AGAGCGGCAT 1400 |
| | | CCTGGGCCCC CTGCTGTACG GCGAGGTGGG CGACACCCTG CTGATCATCT 1450 |
| | | TCAAGAACCA GGCCAGCCGC CCCTACAACA TCTACCCCCA CGGCATCACC 1500 |
| | | GACGTGCGCC CCCTGTACAG CCGCCGCCTG CCCAAGGGCG TGAAGCACCT 1550 |
| | | GAAGGACTTC CCCATCCTGC CCGGCGAGAT CTTCAAGTAC AAGTGGACCG 1600 |
| | | TGACCGTGGA GGACGGCCCC ACCAAGAGCG ACCCCCGCTG CCTGACCCGC 1650 |
| | | TACTACAGCA GCTTCGTGAA CATGGAGCGC GACCTGGCCA GCGGCCTGAT 1700 |
| | | CGGCCCCCTG CTGATCTGCT ACAAGGAGAG CGTGGACCAG CGCGGCAACC 1750 |
| | | AGATCATGAG CGACAAGCGC AACGTGATCC TGTTCAGCGT GTTCGACGAG 1800 |
| | | AACCGCAGCT GGTACCTGAC CGAGAACATC CAGCGCTTCC TGCCCAACCC 1850 |
| | | CGCCGGCGTG CAGCTGGAGG ACCCCGAGTT CCAGGCCAGC AACATCATGC 1900 |
| | | ACAGCATCAA CGGCTACGTG TTCGACAGCC TGCAGCTGAG CGTGTGCCTG 1950 |
| | | CACGAGGTGG CCTACTGGTA CATCCTGAGC ATCGGCGCCC AGACCGACTT 2000 |
| | | CCTGAGCGTG TTCTTCAGCG GCTACACCTT CAAGCACAAG ATGGTGTACG 2050 |
| | | AGGACACCCT GACCCTGTTC CCCTTCAGCG GCGAGACCGT GTTCATGAGC 2100 |
| | | ATGGAGAACC CCGGCCTGTG GATCCTGGGC TGCCACAACA GCGACTTCCG 2150 |
| | | CAACCGCGGC ATGACCGCCC TGCTGAAGGT GAGCAGCTGC GACAAGAACA 2200 |
| | | CCGGCGACTA CTACGAGGAC AGCTACGAGG ACATCAGCGC CTACCTGCTG 2250 |
| | | AGCAAGAACA ACGCCATCGA GCCCCGCAGC TTCAGCCAGA ACCCCCCCGT 2300 |
| | | GCTGAAGCGC CACCAGCGCG AGATCACCCG CACCACCCTG CAGAGCGACC 2350 |
| | | AGGAGGAGAT CGACTACGAC GACACCATCA GCGTGGAGAT GAAGAAGGAG 2400 |
| | | GACTTCGACA TCTACGACGA GGACGAGAAC CAGAGCCCCC GCAGCTTCCA 2450 |
| | | GAAGAAGACC CGCCACTACT TCATCGCCGC CGTGGAGCGC CTGTGGGACT 2500 |
| | | ACGGCATGAG CAGCAGCCCC CACGTGCTGC GCAACCGCGC CCAGAGCGGC 2550 |
| | | AGCGTGCCCC AGTTCAAGAA GGTGGTGTTC CAGGAGTTCA CCGACGGCAG 2600 |
| | | CTTCACCCAG CCCCTGTACC GCGGCGAGCT GAACGAGCAC CTGGGCCTGC 2650 |
| | | TGGGCCCCTA CATCCGCGCC GAGGTGGAGG ACAACATCAT GGTGACCTTC 2700 |
| | | CGCAACCAGG CCAGCCGCCC CTACAGCTTC TACAGCAGCC TGATCAGCTA 2750 |
| | | CGAGGAGGAC CAGCGCCAGG GCGCCGAGCC CCGCAAGAAC TTCGTGAAGC 2800 |

FIG. 24O

Table 8 (continued)

| | | |
|---|---|---|
| | | CCAACGAGAC CAAGACCTAC TTCTGGAAGG TGCAGCACCA CATGGCCCCC 2850 |
| | | ACCAAGGACG AGTTCGACTG CAAGGCCTGG GCCTACTTCA GCGACGTGGA 2900 |
| | | CCTGGAGAAG GACGTGCACA GCGGCCTGAT CGGCCCCCTG CTGGTGTGCC 2950 |
| | | ACACCAACAC CCTGAACCCC GCCCACGGCC GCCAGGTGAC CGTGCAGGAG 3000 |
| | | TTCGCCCTGT TCTTCACCAT CTTCGACGAG ACCAAGAGCT GGTACTTCAC 3050 |
| | | CGAGAACATG GAGCGCAACT GCCGCGCCCC CTGCAACATC CAGATGGAGG 3100 |
| | | ACCCCACCTT CAAGGAGAAC TACCGCTTCC ACGCCATCAA CGGCTACATC 3150 |
| | | ATGGACACCC TGCCCGGCCT GGTGATGGCC CAGGACCAGC GCATCCGCTG 3200 |
| | | GTACCTGCTG AGCATGGGCA GCAACGAGAA CATCCACAGC ATCCACTTCA 3250 |
| | | GCGGCCACGT GTTCACCGTG CGCAAGAAGG AGGAGTACAA GATGGCCCTG 3300 |
| | | TACAACCTGT ACCCCGGCGT GTTCGAGACC GTGGAGATGC TGCCCAGCAA 3350 |
| | | GGCCGGCATC TGGCGCGTGG AGTGCCTGAT CGGCGAGCAC CTGCACGCCG 3400 |
| | | GCATGAGCAC CCTGTTCCTG GTGTACAGCA ACAAGTGCCA GACCCCCCTG 3450 |
| | | GGCATGGCCA GCGGCCACAT CCGCGACTTC CAGATCACCG CCAGCGGCCA 3500 |
| | | GTACGGCCAG TGGGCCCCCA AGCTGGCCCG CCTGCACTAC AGCGGCAGCA 3550 |
| | | TCAACGCCTG GAGCACCAAG GAGCCCTTCA GCTGGATCAA GGTGGACCTG 3600 |
| | | CTGGCCCCCA TGATCATCCA CGGCATCAAG ACCCAGGGCG CCCGCCAGAA 3650 |
| | | GTTCAGCAGC CTGTACATCA GCCAGTTCAT CATCATGTAC AGCCTGGACG 3700 |
| | | GCAAGAAGTG GCAGACCTAC CGCGGCAACA GCACCGGCAC CCTGATGGTG 3750 |
| | | TTCTTCGGCA ACGTGGACAG CAGCGGCATC AAGCACAACA TCTTCAACCC 3800 |
| | | CCCCATCATC GCCCGCTACA TCCGCCTGCA CCCCACCCAC TACAGCATCC 3850 |
| | | GCAGCACCCT GCGCATGGAG CTGATGGGCT GCGACCTGAA CAGCTGCAGC 3900 |
| | | ATGCCCCTGG GCATGGAGAG CAAGGCCATC AGCGACGCCC AGATCACCGC 3950 |
| | | CAGCAGCTAC TTCACCAACA TGTTCGCCAC CTGGAGCCCC AGCAAGGCCC 4000 |
| | | GCCTGCACCT GCAGGGCCGC AGCAACGCCT GGCGCCCCCA GGTGAACAAC 4050 |
| | | CCCAAGGAGT GGCTGCAGGT GGACTTCCAG AAGACCATGA AGGTGACCGG 4100 |
| | | CGTGACCACC CAGGGCGTGA AGAGCCTGCT GACCAGCATG TACGTGAAGG 4150 |
| | | AGTTCCTGAT CAGCAGCAGC CAGGACGGCC ACCAGTGGAC CCTGTTCTTC 4200 |
| | | CAGAACGGCA AGGTGAAGGT GTTCCAGGGC AACCAGGACA GCTTCACCCC 4250 |
| | | CGTGGTGAAC AGCCTGGACC CCCCCCTGCT GACCCGCTAC CTGCGCATCC 4300 |
| | | ACCCCCAGAG CTGGGTGCAC CAGATCGCCC TGCGCATGGA GGTGCTGGGC 4350 |
| | | TGCGAGGCCC AGGACCTGTA CTGA 4374 |
| 15 | rhFVIII-BDD CO6 | ATGCAGATTG AGCTGAGCAC CTGTTTCTTC CTGTGCCTGC TGAGATTTTG 50 |
| | | CTTCTCAGCT ACCCGCAGGT ACTACCTGGG AGCCGTTGAG CTGTCCTGGG 100 |
| | | ATTACATGCA GTCAGATCTG GGGGAGCTGC CTGTGGACGC TCGGTTTCCC 150 |
| | | CCCAGAGTGC CAAAGTCCTT TCCCTTCAAC ACCAGCGTGG TGTACAAAAA 200 |
| | | GACACTTTTT GTTGAATTTA CTGACCACTT GTTCAACATC GCCAAGCCAC 250 |
| | | GACCCCCATG GATGGGCCTG CTGGGGCCAA CCATTCAGGC AGAGGTTTAC 300 |
| | | GACACAGTCG TGATCACACT GAAGAACATG GCCTCCCATC CAGTGTCTCT 350 |
| | | GCACGCCGTC GGTGTGTCCT ACTGGAAAGC ATCCGAGGGC GCCGAGTATG 400 |
| | | ACGACCAGAC CAGCCAGAGA GAGAAAGAGG ACGACAAAGT GTTCCCTGGA 450 |
| | | GGCAGCCACA CCTACGTGTG GCAGGTGTTG AAGGAAAATG GCCCCATGGC 500 |
| | | CAGTGACCCT TTGTGTCTGA CTTACTCATA CCTGTCTCAT GTGGATCTAG 550 |
| | | TCAAGGACCT GAATTCTGGA CTGATTGGGG CACTGCTTGT GTGCCGCGAA 600 |
| | | GGCAGCCTGG CCAAAGAAAA GACACAGACC CTTCACAAGT TCATCCTGCT 650 |
| | | GTTCGCCGTG TTCGACGAAG GCAAATCCTG GCACTCAGAA ACCAAAAACT 700 |
| | | CACTGATGCA GGACCGGGAT GCCGCCTCTG CCCGCGCATG GCCAAAAATG 750 |
| | | CACACCGTCA ACGGCTATGT CAATAGAAGT TTGCCCGGCC TCATTGGATG 800 |
| | | TCACAGGAAA AGCGTCTATT GGCATGTAAT CGGGATGGGA ACCACACCTG 850 |
| | | AGGTCCACAG CATATTTCTG GAAGGCCACA CATTTCTGGT GAGAAATCAT 900 |
| | | CGCCAGGCTT CCCTGGAAAT TTCCCCCATC ACCTTCTTGA CCGCCCAGAC 950 |
| | | ACTGCTCATG GATCTTGGGC AGTTTCTGCT GTTTTGTCAT ATTTCTTCTC 1000 |
| | | ACCAACACGA CGGAATGGAG GCCTACGTTA AGGTCGATAG TTGCCCTGAA 1050 |
| | | GAACCTCAGC TGAGGATGAA GAACAACGAG GAAGCCGAGG ACTACGATGA 1100 |
| | | CGATTTGACC GATTCCGAAA TGGACGTGGT GCGCTTTGAT GATGACAATT 1150 |
| | | CTCCATCCTT CATTCAGATT AGATCCGTCG CCAAGAAGCA CCCCAAGACC 1200 |
| | | TGGGTGCACT ACATTGCAGC CGAGGAGGAG GATTGGGACT ACGCCCCCCT 1250 |

FIG. 24P

Table 8 (continued)

| | | |
|---|---|---|
| | | GGTGCTGGCA CCCGACGACC GAAGCTACAA ATCTCAGTAC CTGAACAATG 1300 |
| | | GTCCACAACG GATCGGCAGG AAGTACAAGA AAGTGCGGTT CATGGCCTAT 1350 |
| | | ACAGACGAAA CCTTCAAAAC CAGGGAGGCT ATCCAGCACG AGTCTGGGAT 1400 |
| | | TCTGGGACCA CTCCTGTACG GCGAAGTGGG CGACACCTTG TTAATTATCT 1450 |
| | | TCAAGAACCA GGCTAGTAGA CCTTATAACA TTTATCCCCA CGGCATTACC 1500 |
| | | GATGTGCGGC CTCTCTACTC TAGGCGGCTT CCAAAGGGGG TGAAACACCT 1550 |
| | | GAAGGACTTT CCCATCCTCC CTGGCGAAAT CTTTAAGTAT AAGTGGACAG 1600 |
| | | TGACCGTGGA GGATGGACCA ACCAAGAGCG ACCCCAGGTG CCTGACACGC 1650 |
| | | TATTATTCAA GCTTCGTGAA TATGGAAAGG GACCTCGCAT CTGGCTTGAT 1700 |
| | | CGGCCCTCTG CTGATATGTT ACAAGGAAAG CGTCGATCAG AGAGGAAATC 1750 |
| | | AGATCATGTC AGACAAAAGG AATGTGATCC TGTTCTCCGT CTTCGATGAA 1800 |
| | | AACAGGAGCT GGTATCTGAC AGAGAACATC CAGAGATTCC TGCCAAATCC 1850 |
| | | CGCCGGCGTC CAGCTGGAGG ACCCGGAGTT TCAGGCATCT AACATCATGC 1900 |
| | | ATTCCATTAA TGGTTACGTG TTCGACTCCC TGCAGCTGAG CGTGTGCCTC 1950 |
| | | CACGAGGTGG CCTACTGGTA CATCTTGAGC ATCGGCGCCC AGACCGACTT 2000 |
| | | TCTGAGCGTC TTTTTCTCCG GGTATACTTT CAAACATAAG ATGGTGTACG 2050 |
| | | AAGATACTCT GACGCTGTTC CCTTTCTCTG GGGAGACTGT GTTTATGTCT 2100 |
| | | ATGGAGAACC CTGGACTGTG GATTCTCGGA TGCCACAACA GTGACTTTCG 2150 |
| | | TAATAGAGGG ATGACTGCAC TGCTGAAGGT GTCCAGCTGT GATAAAAATA 2200 |
| | | CTGGCGACTA CTACGAAGAT AGCTATGAGG ATATCTCAGC ATACCTGCTG 2250 |
| | | AGCAAGAATA ACGCCATCGA GCCCCGAAGC TTCTCACAGA ATCCCCCTGT 2300 |
| | | CCTCAAGAGG CACCAGCGAG AGATCACAAG GACCACACTC CAGTCCGACC 2350 |
| | | AGGAGGAGAT TGACTACGAT GACACGATTT CTGTGGAGAT GAAAAAAGAG 2400 |
| | | GACTTTGACA TCTACGATGA GGATGAAAAC CAGAGCCCTA GGTCGTTCCA 2450 |
| | | GAAGAAAACA AGGCACTACT TCATTGCCGC CGTGGAGAGA CTGTGGGACT 2500 |
| | | ACGGAATGAG TAGTTCCCCA CACGTGTTGC GGAACAGAGC CCAGAGTGGG 2550 |
| | | TCCGTCCCAC AGTTCAAGAA GGTTGTTTTC CAGGAGTTCA CAGATGGCTC 2600 |
| | | CTTCACTCAG CCACTGTATC GCGGCGAGCT GAATGAGCAC TTGGGCTTAT 2650 |
| | | TGGGCCCCTA CATTCGCGCA GAAGTCGAAG ATAATATTAT GGTGACCTTC 2700 |
| | | CGCAACCAGG CCAGCCGGCC TTACTCATTC TACTCCTCTC TCATCTCTTA 2750 |
| | | TGAGGAGGAT CAGCGCCAGG GCGCCGAACC CCGGAAGAAC TTTGTGAAGC 2800 |
| | | CCAATGAAAC CAAAACTTAC TTTTGGAAGG TGCAGCACCA TATGGCGCCG 2850 |
| | | ACGAAAGACG AATTTGACTG CAAAGCCTGG GCCTACTTCA GCGACGTCGA 2900 |
| | | CTTGGAGAAG GACGTCCACA GCGGCCTGAT TGGCCCTTTG TTGGTCTGCC 2950 |
| | | ATACCAATAC ACTCAACCCT GCCCACGGGA GGCAGGTGAC CGTGCAGGAG 3000 |
| | | TTTGCCTTGT TCTTCACCAT CTTCGACGAA ACCAAGAGCT GGTACTTCAC 3050 |
| | | AGAGAACATG GAGAGGAACT GCAGAGCACC CTGTAACATC CAGATGGAGG 3100 |
| | | ACCCTACTTT CAAGGAAAAT TACAGGTTCC ATGCCATTAA TGGCTACATC 3150 |
| | | ATGGATACCC TCCCCGGGCT TGTGATGGCT CAGGACCAGC GCATCCGCTG 3200 |
| | | GTACCTGCTC TCAATGGGCT CCAACGAGAA CATTCATAGC ATCCACTTTA 3250 |
| | | GTGGCCACGT GTTTACCGTG CGCAAGAAGG AGGAGTACAA GATGGCACTG 3300 |
| | | TACAACCTGT ACCCTGGCGT GTTTGAGACA GTGGAGATGC TGCCATCCAA 3350 |
| | | GGCCGGCATC TGGCGCGTGG AGTGCCTCAT TGGGGAGCAC CTCCATGCTG 3400 |
| | | GCATGTCTAC ACTGTTCCTG GTGTACAGCA ACAAGTGTCA GACTCCACTC 3450 |
| | | GGAATGGCCT CCGGGCATAT CCGCGATTTT CAGATCACGG CCTCTGGCCA 3500 |
| | | GTATGGCCAA TGGGCTCCCA AGCTGGCCAG GCTGCACTAC AGTGGGAGTA 3550 |
| | | TCAACGCTTG GAGCACCAAG GAGCCTTTCT CCTGGATCAA GGTGGACCTG 3600 |
| | | CTTGCCCCCA TGATTATTCA CGGCATTAAG ACACAGGGGG CCAGGCAGAA 3650 |
| | | ATTCTCCTCC CTGTACATCT CCCAGTTCAT CATCATGTAC AGTCTGGACG 3700 |
| | | GCAAAAAGTG GCAGACCTAC CGCGGGAACA GTACCGGGAC ATTGATGGTG 3750 |
| | | TTCTTCGGGA ACGTGGACTC TAGCGGCATT AAACACAACA TTTTCAACCC 3800 |
| | | CCCCATCATT GCTAGGTATA TCAGGCTCCA TCCCACCCAC TATAGCATCA 3850 |
| | | GGTCCACTCT GCGGATGGAG CTGATGGGCT GCGACCTTAA TTCATGCAGC 3900 |
| | | ATGCCGCTGG GCATGGAGTC AAAGGCCATC TCCGACGCCC AAATCACCGC 3950 |
| | | CTCCAGCTAC TTCACCAATA TGTTCGCCAC CTGGAGCCCC AGCAAGGCCC 4000 |
| | | GGCTGCACCT GCAGGGCCGC AGCAACGCCT GGCGGCCTCA GGTGAACAAC 4050 |
| | | CCCAAGGAGT GGCTGCAGGT GGACTTCCAG AAAACCATGA AGGTGACTGG 4100 |

FIG. 24Q

Table 8 (continued)

| | | |
|---|---|---|
| | | GGTCACCACC CAGGGAGTCA AGAGCCTGCT GACCAGCATG TATGTGAAGG 4150<br>AGTTCTTGAT CAGCTCGTCA CAGGATGGCC ACCAGTGGAC TTTGTTCTTT 4200<br>CAGAACGGTA AGGTGAAAGT GTTCCAGGGA AACCAAGATT CCTTTACACC 4250<br>AGTGGTCAAC TCTCTGGATC CTCCCCTGCT GACACGGTAC CTGCGGATCC 4300<br>ATCCCCAGTC ATGGGTGCAC CAGATTGCTC TGCGCATGGA GGTGCTTGGC 4350<br>TGCGAGGCCC AGGACCTGTA CTGA 4374 |
| **16** | rhFVIII-BDD CO6 sc2 | ATGCAGATTG AGCTGAGCAC CTGTTTCTTC CTGTGCCTGC TGAGATTTTG 50<br>CTTCTCAGCT ACCCGCAGGT ACTACCTGGG AGCCGTTGAG CTGTCCTGGG 100<br>ATTACATGCA GTCAGATCTG GGGGAGCTGC CTGTGGACGC TCGGTTTCCC 150<br>CCCAGAGTGC CAAAGTCCTT TCCCTTCAAC ACCAGCGTGG TGTACAAAAA 200<br>GACACTTTTT GTTGAATTTA CTGACCACTT GTTCAACATC GCCAAGCCAC 250<br>GACCCCCATG GATGGGCCTG CTGGGGCCAA CCATTCAGGC AGAGGTTTAC 300<br>GACACAGTCG TGATCACACT GAAGAACATG GCCTCCCATC CAGTGTCTCT 350<br>GCACGCCGTC GGTGTGTCCT ACTGGAAAGC ATCCGAGGGC GCCGAGTATG 400<br>ACGACCAGAC CAGCCAGAGA GAGAAAGAGG ACGACAAAGT GTTCCCTGGA 450<br>GGCAGCCACA CCTACGTGTG GCAGGTGTTG AAGGAAAATG GCCCCATGGC 500<br>CAGTGACCCT TTGTGTCTGA CTTACTCATA CCTGTCTCAT GTGGATCTAG 550<br>TCAAGGACCT GAATTCTGGA CTGATTGGGG CACTGCTTGT GTGCCGCGAA 600<br>GGCAGCCTGG CCAAAGAAAA GACACAGACC CTTCACAAGT TCATCCTGCT 650<br>GTTCGCCGTG TTCGACGAAG GCAAATCCTG GCACTCAGAA ACCAAAAACT 700<br>CACTGATGCA GGACCGGGAT GCCGCCTCTG CCCGCGCATG GCCAAAAATG 750<br>CACACCGTCA ACGGCTATGT CAATAGAAGT TTGCCCGGCC TCATTGGATG 800<br>TCACAGGAAA AGCGTCTATT GGCATGTAAT CGGGATGGGA ACCACACCTG 850<br>AGGTCCACAG CATATTTCTG GAAGGCCACA CATTTCTGGT GAGAAATCAT 900<br>CGCCAGGCTT CCCTGGAAAT TTCCCCCATC ACCTTCTTGA CCGCCCAGAC 950<br>ACTGCTCATG GATCTTGGGC AGTTTCTGCT GTTTTGTCAT ATTTCTTCTC 1000<br>ACCAACACGA CGGAATGGAG GCCTACGTTA AGGTCGATAG TTGCCCTGAA 1050<br>GAACCTCAGC TGAGGATGAA GAACAACGAG GAAGCCGAGG ACTACGATGA 1100<br>CGATTTGACC GATTCCGAAA TGGACGTGGT GCGCTTTGAT GATGACAATT 1150<br>CTCCATCCTT CATTCAGATT AGATCCGTCG CCAAGAAGCA CCCCAAGACC 1200<br>TGGGTGCACT ACATTGCAGC CGAGGAGGAG GATTGGGACT ACGCCCCCCT 1250<br>GGTGCTGGCA CCCGACGACC GAAGCTACAA ATCTCAGTAC CTGAACAATG 1300<br>GTCCACAACG GATCGGCAGG AAGTACAAGA AAGTGCGGTT CATGGCCTAT 1350<br>ACAGACGAAA CCTTCAAAAC CAGGGAGGCT ATCCAGCACG AGTCTGGGAT 1400<br>TCTGGGACCA CTCCTGTACG GCGAAGTGGG CGACACCTTG TTAATTATCT 1450<br>TCAAGAACCA GGCTAGTAGA CCTTATAACA TTTATCCCCA CGGCATTACC 1500<br>GATGTGCGGC CTCTCTACTC TAGGCGGCTT CCAAAGGGGG TGAAACACCT 1550<br>GAAGGACTTT CCCATCCTCC CTGGCGAAAT CTTTAAGTAT AAGTGGACAG 1600<br>TGACCGTGGA GGATGGACCA ACCAAGAGCG ACCCCAGGTG CCTGACACGC 1650<br>TATTATTCAA GCTTCGTGAA TATGGAAAGG GACCTCGCAT CTGGCTTGAT 1700<br>CGGCCCTCTG CTGATATGTT ACAAGGAAAG CGTCGATCAG AGAGGAAATC 1750<br>AGATCATGTC AGACAAAAGG AATGTGATCC TGTTCTCCGT CTTCGATGAA 1800<br>AACAGGAGCT GGTATCTGAC AGAGAACATC CAGAGATTCC TGCCAAATCC 1850<br>CGCCGGCGTC CAGCTGGAGG ACCCGGAGTT TCAGGCATCT AACATCATGC 1900<br>ATTCCATTAA TGGTTACGTG TTCGACTCCC TGCAGCTGAG CGTGTGCCTC 1950<br>CACGAGGTGG CCTACTGGTA CATCTTGAGC ATCGGCGCCC AGACCGACTT 2000<br>TCTGAGCGTC TTTTTCTCCG GGTATACTTT CAAACATAAG ATGGTGTACG 2050<br>AAGATACTCT GACGCTGTTC CCTTTCTCTG GGGAGACTGT GTTTATGTCT 2100<br>ATGGAGAACC CTGGACTGTG GATTCTCGGA TGCCACAACA GTGACTTTCG 2150<br>TAATAGAGGG ATGACTGCAC TGCTGAAGGT GTCCAGCTGT GATAAAAATA 2200<br>CTGGCGACTA CTACGAAGAT AGCTATGAGG ATATCTCAGC ATACCTGCTG 2250<br>AGCAAGAATA ACGCCATCGA GCCCCGAAGC TTCTCACAGA ATCCCCCTGT 2300<br>CCTCAAGGCC CACCAGGCGG AGATCACAAG GACCACACTC CAGTCCGACC 2350<br>AGGAGGAGAT TGACTACGAT GACACGATTT CTGTGGAGAT GAAAAAAGAG 2400<br>GACTTTGACA TCTACGATGA GGATGAAAAC CAGAGCCCTA GGTCGTTCCA 2450<br>GAAGAAAACA AGGCACTACT TCATTGCCGC CGTGGAGAGA CTGTGGGACT 2500<br>ACGGAATGAG TAGTTCCCCA CACGTGTTGC GGAACAGAGC CCAGAGTGGG 2550 |

FIG. 24R

Table 8 (continued)

| | | |
|---|---|---|
| | | TCCGTCCCAC AGTTCAAGAA GGTTGTTTTC CAGGAGTTCA CAGATGGCTC 2600<br>CTTCACTCAG CCACTGTATC GCGGCGAGCT GAATGAGCAC TTGGGCTTAT 2650<br>TGGGCCCCTA CATTCGCGCA GAAGTCGAAG ATAATATTAT GGTGACCTTC 2700<br>CGCAACCAGG CCAGCCGGCC TTACTCATTC TACTCCTCTC TCATCTCTTA 2750<br>TGAGGAGGAT CAGCGCCAGG GCGCCGAACC CCGGAAGAAC TTTGTGAAGC 2800<br>CCAATGAAAC CAAAACTTAC TTTTGGAAGG TGCAGCACCA TATGGCGCCG 2850<br>ACGAAAGACG AATTTGACTG CAAAGCCTGG GCCTACTTCA GCGACGTCGA 2900<br>CTTGGAGAAG GACGTCCACA GCGGCCTGAT TGGCCCTTTG TTGGTCTGCC 2950<br>ATACCAATAC ACTCAACCCT GCCCACGGGA GGCAGGTGAC CGTGCAGGAG 3000<br>TTTGCCTTGT TCTTCACCAT CTTCGACGAA ACCAAGAGCT GGTACTTCAC 3050<br>AGAGAACATG GAGAGGAACT GCAGAGCACC CTGTAACATC CAGATGGAGG 3100<br>ACCCTACTTT CAAGGAAAAT TACAGGTTCC ATGCCATTAA TGGCTACATC 3150<br>ATGGATACCC TCCCCGGGCT TGTGATGGCT CAGGACCAGC GCATCCGCTG 3200<br>GTACCTGCTC TCAATGGGCT CCAACGAGAA CATTCATAGC ATCCACTTTA 3250<br>GTGGCCACGT GTTTACCGTG CGCAAGAAGG AGGAGTACAA GATGGCACTG 3300<br>TACAACCTGT ACCCTGGCGT GTTTGAGACA GTGGAGATGC TGCCATCCAA 3350<br>GGCCGGCATC TGGCGCGTGG AGTGCCTCAT TGGGGAGCAC CTCCATGCTG 3400<br>GCATGTCTAC ACTGTTCCTG GTGTACAGCA ACAAGTGTCA GACTCCACTC 3450<br>GGAATGGCCT CCGGGCATAT CCGCGATTTT CAGATCACGG CCTCTGGCCA 3500<br>GTATGGCCAA TGGGCTCCCA AGCTGGCCAG GCTGCACTAC AGTGGGAGTA 3550<br>TCAACGCTTG GAGCACCAAG GAGCCTTTCT CCTGGATCAA GGTGGACCTG 3600<br>CTTGCCCCCA TGATTATTCA CGGCATTAAG ACACAGGGGG CCAGGCAGAA 3650<br>ATTCTCCTCC CTGTACATCT CCCAGTTCAT CATCATGTAC AGTCTGGACG 3700<br>GCAAAAAGTG GCAGACCTAC CGCGGGAACA GTACCGGGAC ATTGATGGTG 3750<br>TTCTTCGGGA ACGTGGACTC TAGCGGCATT AAACACAACA TTTTCAACCC 3800<br>CCCCATCATT GCTAGGTATA TCAGGCTCCA TCCCACCCAC TATAGCATCA 3850<br>GGTCCACTCT GCGGATGGAG CTGATGGGCT GCGACCTTAA TTCATGCAGC 3900<br>ATGCCGCTGG GCATGGAGTC AAAGGCCATC TCCGACGCCC AAATCACCGC 3950<br>CTCCAGCTAC TTCACCAATA TGTTCGCCAC CTGGAGCCCC AGCAAGGCCC 4000<br>GGCTGCACCT GCAGGGCCGC AGCAACGCCT GGCGGCCTCA GGTGAACAAC 4050<br>CCCAAGGAGT GGCTGCAGGT GGACTTCCAG AAAACCATGA AGGTGACTGG 4100<br>GGTCACCACC CAGGGAGTCA AGAGCCTGCT GACCAGCATG TATGTGAAGG 4150<br>AGTTCTTGAT CAGCTCGTCA CAGGATGGCC ACCAGTGGAC TTTGTTCTTT 4200<br>CAGAACGGTA AGGTGAAAGT GTTCCAGGGA AACCAAGATT CCTTTACACC 4250<br>AGTGGTCAAC TCTCTGGATC CTCCCCTGCT GACACGGTAC CTGCGGATCC 4300<br>ATCCCCAGTC ATGGGTGCAC CAGATTGCTC TGCGCATGGA GGTGCTTGGC 4350<br>TGCGAGGCCC AGGACCTGTA CTGA 4374 |
| **17** | rhScFVIII-BDD Addback (AHQA) | ATGCAGATTG AGCTGAGCAC CTGTTTCTTC CTGTGCCTGC TGAGATTTTG 50<br>CTTCTCAGCT ACCCGCAGGT ACTACCTGGG AGCCGTTGAG CTGTCCTGGG 100<br>ATTACATGCA GTCAGATCTG GGGGAGCTGC CTGTGGACGC TCGGTTTCCC 150<br>CCCAGAGTGC CAAAGTCCTT TCCCTTCAAC ACCAGCGTGG TGTACAAAAA 200<br>GACACTTTTT GTTGAATTTA CTGACCACTT GTTCAACATC GCCAAGCCAC 250<br>GACCCCCATG GATGGGCCTG CTGGGGCCAA CCATTCAGGC AGAGGTTTAC 300<br>GACACAGTCG TGATCACACT GAAGAACATG GCCTCCCATC CAGTGTCTCT 350<br>GCACGCCGTC GGTGTGTCCT ACTGGAAAGC ATCCGAGGGC GCCGAGTATG 400<br>ACGACCAGAC CAGCCAGAGA GAGAAAGAGG ACGACAAAGT GTTCCCTGGA 450<br>GGCAGCCACA CCTACGTGTG GCAGGTGTTG AAGGAAAATG GGCCCATGGC 500<br>CAGTGACCCT TTGTGTCTGA CTTACTCATA CCTGTCTCAT GTGGATCTAG 550<br>TCAAGGACCT GAATTCTGGA CTGATTGGGG CACTGCTTGT GTGCCGCGAA 600<br>GGCAGCCTGG CCAAAGAAAA GACACAGACC CTTCACAAGT TCATCCTGCT 650<br>GTTCGCCGTG TTCGACGAAG GCAAATCCTG GCACTCAGAA ACCAAAAACT 700<br>CACTGATGCA GGACCGGGAT GCCGCCTCTG CCCGCGCATG GCCAAAAATG 750<br>CACACCGTCA ACGGCTATGT CAATAGAAGT TTGCCCGGCC TCATTGGATG 800<br>TCACAGGAAA AGCGTCTATT GGCATGTAAT CGGGATGGGA ACCACACCTG 850<br>AGGTCCACAG CATATTTCTG GAAGGCCACA CATTTCTGGT GAGAAATCAT 900<br>CGCCAGGCTT CCCTGGAAAT TTCCCCCATC ACCTTCTTGA CCGCCCAGAC 950<br>ACTGCTCATG GATCTTGGGC AGTTTCTGCT GTTTTGTCAT ATTTCTTCTC 1000 |

FIG. 24S

Table 8 (continued)

| | | |
|---|---|---|
| | | ACCAACACGA CGGAATGGAG GCCTACGTTA AGGTCGATAG TTGCCCTGAA 1050 |
| | | GAACCTCAGC TGAGGATGAA GAACAACGAG GAAGCCGAGG ACTACGATGA 1100 |
| | | CGATTTGACC GATTCCGAAA TGGACGTGGT GCGCTTTGAT GATGACAATT 1150 |
| | | CTCCATCCTT CATTCAGATT AGATCCGTCG CCAAGAAGCA CCCCAAGACC 1200 |
| | | TGGGTGCACT ACATTGCAGC CGAGGAGGAG GATTGGGACT ACGCCCCCCT 1250 |
| | | GGTGCTGGCA CCCGACGACC GAAGCTACAA ATCTCAGTAC CTGAACAATG 1300 |
| | | GTCCACAACG GATCGGCAGG AAGTACAAGA AAGTGCGGTT CATGGCCTAT 1350 |
| | | ACAGACGAAA CCTTCAAAAC CAGGGAGGCT ATCCAGCACG AGTCTGGGAT 1400 |
| | | TCTGGGACCA CTCCTGTACG GCGAAGTGGG CGACACCTTG TTAATTATCT 1450 |
| | | TCAAGAACCA GGCTAGTAGA CCTTATAACA TTTATCCCCA CGGCATTACC 1500 |
| | | GATGTGCGGC CTCTCTACTC TAGGCGGCTT CCAAAGGGGG TGAAACACCT 1550 |
| | | GAAGGACTTT CCCATCCTCC CTGGCGAAAT CTTTAAGTAT AAGTGGACAG 1600 |
| | | TGACCGTGGA GGATGGACCA ACCAAGAGCG ACCCCAGGTG CCTGACACGC 1650 |
| | | TATTATTCAA GCTTCGTGAA TATGGAAAGG GACCTCGCAT CTGGCTTGAT 1700 |
| | | CGGCCCTCTG CTGATATGTT ACAAGGAAAG CGTCGATCAG AGAGGAAATC 1750 |
| | | AGATCATGTC AGACAAAAGG AATGTGATCC TGTTCTCCGT CTTCGATGAA 1800 |
| | | AACAGGAGCT GGTATCTGAC AGAGAACATC CAGAGATTCC TGCCAAATCC 1850 |
| | | CGCCGGCGTC CAGCTGGAGG ACCCGGAGTT TCAGGCATCT AACATCATGC 1900 |
| | | ATTCCATTAA TGGTTACGTG TTCGACTCCC TGCAGCTGAG CGTGTGCCTC 1950 |
| | | CACGAGGTGG CCTACTGGTA CATCTTGAGC ATCGGCGCCC AGACCGACTT 2000 |
| | | TCTGAGCGTC TTTTTCTCCG GGTATACTTT CAAACATAAG ATGGTGTACG 2050 |
| | | AAGATACTCT GACGCTGTTC CCTTTCTCTG GGGAGACTGT GTTTATGTCT 2100 |
| | | ATGGAGAACC CTGGACTGTG GATTCTCGGA TGCCACAACA GTGACTTTCG 2150 |
| | | TAATAGAGGG ATGACTGCAC TGCTGAAGGT GTCCAGCTGT GATAAAAATA 2200 |
| | | CTGGCGACTA CTACGAAGAT AGCTATGAGG ATATCTCAGC ATACCTGCTG 2250 |
| | | AGCAAGAATA ACGCCATCGA GCCCCGAAGC TTCTCACAGA ATGCCACCAA 2300 |
| | | CGTGAGCAAC AACAGCAACA CCAGCAACGA CAGCAACGTG AGCCCCCCTG 2350 |
| | | TCCTCAAGGC CCACCAGGCG GAGATCACAA GGACCACACT CCAGTCCGAC 2400 |
| | | CAGGAGGAGA TTGACTACGA TGACACGATT TCTGTGGAGA TGAAAAAAGA 2450 |
| | | GGACTTTGAC ATCTACGATG AGGATGAAAA CCAGAGCCCT AGGTCGTTCC 2500 |
| | | AGAAGAAAAC AAGGCACTAC TTCATTGCCG CCGTGGAGAG ACTGTGGGAC 2550 |
| | | TACGGAATGA GTAGTTCCCC ACACGTGTTG CGGAACAGAG CCCAGAGTGG 2600 |
| | | GTCCGTCCCA CAGTTCAAGA AGGTTGTTTT CCAGGAGTTC ACAGATGGCT 2650 |
| | | CCTTCACTCA GCCACTGTAT CGCGGCGAGC TGAATGAGCA CTTGGGCTTA 2700 |
| | | TTGGGCCCCT ACATTCGCGC AGAAGTCGAA GATAATATTA TGGTGACCTT 2750 |
| | | CCGCAACCAG GCCAGCCGGC CTTACTCATT CTACTCCTCT CTCATCTCTT 2800 |
| | | ATGAGGAGGA TCAGCGCCAG GGCGCCGAAC CCCGGAAGAA CTTTGTGAAG 2850 |
| | | CCCAATGAAA CCAAAACTTA CTTTTGGAAG GTGCAGCACC ATATGGCGCC 2900 |
| | | GACGAAAGAC GAATTTGACT GCAAAGCCTG GGCCTACTTC AGCGACGTCG 2950 |
| | | ACTTGGAGAA GGACGTCCAC AGCGGCCTGA TTGGCCCTTT GTTGGTCTGC 3000 |
| | | CATACCAATA CACTCAACCC TGCCCACGGG AGGCAGGTGA CCGTGCAGGA 3050 |
| | | GTTTGCCTTG TTCTTCACCA TCTTCGACGA AACCAAGAGC TGGTACTTCA 3100 |
| | | CAGAGAACAT GGAGAGGAAC TGCAGAGCAC CCTGTAACAT CCAGATGGAG 3150 |
| | | GACCCTACTT TCAAGGAAAA TTACAGGTTC CATGCCATTA ATGGCTACAT 3200 |
| | | CATGGATACC CTCCCCGGGC TTGTGATGGC TCAGGACCAG CGCATCCGCT 3250 |
| | | GGTACCTGCT CTCAATGGGC TCCAACGAGA ACATTCATAG CATCCACTTT 3300 |
| | | AGTGGCCACG TGTTTACCGT GCGCAAGAAG GAGGAGTACA AGATGGCACT 3350 |
| | | GTACAACCTG TACCCTGGCG TGTTTGAGAC AGTGGAGATG CTGCCATCCA 3400 |
| | | AGGCCGGCAT CTGGCGCGTG GAGTGCCTCA TTGGGGAGCA CCTCCATGCT 3450 |
| | | GGCATGTCTA CACTGTTCCT GGTGTACAGC AACAAGTGTC AGACTCCACT 3500 |
| | | CGGAATGGCC TCCGGGCATA TCCGCGATTT TCAGATCACG GCCTCTGGCC 3550 |
| | | AGTATGGCCA ATGGGCTCCC AAGCTGGCCA GGCTGCACTA CAGTGGGAGT 3600 |
| | | ATCAACGCTT GGAGCACCAA GGAGCCTTTC TCCTGGATCA AGGTGGACCT 3650 |
| | | GCTTGCCCCC ATGATTATTC ACGGCATTAA GACACAGGGG GCCAGGCAGA 3700 |
| | | AATTCTCCTC CCTGTACATC TCCCAGTTCA TCATCATGTA CAGTCTGGAC 3750 |
| | | GGCAAAAAGT GGCAGACCTA CCGCGGGAAC AGTACCGGGA CATTGATGGT 3800 |
| | | GTTCTTCGGG AACGTGGACT CTAGCGGCAT TAAACACAAC ATTTTCAACC 3850 |

FIG. 24T

Table 8 (continued)

| | | |
|---|---|---|
| | | CCCCCATCAT TGCTAGGTAT ATCAGGCTCC ATCCCACCCA CTATAGCATC 3900<br>AGGTCCACTC TGCGGATGGA GCTGATGGGC TGCGACCTTA ATTCATGCAG 3950<br>CATGCCGCTG GGCATGGAGT CAAAGGCCAT CTCCGACGCC CAAATCACCG 4000<br>CCTCCAGCTA CTTCACCAAT ATGTTCGCCA CCTGGAGCCC CAGCAAGGCC 4050<br>CGGCTGCACC TGCAGGGCCG CAGCAACGCC TGGCGGCCTC AGGTGAACAA 4100<br>CCCCAAGGAG TGGCTGCAGG TGGACTTCCA GAAAACCATG AAGGTGACTG 4150<br>GGGTCACCAC CCAGGGAGTC AAGAGCCTGC TGACCAGCAT GTATGTGAAG 4200<br>GAGTTCTTGA TCAGCTCGTC ACAGGATGGC CACCAGTGGA CTTTGTTCTT 4250<br>TCAGAACGGT AAGGTGAAAG TGTTCCAGGG AAACCAAGAT TCCTTTACAC 4300<br>CAGTGGTCAA CTCTCTGGAT CCTCCCCTGC TGACACGGTA CCTGCGGATC 4350<br>CATCCCCAGT CATGGGTGCA CCAGATTGCT CTGCGCATGG AGGTGCTTGG 4400<br>CTGCGAGGCC CAGGACCTGT ACTAA 4425 |

Table 9: FIX coding sequences expressed in ARPE-19 cells

| SEQ ID NO. | Sequence Name | Nucleotide Sequence |
|---|---|---|
| 18 | rhFIX Padua | ATGCAGCGCG TGAACATGAT CATGGCAGAA TCACCAGGCC TCATCACCAT 50<br>CTGCCTTTTA GGATATCTAC TCAGTGCTGA ATGTACAGTT TTTCTTGATC 100<br>ATGAAAACGC CAACAAAATT CTGAATCGGC CAAAGAGGTA TAATTCAGGT 150<br>AAATTGGAAG AGTTTGTTCA AGGGAACCTT GAGAGAGAAT GTATGGAAGA 200<br>AAAGTGTAGT TTTGAAGAAG CACGAGAAGT TTTTGAAAAC ACTGAAAGAA 250<br>CAACTGAATT TTGGAAGCAG TATGTTGATG GAGATCAGTG TGAGTCCAAT 300<br>CCATGTTTAA ATGGCGGCAG TTGCAAGGAT GACATTAATT CCTATGAATG 350<br>TTGGTGTCCC TTTGGATTTG AAGGAAAGAA CTGTGAATTA GATGTAACAT 400<br>GTAACATTAA GAATGGCAGA TGCGAGCAGT TTTGTAAAAA TAGTGCTGAT 450<br>AACAAGGTGG TTTGCTCCTG TACTGAGGGA TATCGACTTG CAGAAAACCA 500<br>GAAGTCCTGT GAACCAGCAG TGCCATTTCC ATGTGGAAGA GTTTCTGTTT 550<br>CACAAACTTC TAAGCTCACC CGTGCTGAGA CTGTTTTTCC TGATGTGGAC 600<br>TATGTAAATT CTACTGAAGC TGAAACCATT TTGGATAACA TCACTCAAAG 650<br>CACCCAATCA TTTAATGACT TCACTCGGGT TGTTGGTGGA GAAGATGCCA 700<br>AACCAGGTCA ATTCCCTTGG CAGGTTGTTT TGAATGGTAA AGTTGATGCA 750<br>TTCTGTGGAG GCTCTATCGT TAATGAAAAA TGGATTGTAA CTGCTGCCCA 800<br>CTGTGTTGAA ACTGGTGTTA AAATTACAGT TGTCGCAGGT GAACATAATA 850<br>TTGAGGAGAC AGAACATACA GAGCAAAAGC GAAATGTGAT TCGAATTATT 900<br>CCTCACCACA ACTACAATGC AGCTATTAAT AAGTACAACC ATGACATTGC 950<br>CCTTCTGGAA CTGGACGAAC CCTTAGTGCT AAACAGCTAC GTTACACCTA 1000<br>TTTGCATTGC TGACAAGGAA TACACGAACA TCTTCCTCAA ATTTGGATCT 1050<br>GGCTATGTAA GTGGCTGGGG AAGAGTCTTC CACAAAGGGA GATCAGCTTT 1100<br>AGTTCTTCAG TACCTTAGAG TTCCACTTGT TGACCGAGCC ACATGTCTTC 1150<br>TGTCTACAAA GTTCACCATC TATAACAACA TGTTCTGTGC TGGCTTCCAT 1200<br>GAAGGAGGTA GAGATTCATG TCAAGGAGAT AGTGGGGGAC CCCATGTTAC 1250<br>TGAAGTGGAA GGGACCAGTT TCTTAACTGG AATTATTAGC TGGGGTGAAG 1300<br>AGTGTGCAAT GAAAGGCAAA TATGGAATAT ATACCAAGGT ATCCCGGTAT 1350<br>GTCAACTGGA TTAAGGAAAA AACAAAGCTC ACTTAA 1386 |
| 19 | rhFIX Padua CO2 | ATGCAGCGCG TGAACATGAT TATGGCCGAG TCTCCCGGCC TGATCACCAT 50<br>CTGTCTGCTG GGCTATCTGC TGAGCGCCGA GTGCACCGTG TTTCTGGATC 100<br>ACGAGAACGC CAACAAGATC CTGAACAGAC CCAAGCGGTA CAACAGCGGC 150<br>AAGCTGGAAG AGTTCGTGCA GGGCAACCTG GAACGCGAGT GCATGGAAGA 200<br>GAAGTGCAGC TTCGAAGAGG CCAGAGAGGT GTTCGAGAAC ACCGAGAGAA 250<br>CCACCGAGTT CTGGAAGCAG TACGTGGACG GCGATCAGTG CGAGAGCAAC 300<br>CCTTGTCTGA ATGGCGGCAG CTGCAAGGAC GACATCAACA GCTACGAGTG 350<br>CTGGTGCCCC TTCGGCTTCG AGGGCAAGAA TTGCGAGCTG GACGTGACCT 400<br>GCAACATCAA GAACGGCAGA TGCGAGCAGT TCTGCAAGAA CAGCGCCGAC 450<br>AACAAGGTCG TGTGCTCCTG CACAGAGGGC TACAGACTGG CCGAGAACCA 500<br>GAAGTCTTGC GAGCCCGCTG TGCCCTTTCC ATGTGGCAGA GTGTCTGTGT 550 |

FIG. 24U

Table 9 (continued)

| | | |
|---|---|---|
| | | CCCAGACCAG CAAGCTGACC AGAGCCGAGA CAGTGTTCCC CGACGTGGAC 600<br>TACGTGAACA GCACCGAGGC CGAGACAATC CTGGACAACA TCACCCAGAG 650<br>CACCCAGTCC TTCAACGACT TCACCAGAGT CGTCGGCGGC GAGGATGCTA 700<br>AGCCTGGACA GTTTCCTTGG CAAGTGGTGC TGAACGGCAA GGTGGACGCT 750<br>TTTTGTGGCG GCTCCATCGT GAACGAGAAG TGGATCGTGA CCGCCGCTCA 800<br>CTGTGTGGAA ACCGGCGTGA AGATTACAGT GGTGGCCGGC GAGCACAACA 850<br>TCGAGGAAAC AGAGCACACC GAGCAGAAAC GGAACGTGAT CAGAATCATC 900<br>CCTCACCACA ACTACAACGC CGCCATCAAC AAGTACAACC ACGATATCGC 950<br>CCTGCTGGAA CTGGACGAGC CCCTGGTCCT GAACTCTTAC GTGACCCCTA 1000<br>TCTGTATCGC CGACAAAGAG TACACCAACA TCTTTCTGAA GTTCGGCAGC 1050<br>GGCTACGTGT CCGGCTGGGG AAGAGTTTTC CACAAGGGCA GATCAGCCCT 1100<br>GGTGCTGCAG TACCTGAGAG TGCCCCTGGT GGATAGAGCC ACATGCCTGC 1150<br>TGAGCACCAA GTTCACCATC TACAACAACA TGTTCTGCGC CGGCTTCCAC 1200<br>GAAGGCGGCA GAGATTCTTG TCAAGGCGAT TCTGGCGGCC CTCACGTGAC 1250<br>AGAGGTTGAG GGCACAAGCT TTCTGACCGG CATCATCAGC TGGGGCGAAG 1300<br>AGTGTGCCAT GAAGGGGAAG TACGGCATCT ACACCAAGGT GTCCAGATAC 1350<br>GTGAACTGGA TCAAAGAAAA GACCAAGCTC ACCTGA 1386 |
| 20 | rHFIX Padua CO3 | ATGCAGCGCG TGAACATGAT CATGGCCGAG AGCCCCGGCC TGATCACCAT 50<br>CTGCCTGCTG GGCTACCTGC TGAGCGCCGA GTGCACCGTG TTCCTGGACC 100<br>ACGAGAACGC CAACAAGATC CTGAACCGCC CCAAGCGCTA CAACAGCGGC 150<br>AAGCTGGAGG AGTTCGTGCA GGGCAACCTG GAGCGCGAGT GCATGGAGGA 200<br>GAAGTGCAGC TTCGAGGAGG CCCGCGAGGT GTTCGAGAAC ACCGAGCGCA 250<br>CCACCGAGTT CTGGAAGCAG TACGTGGACG GCGACCAGTG CGAGAGCAAC 300<br>CCCTGCCTGA ACGGCGGCAG CTGCAAGGAC GACATCAACA GCTACGAGTG 350<br>CTGGTGCCCC TTCGGCTTCG AGGGCAAGAA CTGCGAGCTG GACGTGACCT 400<br>GCAACATCAA GAACGGCCGC TGCGAGCAGT TCTGCAAGAA CAGCGCCGAC 450<br>AACAAGGTGG TGTGCAGCTG CACCGAGGGC TACCGCCTGG CCGAGAACCA 500<br>GAAGAGCTGC GAGCCCGCCG TGCCCTTCCC CTGCGGCCGC GTGAGCGTGA 550<br>GCCAGACCAG CAAGCTGACC CGCGCCGAGA CTGTGTTCCC CGACGTGGAC 600<br>TACGTGAACA GCACCGAGGC CGAAACGATC CTGGACAACA TCACCCAGAG 650<br>CACCCAGAGC TTCAACGACT TCACCCGCGT GGTGGGCGGC GAGGACGCCA 700<br>AGCCCGGCCA GTTCCCCTGG CAGGTGGTGC TGAACGGCAA GGTGGACGCC 750<br>TTCTGCGGCG GCAGCATCGT GAACGAGAAG TGGATCGTGA CCGCCGCCCA 800<br>CTGCGTGGAA ACCGGCGTGA AGATCACCGT GGTGGCCGGC GAGCACAACA 850<br>TCGAGGAAAC CGAGCACACC GAGCAGAAGC GCAACGTGAT CCGCATCATC 900<br>CCCCACCACA ACTACAACGC CGCCATCAAC AAGTACAACC ACGACATCGC 950<br>CCTGCTGGAG CTGGACGAGC CCCTGGTGCT GAACAGCTAC GTGACCCCCA 1000<br>TCTGCATCGC CGACAAGGAG TACACCAACA TCTTCCTGAA GTTCGGCAGC 1050<br>GGCTACGTGA GCGGCTGGGG CCGCGTGTTC CACAAGGGCC GCAGCGCCCT 1100<br>GGTGCTGCAG TACCTGCGCG TGCCCCTGGT GGACCGCGCC ACCTGCCTGC 1150<br>TGAGCACCAA GTTCACCATC TACAACAACA TGTTCTGCGC CGGCTTCCAC 1200<br>GAGGGCGGCC GCGACAGCTG CCAGGGCGAC AGCGGCGGCC CCCACGTGAC 1250<br>CGAGGTGGAG GGCACCAGCT TCCTGACCGG CATCATCAGC TGGGGCGAGG 1300<br>AGTGCGCCAT GAAGGGCAAG TACGGCATCT ACACCAAGGT GAGCCGCTAC 1350<br>GTGAACTGGA TCAAGGAGAA AACCAAGCTG ACCTAA 1386 |
| 21 | rhFIX Padua CO5 | ATGCAGCGGG TGAACATGAT CATGGCCGAG AGCCCCGGGC TGATCACCAT 50<br>CTGTCTGCTG GGGTACCTGC TGTCCGCCGA GTGCACCGTG TTCCTGGACC 100<br>ACGAGAACGC CAACAAGATC CTGAATCGCC CCAAGAGATA CAATTCCGGA 150<br>AAGCTGGAAG AGTTTGTGCA GGGCAACCTG GAGAGAGAGT GCATGGAAGA 200<br>GAAGTGCTCC TTCGAGGAGG CCCGGGAGGT GTTCGAGAAT ACTGAACGGA 250<br>CAACAGAGTT CTGGAAGCAG TATGTGGACG GCGACCAGTG TGAGAGCAAC 300<br>CCCTGTCTGA ACGGCGGGAG CTGCAAGGAC GACATTAATT CCTACGAATG 350<br>CTGGTGCCCA TTCGGCTTCG AGGGCAAGAA CTGCGAGCTG GACGTGACCT 400<br>GCAACATCAA GAACGGCCGC TGCGAGCAGT TTTGCAAGAA CTCCGCCGAC 450<br>AACAAGGTGG TGTGTTCTTG CACCGAGGGC TACCGCCTGG CCGAAAACCA 500<br>GAAGAGCTGT GAGCCTGCCG TGCCCTTCCC CTGCGGCCGG GTGTCTGTGT 550<br>CCCAGACCTC CAAGCTGACC AGAGCCGAAA CCGTGTTTCC AGATGTGGAC 600 |

FIG. 24V

Table 9 (continued)

| | | |
|---|---|---|
| | | TACGTGAATA GCACCGAGGC CGAGACTATC CTCGACAACA TCACCCAGTC 650<br>CACCCAGAGC TTTAACGACT TCACCCGCGT GGTGGGCGGC GAGGACGCCA 700<br>AGCCCGGCCA GTTCCCCTGG CAGGTGGTGC TCAACGGAAA GGTGGACGCC 750<br>TTCTGCGGAG GCAGCATCGT GAATGAAAAG TGGATCGTGA CAGCCGCCCA 800<br>CTGCGTGGAA ACAGGGGTGA AGATCACCGT GGTGGCTGGA GAGCACAACA 850<br>TCGAGGAGAC AGAGCACACC GAACAGAAGA GGAATGTGAT CAGGATCATC 900<br>CCCCACCACA ACTATAATGC CGCCATCAAC AAGTACAACC ACGACATCGC 950<br>CCTGCTGGAG CTGGATGAGC CCCTGGTGCT CAACAGCTAC GTGACCCCCA 1000<br>TCTGCATCGC TGACAAGGAG TACACCAACA TCTTCCTGAA GTTCGGCTCC 1050<br>GGCTACGTGT CTGGCTGGGG CCGCGTGTTC CACAAGGGAA GAAGCGCCCT 1100<br>CGTGCTGCAG TACCTGCGGG TGCCACTGGT GGACAGGGCC ACCTGCCTGC 1150<br>TGAGCACTAA GTTCACCATT TACAACAACA TGTTCTGCGC CGGCTTCCAC 1200<br>GAGGGCGGCA GGGACTCCTG CCAGGGCGAC AGCGGCGGCC CCCATGTGAC 1250<br>CGAGGTGGAG GGCACCTCCT TTCTGACTGG CATTATCTCC TGGGGCGAGG 1300<br>AGTGCGCCAT GAAGGGGAAG TATGGCATCT ACACCAAGGT GTCCCGCTAC 1350<br>GTGAACTGGA TTAAGGAGAA AACCAAGCTG ACCTGA 1386 |

Table 10: Expression Vector Sequences

| SEQ ID NO. | Component | Nucleotide Sequence |
|---|---|---|
| 22 | 5′ ITR | TTAACCCTAG AAAGATAGTC TGCGTAAAAT TGACGCATGC ATTCTTGAAA<br>TATTGCTCTC TCTTTCTAAA TAGCGCGAAT CCGTCGCTGT GCATTTAGGA<br>CATCTCAGTC GCCGCTTGGA GCTCCCGTGA GGCGTGCTTG TCAATGCGGT<br>AAGTGTCACT GATTTTGAAC TATAACGACC GCGTGAGTCA AAATGACGCA<br>TGATTATCTT TTACGTGACT TTTAAGATTT AACTCATACG ATAATTATAT<br>TGTTATTTCA TGTTCTACTT ACGTGATAAC TTATTATATA TATATTTTCT<br>TGTTATAGAT ATC |
| 23 | CAG Promoter | CTCGACATTG ATTATTGACT AGTTATTAAT AGTAATCAAT TACGGGGTCA<br>TTAGTTCATA GCCCATATAT GGAGTTCCGC GTTACATAAC TTACGGTAAA<br>TGGCCCGCCT GGCTGACCGC CCAACGACCC CCGCCCATTG ACGTCAATAA<br>TGACGTATGT TCCCATAGTA ACGCCAATAG GGACTTTCCA TTGACGTCAA<br>TGGGTGGAGT ATTTACGGTA AACTGCCCAC TTGGCAGTAC ATCAAGTGTA<br>TCATATGCCA AGTACGCCCC CTATTGACGT CAATGACGGT AAATGGCCCG<br>CCTGGCATTA TGCCCAGTAC ATGACCTTAT GGGACTTTCC TACTTGGCAG<br>TACATCTACG TATTAGTCAT CGCTATTACC ATGGTCGAGG TGAGCCCCAC<br>GTTCTGCTTC ACTCTCCCCA TCTCCCCCCC CTCCCCACCC CCAATTTTGT<br>ATTTATTTAT TTTTTAATTA TTTTGTGCAG CGATGGGGGC GGGGGGGGGG<br>GGGGGGCGCG CGCCAGGCGG GGCGGGGCGG GGCGAGGGGC GGGGCGGGGC<br>GAGGCGGAGA GGTGCGGCGG CAGCCAATCA GAGCGGCGCG CTCCGAAAGT<br>TTCCTTTTAT GGCGAGGCGG CGGCGGCGGC GGCCCTATAA AAAGCGAAGC<br>GCGCGGCGGG CGGGAGTCGC TGCGCGCTGC CTTCGCCCCG TGCCCCGCTC<br>CGCCGCCGCC TCGCGCCGCC CGCCCCGGCT CTGACTGACC GCGTTACTCC<br>CACAGGTGAG CGGGCGGGAC GGCCCTTCTC CTCCGGGCTG TAATTAGCGC<br>TTGGTTTAAT GACGGCTTGT TTCTTTTCTG TGGCTGCGTG AAAGCCTTGA<br>GGGGCTCCGG GAGGGCCCTT TGTGCGGGGG GAGCGGCTCG GGGGGTGCGT<br>GCGTGTGTGT GTGCGTGGGG AGCGCCGCGT GCGGCTCCGC GCTGCCCGGC<br>GGCTGTGAGC GCTGCGGGCG CGGCGCGGGG CTTTGTGCGC TCCGCAGTGT<br>GCGCGAGGGG AGCGCGGCCG GGGGCGGTGC CCCGCGGTGC GGGGGGGGCT<br>GCGAGGGGAA CAAAGGCTGC GTGCGGGGTG TGTGCGTGGG GGGGTGAGCA<br>GGGGGTGTGG GCGCGTCGGT CGGGCTGCAA CCCCCCCTGC ACCCCCCTCC<br>CCGAGTTGCT GAGCACGGCC CGGCTTCGGG TGCGGGGCTC CGTACGGGGC<br>GTGGCGCGGG GCTCGCCGTG CCGGGCGGGG GGTGGCGGCA GGTGGGGGTG<br>CCGGGCGGGG CGGGGCCGCC TCGGGCCGGG GAGGGCTCGG GGGAGGGGCG |

FIG. 24W

Table 10 (continued)

| | | |
|---|---|---|
| | | CGGCGGCCCC CGGAGCGCCG GCGGCTGTCG AGGCGCGGCG AGCCGCAGCC ATTGCCTTTT ATGGTAATCG TGCGAGAGGG CGCAGGGACT TCCTTTGTCC CAAATCTGTG CGGAGCCGAA ATCTGGGAGG CGCCGCCGCA CCCCCTCTAG CGGGCGCGGG GCGAAGCGGT GCGGCGCCGG CAGGAAGGAA ATGGGCGGGG AGGGCCTTCG TGCGTCGCCG CGCCGCCGTC CCCTTCTCCC TCTCCAGCCT CGGGGCTGTC CGCGGGGGGA CGGCTGCCTT CGGGGGGGAC GGGGCAGGGC GGGGTTCGGC TTCTGGCGTG TGACCGGCGG CTCTAGAGCC TCTGCTAACC ATGTTCATGC CTTCTTCTTT TTCCTACAGC TCCTGGGCAA CGTGCTGGTT ATTGTGCTGT CTCATCATTT TGGCAAAGAA TTG |
| 24 | rBG pA | TCCTCAGGTG CAGGCTGCCT ATCAGAAGGT GGTGGCTGGT GTGGCCAATG CCCTGGCTCA CAAATACCAC TGAGATCTTT TTCCCTCTGC CAAAAATTAT GGGGACATCA TGAAGCCCCT TGAGCATCTG ACTTCTGGCT AATAAAGGAA ATTTATTTTC ATTGCAATAG TGTGTTGGAA TTTTTTGTGT CTCTCACTCG GAAGGACATA TGGGAGGGCA AATCATTTAA AACATCAGAA TGAGTATTTG GTTTAGAGTT TGGCAACATA TGCCCATATG CTGGCTGCCA TGAACAAAGG TTGGCTATAA AGAGGTCATC AGTATATGAA ACAGCCCCCT GCTGTCCATT CCTTATTCCA TAGAAAAGCC TTGACTTGAG GTTAGATTTT TTTTATATTT TGTTTTGTGT TATTTTTTTC TTTAACATCC CTAAAATTTT CCTTACATGT TTTACTAGCC AGATTTTTCC TCCTCTCCTG ACTACTCCCA GTCATAGCTG TCCCTCTTCT CTTATGGAGA TC |
| 25 | 3' ITR | TTAACCCTAG AAAGATAATC ATATTGTGAC GTACGTTAAA GATAATCATG CGTAAAATTG ACGCATGTGT TTTATCGGTC TGTATATCGA GGTTTATTTA TTAATTTGAA TAGATATTAA GTTTTATTAT ATTTACACTT ACATACTAAT AATAAATTCA ACAAACAATT TATTTATGTT TATTTATTTA TTAAAAAAAA ACAAAAACTC AAAATTTCTT CTATAAAGTA ACAAA |
| 26 | Vector | TTAACCCTAG AAAGATAGTC TGCGTAAAAT TGACGCATGC ATTCTTGAAA TATTGCTCTC TCTTTCTAAA TAGCGCGAAT CCGTCGCTGT GCATTTAGGA CATCTCAGTC GCCGCTTGGA GCTCCCGTGA GGCGTGCTTG TCAATGCGGT AAGTGTCACT GATTTTGAAC TATAACGACC GCGTGAGTCA AAATGACGCA TGATTATCTT TTACGTGACT TTTAAGATTT AACTCATACG ATAATTATAT TGTTATTTCA TGTTCTACTT ACGTGATAAC TTATTATATA TATATTTTCT TGTTATAGAT ATCATCAACT TTGTATAGAA AAGTTGCTCG ACATTGATTA TTGACTAGTT ATTAATAGTA ATCAATTACG GGGTCATTAG TTCATAGCCC ATATATGGAG TTCCGCGTTA CATAACTTAC GGTAAATGGC CCGCCTGGCT GACCGCCCAA CGACCCCCGC CCATTGACGT CAATAATGAC GTATGTTCCC ATAGTAACGC CAATAGGGAC TTTCCATTGA CGTCAATGGG TGGAGTATTT ACGGTAAACT GCCCACTTGG CAGTACATCA AGTGTATCAT ATGCCAAGTA CGCCCCCTAT TGACGTCAAT GACGGTAAAT GGCCCGCCTG GCATTATGCC CAGTACATGA CCTTATGGGA CTTTCCTACT TGGCAGTACA TCTACGTATT AGTCATCGCT ATTACCATGG TCGAGGTGAG CCCCACGTTC TGCTTCACTC TCCCCATCTC CCCCCCCTCC CCACCCCCAA TTTTGTATTT ATTTATTTTT TAATTATTTT GTGCAGCGAT GGGGGCGGGG GGGGGGGGGG GGCGCGCGCC AGGCGGGGCG GGGCGGGGCG AGGGGCGGGG CGGGGCGAGG CGGAGAGGTG CGGCGGCAGC CAATCAGAGC GGCGCGCTCC GAAAGTTTCC TTTTATGGCG AGGCGGCGGC GGCGGCGGCC CTATAAAAAG CGAAGCGCGC GGCGGGCGGG AGTCGCTGCG CGCTGCCTTC GCCCCGTGCC CCGCTCCGCC GCCGCCTCGC GCCGCCCGCC CCGGCTCTGA CTGACCGCGT TACTCCCACA GGTGAGCGGG CGGGACGGCC CTTCTCCTCC GGGCTGTAAT TAGCGCTTGG TTTAATGACG GCTTGTTTCT TTTCTGTGGC TGCGTGAAAG CCTTGAGGGG CTCCGGGAGG GCCCTTTGTG CGGGGGGAGC GGCTCGGGGG GTGCGTGCGT GTGTGTGTGC GTGGGGAGCG CCGCGTGCGG CTCCGCGCTG CCCGGCGGCT GTGAGCGCTG CGGGCGCGGC GCGGGGCTTT GTGCGCTCCG CAGTGTGCGC GAGGGGAGCG CGGCCGGGGG CGGTGCCCCG CGGTGCGGGG GGGGCTGCGA GGGGAACAAA GGCTGCGTGC GGGGTGTGTG CGTGGGGGGG TGAGCAGGGG GTGTGGGCGC GTCGGTCGGG CTGCAACCCC CCCTGCACCC CCCTCCCCGA GTTGCTGAGC ACGGCCCGGC TTCGGGTGCG GGGCTCCGTA CGGGGCGTGG CGCGGGGCTC |

FIG. 24X

Table 10 (continued)

| | | |
|---|---|---|
| | | GCCGTGCCGG GCGGGGGGTG GCGGCAGGTG GGGGTGCCGG GCGGGGCGGG |
| | | GCCGCCTCGG GCCGGGGAGG GCTCGGGGGA GGGGCGCGGC GGCCCCCGGA |
| | | GCGCCGGCGG CTGTCGAGGC GCGGCGAGCC GCAGCCATTG CCTTTTATGG |
| | | TAATCGTGCG AGAGGGCGCA GGGACTTCCT TTGTCCCAAA TCTGTGCGGA |
| | | GCCGAAATCT GGGAGGCGCC GCCGCACCCC CTCTAGCGGG CGCGGGGCGA |
| | | AGCGGTGCGG CGCCGGCAGG AAGGAAATGG GCGGGGAGGG CCTTCGTGCG |
| | | TCGCCGCGCC GCCGTCCCCT TCTCCCTCTC CAGCCTCGGG GCTGTCCGCG |
| | | GGGGGACGGC TGCCTTCGGG GGGGACGGGG CAGGGCGGGG TTCGGCTTCT |
| | | GGCGTGTGAC CGGCGGCTCT AGAGCCTCTG CTAACCATGT TCATGCCTTC |
| | | TTCTTTTTCC TACAGCTCCT GGGCAACGTG CTGGTTATTG TGCTGTCTCA |
| | | TCATTTTGGC AAAGAATTGC AAGTTTGTAC AAAAAAGCAG GCTGCCACCG |
| | | AATTCGCGGC CGCTAAACCC AGCTTTCTTG TACAAAGTGG CAACTTTATT |
| | | ATACATAGTT GATCCTCAGG TGCAGGCTGC CTATCAGAAG GTGGTGGCTG |
| | | GTGTGGCCAA TGCCCTGGCT CACAAATACC ACTGAGATCT TTTTCCCTCT |
| | | GCCAAAAATT ATGGGGACAT CATGAAGCCC CTTGAGCATC TGACTTCTGG |
| | | CTAATAAAGG AAATTTATTT TCATTGCAAT AGTGTGTTGG AATTTTTTGT |
| | | GTCTCTCACT CGGAAGGACA TATGGGAGGG CAAATCATTT AAAACATCAG |
| | | AATGAGTATT TGGTTTAGAG TTTGGCAACA TATGCCCATA TGCTGGCTGC |
| | | CATGAACAAA GGTTGGCTAT AAAGAGGTCA TCAGTATATG AAACAGCCCC |
| | | CTGCTGTCCA TTCCTTATTC CATAGAAAAG CCTTGACTTG AGGTTAGATT |
| | | TTTTTTATAT TTTGTTTTGT GTTATTTTTT TCTTTAACAT CCCTAAAATT |
| | | TTCCTTACAT GTTTTACTAG CCAGATTTTT CCTCCTCTCC TGACTACTCC |
| | | CAGTCATAGC TGTCCCTCTT CTCTTATGGA GATCCCTCGA CCTGCAGCCC |
| | | AAGCTTGGAT CCCTCGAGTT AATTAACGAG AGCATAATAT TGATATGTGC |
| | | CAAAGTTGTT TCTGACTGAC TAATAAGTAT AATTTGTTTC TATTATGTAT |
| | | AGGTTAAGCT AATTACTTAT TTTATAATAC AACATGACTG TTTTTAAAGT |
| | | ACAAAATAAG TTTATTTTTG TAAAAGAGAG AATGTTTAAA AGTTTTGTTA |
| | | CTTTATAGAA GAAATTTTGA GTTTTTGTTT TTTTTTAATA AATAAATAAA |
| | | CATAAATAAA TTGTTTGTTG AATTTATTAT TAGTATGTAA GTGTAAATAT |
| | | AATAAAACTT AATATCTATT CAAATTAATA AATAAACCTC GATATACAGA |
| | | CCGATAAAAC ACATGCGTCA ATTTTACGCA TGATTATCTT TAACGTACGT |
| | | CACAATATGA TTATCTTTCT AGGGTTAAAT AATAGTTTCT AATTTTTTTA |
| | | TTATTCAGCC TGCTGTCGTG AATACCGAGC TCCAATTCGC CCTATAGTGA |
| | | GTCGTATTAC AATTCACTGG CCGTCGTTTT ACAACGTCGT GACTGGGAAA |
| | | ACCCTGGCGT TACCCAACTT AATCGCCTTG CAGCACATCC CCCTTTCGCC |
| | | AGCTGGCGTA ATAGCGAAGA GGCCCGCACC GATCGCCCTT CCCAACAGTT |
| | | GCGCAGCCTG AATGGCGAAT GGGACGCGCC CTGTAGCGGC GCATTAAGCG |
| | | CGGCGGGTGT GGTGGTTACG CGCAGCGTGA CCGCTACACT TGCCAGCGCC |
| | | CTAGCGCCCG CTCCTTTCGC TTTCTTCCCT TCCTTTCTCG CCACGTTCGC |
| | | CGGCTTTCCC CGTCAAGCTC TAAATCGGGG GCTCCCTTTA GGGTTCCGAT |
| | | TTAGTGCTTT ACGGCACCTC GACCCCAAAA AACTTGATTA GGGTGATGGT |
| | | TCACGTAGTG GGCCATCGCC CTGATAGACG GTTTTTCGCC CTTTGACGTT |
| | | GGAGTCCACG TTCTTTAATA GTGGACTCTT GTTCCAAACT GGAACAACAC |
| | | TCAACCCTAT CTCGGTCTAT TCTTTTGATT TATAAGGGAT TTTGCCGATT |
| | | TCGGCCTATT GGTTAAAAAA TGAGCTGATT TAACAAAAAT TTAACGCGAA |
| | | TTTTAACAAA ATATTAACGC TTACAATTTA GGTGGCACTT TTCGGGGAAA |
| | | TGTGCGCGGA ACCCCTATTT GTTTATTTTT CTAAATACAT TCAAATATGT |
| | | ATCCGCTCAT GAGACAATAA CCCTGATAAA TGCTTCAATA ATATTGAAAA |
| | | AGGAAGAGTA TGAGTATTCA ACATTTCCGT GTCGCCCTTA TTCCCTTTTT |
| | | TGCGGCATTT TGCCTTCCTG TTTTTGCTCA CCCAGAAACG CTGGTGAAAG |
| | | TAAAAGATGC TGAAGATCAG TTGGGTGCAC GAGTGGGTTA CATCGAACTG |
| | | GATCTCAACA GCGGTAAGAT CCTTGAGAGT TTTCGCCCCG AAGAACGTTT |
| | | TCCAATGATG AGCACTTTTA AAGTTCTGCT ATGTGGCGCG GTATTATCCC |
| | | GTATTGACGC CGGGCAAGAG CAACTCGGTC GCCGCATACA CTATTCTCAG |
| | | AATGACTTGG TTGAGTACTC ACCAGTCACA GAAAAGCATC TTACGGATGG |
| | | CATGACAGTA AGAGAATTAT GCAGTGCTGC CATAACCATG AGTGATAACA |
| | | CTGCGGCCAA CTTACTTCTG ACAACGATCG GAGGACCGAA GGAGCTAACC |

FIG. 24Y

Table 10 (continued)

| | | |
|---|---|---|
| | | GCTTTTTTGC ACAACATGGG GGATCATGTA ACTCGCCTTG ATCGTTGGGA ACCGGAGCTG AATGAAGCCA TACCAAACGA CGAGCGTGAC ACCACGATGC CTGTAGCAAT GGCAACAACG TTGCGCAAAC TATTAACTGG CGAACTACTT ACTCTAGCTT CCCGGCAACA ATTAATAGAC TGGATGGAGG CGGATAAAGT TGCAGGACCA CTTCTGCGCT CGGCCCTTCC GGCTGGCTGG TTTATTGCTG ATAAATCTGG AGCCGGTGAG CGTGGGTCTC GCGGTATCAT TGCAGCACTG GGGCCAGATG GTAAGCCCTC CCGTATCGTA GTTATCTACA CGACGGGGAG TCAGGCAACT ATGGATGAAC GAAATAGACA GATCGCTGAG ATAGGTGCCT CACTGATTAA GCATTGGTAA CTGTCAGACC AAGTTTACTC ATATATACTT TAGATTGATT TAAAACTTCA TTTTTAATTT AAAAGGATCT AGGTGAAGAT CCTTTTTGAT AATCTCATGA CCAAAATCCC TTAACGTGAG TTTTCGTTCC ACTGAGCGTC AGACCCCGTA GAAAAGATCA AAGGATCTTC TTGAGATCCT TTTTTTCTGC GCGTAATCTG CTGCTTGCAA ACAAAAAAAC CACCGCTACC AGCGGTGGTT TGTTTGCCGG ATCAAGAGCT ACCAACTCTT TTTCCGAAGG TAACTGGCTT CAGCAGAGCG CAGATACCAA ATACTGTTCT TCTAGTGTAG CCGTAGTTAG GCCACCACTT CAAGAACTCT GTAGCACCGC CTACATACCT CGCTCTGCTA ATCCTGTTAC CAGTGGCTGC TGCCAGTGGC GATAAGTCGT GTCTTACCGG GTTGGACTCA AGACGATAGT TACCGGATAA GGCGCAGCGG TCGGGCTGAA CGGGGGGTTC GTGCACACAG CCCAGCTTGG AGCGAACGAC CTACACCGAA CTGAGATACC TACAGCGTGA GCTATGAGAA AGCGCCACGC TTCCCGAAGA GAGAAAGGCG GACAGGTATC CGGTAAGCGG CAGGGTCGGA ACAGGAGAGC GCACGAGGGA GCTTCCAGGG GGAAACGCCT GGTATCTTTA TAGTCCTGTC GGGTTTCGCC ACCTCTGACT TGAGCGTCGA TTTTTGTGAT GCTCGTCAGG GGGGCGGAGC CTATGGAAAA ACGCCAGCAA CGCGGCCTTT TTACGGTTCC TGGCCTTTTG CTGGCCTTTT GCTCACATGT TCTTTCCTGC GTTATCCCCT GATTCTGTGG ATAACCGTAT TACCGCCTTT GAGTGAGCTG ATACCGCTCG CCGCAGCCGA ACGACCGAGC GCAGCGAGTC AGTGAGCGAG GAAGCGGAAG AGCGCCCAAT ACGCAAACCG CCTCTCCCCG CGCGTTGGCC GATTCATTAA TGCAGCTGGC ACGACAGGTT TCCCGACTGG AAAGCGGGCA GTGAGCGCAA CGCAATTAAT GTGAGTTAGC TCACTCATTA GGCACCCCAG GCTTTACACT TTATGCTTCC GGCTCGTATG TTGTGTGGAA TTGTGAGCGG ATAACAATTT CACACAGGAA ACAGCTATGA CCATGATTAC GCCAAGCTCG AAATTAACCC TCACTAAAGG GAACAAAAGC TGGTACCTCG CGCGACTTGG TTTGCCATTC TTTAGCGCGC GTCGCGTCAC ACAGCTTGGC CACAATGTGG TTTTTGTCAA ACGAAGATTC TATGACGTGT TTAAAGTTTA GGTCGAGTAA AGCGCAAATC TTTT |
| 27 | Transcription Unit for rhScFVIIIBDD CO6 | CTCGACATTG ATTATTGACT AGTTATTAAT AGTAATCAAT TACGGGGTCA TTAGTTCATA GCCCATATAT GGAGTTCCGC GTTACATAAC TTACGGTAAA TGGCCCGCCT GGCTGACCGC CCAACGACCC CCGCCCATTG ACGTCAATAA TGACGTATGT TCCCATAGTA ACGCCAATAG GGACTTTCCA TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT AAATGGCCCG CCTGGCATTA TGCCCAGTAC ATGACCTTAT GGGACTTTCC TACTTGGCAG TACATCTACG TATTAGTCAT CGCTATTACC ATGGTCGAGG TGAGCCCCAC GTTCTGCTTC ACTCTCCCCA TCTCCCCCCC CTCCCCACCC CCAATTTTGT ATTTATTTAT TTTTTAATTA TTTTGTGCAG CGATGGGGGC GGGGGGGGGG GGGGGGCGCG CGCCAGGCGG GGCGGGGCGG GGCGAGGGGC GGGGCGGGGC GAGGCGGAGA GGTGCGGCGG CAGCCAATCA GAGCGGCGCG CTCCGAAAGT TTCCTTTTAT GGCGAGGCGG CGGCGGCGGC GGCCCTATAA AAAGCGAAGC GCGCGGCGGG CGGGAGTCGC TGCGCGCTGC CTTCGCCCCG TGCCCCGCTC CGCCGCCGCC TCGCGCCGCC CGCCCCGGCT CTGACTGACC GCGTTACTCC CACAGGTGAG CGGGCGGGAC GGCCCTTCTC CTCCGGGCTG TAATTAGCGC TTGGTTTAAT GACGGCTTGT TTCTTTTCTG TGGCTGCGTG AAAGCCTTGA GGGGCTCCGG GAGGGCCCTT TGTGCGGGGG GAGCGGCTCG GGGGGTGCGT GCGTGTGTGT GTGCGTGGGG AGCGCCGCGT GCGGCTCCGC GCTGCCCGGC GGCTGTGAGC GCTGCGGGCG CGGCGCGGGG CTTTGTGCGC TCCGCAGTGT GCGCGAGGGG AGCGCGGCCG GGGGCGGTGC CCCGCGGTGC GGGGGGGGCT |

FIG. 24Z

Table 10 (continued)

| | | |
|---|---|---|
| | | GCGAGGGGAA CAAAGGCTGC GTGCGGGGTG TGTGCGTGGG GGGGTGAGCA |
| | | GGGGGTGTGG GCGCGTCGGT CGGGCTGCAA CCCCCCCTGC ACCCCCCTCC |
| | | CCGAGTTGCT GAGCACGGCC CGGCTTCGGG TGCGGGGCTC CGTACGGGGC |
| | | GTGGCGCGGG GCTCGCCGTG CCGGGCGGGG GGTGGCGGCA GGTGGGGGTG |
| | | CCGGGCGGGG CGGGGCCGCC TCGGGCCGGG GAGGGCTCGG GGGAGGGGCG |
| | | CGGCGGCCCC CGGAGCGCCG GCGGCTGTCG AGGCGCGGCG AGCCGCAGCC |
| | | ATTGCCTTTT ATGGTAATCG TGCGAGAGGG CGCAGGGACT TCCTTTGTCC |
| | | CAAATCTGTG CGGAGCCGAA ATCTGGGAGG CGCCGCCGCA CCCCCTCTAG |
| | | CGGGCGCGGG GCGAAGCGGT GCGGCGCCGG CAGGAAGGAA ATGGGCGGGG |
| | | AGGGCCTTCG TGCGTCGCCG CGCCGCCGTC CCCTTCTCCC TCTCCAGCCT |
| | | CGGGGCTGTC CGCGGGGGGA CGGCTGCCTT CGGGGGGGAC GGGGCAGGGC |
| | | GGGGTTCGGC TTCTGGCGTG TGACCGGCGG CTCTAGAGCC TCTGCTAACC |
| | | ATGTTCATGC CTTCTTCTTT TTCCTACAGC TCCTGGGCAA CGTGCTGGTT |
| | | ATTGTGCTGT CTCATCATTT TGGCAAAGAA TTGCAAGTTT GTACAAAAAA |
| | | GCAGGCTGCC ACCATGCAGA TTGAGCTGAG CACCTGTTTC TTCCTGTGCC |
| | | TGCTGAGATT TTGCTTCTCA GCTACCCGCA GGTACTACCT GGGAGCCGTT |
| | | GAGCTGTCCT GGGATTACAT GCAGTCAGAT CTGGGGGAGC TGCCTGTGGA |
| | | CGCTCGGTTT CCCCCCAGAG TGCCAAAGTC CTTTCCCTTC AACACCAGCG |
| | | TGGTGTACAA AAAGACACTT TTTGTTGAAT TTACTGACCA CTTGTTCAAC |
| | | ATCGCCAAGC CACGACCCCC ATGGATGGGC CTGCTGGGGC CAACCATTCA |
| | | GGCAGAGGTT TACGACACAG TCGTGATCAC ACTGAAGAAC ATGGCCTCCC |
| | | ATCCAGTGTC TCTGCACGCC GTCGGTGTGT CCTACTGGAA AGCATCCGAG |
| | | GGCGCCGAGT ATGACGACCA GACCAGCCAG AGAGAGAAAG AGGACGACAA |
| | | AGTGTTCCCT GGAGGCAGCC ACACCTACGT GTGGCAGGTG TTGAAGGAAA |
| | | ATGGGCCCAT GGCCAGTGAC CCTTTGTGTC TGACTTACTC ATACCTGTCT |
| | | CATGTGGATC TAGTCAAGGA CCTGAATTCT GGACTGATTG GGGCACTGCT |
| | | TGTGTGCCGC GAAGGCAGCC TGGCCAAAGA AAAGACACAG ACCCTTCACA |
| | | AGTTCATCCT GCTGTTCGCC GTGTTCGACG AAGGCAAATC CTGGCACTCA |
| | | GAAACCAAAA ACTCACTGAT GCAGGACCGG GATGCCGCCT CTGCCCGCGC |
| | | ATGGCCAAAA ATGCACACCG TCAACGGCTA TGTCAATAGA AGTTTGCCCG |
| | | GCCTCATTGG ATGTCACAGG AAAAGCGTCT ATTGGCATGT AATCGGGATG |
| | | GGAACCACAC CTGAGGTCCA CAGCATATTT CTGGAAGGCC ACACATTTCT |
| | | GGTGAGAAAT CATCGCCAGG CTTCCCTGGA AATTTCCCCC ATCACCTTCT |
| | | TGACCGCCCA GACACTGCTC ATGGATCTTG GGCAGTTTCT GCTGTTTTGT |
| | | CATATTTCTT CTCACCAACA CGACGGAATG GAGGCCTACG TTAAGGTCGA |
| | | TAGTTGCCCT GAAGAACCTC AGCTGAGGAT GAAGAACAAC GAGGAAGCCG |
| | | AGGACTACGA TGACGATTTG ACCGATTCCG AAATGGACGT GGTGCGCTTT |
| | | GATGATGACA ATTCTCCATC CTTCATTCAG ATTAGATCCG TCGCCAAGAA |
| | | GCACCCCAAG ACCTGGGTGC ACTACATTGC AGCCGAGGAG GAGGATTGGG |
| | | ACTACGCCCC CCTGGTGCTG GCACCCGACG ACCGAAGCTA CAAATCTCAG |
| | | TACCTGAACA ATGGTCCACA ACGGATCGGC AGGAAGTACA AGAAAGTGCG |
| | | GTTCATGGCC TATACAGACG AAACCTTCAA AACCAGGGAG GCTATCCAGC |
| | | ACGAGTCTGG GATTCTGGGA CCACTCCTGT ACGGCGAAGT GGGCGACACC |
| | | TTGTTAATTA TCTTCAAGAA CCAGGCTAGT AGACCTTATA ACATTTATCC |
| | | CCACGGCATT ACCGATGTGC GGCCTCTCTA CTCTAGGCGG CTTCCAAAGG |
| | | GGGTGAAACA CCTGAAGGAC TTTCCCATCC TCCCTGGCGA AATCTTTAAG |
| | | TATAAGTGGA CAGTGACCGT GGAGGATGGA CCAACCAAGA GCGACCCCAG |
| | | GTGCCTGACA CGCTATTATT CAAGCTTCGT GAATATGGAA AGGGACCTCG |
| | | CATCTGGCTT GATCGGCCCT CTGCTGATAT GTTACAAGGA AAGCGTCGAT |
| | | CAGAGAGGAA ATCAGATCAT GTCAGACAAA AGGAATGTGA TCCTGTTCTC |
| | | CGTCTTCGAT GAAAACAGGA GCTGGTATCT GACAGAGAAC ATCCAGAGAT |
| | | TCCTGCCAAA TCCCGCCGGC GTCCAGCTGG AGGACCCGGA GTTTCAGGCA |
| | | TCTAACATCA TGCATTCCAT TAATGGTTAC GTGTTCGACT CCCTGCAGCT |
| | | GAGCGTGTGC CTCCACGAGG TGGCCTACTG GTACATCTTG AGCATCGGCG |
| | | CCCAGACCGA CTTTCTGAGC GTCTTTTTCT CCGGGTATAC TTTCAAACAT |
| | | AAGATGGTGT ACGAAGATAC TCTGACGCTG TTCCCTTTCT CTGGGGAGAC |
| | | TGTGTTTATG TCTATGGAGA ACCCTGGACT GTGGATTCTC GGATGCCACA |

FIG. 24AA

Table 10 (continued)

| | | |
|---|---|---|
| | | ACAGTGACTT TCGTAATAGA GGGATGACTG CACTGCTGAA GGTGTCCAGC<br>TGTGATAAAA ATACTGGCGA CTACTACGAA GATAGCTATG AGGATATCTC<br>AGCATACCTG CTGAGCAAGA ATAACGCCAT CGAGCCCCGA AGCTTCTCAC<br>AGAATCCCCC TGTCCTCAAG GCCCACCAGG CGGAGATCAC AAGGACCACA<br>CTCCAGTCCG ACCAGGAGGA GATTGACTAC GATGACACGA TTTCTGTGGA<br>GATGAAAAAA GAGGACTTTG ACATCTACGA TGAGGATGAA AACCAGAGCC<br>CTAGGTCGTT CCAGAAGAAA ACAAGGCACT ACTTCATTGC CGCCGTGGAG<br>AGACTGTGGG ACTACGGAAT GAGTAGTTCC CCACACGTGT TGCGGAACAG<br>AGCCCAGAGT GGGTCCGTCC CACAGTTCAA GAAGGTTGTT TTCCAGGAGT<br>TCACAGATGG CTCCTTCACT CAGCCACTGT ATCGCGGCGA GCTGAATGAG<br>CACTTGGGCT TATTGGGCCC CTACATTCGC GCAGAAGTCG AAGATAATAT<br>TATGGTGACC TTCCGCAACC AGGCCAGCCG GCCTTACTCA TTCTACTCCT<br>CTCTCATCTC TTATGAGGAG GATCAGCGCC AGGGCGCCGA ACCCCGGAAG<br>AACTTTGTGA AGCCCAATGA AACCAAAACT TACTTTTGGA AGGTGCAGCA<br>CCATATGGCG CCGACGAAAG ACGAATTTGA CTGCAAAGCC TGGGCCTACT<br>TCAGCGACGT CGACTTGGAG AAGGACGTCC ACAGCGGCCT GATTGGCCCT<br>TTGTTGGTCT GCCATACCAA TACACTCAAC CCTGCCCACG GGAGGCAGGT<br>GACCGTGCAG GAGTTTGCCT TGTTCTTCAC CATCTTCGAC GAAACCAAGA<br>GCTGGTACTT CACAGAGAAC ATGGAGAGGA ACTGCAGAGC ACCCTGTAAC<br>ATCCAGATGG AGGACCCTAC TTTCAAGGAA AATTACAGGT TCCATGCCAT<br>TAATGGCTAC ATCATGGATA CCCTCCCCGG GCTTGTGATG GCTCAGGACC<br>AGCGCATCCG CTGGTACCTG CTCTCAATGG GCTCCAACGA GAACATTCAT<br>AGCATCCACT TTAGTGGCCA CGTGTTTACC GTGCGCAAGA AGGAGGAGTA<br>CAAGATGGCA CTGTACAACC TGTACCCTGG CGTGTTTGAG ACAGTGGAGA<br>TGCTGCCATC CAAGGCCGGC ATCTGGCGCG TGGAGTGCCT CATTGGGGAG<br>CACCTCCATG CTGGCATGTC TACACTGTTC CTGGTGTACA GCAACAAGTG<br>TCAGACTCCA CTCGGAATGG CCTCCGGGCA TATCCGCGAT TTTCAGATCA<br>CGGCCTCTGG CCAGTATGGC CAATGGGCTC CCAAGCTGGC CAGGCTGCAC<br>TACAGTGGGA GTATCAACGC TTGGAGCACC AAGGAGCCTT TCTCCTGGAT<br>CAAGGTGGAC CTGCTTGCCC CCATGATTAT TCACGGCATT AAGACACAGG<br>GGGCCAGGCA GAAATTCTCC TCCCTGTACA TCTCCCAGTT CATCATCATG<br>TACAGTCTGG ACGGCAAAAA GTGGCAGACC TACCGCGGGA ACAGTACCGG<br>GACATTGATG GTGTTCTTCG GGAACGTGGA CTCTAGCGGC ATTAAACACA<br>ACATTTTCAA CCCCCCCATC ATTGCTAGGT ATATCAGGCT CCATCCCACC<br>CACTATAGCA TCAGGTCCAC TCTGCGGATG GAGCTGATGG GCTGCGACCT<br>TAATTCATGC AGCATGCCGC TGGGCATGGA GTCAAAGGCC ATCTCCGACG<br>CCCAAATCAC CGCCTCCAGC TACTTCACCA ATATGTTCGC CACCTGGAGC<br>CCCAGCAAGG CCCGGCTGCA CCTGCAGGGC CGCAGCAACG CCTGGCGGCC<br>TCAGGTGAAC AACCCCAAGG AGTGGCTGCA GGTGGACTTC CAGAAAACCA<br>TGAAGGTGAC TGGGGTCACC ACCCAGGGAG TCAAGAGCCT GCTGACCAGC<br>ATGTATGTGA AGGAGTTCTT GATCAGCTCG TCACAGGATG GCCACCAGTG<br>GACTTTGTTC TTTCAGAACG GTAAGGTGAA AGTGTTCCAG GGAAACCAAG<br>ATTCCTTTAC ACCAGTGGTC AACTCTCTGG ATCCTCCCCT GCTGACACGG<br>TACCTGCGGA TCCATCCCCA GTCATGGGTG CACCAGATTG CTCTGCGCAT<br>GGAGGTGCTT GGCTGCGAGG CCCAGGACCT GTACTGAAAT TCGCGGCCGC<br>TAAACCCAGC TTTCTTGTAC AAAGTGGCAA CTTTATTATA CATAGTTGAT<br>CCTCAGGTGC AGGCTGCCTA TCAGAAGGTG GTGGCTGGTG TGGCCAATGC<br>CCTGGCTCAC AAATACCACT GAGATCTTTT TCCCTCTGCC AAAAATTATG<br>GGGACATCAT GAAGCCCCTT GAGCATCTGA CTTCTGGCTA ATAAAGGAAA<br>TTTATTTTCA TTGCAATAGT GTGTTGGAAT TTTTTGTGTC TCTCACTCGG<br>AAGGACATAT GGGAGGGCAA ATCATTTAAA ACATCAGAAT GAGTATTTGG<br>TTTAGAGTTT GGCAACATAT GCCCATATGC TGGCTGCCAT GAACAAAGGT<br>TGGCTATAAA GAGGTCATCA GTATATGAAA CAGCCCCCTG CTGTCCATTC<br>CTTATTCCAT AGAAAAGCCT TGACTTGAGG TTAGATTTTT TTTATATTTT<br>GTTTTGTGTT ATTTTTTTCT TTAACATCCC TAAAATTTTC CTTACATGTT<br>TTACTAGCCA GATTTTTCCT CCTCTCCTGA CTACTCCCAG TCATAGCTGT<br>CCCTCTTCTC TTATGGAGAT C |

FIG. 24BB

Table 10 (continued)

| | | |
|---|---|---|
| 28 | Transcription Unit for rhFIX Padua CO2 | CTCGACATTG ATTATTGACT AGTTATTAAT AGTAATCAAT TACGGGGTCA<br>TTAGTTCATA GCCCATATAT GGAGTTCCGC GTTACATAAC TTACGGTAAA<br>TGGCCCGCCT GGCTGACCGC CCAACGACCC CCGCCCATTG ACGTCAATAA<br>TGACGTATGT TCCCATAGTA ACGCCAATAG GGACTTTCCA TTGACGTCAA<br>TGGGTGGAGT ATTTACGGTA AACTGCCCAC TTGGCAGTAC ATCAAGTGTA<br>TCATATGCCA AGTACGCCCC CTATTGACGT CAATGACGGT AAATGGCCCG<br>CCTGGCATTA TGCCCAGTAC ATGACCTTAT GGGACTTTCC TACTTGGCAG<br>TACATCTACG TATTAGTCAT CGCTATTACC ATGGTCGAGG TGAGCCCCAC<br>GTTCTGCTTC ACTCTCCCCA TCTCCCCCCC CTCCCCACCC CCAATTTTGT<br>ATTTATTTAT TTTTTAATTA TTTTGTGCAG CGATGGGGGC GGGGGGGGGG<br>GGGGGGCGCG CGCCAGGCGG GGCGGGGCGG GGCGAGGGGC GGGGCGGGGC<br>GAGGCGGAGA GGTGCGGCGG CAGCCAATCA GAGCGGCGCG CTCCGAAAGT<br>TTCCTTTTAT GGCGAGGCGG CGGCGGCGGC GGCCCTATAA AAAGCGAAGC<br>GCGCGGCGGG CGGGAGTCGC TGCGCGCTGC CTTCGCCCCG TGCCCCGCTC<br>CGCCGCCGCC TCGCGCCGCC CGCCCCGGCT CTGACTGACC GCGTTACTCC<br>CACAGGTGAG CGGGCGGGAC GGCCCTTCTC CTCCGGGCTG TAATTAGCGC<br>TTGGTTTAAT GACGGCTTGT TTCTTTTCTG TGGCTGCGTG AAAGCCTTGA<br>GGGGCTCCGG GAGGGCCCTT TGTGCGGGGG GAGCGGCTCG GGGGGTGCGT<br>GCGTGTGTGT GTGCGTGGGG AGCGCCGCGT GCGGCTCCGC GCTGCCCGGC<br>GGCTGTGAGC GCTGCGGGCG CGGCGCGGGG CTTTGTGCGC TCCGCAGTGT<br>GCGCGAGGGG AGCGCGGCCG GGGGCGGTGC CCCGCGGTGC GGGGGGGGCT<br>GCGAGGGGAA CAAAGGCTGC GTGCGGGGTG TGTGCGTGGG GGGGTGAGCA<br>GGGGGTGTGG GCGCGTCGGT CGGGCTGCAA CCCCCCCTGC ACCCCCCTCC<br>CCGAGTTGCT GAGCACGGCC CGGCTTCGGG TGCGGGGCTC CGTACGGGGC<br>GTGGCGCGGG GCTCGCCGTG CCGGGCGGGG GGTGGCGGCA GGTGGGGGTG<br>CCGGGCGGGG CGGGGCCGCC TCGGGCCGGG GAGGGCTCGG GGGAGGGGCG<br>CGGCGGCCCC CGGAGCGCCG GCGGCTGTCG AGGCGCGGCG AGCCGCAGCC<br>ATTGCCTTTT ATGGTAATCG TGCGAGAGGG CGCAGGGACT TCCTTTGTCC<br>CAAATCTGTG CGGAGCCGAA ATCTGGGAGG CGCCGCCGCA CCCCCTCTAG<br>CGGGCGCGGG GCGAAGCGGT GCGGCGCCGG CAGGAAGGAA ATGGGCGGGG<br>AGGGCCTTCG TGCGTCGCCG CGCCGCCGTC CCCTTCTCCC TCTCCAGCCT<br>CGGGGCTGTC CGCGGGGGGA CGGCTGCCTT CGGGGGGGAC GGGGCAGGGC<br>GGGGTTCGGC TTCTGGCGTG TGACCGGCGG CTCTAGAGCC TCTGCTAACC<br>ATGTTCATGC CTTCTTCTTT TTCCTACAGC TCCTGGGCAA CGTGCTGGTT<br>ATTGTGCTGT CTCATCATTT TGGCAAAGAA TTGCAAGTTT GTACAAAAAA<br>GCAGGCTGCC ACCATGCAGC GCGTGAACAT GATTATGGCC GAGTCTCCCG<br>GCCTGATCAC CATCTGTCTG CTGGGCTATC TGCTGAGCGC CGAGTGCACC<br>GTGTTTCTGG ATCACGAGAA CGCCAACAAG ATCCTGAACA GACCCAAGCG<br>GTACAACAGC GGCAAGCTGG AAGAGTTCGT GCAGGGCAAC CTGGAACGCG<br>AGTGCATGGA AGAGAAGTGC AGCTTCGAAG AGGCCAGAGA GGTGTTCGAG<br>AACACCGAGA GAACCACCGA GTTCTGGAAG CAGTACGTGG ACGGCGATCA<br>GTGCGAGAGC AACCCTTGTC TGAATGGCGG CAGCTGCAAG GACGACATCA<br>ACAGCTACGA GTGCTGGTGC CCCTTCGGCT TCGAGGGCAA GAATTGCGAG<br>CTGGACGTGA CCTGCAACAT CAAGAACGGC AGATGCGAGC AGTTCTGCAA<br>GAACAGCGCC GACAACAAGG TCGTGTGCTC CTGCACAGAG GGCTACAGAC<br>TGGCCGAGAA CCAGAAGTCT TGCGAGCCCG CTGTGCCCTT TCCATGTGGC<br>AGAGTGTCTG TGTCCCAGAC CAGCAAGCTG ACCAGAGCCG AGACAGTGTT<br>CCCCGACGTG GACTACGTGA ACAGCACCGA GGCCGAGACA ATCCTGGACA<br>ACATCACCCA GAGCACCCAG TCCTTCAACG ACTTCACCAG AGTCGTCGGC<br>GGCGAGGATG CTAAGCCTGG ACAGTTTCCT TGGCAAGTGG TGCTGAACGG<br>CAAGGTGGAC GCTTTTTGTG GCGGCTCCAT CGTGAACGAG AAGTGGATCG<br>TGACCGCCGC TCACTGTGTG GAAACCGGCG TGAAGATTAC AGTGGTGGCC<br>GGCGAGCACA ACATCGAGGA AACAGAGCAC ACCGAGCAGA AACGGAACGT<br>GATCAGAATC ATCCCTCACC ACAACTACAA CGCCGCCATC AACAAGTACA<br>ACCACGATAT CGCCCTGCTG GAACTGGACG AGCCCCTGGT CCTGAACTCT<br>TACGTGACCC CTATCTGTAT CGCCGACAAA GAGTACACCA ACATCTTTCT<br>GAAGTTCGGC AGCGGCTACG TGTCCGGCTG GGGAAGAGTT TTCCACAAGG |

FIG. 24CC

Table 10 (continued)

| | | |
|---|---|---|
| | | GCAGATCAGC CCTGGTGCTG CAGTACCTGA GAGTGCCCCT GGTGGATAGA<br>GCCACATGCC TGCTGAGCAC CAAGTTCACC ATCTACAACA ACATGTTCTG<br>CGCCGGCTTC CACGAAGGCG GCAGAGATTC TTGTCAAGGC GATTCTGGCG<br>GCCCTCACGT GACAGAGGTT GAGGGCACAA GCTTTCTGAC CGGCATCATC<br>AGCTGGGGCG AAGAGTGTGC CATGAAGGGG AAGTACGGCA TCTACACCAA<br>GGTGTCCAGA TACGTGAACT GGATCAAAGA AAAGACCAAG CTCACCTGAA<br>ATTCGCGGCC GCTAAACCCA GCTTTCTTGT ACAAAGTGGC AACTTTATTA<br>TACATAGTTG ATCCTCAGGT GCAGGCTGCC TATCAGAAGG TGGTGGCTGG<br>TGTGGCCAAT GCCCTGGCTC ACAAATACCA CTGAGATCTT TTTCCCTCTG<br>CCAAAAATTA TGGGGACATC ATGAAGCCCC TTGAGCATCT GACTTCTGGC<br>TAATAAAGGA AATTTATTTT CATTGCAATA GTGTGTTGGA ATTTTTTGTG<br>TCTCTCACTC GGAAGGACAT ATGGGAGGGC AAATCATTTA AAACATCAGA<br>ATGAGTATTT GGTTTAGAGT TTGGCAACAT ATGCCCATAT GCTGGCTGCC<br>ATGAACAAAG GTTGGCTATA AAGAGGTCAT CAGTATATGA AACAGCCCCC<br>TGCTGTCCAT TCCTTATTCC ATAGAAAAGC CTTGACTTGA GGTTAGATTT<br>TTTTTATATT TTGTTTTGTG TTATTTTTTT CTTTAACATC CCTAAAATTT<br>TCCTTACATG TTTTACTAGC CAGATTTTTC CTCCTCTCCT GACTACTCCC<br>AGTCATAGCT GTCCCTCTTC TCTTATGGAG ATC |

Table 11: Additional Amino Acid Sequences

| SEQ ID NO. | Protein Name | mino Acid Sequence |
|---|---|---|
| 29 | Interleukin-2 | MYRMQLLSCI ALSLALVTNS APTSSSTKKT QLQLEHLLLD LQMILNGINN 50<br>YKNPKLTRML TFKFYMPKKA TELKHLQCLE EELKPLEEVL NLAQSKNFHL 100<br>RPRDLISNIN VIVLELKGSE TTFMCEYADE TATIVEFLNR WITFCQSIIS 150<br>TLT 153 |
| 30 | Parathyroid hormone, Truncated | MIPAKDMAKV MIVMLAICFL TKSDGKSVKK RSVSEIQLMH NLGKHLNSME 50<br>RVEWLRKKLQ DVHNF 65 |
| 31 | Parathyroid hormone | MIPAKDMAKV MIVMLAICFL TKSDGKSVKK RSVSEIQLMH NLGKHLNSME 50<br>RVEWLRKKLQ DVHNFVALGA PLAPRDAGSQ RPRKKEDNVL VESHEKSLGE 100<br>ADKADVNVLT KAKSQ 115 |
| 32 | Von Willebrand Factor, Truncated 1 | MIPARFAGVL LALALILPGT LCSLSCRPP MVKLVCPADN LRAEGLECTK 49<br>TCQNYDLECM SMGCVSGCLC PPGMVRHENR CVALERCPCF HQGKEYAPGE 99<br>TVKIGCNTCV CRDRKWNCTD HVCDATCSTI GMAHYLTFDG LKYLFPGECQ 149<br>YVLVQDYCGS NPGTFRILVG NKGCSHPSVK CKKRVTILVE GGEIELFDGE 199<br>VNVKRPMKDE THFEVVESGR YIILLLGKAL SVVWDRHLSI SVVLKQTYQE 249<br>KVCGLCGNFD GIQNNDLTSS NLQVEEDPVD FGNSWKVSSQ CADTRKVPLD 299<br>SSPATCHNNI MKQTMVDSSC RILTSDVFQD CNKLVDPEPY LDVCIYDTCS 349<br>CESIGDCACF CDTIAAYAHV CAQHGKVVTW RTATLCPQSC EERNLRENGY 399<br>ECEWRYNSCA PACQVTCQHP EPLACPVQCV EGCHAHCPPG KILDELLQTC 449<br>VDPEDCPVCE VAGRRFASGK KVTLNPSDPE HCQICHCDVV NLTCEACQEP 499<br>GGLVVPP 506 |
| 33 | Von Willebrand Factor, Truncated 2 | MIPARFAGVL LALALILPGT LCAEGTRGRS STARCSLFGS DFVNTFDGSM 50<br>YSFAGYCSYL LAGGCQKRSF SIIGDFQNGK RVSLSVYLGE FFDIHLFVNG 100<br>TVTQGDQRVS MPYASKGLYL ETEAGYYKLS GEAYGFVARI DGSGNFQVLL 150<br>SDRYFNKTCG LCGNFNIFAE DDFMTQEGTL TSDPYDFANS WALSSGEQWC 200<br>ERASPPSSSC NISSGEMQKG LWEQCQLLKS TSVFARCHPL VDPEPFVALC 250<br>EKTLCECAGG LECACPALLE YARTCAQEGM VLYGWTDHSA CSPVCPAGME 300<br>YRQCVSPCAR TCQSLHINEM CQERCVDGCS CPEGQLLDEG LCVESTECPC 350<br>VHSGKRYPPG TSLSRDCNTC ICRNSQWICS NEECPGECLV TGQSHFKSFD 400<br>NRYFTFSGIC QYLLARDCQD HSFSIVIETV QCADDRDAVC TRSVTVRLPG 450<br>LHNSLVKLKH GAGVAMDGQD VQLPLLKGDL RIQHTVTASV RLSYGEDLQM 500 |

FIG. 24DD

Table 11 (continued)

| | | |
|---|---|---|
| | | DWDGRGRLLV KLSPVYAGKT CGLCGNYNGN QGDDFLTPSG LAEPRVEDFG 550<br>NAWKLHGDCQ DLQKQHSDPC ALNPRMTRFS EEACAVLTSP TFEACHRAVS 600<br>FLPYLRNCRY DVCSCSDGRE CLCGALASYA AACAGRGVRV AWREPGRCEL 650<br>NCPKGQVYLQ CGTPCNLTCR SLSYPDEECN EACLEGCFCP PGLYMDERGD 700<br>CVPKAQCPCY YDGEIFQPED IFSDHHTMCY CEDGFMHCTM SGVPGSLLPD 750<br>AVLSSPLSHR SKRSLSCRPP MVKLVCPADN LRAEGLECTK TCQNYDLECM 800<br>SMGCVSGCLC PPGMVRHENR CVALERCPCF HQGKEYAPGE TVKIGCNTCV 850<br>CRDRKWNCTD HVCDATCSTI GMAHYLTFDG LKYLFPGECQ YVLVQDYCGS 900<br>NPGTFRILVG NKGCSHPSVK CKKRVTILVE GGEIELFDGE VNVKRPMKDE 950<br>THFEVVESGR YIILLLGKAL SVVWDRHLSI SVVLKQTYQE KVCGLCGNFD 1000<br>GIQNNDLTSS NLQVEEDPVD FGNSWKVSSQ CADTRKVPLD SSPATCHNNI 1050<br>MKQTMVDSSC RILTSDVFQD CNKLVDPEPY LDVCIYDTCS CESIGDCACF 1100<br>CDTIAAYAHV CAQHGKVVTW RTATLCPQSC EERNLRENGY ECEWRYNSCA 1150<br>PACQVTCQHP EPLACPVQCV EGCHAHCPPG KILDELLQTC VDPEDCPVCE 1200<br>VAGRRFASGK KVTLNPSDPE HCQICHCDVV NLTCEACQEP GGLVVPP 1247 |
| 34 | Fc | EPKSCDKTHT CPPCPAPELL GGPSVFLFPP KPKDTLMISR TPEVTCVVVD 50<br>VSHEDPEVKF NWYVDGVEVH NAKTKPREEQ YNSTYRVVSV LTVLHQDWLN 100<br>GKEYKCKVSN KALPAPIEKT ISKAKGQPRE PQVYTLPPSR DELTKNQVSL 150<br>TCLVKGFYPS DIAVEWESNG QPENNYKTTP PVLDSDGSFF LYSKLTVDKS 200<br>RWQQGNVFSC SVMHEALHNH YTQKSLSLSP GK 232 |
| 35 | Albumin | DAHKSEVAHR FKDLGEENFK ALVLIAFAQY LQQCPFEDHV KLVNEVTEFA 50<br>KTCVADESAE NCDKSLHTLF GDKLCTVATL RETYGEMADC CAKQEPERNE 100<br>CFLQHKDDNP NLPRLVRPEV DVMCTAFHDN EETFLKKYLY EIARRHPYFY 150<br>APELLFFAKR YKAAFTECCQ AADKAACLLP KLDELRDEGK ASSAKQRLKC 200<br>ASLQKFGERA FKAWAVARLS QRFPKAEFAE VSKLVTDLTK VHTECCHGDL 250<br>LECADDRADL AKYICENQDS ISSKLKECCE KPLLEKSHCI AEVENDEMPA 300<br>DLPSLAADFV ESKDVCKNYA EAKDVFLGMF LYEYARRHPD YSVVLLLRLA 350<br>KTYETTLEKC CAAADPHECY AKVFDEFKPL VEEPQNLIKQ NCELFEQLGE 400<br>YKFQNALLVR YTKKVPQVST PTLVEVSRNL GKVGSKCCKH PEAKRMPCAE 450<br>DYLSVVLNQL CVLHEKTPVS DRVTKCCTES LVNRRPCFSA LEVDETYVPK 500<br>EFNAETFTFH ADICTLSEKE RQIKKQTALV ELVKHKPKAT KEQLKAVMDD 550<br>FAAFVEKCCK ADDKETCFAE EGKKLVAASQ AALGL 585 |
| 36 | FIX-Padua | MQRVNMIMAE SPGLITICLL GYLLSAECTV FLDHENANKI LNRPKRYNSG<br>KLEEFVQGNL ERECMEEKCS FEEAREVFEN TERTTEFWKQ YVDGDQCESN<br>PCLNGGSCKD DINSYECWCP FGFEGKNCEL DVTCNIKNGR CEQFCKNSAD<br>NKVVCSCTEG YRLAENQKSC EPAVPFPCGR VSVSQTSKLT RAETVFPDVD<br>YVNSTEAETI LDNITQSTQS FNDFTRVVGG EDAKPGQFPW QVVLNGKVDA<br>FCGGSIVNEK WIVTAAHCVE TGVKITVVAG EHNIEETEHT EQKRNVIRII<br>PHHNYNAAIN KYNHDIALLE LDEPLVLNSY VTPICIADKE YTNIFLKFGS<br>GYVSGWGRVF HKGRSALVLQ YLRVPLVDRA TCLLSTKFTI YNNMFCAGFH<br>EGGRDSCQGD SGGPHVTEVE GTSFLTGIIS WGEECAMKGK YGIYTKVSRY<br>VNWIKEKTKL T |

SEQUENCE LISTING

<160> NUMBER OF SEQ ID NOS: 70

<210> SEQ ID NO 1
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 1

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350
```

-continued

```
Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765
```

-continued

```
Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170
```

```
Lys Leu  Ala Arg Leu His Tyr  Ser Gly Ser Ile Asn  Ala Trp Ser
    1175                 1180                 1185

Thr Lys  Glu Pro Phe Ser Trp  Ile Lys Val Asp Leu  Leu Ala Pro
    1190                 1195                 1200

Met Ile  Ile His Gly Ile Lys  Thr Gln Gly Ala Arg  Gln Lys Phe
    1205                 1210                 1215

Ser Ser  Leu Tyr Ile Ser Gln  Phe Ile Ile Met Tyr  Ser Leu Asp
    1220                 1225                 1230

Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455


<210> SEQ ID NO 2
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45
```

-continued

```
Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```

<210> SEQ ID NO 3
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

<400> SEQUENCE: 3

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

-continued

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys His His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830
```

-continued

```
Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230
```

Gly Lys Lys Trp Gln Thr Tyr Arg Gly Asn Ser Thr Gly Thr Leu
1235 1240 1245

Met Val Phe Phe Gly Asn Val Asp Ser Ser Gly Ile Lys His Asn
1250 1255 1260

Ile Phe Asn Pro Pro Ile Ile Ala Arg Tyr Ile Arg Leu His Pro
1265 1270 1275

Thr His Tyr Ser Ile Arg Ser Thr Leu Arg Met Glu Leu Met Gly
1280 1285 1290

Cys Asp Leu Asn Ser Cys Ser Met Pro Leu Gly Met Glu Ser Lys
1295 1300 1305

Ala Ile Ser Asp Ala Gln Ile Thr Ala Ser Ser Tyr Phe Thr Asn
1310 1315 1320

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr
1445 1450 1455

<210> SEQ ID NO 4
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

-continued

```
His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525
```

-continued

```
Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Ala His Gln Ala Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940
```

```
Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                 1005

Asp Glu  Thr Lys Ser Trp Tyr  Phe Thr Glu Asn Met  Glu Arg Asn
    1010                 1015                 1020

Cys Arg  Ala Pro Cys Asn Ile  Gln Met Glu Asp Pro  Thr Phe Lys
    1025                 1030                 1035

Glu Asn  Tyr Arg Phe His Ala  Ile Asn Gly Tyr Ile  Met Asp Thr
    1040                 1045                 1050

Leu Pro  Gly Leu Val Met Ala  Gln Asp Gln Arg Ile  Arg Trp Tyr
    1055                 1060                 1065

Leu Leu  Ser Met Gly Ser Asn  Glu Asn Ile His Ser  Ile His Phe
    1070                 1075                 1080

Ser Gly  His Val Phe Thr Val  Arg Lys Lys Glu Glu  Tyr Lys Met
    1085                 1090                 1095

Ala Leu  Tyr Asn Leu Tyr Pro  Gly Val Phe Glu Thr  Val Glu Met
    1100                 1105                 1110

Leu Pro  Ser Lys Ala Gly Ile  Trp Arg Val Glu Cys  Leu Ile Gly
    1115                 1120                 1125

Glu His  Leu His Ala Gly Met  Ser Thr Leu Phe Leu  Val Tyr Ser
    1130                 1135                 1140

Asn Lys  Cys Gln Thr Pro Leu  Gly Met Ala Ser Gly  His Ile Arg
    1145                 1150                 1155

Asp Phe  Gln Ile Thr Ala Ser  Gly Gln Tyr Gly Gln  Trp Ala Pro
    1160                 1165                 1170

Lys Leu  Ala Arg Leu His Tyr  Ser Gly Ser Ile Asn  Ala Trp Ser
    1175                 1180                 1185

Thr Lys  Glu Pro Phe Ser Trp  Ile Lys Val Asp Leu  Leu Ala Pro
    1190                 1195                 1200

Met Ile  Ile His Gly Ile Lys  Thr Gln Gly Ala Arg  Gln Lys Phe
    1205                 1210                 1215

Ser Ser  Leu Tyr Ile Ser Gln  Phe Ile Ile Met Tyr  Ser Leu Asp
    1220                 1225                 1230

Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335
```

```
Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455


<210> SEQ ID NO 5
<211> LENGTH: 1453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220
```

-continued

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640
```

```
Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Glu Ile Thr Arg Thr Thr Leu Gln Ser Asp Gln Glu Glu Ile Asp
    770                 775                 780

Tyr Asp Asp Thr Ile Ser Val Glu Met Lys Lys Glu Asp Phe Asp Ile
785                 790                 795                 800

Tyr Asp Glu Asp Glu Asn Gln Ser Pro Arg Ser Phe Gln Lys Lys Thr
                805                 810                 815

Arg His Tyr Phe Ile Ala Ala Val Glu Arg Leu Trp Asp Tyr Gly Met
            820                 825                 830

Ser Ser Ser Pro His Val Leu Arg Asn Arg Ala Gln Ser Gly Ser Val
        835                 840                 845

Pro Gln Phe Lys Lys Val Val Phe Gln Glu Phe Thr Asp Gly Ser Phe
    850                 855                 860

Thr Gln Pro Leu Tyr Arg Gly Glu Leu Asn Glu His Leu Gly Leu Leu
865                 870                 875                 880

Gly Pro Tyr Ile Arg Ala Glu Val Glu Asp Asn Ile Met Val Thr Phe
                885                 890                 895

Arg Asn Gln Ala Ser Arg Pro Tyr Ser Phe Tyr Ser Ser Leu Ile Ser
            900                 905                 910

Tyr Glu Glu Asp Gln Arg Gln Gly Ala Glu Pro Arg Lys Asn Phe Val
        915                 920                 925

Lys Pro Asn Glu Thr Lys Thr Tyr Phe Trp Lys Val Gln His His Met
    930                 935                 940

Ala Pro Thr Lys Asp Glu Phe Asp Cys Lys Ala Trp Ala Tyr Phe Ser
945                 950                 955                 960

Asp Val Asp Leu Glu Lys Asp Val His Ser Gly Leu Ile Gly Pro Leu
                965                 970                 975

Leu Val Cys His Thr Asn Thr Leu Asn Pro Ala His Gly Arg Gln Val
            980                 985                 990

Thr Val Gln Glu Phe Ala Leu Phe  Phe Thr Ile Phe Asp  Glu Thr Lys
        995                 1000                1005

Ser Trp  Tyr Phe Thr Glu Asn  Met Glu Arg Asn Cys  Arg Ala Pro
    1010                1015                1020

Cys Asn  Ile Gln Met Glu Asp  Pro Thr Phe Lys Glu  Asn Tyr Arg
    1025                1030                1035

Phe His  Ala Ile Asn Gly Tyr  Ile Met Asp Thr Leu  Pro Gly Leu
    1040                1045                1050
```

-continued

```
Val Met  Ala Gln Asp Gln Arg  Ile Arg Trp Tyr Leu  Leu Ser Met
    1055                1060                 1065

Gly Ser  Asn Glu Asn Ile His  Ser Ile His Phe Ser  Gly His Val
    1070                1075                 1080

Phe Thr  Val Arg Lys Lys Glu  Glu Tyr Lys Met Ala  Leu Tyr Asn
    1085                1090                 1095

Leu Tyr  Pro Gly Val Phe Glu  Thr Val Glu Met Leu  Pro Ser Lys
    1100                1105                 1110

Ala Gly  Ile Trp Arg Val Glu  Cys Leu Ile Gly Glu  His Leu His
    1115                1120                 1125

Ala Gly  Met Ser Thr Leu Phe  Leu Val Tyr Ser Asn  Lys Cys Gln
    1130                1135                 1140

Thr Pro  Leu Gly Met Ala Ser  Gly His Ile Arg Asp  Phe Gln Ile
    1145                1150                 1155

Thr Ala  Ser Gly Gln Tyr Gly  Gln Trp Ala Pro Lys  Leu Ala Arg
    1160                1165                 1170

Leu His  Tyr Ser Gly Ser Ile  Asn Ala Trp Ser Thr  Lys Glu Pro
    1175                1180                 1185

Phe Ser  Trp Ile Lys Val Asp  Leu Leu Ala Pro Met  Ile Ile His
    1190                1195                 1200

Gly Ile  Lys Thr Gln Gly Ala  Arg Gln Lys Phe Ser  Ser Leu Tyr
    1205                1210                 1215

Ile Ser  Gln Phe Ile Ile Met  Tyr Ser Leu Asp Gly  Lys Lys Trp
    1220                1225                 1230

Gln Thr  Tyr Arg Gly Asn Ser  Thr Gly Thr Leu Met  Val Phe Phe
    1235                1240                 1245

Gly Asn  Val Asp Ser Ser Gly  Ile Lys His Asn Ile  Phe Asn Pro
    1250                1255                 1260

Pro Ile  Ile Ala Arg Tyr Ile  Arg Leu His Pro Thr  His Tyr Ser
    1265                1270                 1275

Ile Arg  Ser Thr Leu Arg Met  Glu Leu Met Gly Cys  Asp Leu Asn
    1280                1285                 1290

Ser Cys  Ser Met Pro Leu Gly  Met Glu Ser Lys Ala  Ile Ser Asp
    1295                1300                 1305

Ala Gln  Ile Thr Ala Ser Ser  Tyr Phe Thr Asn Met  Phe Ala Thr
    1310                1315                 1320

Trp Ser  Pro Ser Lys Ala Arg  Leu His Leu Gln Gly  Arg Ser Asn
    1325                1330                 1335

Ala Trp  Arg Pro Gln Val Asn  Asn Pro Lys Glu Trp  Leu Gln Val
    1340                1345                 1350

Asp Phe  Gln Lys Thr Met Lys  Val Thr Gly Val Thr  Thr Gln Gly
    1355                1360                 1365

Val Lys  Ser Leu Leu Thr Ser  Met Tyr Val Lys Glu  Phe Leu Ile
    1370                1375                 1380

Ser Ser  Ser Gln Asp Gly His  Gln Trp Thr Leu Phe  Phe Gln Asn
    1385                1390                 1395

Gly Lys  Val Lys Val Phe Gln  Gly Asn Gln Asp Ser  Phe Thr Pro
    1400                1405                 1410

Val Val  Asn Ser Leu Asp Pro  Pro Leu Leu Thr Arg  Tyr Leu Arg
    1415                1420                 1425
```

```
Ile His Pro Gln Ser Trp Val His Gln Ile Ala Leu Arg Met Glu
    1430                1435                1440

Val Leu Gly Cys Glu Ala Gln Asp Leu Tyr
    1445                1450


<210> SEQ ID NO 6
<211> LENGTH: 1454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320
```

-continued

```
Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735
```

-continued

```
Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg Glu Ile Thr Arg Thr Thr Leu Gln Ser Asp Gln Glu Glu Ile
    770                 775                 780

Asp Tyr Asp Asp Thr Ile Ser Val Glu Met Lys Lys Glu Asp Phe Asp
785                 790                 795                 800

Ile Tyr Asp Glu Asp Glu Asn Gln Ser Pro Arg Ser Phe Gln Lys Lys
                805                 810                 815

Thr Arg His Tyr Phe Ile Ala Ala Val Glu Arg Leu Trp Asp Tyr Gly
            820                 825                 830

Met Ser Ser Ser Pro His Val Leu Arg Asn Arg Ala Gln Ser Gly Ser
        835                 840                 845

Val Pro Gln Phe Lys Lys Val Val Phe Gln Glu Phe Thr Asp Gly Ser
    850                 855                 860

Phe Thr Gln Pro Leu Tyr Arg Gly Glu Leu Asn Glu His Leu Gly Leu
865                 870                 875                 880

Leu Gly Pro Tyr Ile Arg Ala Glu Val Glu Asp Asn Ile Met Val Thr
                885                 890                 895

Phe Arg Asn Gln Ala Ser Arg Pro Tyr Ser Phe Tyr Ser Ser Leu Ile
            900                 905                 910

Ser Tyr Glu Glu Asp Gln Arg Gln Gly Ala Glu Pro Arg Lys Asn Phe
        915                 920                 925

Val Lys Pro Asn Glu Thr Lys Thr Tyr Phe Trp Lys Val Gln His His
    930                 935                 940

Met Ala Pro Thr Lys Asp Glu Phe Asp Cys Lys Ala Trp Ala Tyr Phe
945                 950                 955                 960

Ser Asp Val Asp Leu Glu Lys Asp Val His Ser Gly Leu Ile Gly Pro
                965                 970                 975

Leu Leu Val Cys His Thr Asn Thr Leu Asn Pro Ala His Gly Arg Gln
            980                 985                 990

Val Thr Val Gln Glu Phe Ala Leu  Phe Phe Thr Ile Phe  Asp Glu Thr
        995                 1000                1005

Lys Ser  Trp Tyr Phe Thr Glu  Asn Met Glu Arg Asn  Cys Arg Ala
    1010                1015                1020

Pro Cys  Asn Ile Gln Met Glu  Asp Pro Thr Phe Lys  Glu Asn Tyr
    1025                1030                1035

Arg Phe  His Ala Ile Asn Gly  Tyr Ile Met Asp Thr  Leu Pro Gly
    1040                1045                1050

Leu Val  Met Ala Gln Asp Gln  Arg Ile Arg Trp Tyr  Leu Leu Ser
    1055                1060                1065

Met Gly  Ser Asn Glu Asn Ile  His Ser Ile His Phe  Ser Gly His
    1070                1075                1080

Val Phe  Thr Val Arg Lys Lys  Glu Glu Tyr Lys Met  Ala Leu Tyr
    1085                1090                1095

Asn Leu  Tyr Pro Gly Val Phe  Glu Thr Val Glu Met  Leu Pro Ser
    1100                1105                1110

Lys Ala  Gly Ile Trp Arg Val  Glu Cys Leu Ile Gly  Glu His Leu
    1115                1120                1125

His Ala  Gly Met Ser Thr Leu  Phe Leu Val Tyr Ser  Asn Lys Cys
    1130                1135                1140
```

```
Gln Thr  Pro Leu Gly Met Ala  Ser Gly His Ile Arg  Asp Phe Gln
    1145                 1150                 1155

Ile Thr  Ala Ser Gly Gln Tyr  Gly Gln Trp Ala Pro  Lys Leu Ala
    1160                 1165                 1170

Arg Leu  His Tyr Ser Gly Ser  Ile Asn Ala Trp Ser  Thr Lys Glu
    1175                 1180                 1185

Pro Phe  Ser Trp Ile Lys Val  Asp Leu Leu Ala Pro  Met Ile Ile
    1190                 1195                 1200

His Gly  Ile Lys Thr Gln Gly  Ala Arg Gln Lys Phe  Ser Ser Leu
    1205                 1210                 1215

Tyr Ile  Ser Gln Phe Ile Ile  Met Tyr Ser Leu Asp  Gly Lys Lys
    1220                 1225                 1230

Trp Gln  Thr Tyr Arg Gly Asn  Ser Thr Gly Thr Leu  Met Val Phe
    1235                 1240                 1245

Phe Gly  Asn Val Asp Ser Ser  Gly Ile Lys His Asn  Ile Phe Asn
    1250                 1255                 1260

Pro Pro  Ile Ile Ala Arg Tyr  Ile Arg Leu His Pro  Thr His Tyr
    1265                 1270                 1275

Ser Ile  Arg Ser Thr Leu Arg  Met Glu Leu Met Gly  Cys Asp Leu
    1280                 1285                 1290

Asn Ser  Cys Ser Met Pro Leu  Gly Met Glu Ser Lys  Ala Ile Ser
    1295                 1300                 1305

Asp Ala  Gln Ile Thr Ala Ser  Ser Tyr Phe Thr Asn  Met Phe Ala
    1310                 1315                 1320

Thr Trp  Ser Pro Ser Lys Ala  Arg Leu His Leu Gln  Gly Arg Ser
    1325                 1330                 1335

Asn Ala  Trp Arg Pro Gln Val  Asn Asn Pro Lys Glu  Trp Leu Gln
    1340                 1345                 1350

Val Asp  Phe Gln Lys Thr Met  Lys Val Thr Gly Val  Thr Thr Gln
    1355                 1360                 1365

Gly Val  Lys Ser Leu Leu Thr  Ser Met Tyr Val Lys  Glu Phe Leu
    1370                 1375                 1380

Ile Ser  Ser Ser Gln Asp Gly  His Gln Trp Thr Leu  Phe Phe Gln
    1385                 1390                 1395

Asn Gly  Lys Val Lys Val Phe  Gln Gly Asn Gln Asp  Ser Phe Thr
    1400                 1405                 1410

Pro Val  Val Asn Ser Leu Asp  Pro Pro Leu Leu Thr  Arg Tyr Leu
    1415                 1420                 1425

Arg Ile  His Pro Gln Ser Trp  Val His Gln Ile Ala  Leu Arg Met
    1430                 1435                 1440

Glu Val  Leu Gly Cys Glu Ala  Gln Asp Leu Tyr
    1445                 1450
```

```
<210> SEQ ID NO 7
<211> LENGTH: 1474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Gln Ile Glu Leu Ser Thr Cys Phe Phe Leu Cys Leu Leu Arg Phe
1               5                   10                  15
```

-continued

```
Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430
```

-continued

```
Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ala Thr Asn Val
        755                 760                 765

Ser Asn Asn Ser Asn Thr Ser Asn Asp Ser Asn Val Ser Pro Pro Val
    770                 775                 780

Leu Lys Arg His Gln Arg Glu Ile Thr Arg Thr Thr Leu Gln Ser Asp
785                 790                 795                 800

Gln Glu Glu Ile Asp Tyr Asp Asp Thr Ile Ser Val Glu Met Lys Lys
                805                 810                 815

Glu Asp Phe Asp Ile Tyr Asp Glu Asp Glu Asn Gln Ser Pro Arg Ser
            820                 825                 830

Phe Gln Lys Lys Thr Arg His Tyr Phe Ile Ala Ala Val Glu Arg Leu
        835                 840                 845
```

-continued

```
Trp Asp Tyr Gly Met Ser Ser Ser Pro His Val Leu Arg Asn Arg Ala
    850                 855                 860

Gln Ser Gly Ser Val Pro Gln Phe Lys Lys Val Val Phe Gln Glu Phe
865                 870                 875                 880

Thr Asp Gly Ser Phe Thr Gln Pro Leu Tyr Arg Gly Glu Leu Asn Glu
                885                 890                 895

His Leu Gly Leu Leu Gly Pro Tyr Ile Arg Ala Glu Val Glu Asp Asn
            900                 905                 910

Ile Met Val Thr Phe Arg Asn Gln Ala Ser Arg Pro Tyr Ser Phe Tyr
        915                 920                 925

Ser Ser Leu Ile Ser Tyr Glu Glu Asp Gln Arg Gln Gly Ala Glu Pro
    930                 935                 940

Arg Lys Asn Phe Val Lys Pro Asn Glu Thr Lys Thr Tyr Phe Trp Lys
945                 950                 955                 960

Val Gln His His Met Ala Pro Thr Lys Asp Glu Phe Asp Cys Lys Ala
                965                 970                 975

Trp Ala Tyr Phe Ser Asp Val Asp Leu Glu Lys Asp Val His Ser Gly
            980                 985                 990

Leu Ile Gly Pro Leu Leu Val Cys  His Thr Asn Thr Leu  Asn Pro Ala
        995                 1000                1005

His Gly  Arg Gln Val Thr Val  Gln Glu Phe Ala Leu  Phe Phe Thr
    1010                1015                1020

Ile Phe  Asp Glu Thr Lys Ser  Trp Tyr Phe Thr Glu  Asn Met Glu
    1025                1030                1035

Arg Asn  Cys Arg Ala Pro Cys  Asn Ile Gln Met Glu  Asp Pro Thr
    1040                1045                1050

Phe Lys  Glu Asn Tyr Arg Phe  His Ala Ile Asn Gly  Tyr Ile Met
    1055                1060                1065

Asp Thr  Leu Pro Gly Leu Val  Met Ala Gln Asp Gln  Arg Ile Arg
    1070                1075                1080

Trp Tyr  Leu Leu Ser Met Gly  Ser Asn Glu Asn Ile  His Ser Ile
    1085                1090                1095

His Phe  Ser Gly His Val Phe  Thr Val Arg Lys Lys  Glu Glu Tyr
    1100                1105                1110

Lys Met  Ala Leu Tyr Asn Leu  Tyr Pro Gly Val Phe  Glu Thr Val
    1115                1120                1125

Glu Met  Leu Pro Ser Lys Ala  Gly Ile Trp Arg Val  Glu Cys Leu
    1130                1135                1140

Ile Gly  Glu His Leu His Ala  Gly Met Ser Thr Leu  Phe Leu Val
    1145                1150                1155

Tyr Ser  Asn Lys Cys Gln Thr  Pro Leu Gly Met Ala  Ser Gly His
    1160                1165                1170

Ile Arg  Asp Phe Gln Ile Thr  Ala Ser Gly Gln Tyr  Gly Gln Trp
    1175                1180                1185

Ala Pro  Lys Leu Ala Arg Leu  His Tyr Ser Gly Ser  Ile Asn Ala
    1190                1195                1200

Trp Ser  Thr Lys Glu Pro Phe  Ser Trp Ile Lys Val  Asp Leu Leu
    1205                1210                1215

Ala Pro  Met Ile Ile His Gly  Ile Lys Thr Gln Gly  Ala Arg Gln
    1220                1225                1230

Lys Phe  Ser Ser Leu Tyr Ile  Ser Gln Phe Ile Ile  Met Tyr Ser
    1235                1240                1245
```

```
Leu Asp  Gly Lys Lys Trp Gln  Thr Tyr Arg Gly Asn  Ser Thr Gly
    1250                 1255                 1260

Thr Leu  Met Val Phe Phe Gly  Asn Val Asp Ser Ser  Gly Ile Lys
    1265                 1270                 1275

His Asn  Ile Phe Asn Pro Pro  Ile Ile Ala Arg Tyr  Ile Arg Leu
    1280                 1285                 1290

His Pro  Thr His Tyr Ser Ile  Arg Ser Thr Leu Arg  Met Glu Leu
    1295                 1300                 1305

Met Gly  Cys Asp Leu Asn Ser  Cys Ser Met Pro Leu  Gly Met Glu
    1310                 1315                 1320

Ser Lys  Ala Ile Ser Asp Ala  Gln Ile Thr Ala Ser  Ser Tyr Phe
    1325                 1330                 1335

Thr Asn  Met Phe Ala Thr Trp  Ser Pro Ser Lys Ala  Arg Leu His
    1340                 1345                 1350

Leu Gln  Gly Arg Ser Asn Ala  Trp Arg Pro Gln Val  Asn Asn Pro
    1355                 1360                 1365

Lys Glu  Trp Leu Gln Val Asp  Phe Gln Lys Thr Met  Lys Val Thr
    1370                 1375                 1380

Gly Val  Thr Thr Gln Gly Val  Lys Ser Leu Leu Thr  Ser Met Tyr
    1385                 1390                 1395

Val Lys  Glu Phe Leu Ile Ser  Ser Ser Gln Asp Gly  His Gln Trp
    1400                 1405                 1410

Thr Leu  Phe Phe Gln Asn Gly  Lys Val Lys Val Phe  Gln Gly Asn
    1415                 1420                 1425

Gln Asp  Ser Phe Thr Pro Val  Val Asn Ser Leu Asp  Pro Pro Leu
    1430                 1435                 1440

Leu Thr  Arg Tyr Leu Arg Ile  His Pro Gln Ser Trp  Val His Gln
    1445                 1450                 1455

Ile Ala  Leu Arg Met Glu Val  Leu Gly Cys Glu Ala  Gln Asp Leu
    1460                 1465                 1470

Tyr
```

<210> SEQ ID NO 8
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
atgcaaatag agctctccac ctgcttcttt ctgtgccttt tgcgattctg ctttagtgcc      60

accagaagat actacctggg tgcagtggaa ctgtcatggg actatatgca aagtgatctc     120

ggtgagctgc ctgtggacgc aagatttcct cctagagtgc caaaatcttt tccattcaac     180

acctcagtcg tgtacaaaaa gactctgttt gtagaattca cggatcacct tttcaacatc     240

gctaagccaa ggccaccctg gatgggtctg ctaggtccta ccatccaggc tgaggtttat     300

gatacagtgg tcattacact taagaacatg gcttcccatc ctgtcagtct tcatgctgtt     360

ggtgtatcct actggaaagc ttctgaggga gctgaatatg atgatcagac cagtcaaagg     420

gagaaagaag atgataaagt cttccctggt ggaagccata catatgtctg gcaggtcctg     480

aaagagaatg gtccaatggc ctctgaccca ctgtgcctta cctactcata tctttctcat     540

gtggacctgg taaaagactt gaattcaggc ctcattggag ccctactagt atgtagagaa     600
```

-continued

```
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
```

tttgctctgt ttttcaccat ctttgatgag accaaaagct ggtacttcac tgaaaatatg 3060
gaaagaaact gcagggctcc ctgcaatatc cagatggaag atcccacttt taaagagaat 3120
tatcgcttcc atgcaatcaa tggctacata atggatacac tacctggctt agtaatggct 3180
caggatcaaa ggattcgatg gtatctgctc agcatgggca gcaatgaaaa catccattct 3240
attcatttca gtggacatgt gttcactgta cgaaaaaaag aggagtataa aatggcactg 3300
tacaatctct atccaggtgt ttttgagaca gtggaaatgt taccatccaa agctggaatt 3360
tggcgggtgg aatgccttat tggcgagcat ctacatgctg ggatgagcac actttttctg 3420
gtgtacagca ataagtgtca gactcccctg ggaatggctt ctggacacat tagagatttt 3480
cagattacag cttcaggaca atatggacag tgggccccaa agctggccag acttcattat 3540
tccggatcaa tcaatgcctg gagcaccaag gagccctttt cttggatcaa ggtggatctg 3600
ttggcaccaa tgattattca cggcatcaag acccagggtg cccgtcagaa gttctccagc 3660
ctctacatct ctcagtttat catcatgtat agtcttgatg ggaagaagtg gcagacttat 3720
cgaggaaatt ccactggaac cttaatggtc ttctttggca atgtggattc atctgggata 3780
aaacacaata tttttaaccc tccaattatt gctcgataca tccgtttgca cccaactcat 3840
tatagcattc gcagcactct tcgcatggag ttgatgggct gtgatttaaa tagttgcagc 3900
atgccattgg gaatggagag taaagcaata tcagatgcac agattactgc ttcatcctac 3960
tttaccaata tgtttgccac ctggtctcct tcaaaagctc gacttcacct ccaagggagg 4020
agtaatgcct ggagacctca ggtgaataat ccaaaagagt ggctgcaagt ggacttccag 4080
aagacaatga aagtcacagg agtaactact cagggagtaa aatctctgct taccagcatg 4140
tatgtgaagg agttcctcat ctccagcagt caagatggcc atcagtggac tctctttttt 4200
cagaatggca aagtaaaggt ttttcaggga aatcaagact ccttcacacc tgtggtgaac 4260
tctctagacc caccgttact gactcgctac cttcgaattc acccccagag ttgggtgcac 4320
cagattgccc tgaggatgga ggttctgggc tgcgaggcac aggacctcta ctga 4374

<210> SEQ ID NO 9
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9
atgcaaatag agctctccac ctgcttcttt ctgtgccttt tgcgattctg ctttagtgcc 60
accagaagat actacctggg tgcagtggaa ctgtcatggg actatatgca aagtgatctc 120
ggtgagctgc ctgtggacgc aagatttcct cctagagtgc caaaatcttt tccattcaac 180
acctcagtcg tgtacaaaaa gactctgttt gtagaattca cggatcacct tttcaacatc 240
gctaagccaa ggccaccctg gatgggtctg ctaggtccta ccatccaggc tgaggtttat 300
gatacagtgg tcattacact taagaacatg gcttcccatc ctgtcagtct tcatgctgtt 360
ggtgtatcct actggaaagc ttctgaggga gctgaatatg atgatcagac cagtcaaagg 420
gagaaagaag atgataaagt cttccctggt ggaagccata catatgtctg gcaggtcctg 480
aaagagaatg gtccaatggc ctctgaccca ctgtgcctta cctactcata tctttctcat 540
gtggacctgg taaaagactt gaattcaggc ctcattggag ccctactagt atgtagagaa 600

-continued

```
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaacac catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
```

```
tttgctctgt ttttcaccat ctttgatgag accaaaagct ggtacttcac tgaaaatatg   3060

gaaagaaact gcagggctcc ctgcaatatc cagatggaag atcccacttt taaagagaat   3120

tatcgcttcc atgcaatcaa tggctacata atggatacac tacctggctt agtaatggct   3180

caggatcaaa ggattcgatg gtatctgctc agcatgggca gcaatgaaaa catccattct   3240

attcatttca gtggacatgt gttcactgta cgaaaaaaag aggagtataa aatggcactg   3300

tacaatctct atccaggtgt ttttgagaca gtggaaatgt taccatccaa agctggaatt   3360

tggcgggtgg aatgccttat tggcgagcat ctacatgctg ggatgagcac actttttctg   3420

gtgtacagca ataagtgtca gactcccctg ggaatggctt ctggacacat tagagatttt   3480

cagattacag cttcaggaca atatggacag tgggccccaa agctggccag acttcattat   3540

tccggatcaa tcaatgcctg gagcaccaag gagccctttt cttggatcaa ggtggatctg   3600

ttggcaccaa tgattattca cggcatcaag acccagggtg cccgtcagaa gttctccagc   3660

ctctacatct ctcagtttat catcatgtat agtcttgatg ggaagaagtg gcagacttat   3720

cgaggaaatt ccactggaac cttaatggtc ttctttggca atgtggattc atctgggata   3780

aaacacaata tttttaaccc tccaattatt gctcgataca tccgtttgca cccaactcat   3840

tatagcattc gcagcactct tcgcatggag ttgatgggct gtgatttaaa tagttgcagc   3900

atgccattgg gaatggagag taaagcaata tcagatgcac agattactgc ttcatcctac   3960

tttaccaata tgtttgccac ctggtctcct tcaaaagctc gacttcacct ccaagggagg   4020

agtaatgcct ggagacctca ggtgaataat ccaaaagagt ggctgcaagt ggacttccag   4080

aagacaatga aagtcacagg agtaactact cagggagtaa aatctctgct taccagcatg   4140

tatgtgaagg agttcctcat ctccagcagt caagatggcc atcagtggac tctctttttt   4200

cagaatggca aagtaaaggt tttcagggga aatcaagact ccttcacacc tgtggtgaac   4260

tctctagacc caccgttact gactcgctac cttcgaattc acccccagag ttgggtgcac   4320

cagattgccc tgaggatgga ggttctgggc tgcgaggcac aggacctcta ctga         4374
```

```
<210> SEQ ID NO 10
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
```

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600
```

-continued

```
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaagcc catcaagcgg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
```

```
tttgctctgt ttttcaccat ctttgatgag accaaaagct ggtacttcac tgaaaatatg   3060

gaaagaaact gcagggctcc ctgcaatatc cagatggaag atcccacttt taaagagaat   3120

tatcgcttcc atgcaatcaa tggctacata atggatacac tacctggctt agtaatggct   3180

caggatcaaa ggattcgatg gtatctgctc agcatgggca gcaatgaaaa catccattct   3240

attcatttca gtggacatgt gttcactgta cgaaaaaaag aggagtataa aatggcactg   3300

tacaatctct atccaggtgt ttttgagaca gtggaaatgt taccatccaa agctggaatt   3360

tggcgggtgg aatgccttat tggcgagcat ctacatgctg ggatgagcac actttttctg   3420

gtgtacagca ataagtgtca gactcccctg ggaatggctt ctggacacat tagagatttt   3480

cagattacag cttcaggaca atatggacag tgggccccaa agctggccag acttcattat   3540

tccggatcaa tcaatgcctg gagcaccaag gagccctttt cttggatcaa ggtggatctg   3600

ttggcaccaa tgattattca cggcatcaag acccagggtg cccgtcagaa gttctccagc   3660

ctctacatct ctcagtttat catcatgtat agtcttgatg ggaagaagtg gcagacttat   3720

cgaggaaatt ccactggaac cttaatggtc ttctttggca atgtggattc atctgggata   3780

aaacacaata tttttaaccc tccaattatt gctcgataca tccgtttgca cccaactcat   3840

tatagcattc gcagcactct tcgcatggag ttgatgggct gtgatttaaa tagttgcagc   3900

atgccattgg gaatggagag taaagcaata tcagatgcac agattactgc ttcatcctac   3960

tttaccaata tgtttgccac ctggtctcct tcaaaagctc gacttcacct ccaagggagg   4020

agtaatgcct ggagacctca ggtgaataat ccaaaagagt ggctgcaagt ggacttccag   4080

aagacaatga aagtcacagg agtaactact cagggagtaa aatctctgct taccagcatg   4140

tatgtgaagg agttcctcat ctccagcagt caagatggcc atcagtggac tctctttttt   4200

cagaatggca aagtaaaggt ttttcaggga aatcaagact ccttcacacc tgtggtgaac   4260

tctctagacc caccgttact gactcgctac cttcgaattc acccccagag ttgggtgcac   4320

cagattgccc tgaggatgga ggttctgggc tgcgaggcac aggacctcta ctga         4374
```

<210> SEQ ID NO 11
<211> LENGTH: 4362
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600
```

-continued

```
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaagaa ataactcgta ctactcttca gtcagatcaa   2340
gaggaaattg actatgatga taccatatca gttgaaatga agaaggaaga ttttgacatt   2400
tatgatgagg atgaaaatca gagcccccgc agctttcaaa agaaaacacg acactatttt   2460
attgctgcag tggagaggct ctgggattat gggatgagta gctccccaca tgttctaaga   2520
aacagggctc agagtggcag tgtccctcag ttcaagaaag ttgttttcca ggaatttact   2580
gatggctcct ttactcagcc cttataccgt ggagaactaa atgaacattt gggactcctg   2640
gggccatata taagagcaga agttgaagat aatatcatgg taactttcag aaatcaggcc   2700
tctcgtccct attccttcta ttctagcctt atttcttatg aggaagatca gaggcaagga   2760
gcagaaccta gaaaaaactt tgtcaagcct aatgaaacca aaacttactt ttggaaagtg   2820
caacatcata tggcacccac taaagatgag tttgactgca aagcctgggc ttatttctct   2880
gatgttgacc tggaaaaaga tgtgcactca ggcctgattg gaccccttct ggtctgccac   2940
actaacacac tgaaccctgc tcatgggaga caagtgacag tacaggaatt tgctctgttt   3000
```

```
ttcaccatct ttgatgagac caaaagctgg tacttcactg aaaatatgga aagaaactgc   3060

agggctccct gcaatatcca gatggaagat cccactttta aagagaatta tcgcttccat   3120

gcaatcaatg gctacataat ggatacacta cctggcttag taatggctca ggatcaaagg   3180

attcgatggt atctgctcag catgggcagc aatgaaaaca tccattctat tcatttcagt   3240

ggacatgtgt tcactgtacg aaaaaaagag gagtataaaa tggcactgta caatctctat   3300

ccaggtgttt ttgagacagt ggaaatgtta ccatccaaag ctggaatttg gcgggtggaa   3360

tgccttattg gcgagcatct acatgctggg atgagcacac tttttctggt gtacagcaat   3420

aagtgtcaga ctcccctggg aatggcttct ggacacatta gagattttca gattacagct   3480

tcaggacaat atggacagtg ggccccaaag ctggccagac ttcattattc cggatcaatc   3540

aatgcctgga gcaccaagga gcccttttct tggatcaagg tggatctgtt ggcaccaatg   3600

attattcacg gcatcaagac ccagggtgcc cgtcagaagt tctccagcct ctacatctct   3660

cagtttatca tcatgtatag tcttgatggg aagaagtggc agacttatcg aggaaattcc   3720

actggaacct taatggtctt ctttggcaat gtggattcat ctgggataaa acacaatatt   3780

tttaaccctc caattattgc tcgatacatc cgtttgcacc caactcatta tagcattcgc   3840

agcactcttc gcatggagtt gatgggctgt gatttaaata gttgcagcat gccattggga   3900

atggagagta aagcaatatc agatgcacag attactgctt catcctactt taccaatatg   3960

tttgccacct ggtctccttc aaaagctcga cttcacctcc aagggaggag taatgcctgg   4020

agacctcagg tgaataatcc aaaagagtgg ctgcaagtgg acttccagaa gacaatgaaa   4080

gtcacaggag taactactca gggagtaaaa tctctgctta ccagcatgta tgtgaaggag   4140

ttcctcatct ccagcagtca agatggccat cagtggactc tcttttttca gaatggcaaa   4200

gtaaaggttt ttcagggaaa tcaagactcc ttcacacctg tggtgaactc tctagaccca   4260

ccgttactga ctcgctacct tcgaattcac ccccagagtt gggtgcacca gattgccctg   4320

aggatggagg ttctgggctg cgaggcacag gacctctact ga                      4362
```

```
<210> SEQ ID NO 12
<211> LENGTH: 4365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
```

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600
```

-continued

```
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaaa acccaccagt cttgaaacgc gaaataactc gtactactct tcagtcagat   2340
caagaggaaa ttgactatga tgataccata tcagttgaaa tgaagaagga agattttgac   2400
atttatgatg aggatgaaaa tcagagcccc cgcagctttc aaaagaaaac acgacactat   2460
tttattgctg cagtggagag gctctgggat tatgggatga gtagctcccc acatgttcta   2520
agaaacaggg ctcagagtgg cagtgtccct cagttcaaga aagttgtttt ccaggaattt   2580
actgatggct cctttactca gcccttatac cgtggagaac taaatgaaca tttgggactc   2640
ctggggccat atataagagc agaagttgaa gataatatca tggtaacttt cagaaatcag   2700
gcctctcgtc cctattcctt ctattctagc cttatttctt atgaggaaga tcagaggcaa   2760
ggagcagaac ctagaaaaaa ctttgtcaag cctaatgaaa ccaaaactta cttttggaaa   2820
gtgcaacatc atatggcacc cactaaagat gagtttgact gcaaagcctg ggcttatttc   2880
tctgatgttg acctggaaaa agatgtgcac tcaggcctga ttggacccct tctggtctgc   2940
cacactaaca cactgaaccc tgctcatggg agacaagtga cagtacagga atttgctctg   3000
```

```
tttttcacca tctttgatga gaccaaaagc tggtacttca ctgaaaatat ggaaagaaac   3060

tgcagggctc cctgcaatat ccagatggaa gatcccactt ttaaagagaa ttatcgcttc   3120

catgcaatca atggctacat aatggataca ctacctggct tagtaatggc tcaggatcaa   3180

aggattcgat ggtatctgct cagcatgggc agcaatgaaa acatccattc tattcatttc   3240

agtggacatg tgttcactgt acgaaaaaaa gaggagtata aaatggcact gtacaatctc   3300

tatccaggtg tttttgagac agtggaaatg ttaccatcca aagctggaat ttggcgggtg   3360

gaatgcctta ttggcgagca tctacatgct gggatgagca cactttttct ggtgtacagc   3420

aataagtgtc agactcccct gggaatggct tctggacaca ttagagattt tcagattaca   3480

gcttcaggac aatatggaca gtgggcccca aagctggcca gacttcatta ttccggatca   3540

atcaatgcct ggagcaccaa ggagcccttt tcttggatca aggtggatct gttggcacca   3600

atgattattc acggcatcaa gacccagggt gcccgtcaga agttctccag cctctacatc   3660

tctcagttta tcatcatgta tagtcttgat gggaagaagt ggcagactta tcgaggaaat   3720

tccactggaa ccttaatggt cttctttggc aatgtggatt catctgggat aaaacacaat   3780

atttttaacc ctccaattat tgctcgatac atccgtttgc acccaactca ttatagcatt   3840

cgcagcactc ttcgcatgga gttgatgggc tgtgatttaa atagttgcag catgccattg   3900

ggaatggaga gtaaagcaat atcagatgca cagattactg cttcatccta ctttaccaat   3960

atgtttgcca cctggtctcc ttcaaaagct cgacttcacc tccaagggag gagtaatgcc   4020

tggagacctc aggtgaataa tccaaaagag tggctgcaag tggacttcca gaagacaatg   4080

aaagtcacag gagtaactac tcagggagta aaatctctgc ttaccagcat gtatgtgaag   4140

gagttcctca tctccagcag tcaagatggc catcagtgga ctctcttttt tcagaatggc   4200

aaagtaaagg tttttcaggg aaatcaagac tccttcacac ctgtggtgaa ctctctagac   4260

ccaccgttac tgactcgcta ccttcgaatt cacccccaga gttgggtgca ccagattgcc   4320

ctgaggatgg aggttctggg ctgcgaggca caggacctct actga                   4365
```

<210> SEQ ID NO 13
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
atgcagatcg agctgtctac ctgcttcttc ctgtgcctgc tgcggttctg cttcagcgcc     60

accagaagat attacctggg cgccgtggaa ctgagctggg actacatgca gtctgacctg    120

ggagagctgc ccgtggacgc tagatttcct ccaagagtgc ccaagagctt ccccttcaac    180

acctccgtgg tgtacaagaa aaccctgttc gtggaattca ccgaccacct gttcaatatc    240

gccaagcctc ggcctccttg gatgggactg ctgggaccta caattcaggc cgaggtgtac    300

gacaccgtgg tcatcaccct gaagaacatg gccagccatc ctgtgtctct gcacgccgtg    360

ggagtgtctt actggaaggc ttctgagggc gccgagtacg acgatcagac aagccagaga    420

gagaaagagg acgacaaggt tttccctggc ggcagccaca cctatgtctg gcaggtcctg    480

aaagaaaacg gccctatggc ctccgatcct ctgtgcctga catacagcta cctgagccac    540

gtggacctgg tcaaggacct gaattctggc ctgatcggag ccctgctcgt gtgtagagaa    600
```

-continued

```
ggcagcctgg ccaaagagaa aacccagaca ctgcacaagt tcatcctgct gttcgccgtg    660
ttcgacgagg gcaagagctg gcacagcgag acaaagaaca gcctgatgca ggacagggat    720
gccgcctctg ctagagcttg gcctaagatg cacaccgtga acggctacgt gaacagaagc    780
ctgcctggac tgatcggctg ccacagaaag tccgtgtact ggcacgtgat cggcatgggc    840
acaacacctg aggtgcacag catctttctg gaaggacaca ccttcctcgt gcggaaccat    900
agacaggcca gcctggaaat cagccctatc accttcctga ccgctcagac cctgctgatg    960
gatctgggcc agtttctgct gttctgccac atcagctccc accagcacga tggcatggaa   1020
gcctacgtga aggtggacag ctgccccgaa gaaccccagc tgcggatgaa gaacaacgag   1080
gaagccgagg actacgacga cgacctgacc gactctgaga tggacgtcgt cagattcgac   1140
gacgataaca gccccagctt catccagatc agaagcgtgg ccaagaagca ccccaagacc   1200
tgggtgcact atatcgccgc cgaggaagag gactgggatt acgctcctct ggtgctggcc   1260
cctgacgaca gaagctacaa gagccagtac ctgaacaacg gccctcagcg gatcggccgg   1320
aagtataaga aagtgcggtt catggcctac accgacgaga cattcaagac cagagaggcc   1380
atccagcacg agagcggaat tctgggccct ctgctgtatg gcgaagtggg cgatacactg   1440
ctgatcatct tcaagaacca ggccagcaga ccctacaaca tctaccctca cggcatcacc   1500
gatgtgcggc ccctgtattc tagaaggctg cccaagggcg tgaagcacct gaaggacttc   1560
cctatcctgc ctggcgagat cttcaagtac aagtggaccg tgaccgtgga agatggcccc   1620
accaagagcg accctagatg tctgacacgg tactacagca gcttcgtgaa catggaacgc   1680
gacctggcca gcggcctgat tggacctctg ctgatctgct acaaagaaag cgtggaccag   1740
cggggcaacc agatcatgag cgacaagcgg aacgtgatcc tgtttagcgt gttcgatgag   1800
aaccggtcct ggtatctgac cgagaacatc cagcggtttc tgcccaatcc tgctggcgtg   1860
cagctggaag atcctgagtt ccaggcctcc aacatcatgc actccatcaa tggctatgtg   1920
ttcgacagcc tgcagctgag cgtgtgcctg cacgaagtgg cctactggta catcctgagc   1980
attggcgccc agaccgactt cctgtccgtg ttctttagcg gctacacctt caagcacaag   2040
atggtgtacg aggataccct gacactgttc ccattcagcg gcgagacagt gttcatgagc   2100
atggaaaacc ccggcctgtg gatcctgggc tgtcacaaca gcgacttccg gaacagaggc   2160
atgacagccc tgctgaaggt gtccagctgc gacaagaaca ccggcgacta ctacgaggac   2220
agctatgagg acatcagcgc ctacctgctg agcaagaaca atgccatcga gcctcggagc   2280
ttcagccaga atcctcctgt gctgaagcgg caccagcgcg agatcaccag aacaaccctg   2340
cagagcgacc aagaggaaat cgattacgac gacaccatca gcgtcgagat gaagaaagaa   2400
gatttcgaca tctacgacga ggacgagaat cagagcccca gaagctttca gaaaaagacc   2460
cggcactact tcattgccgc cgtcgagaga ctgtgggact acggcatgtc tagcagccct   2520
cacgtgctga gaaatagagc ccagagcggc agcgtgcccc agttcaagaa agtggtgttc   2580
caagagttca ccgacggcag cttcacccag ccactgtata gaggcgagct gaacgagcat   2640
ctgggcctgc tgggccctta tatcagagcc gaagtggaag ataacatcat ggtcaccttc   2700
cggaatcagg cctctcggcc ctacagcttc tacagctccc tgatcagcta cgaagaggac   2760
cagagacagg gcgctgagcc cagaaagaac ttcgtgaagc ccaacgagac taagacctac   2820
ttttggaagg tgcagcacca catggcccct acaaaggacg agttcgactg caaggcctgg   2880
gcctactttt ccgatgtgga tctggaaaag gacgtgcaca gcgggctcat cggaccactg   2940
cttgtgtgcc acaccaacac actgaacccc gctcacggca gacaagtgac agtgcaagag   3000
```

ttcgccctgt tcttcaccat cttcgacgaa acaaagagct ggtacttcac cgagaatatg 3060
gaacggaact gcagagcccc ttgcaacatc cagatggaag atcccacctt caaagagaac 3120
taccggttcc acgccatcaa cggctacatc atggacacac tgcccggcct ggttatggct 3180
caggatcaga gaatccggtg gtatctgctg tccatgggct ccaacgagaa tatccacagc 3240
atccacttca gcggccacgt gttcaccgtg cggaaaaaag aagagtacaa aatggccctg 3300
tacaatctgt accctggggt gttcgaaacc gtggaaatgc tgccttccaa ggccggcatt 3360
tggagagtgg aatgtctgat tggagagcac ctccacgccg gaatgagcac cctgtttctg 3420
gtgtacagca acaagtgtca gacccctctc ggcatggcct ctggacacat cagagacttc 3480
cagatcaccg cctctggcca gtacggacag tgggctccta aactggctcg gctgcactac 3540
agcggcagca tcaatgcctg gtccaccaaa gagcccttca gctggatcaa ggtggacctg 3600
ctggctccca tgatcatcca cggaatcaag acccagggcg ccagacagaa gttcagcagc 3660
ctgtacatca gccagttcat catcatgtac agcctggacg gcaagaagtg gcagacctac 3720
agaggcaaca gcaccggcac actcatggtg ttcttcggca acgtggactc cagcggcatt 3780
aagcacaaca tcttcaaccc tccaatcatt gcccggtaca tccggctgca ccccacacac 3840
tacagcatcc ggtctaccct gagaatggaa ctgatgggct gcgacctgaa cagctgcagc 3900
atgcccctcg gaatggaaag caaggccatc agcgacgccc agatcacagc cagcagctac 3960
ttcaccaaca tgttcgccac ttggagcccc tccaaggcta gactgcatct gcagggcaga 4020
agcaacgctt ggaggcccca agtgaacaac cccaaagagt ggctgcaggt cgactttcaa 4080
aagaccatga aagtgaccgg cgtgaccaca cagggcgtca agtctctgct gacctctatg 4140
tacgtgaaag agttcctgat ctccagcagc caggacggcc atcagtggac cctgtttttc 4200
cagaacggca aagtgaaagt gttccagggc aatcaggaca gcttcacacc cgtggtcaac 4260
tccctggatc ctccactgct gaccagatac ctgcggattc accctcagtc ttgggtgcac 4320
cagatcgctc tgcggatgga agtgctgggc tgtgaagctc aggacctcta ctga 4374

<210> SEQ ID NO 14
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
atgcagatcg agctgagcac ctgcttcttc ctgtgcctgc tgcgcttctg cttcagcgcc 60
acccgccgct actacctggg cgccgtggag ctgagctggg actacatgca gagcgacctg 120
ggcgagctgc ccgtggacgc ccgcttcccc ccccgcgtgc ccaagagctt ccccttcaac 180
accagcgtgg tgtacaagaa gaccctgttc gtggagttca ccgaccacct gttcaacatc 240
gccaagcccc gcccccccctg gatgggcctg ctgggcccca ccatccaggc cgaggtgtac 300
gacaccgtgg tgatcaccct gaagaacatg gccagccacc ccgtgagcct gcacgccgtg 360
ggcgtgagct actggaaggc cagcgagggc gccgagtacg acgaccagac cagccagcgc 420
gagaaggagg acgacaaggt gttccccggc ggcagccaca cctacgtgtg gcaggtgctg 480
aaggagaacg gccccatggc cagcgacccc ctgtgcctga cctacagcta cctgagccac 540
gtggacctgg tgaaggacct gaacagcggc ctgatcggcg ccctgctggt gtgccgcgag 600

-continued ggcagcctgg ccaaggagaa gacccagacc ctgcacaagt tcatcctgct gttcgccgtg 660
ttcgacgagg gcaagagctg gcacagcgag accaagaaca gcctgatgca ggaccgcgac 720
gccgccagcg cccgcgcctg gcccaagatg cacaccgtga acggctacgt gaaccgcagc 780
ctgcccggcc tgatcggctg ccaccgcaag agcgtgtact ggcacgtgat cggcatgggc 840
accacccccg aggtgcacag catcttcctg gagggccaca ccttcctggt gcgcaaccac 900
cgccaggcca gcctggagat cagccccatc accttcctga ccgcccagac cctgctgatg 960
gacctgggcc agttcctgct gttctgccac atcagcagcc accagcacga cggcatggag 1020
gcctacgtga aggtggacag ctgccccgag gagccccagc tgcgcatgaa gaacaacgag 1080
gaggccgagg actacgacga cgacctgacc gacagcgaga tggacgtggt gcgcttcgac 1140
gacgacaaca gccccagctt catccagatc cgcagcgtgg ccaagaagca ccccaagacc 1200
tgggtgcact acatcgccgc cgaggaggag gactgggact acgcccccct ggtgctggcc 1260
cccgacgacc gcagctacaa gagccagtac ctgaacaacg gcccccagcg catcggccgc 1320
aagtacaaga aggtgcgctt catggcctac accgacgaga ccttcaagac ccgcgaggcc 1380
atccagcacg agagcggcat cctgggcccc ctgctgtacg gcgaggtggg cgacaccctg 1440
ctgatcatct tcaagaacca ggccagccgc ccctacaaca tctaccccca cggcatcacc 1500
gacgtgcgcc ccctgtacag ccgccgcctg cccaagggcg tgaagcacct gaaggacttc 1560
cccatcctgc ccggcgagat cttcaagtac aagtggaccg tgaccgtgga ggacggcccc 1620
accaagagcg acccccgctg cctgacccgc tactacagca gcttcgtgaa catggagcgc 1680
gacctggcca gcggcctgat cggccccctg ctgatctgct acaaggagag cgtggaccag 1740
cgcggcaacc agatcatgag cgacaagcgc aacgtgatcc tgttcagcgt gttcgacgag 1800
aaccgcagct ggtacctgac cgagaacatc cagcgcttcc tgcccaaccc cgccggcgtg 1860
cagctggagg accccgagtt ccaggccagc aacatcatgc acagcatcaa cggctacgtg 1920
ttcgacagcc tgcagctgag cgtgtgcctg cacgaggtgg cctactggta catcctgagc 1980
atcggcgccc agaccgactt cctgagcgtg ttcttcagcg gctacacctt caagcacaag 2040
atggtgtacg aggacaccct gaccctgttc cccttcagcg gcgagaccgt gttcatgagc 2100
atggagaacc ccggcctgtg gatcctgggc tgccacaaca gcgacttccg caaccgcggc 2160
atgaccgccc tgctgaaggt gagcagctgc gacaagaaca ccggcgacta ctacgaggac 2220
agctacgagg acatcagcgc ctacctgctg agcaagaaca acgccatcga gccccgcagc 2280
ttcagccaga acccccccgt gctgaagcgc caccagcgcg agatcacccg caccaccctg 2340
cagagcgacc aggaggagat cgactacgac gacaccatca gcgtggagat gaagaaggag 2400
gacttcgaca tctacgacga ggacgagaac cagagccccc gcagcttcca gaagaagacc 2460
cgccactact tcatcgccgc cgtggagcgc ctgtgggact acggcatgag cagcagcccc 2520
cacgtgctgc gcaaccgcgc ccagagcggc agcgtgcccc agttcaagaa ggtggtgttc 2580
caggagttca ccgacggcag cttcacccag cccctgtacc gcggcgagct gaacgagcac 2640
ctgggcctgc tgggccccta catccgcgcc gaggtggagg acaacatcat ggtgaccttc 2700
cgcaaccagg ccagccgccc ctacagcttc tacagcagcc tgatcagcta cgaggaggac 2760
cagcgccagg gcgccgagcc ccgcaagaac ttcgtgaagc ccaacgagac caagacctac 2820
ttctggaagg tgcagcacca catggccccc accaaggacg agttcgactg caaggcctgg 2880
gcctacttca gcgacgtgga cctggagaag gacgtgcaca gcggcctgat cggccccctg 2940
ctggtgtgcc acaccaacac cctgaacccc gcccacggcc gccaggtgac cgtgcaggag 3000
ttcgccctgt tcttcaccat cttcgacgag accaagagct ggtacttcac cgagaacatg 3060
gagcgcaact gccgcgcccc ctgcaacatc cagatggagg accccacctt caaggagaac 3120
taccgcttcc acgccatcaa cggctacatc atggacaccc tgcccggcct ggtgatggcc 3180
caggaccagc gcatccgctg gtacctgctg agcatgggca gcaacgagaa catccacagc 3240
atccacttca gcggccacgt gttcaccgtg cgcaagaagg aggagtacaa gatggccctg 3300
tacaacctgt accccggcgt gttcgagacc gtggagatgc tgcccagcaa ggccggcatc 3360
tggcgcgtgg agtgcctgat cggcgagcac ctgcacgccg gcatgagcac cctgttcctg 3420
gtgtacagca acaagtgcca gacccccctg ggcatggcca gcggccacat ccgcgacttc 3480
cagatcaccg ccagcggcca gtacggccag tgggccccca agctggcccg cctgcactac 3540
agcggcagca tcaacgcctg gagcaccaag gagcccttca gctggatcaa ggtggacctg 3600
ctggccccca tgatcatcca cggcatcaag acccagggcg cccgccagaa gttcagcagc 3660
ctgtacatca gccagttcat catcatgtac agcctggacg gcaagaagtg gcagacctac 3720
cgcggcaaca gcaccggcac cctgatggtg ttcttcggca acgtggacag cagcggcatc 3780
aagcacaaca tcttcaaccc ccccatcatc gcccgctaca tccgcctgca ccccacccac 3840
tacagcatcc gcagcaccct gcgcatggag ctgatgggct gcgacctgaa cagctgcagc 3900
atgcccctgg gcatggagag caaggccatc agcgacgccc agatcaccgc cagcagctac 3960
ttcaccaaca tgttcgccac ctggagcccc agcaaggccc gcctgcacct gcagggccgc 4020
agcaacgcct ggcgccccca ggtgaacaac cccaaggagt ggctgcaggt ggacttccag 4080
aagaccatga aggtgaccgg cgtgaccacc cagggcgtga agagcctgct gaccagcatg 4140
tacgtgaagg agttcctgat cagcagcagc caggacggcc accagtggac cctgttcttc 4200
cagaacggca aggtgaaggt gttccagggc aaccaggaca gcttcacccc cgtggtgaac 4260
agcctggacc ccccctgct gacccgctac ctgcgcatcc acccccagag ctgggtgcac 4320
cagatcgccc tgcgcatgga ggtgctgggc tgcgaggccc aggacctgta ctga 4374

<210> SEQ ID NO 15
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
atgcagattg agctgagcac ctgtttcttc ctgtgcctgc tgagattttg cttctcagct 60
acccgcaggt actacctggg agccgttgag ctgtcctggg attacatgca gtcagatctg 120
ggggagctgc ctgtggacgc tcggtttccc cccagagtgc caaagtcctt tcccttcaac 180
accagcgtgg tgtacaaaaa gacacttttt gttgaattta ctgaccactt gttcaacatc 240
gccaagccac gacccccatg gatgggcctg ctggggccaa ccattcaggc agaggtttac 300
gacacagtcg tgatcacact gaagaacatg gcctcccatc cagtgtctct gcacgccgtc 360
ggtgtgtcct actggaaagc atccgagggc gccgagtatg acgaccagac cagccagaga 420
gagaaagagg acgacaaagt gttccctgga ggcagccaca cctacgtgtg gcaggtgttg 480
aaggaaaatg ggcccatggc cagtgaccct ttgtgtctga cttactcata cctgtctcat 540
gtggatctag tcaaggacct gaattctgga ctgattgggg cactgcttgt gtgccgcgaa 600

-continued

```
ggcagcctgg ccaaagaaaa gacacagacc cttcacaagt tcatcctgct gttcgccgtg    660
ttcgacgaag gcaaatcctg gcactcagaa accaaaaact cactgatgca ggaccgggat    720
gccgcctctg cccgcgcatg gccaaaaatg cacaccgtca acggctatgt caatagaagt    780
ttgcccggcc tcattggatg tcacaggaaa agcgtctatt ggcatgtaat cgggatggga    840
accacacctg aggtccacag catatttctg gaaggccaca catttctggt gagaaatcat    900
cgccaggctt ccctggaaat ttcccccatc accttcttga ccgcccagac actgctcatg    960
gatcttgggc agtttctgct gttttgtcat atttcttctc accaacacga cggaatggag   1020
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgcccccct ggtgctggca   1260
cccgacgacc gaagctacaa atctcagtac ctgaacaatg gtccacaacg gatcggcagg   1320
aagtacaaga aagtgcggtt catggcctat acagacgaaa ccttcaaaac cagggaggct   1380
atccagcacg agtctgggat tctgggacca ctcctgtacg gcgaagtggg cgacaccttg   1440
ttaattatct tcaagaacca ggctagtaga ccttataaca tttatcccca cggcattacc   1500
gatgtgcggc ctctctactc taggcggctt ccaaaggggg tgaaacacct gaaggacttt   1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc tttttctccg ggtatacttt caaacataag   2040
atggtgtacg aagatactct gacgctgttc cctttctctg gggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc atacctgctg agcaagaata acgccatcga gccccgaagc   2280
ttctcacaga atccccctgt cctcaagagg caccagcgag agatcacaag gaccacactc   2340
cagtccgacc aggaggagat tgactacgat gacacgattt ctgtggagat gaaaaaagag   2400
gactttgaca tctacgatga ggatgaaaac cagagcccta ggtcgttcca gaagaaaaca   2460
aggcactact tcattgccgc cgtggagaga ctgtgggact acggaatgag tagttcccca   2520
cacgtgttgc ggaacagagc ccagagtggg tccgtcccac agttcaagaa ggttgttttc   2580
caggagttca cagatggctc cttcactcag ccactgtatc gcggcgagct gaatgagcac   2640
ttgggcttat tgggccccta cattcgcgca gaagtcgaag ataatattat ggtgaccttc   2700
cgcaaccagg ccagccggcc ttactcattc tactcctctc tcatctctta tgaggaggat   2760
cagcgccagg gcgccgaacc ccggaagaac tttgtgaagc ccaatgaaac caaaacttac   2820
ttttggaagg tgcagcacca tatggcgccg acgaaagacg aatttgactg caaagcctgg   2880
gcctacttca gcgacgtcga cttggagaag gacgtccaca gcggcctgat tggccctttg   2940
ttggtctgcc ataccaatac actcaaccct gcccacggga ggcaggtgac cgtgcaggag   3000
```

tttgccttgt tcttcaccat cttcgacgaa accaagagct ggtacttcac agagaacatg 3060
gagaggaact gcagagcacc ctgtaacatc cagatggagg accctacttt caaggaaaat 3120
tacaggttcc atgccattaa tggctacatc atggataccc tccccgggct tgtgatggct 3180
caggaccagc gcatccgctg gtacctgctc tcaatgggct ccaacgagaa cattcatagc 3240
atccacttta gtggccacgt gtttaccgtg cgcaagaagg aggagtacaa gatggcactg 3300
tacaacctgt accctggcgt gtttgagaca gtggagatgc tgccatccaa ggccggcatc 3360
tggcgcgtgg agtgcctcat tggggagcac ctccatgctg gcatgtctac actgttcctg 3420
gtgtacagca acaagtgtca gactccactc ggaatggcct ccgggcatat ccgcgatttt 3480
cagatcacgg cctctggcca gtatggccaa tgggctccca agctggccag gctgcactac 3540
agtgggagta tcaacgcttg gagcaccaag gagccttttct cctggatcaa ggtggacctg 3600 cttgcccccca tgattattca cggcattaag acacaggggg ccaggcagaa attctcctcc 3660
ctgtacatct cccagttcat catcatgtac agtctggacg gcaaaaagtg gcagacctac 3720
cgcgggaaca gtaccgggac attgatggtg ttcttcggga acgtggactc tagcggcatt 3780
aaacacaaca ttttcaaccc ccccatcatt gctaggtata tcaggctcca tcccacccac 3840
tatagcatca ggtccactct gcggatggag ctgatgggct gcgaccttaa ttcatgcagc 3900
atgccgctgg gcatggagtc aaaggccatc tccgacgccc aaatcaccgc ctccagctac 3960
ttcaccaata tgttcgccac ctggagcccc agcaaggccc ggctgcacct gcagggccgc 4020
agcaacgcct ggcggcctca ggtgaacaac cccaaggagt ggctgcaggt ggacttccag 4080
aaaaccatga aggtgactgg ggtcaccacc cagggagtca agagcctgct gaccagcatg 4140
tatgtgaagg agttcttgat cagctcgtca caggatggcc accagtggac tttgttcttt 4200
cagaacggta aggtgaaagt gttccaggga aaccaagatt cctttacacc agtggtcaac 4260
tctctggatc ctcccctgct gacacggtac ctgcggatcc atccccagtc atgggtgcac 4320
cagattgctc tgcgcatgga ggtgcttggc tgcgaggccc aggacctgta ctga 4374

<210> SEQ ID NO 16
<211> LENGTH: 4374
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16
atgcagattg agctgagcac ctgtttcttc ctgtgcctgc tgagattttg cttctcagct 60
acccgcaggt actacctggg agccgttgag ctgtcctggg attacatgca gtcagatctg 120
ggggagctgc ctgtggacgc tcggtttccc cccagagtgc caaagtcctt tcccttcaac 180
accagcgtgg tgtacaaaaa gacacttttt gttgaattta ctgaccactt gttcaacatc 240
gccaagccac gacccccatg gatgggcctg ctggggccaa ccattcaggc agaggtttac 300
gacacagtcg tgatcacact gaagaacatg gcctcccatc cagtgtctct gcacgccgtc 360
ggtgtgtcct actggaaagc atccgagggc gccgagtatg acgaccagac cagccagaga 420
gagaaagagg acgacaaagt gttccctgga ggcagccaca cctacgtgtg gcaggtgttg 480
aaggaaaatg ggcccatggc cagtgaccct ttgtgtctga cttactcata cctgtctcat 540
gtggatctag tcaaggacct gaattctgga ctgattgggg cactgcttgt gtgccgcgaa 600

-continued

```
ggcagcctgg ccaaagaaaa gacacagacc cttcacaagt tcatcctgct gttcgccgtg    660
ttcgacgaag gcaaatcctg gcactcagaa accaaaaact cactgatgca ggaccgggat    720
gccgcctctg cccgcgcatg gccaaaaatg cacaccgtca acggctatgt caatagaagt    780
ttgcccggcc tcattggatg tcacaggaaa agcgtctatt ggcatgtaat cgggatggga    840
accacacctg aggtccacag catatttctg gaaggccaca catttctggt gagaaatcat    900
cgccaggctt ccctggaaat ttcccccatc accttcttga ccgcccagac actgctcatg    960
gatcttgggc agtttctgct gttttgtcat atttcttctc accaacacga cggaatggag   1020
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgccccccct ggtgctggca   1260
cccgacgacc gaagctacaa atctcagtac ctgaacaatg gtccacaacg gatcggcagg   1320
aagtacaaga aagtgcggtt catggcctat acagacgaaa ccttcaaaac cagggaggct   1380
atccagcacg agtctgggat tctgggacca ctcctgtacg gcgaagtggg cgacaccttg   1440
ttaattatct tcaagaacca ggctagtaga ccttataaca tttatcccca cggcattacc   1500
gatgtgcggc ctctctactc taggcggctt ccaaaggggg tgaaacacct gaaggacttt   1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc tttttctccg ggtatacttt caaacataag   2040
atggtgtacg aagatactct gacgctgttc cctttctctg ggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc atacctgctg agcaagaata acgccatcga gccccgaagc   2280
ttctcacaga atccccctgt cctcaaggcc caccaggcgg agatcacaag gaccacactc   2340
cagtccgacc aggaggagat tgactacgat gacacgattt ctgtggagat gaaaaaagag   2400
gactttgaca tctacgatga ggatgaaaac cagagcccta ggtcgttcca gaagaaaaca   2460
aggcactact tcattgccgc cgtggagaga ctgtgggact acggaatgag tagttcccca   2520
cacgtgttgc ggaacagagc ccagagtggg tccgtcccac agttcaagaa ggttgttttc   2580
caggagttca cagatggctc cttcactcag ccactgtatc gcggcgagct gaatgagcac   2640
ttgggcttat tgggccccta cattcgcgca gaagtcgaag ataatattat ggtgaccttc   2700
cgcaaccagg ccagccggcc ttactcattc tactcctctc tcatctctta tgaggaggat   2760
cagcgccagg gcgccgaacc ccggaagaac tttgtgaagc ccaatgaaac caaaacttac   2820
ttttggaagg tgcagcacca tatggcgccg acgaaagacg aatttgactg caaagcctgg   2880
gcctacttca gcgacgtcga cttggagaag gacgtccaca gcggcctgat tggccctttg   2940
ttggtctgcc ataccaatac actcaaccct gcccacggga ggcaggtgac cgtgcaggag   3000
```

```
tttgccttgt tcttcaccat cttcgacgaa accaagagct ggtacttcac agagaacatg   3060
gagaggaact gcagagcacc ctgtaacatc cagatggagg accctacttt caaggaaaat   3120
tacaggttcc atgccattaa tggctacatc atggataccc tccccgggct tgtgatggct   3180
caggaccagc gcatccgctg gtacctgctc tcaatgggct ccaacgagaa cattcatagc   3240
atccacttta gtggccacgt gtttaccgtg cgcaagaagg aggagtacaa gatggcactg   3300
tacaacctgt accctggcgt gtttgagaca gtggagatgc tgccatccaa ggccggcatc   3360
tggcgcgtgg agtgcctcat tggggagcac ctccatgctg gcatgtctac actgttcctg   3420
gtgtacagca acaagtgtca gactccactc ggaatggcct ccgggcatat ccgcgatttt   3480
cagatcacgg cctctggcca gtatggccaa tgggctccca agctggccag gctgcactac   3540
agtgggagta tcaacgcttg gagcaccaag gagccttttct cctggatcaa ggtggacctg   3600
cttgccccca tgattattca cggcattaag acacaggggg ccaggcagaa attctcctcc   3660
ctgtacatct cccagttcat catcatgtac agtctggacg gcaaaaagtg gcagacctac   3720
cgcgggaaca gtaccgggac attgatggtg ttcttcggga acgtggactc tagcggcatt   3780
aaacacaaca ttttcaaccc ccccatcatt gctaggtata tcaggctcca tcccacccac   3840
tatagcatca ggtccactct gcggatggag ctgatgggct gcgaccttaa ttcatgcagc   3900
atgccgctgg gcatggagtc aaaggccatc tccgacgccc aaatcaccgc ctccagctac   3960
ttcaccaata tgttcgccac ctggagcccc agcaaggccc ggctgcacct gcagggccgc   4020
agcaacgcct ggcggcctca ggtgaacaac cccaaggagt ggctgcaggt ggacttccag   4080
aaaaccatga aggtgactgg ggtcaccacc cagggagtca agagcctgct gaccagcatg   4140
tatgtgaagg agttcttgat cagctcgtca caggatggcc accagtggac tttgttcttt   4200
cagaacggta aggtgaaagt gttccaggga aaccaagatt cctttacacc agtggtcaac   4260
tctctggatc ctcccctgct gacacggtac ctgcggatcc atccccagtc atgggtgcac   4320
cagattgctc tgcgcatgga ggtgcttggc tgcgaggccc aggacctgta ctga         4374
```

<210> SEQ ID NO 17
<211> LENGTH: 4425
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
atgcagattg agctgagcac ctgtttcttc ctgtgcctgc tgagattttg cttctcagct     60
acccgcaggt actacctggg agccgttgag ctgtcctggg attacatgca gtcagatctg    120
ggggagctgc ctgtggacgc tcggtttccc cccagagtgc caaagtcctt tcccttcaac    180
accagcgtgg tgtacaaaaa gacacttttt gttgaattta ctgaccactt gttcaacatc    240
gccaagccac gacccccatg gatgggcctg ctggggccaa ccattcaggc agaggtttac    300
gacacagtcg tgatcacact gaagaacatg gcctcccatc cagtgtctct gcacgccgtc    360
ggtgtgtcct actggaaagc atccgagggc gccgagtatg acgaccagac cagccagaga    420
gagaaagagg acgacaaagt gttccctgga ggcagccaca cctacgtgtg gcaggtgttg    480
aaggaaaatg ggcccatggc cagtgaccct ttgtgtctga cttactcata cctgtctcat    540
gtggatctag tcaaggacct gaattctgga ctgattgggg cactgcttgt gtgccgcgaa    600
```

-continued

```
ggcagcctgg ccaaagaaaa gacacagacc cttcacaagt tcatcctgct gttcgccgtg    660
ttcgacgaag gcaaatcctg gcactcagaa accaaaaact cactgatgca ggaccgggat    720
gccgcctctg cccgcgcatg gccaaaaatg cacaccgtca acggctatgt caatagaagt    780
ttgcccggcc tcattggatg tcacaggaaa agcgtctatt ggcatgtaat cgggatggga    840
accacacctg aggtccacag catatttctg gaaggccaca catttctggt gagaaatcat    900
cgccaggctt ccctggaaat ttcccccatc accttcttga ccgcccagac actgctcatg    960
gatcttgggc agtttctgct gttttgtcat atttcttctc accaacacga cggaatggag   1020
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgccccct ggtgctggca    1260
cccgacgacc gaagctacaa atctcagtac ctgaacaatg gtccacaacg gatcggcagg   1320
aagtacaaga aagtgcggtt catggcctat acagacgaaa ccttcaaaac cagggaggct   1380
atccagcacg agtctgggat tctgggacca ctcctgtacg gcgaagtggg cgacaccttg   1440
ttaattatct tcaagaacca ggctagtaga ccttataaca tttatcccca cggcattacc   1500
gatgtgcggc ctctctactc taggcggctt ccaaaggggg tgaaacacct gaaggacttt   1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc tttttctccg ggtatacttt caaacataag   2040
atggtgtacg aagatactct gacgctgttc cctttctctg ggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc atacctgctg agcaagaata acgccatcga gccccgaagc   2280
ttctcacaga atgccaccaa cgtgagcaac aacagcaaca ccagcaacga cagcaacgtg   2340
agcccccctg tcctcaaggc ccaccaggcg gagatcacaa ggaccacact ccagtccgac   2400
caggaggaga ttgactacga tgacacgatt tctgtggaga tgaaaaaaga ggactttgac   2460
atctacgatg aggatgaaaa ccagagccct aggtcgttcc agaagaaaac aaggcactac   2520
ttcattgccg ccgtggagag actgtgggac tacggaatga gtagttcccc acacgtgttg   2580
cggaacagag cccagagtgg gtccgtccca cagttcaaga aggttgtttt ccaggagttc   2640
acagatggct ccttcactca gccactgtat cgcggcgagc tgaatgagca cttgggctta   2700
ttgggcccct acattcgcgc agaagtcgaa gataatatta tggtgacctt ccgcaaccag   2760
gccagccggc cttactcatt ctactcctct ctcatctctt atgaggagga tcagcgccag   2820
ggcgccgaac cccggaagaa ctttgtgaag cccaatgaaa ccaaaactta cttttggaag   2880
gtgcagcacc atatggcgcc gacgaaagac gaatttgact gcaaagcctg ggcctacttc   2940
agcgacgtcg acttggagaa ggacgtccac agcggcctga ttggcccttt gttggtctgc   3000
```

```
cataccaata cactcaaccc tgcccacggg aggcaggtga ccgtgcagga gtttgccttg   3060

ttcttcacca tcttcgacga aaccaagagc tggtacttca cagagaacat ggagaggaac   3120

tgcagagcac cctgtaacat ccagatggag gaccctactt tcaaggaaaa ttacaggttc   3180

catgccatta atggctacat catggatacc ctccccgggc ttgtgatggc tcaggaccag   3240

cgcatccgct ggtacctgct ctcaatgggc tccaacgaga acattcatag catccacttt   3300

agtggccacg tgtttaccgt gcgcaagaag gaggagtaca agatggcact gtacaacctg   3360

taccctggcg tgtttgagac agtggagatg ctgccatcca aggccggcat ctggcgcgtg   3420

gagtgcctca ttggggagca cctccatgct ggcatgtcta cactgttcct ggtgtacagc   3480

aacaagtgtc agactccact cggaatggcc tccgggcata tccgcgattt tcagatcacg   3540

gcctctggcc agtatggcca atgggctccc aagctggcca ggctgcacta cagtgggagt   3600

atcaacgctt ggagcaccaa ggagcctttc tcctggatca aggtggacct gcttgccccc   3660

atgattattc acggcattaa gacacagggg gccaggcaga aattctcctc cctgtacatc   3720

tcccagttca tcatcatgta cagtctggac ggcaaaaagt ggcagaccta ccgcgggaac   3780

agtaccggga cattgatggt gttcttcggg aacgtggact ctagcggcat taaacacaac   3840

attttcaacc cccccatcat tgctaggtat atcaggctcc atcccaccca ctatagcatc   3900

aggtccactc tgcggatgga gctgatgggc tgcgacctta attcatgcag catgccgctg   3960

ggcatggagt caaaggccat ctccgacgcc caaatcaccg cctccagcta cttcaccaat   4020

atgttcgcca cctggagccc cagcaaggcc cggctgcacc tgcagggccg cagcaacgcc   4080

tggcggcctc aggtgaacaa ccccaaggag tggctgcagg tggacttcca gaaaaccatg   4140

aaggtgactg gggtcaccac ccagggagtc aagagcctgc tgaccagcat gtatgtgaag   4200

gagttcttga tcagctcgtc acaggatggc caccagtgga ctttgttctt tcagaacggt   4260

aaggtgaaag tgttccaggg aaaccaagat tcctttacac cagtggtcaa ctctctggat   4320

cctcccctgc tgacacggta cctgcggatc catccccagt catgggtgca ccagattgct   4380

ctgcgcatgg aggtgcttgg ctgcgaggcc caggacctgt actaa                   4425
```

<210> SEQ ID NO 18
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
atgcagcgcg tgaacatgat catggcagaa tcaccaggcc tcatcaccat ctgcctttta     60

ggatatctac tcagtgctga atgtacagtt tttcttgatc atgaaaacgc caacaaaatt    120

ctgaatcggc caaagaggta taattcaggt aaattggaag agtttgttca agggaacctt    180

gagagagaat gtatggaaga aaagtgtagt tttgaagaag cacgagaagt tttgaaaac     240

actgaaagaa caactgaatt ttggaagcag tatgttgatg gagatcagtg tgagtccaat    300

ccatgtttaa atggcggcag ttgcaaggat gacattaatt cctatgaatg ttggtgtccc    360

tttggatttg aaggaaagaa ctgtgaatta gatgtaacat gtaacattaa gaatggcaga    420

tgcgagcagt tttgtaaaaa tagtgctgat aacaaggtgg tttgctcctg tactgaggga    480

tatcgacttg cagaaaacca gaagtcctgt gaaccagcag tgccatttcc atgtggaaga    540
```

```
gtttctgttt cacaaacttc taagctcacc cgtgctgaga ctgtttttcc tgatgtggac    600

tatgtaaatt ctactgaagc tgaaaccatt ttggataaca tcactcaaag cacccaatca    660

tttaatgact tcactcgggt tgttggtgga gaagatgcca aaccaggtca attcccttgg    720

caggttgttt tgaatggtaa agttgatgca ttctgtggag gctctatcgt taatgaaaaa    780

tggattgtaa ctgctgccca ctgtgttgaa actggtgtta aaattacagt tgtcgcaggt    840

gaacataata ttgaggagac agaacataca gagcaaaagc gaaatgtgat tcgaattatt    900

cctcaccaca actacaatgc agctattaat aagtacaacc atgacattgc ccttctggaa    960

ctggacgaac ccttagtgct aaacagctac gttacaccta tttgcattgc tgacaaggaa   1020

tacacgaaca tcttcctcaa atttggatct ggctatgtaa gtggctgggg aagagtcttc   1080

cacaaaggga gatcagcttt agttcttcag taccttagag ttccacttgt tgaccgagcc   1140

acatgtcttc tgtctacaaa gttcaccatc tataacaaca tgttctgtgc tggcttccat   1200

gaaggaggta gagattcatg tcaaggagat agtgggggac cccatgttac tgaagtggaa   1260

gggaccagtt tcttaactgg aattattagc tggggtgaag agtgtgcaat gaaaggcaaa   1320

tatggaatat ataccaaggt atcccggtat gtcaactgga ttaaggaaaa aacaaagctc   1380

acttaa                                                              1386
```

```
<210> SEQ ID NO 19
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
```

```
atgcagcgcg tgaacatgat tatggccgag tctcccggcc tgatcaccat ctgtctgctg     60

ggctatctgc tgagcgccga gtgcaccgtg tttctggatc acgagaacgc caacaagatc    120

ctgaacagac ccaagcggta caacagcggc aagctggaag agttcgtgca gggcaacctg    180

gaacgcgagt gcatggaaga gaagtgcagc ttcgaagagg ccagagaggt gttcgagaac    240

accgagagaa ccaccgagtt ctggaagcag tacgtggacg gcgatcagtg cgagagcaac    300

ccttgtctga atggcggcag ctgcaaggac gacatcaaca gctacgagtg ctggtgcccc    360

ttcggcttcg agggcaagaa ttgcgagctg gacgtgacct gcaacatcaa gaacggcaga    420

tgcgagcagt tctgcaagaa cagcgccgac aacaaggtcg tgtgctcctg cacagagggc    480

tacagactgg ccgagaacca gaagtcttgc gagcccgctg tgccctttcc atgtggcaga    540

gtgtctgtgt cccagaccag caagctgacc agagccgaga cagtgttccc cgacgtggac    600

tacgtgaaca gcaccgaggc cgagacaatc ctggacaaca tcacccagag cacccagtcc    660

ttcaacgact tcaccagagt cgtcggcggc gaggatgcta agcctggaca gtttccttgg    720

caagtggtgc tgaacggcaa ggtggacgct ttttgtggcg gctccatcgt gaacgagaag    780

tggatcgtga ccgccgctca ctgtgtggaa accggcgtga agattacagt ggtggccggc    840

gagcacaaca tcgaggaaac agagcacacc gagcagaaac ggaacgtgat cagaatcatc    900

cctcaccaca actacaacgc cgccatcaac aagtacaacc acgatatcgc cctgctggaa    960

ctggacgagc ccctggtcct gaactcttac gtgaccccta tctgtatcgc cgacaaagag   1020

tacaccaaca tctttctgaa gttcggcagc ggctacgtgt ccggctgggg aagagttttc   1080

cacaagggca gatcagccct ggtgctgcag tacctgagag tgcccctggt ggatagagcc   1140
```

acatgcctgc tgagcaccaa gttcaccatc tacaacaaca tgttctgcgc cggcttccac 1200
gaaggcggca gagattcttg tcaaggcgat tctggcggcc ctcacgtgac agaggttgag 1260
ggcacaagct ttctgaccgg catcatcagc tggggcgaag agtgtgccat gaaggggaag 1320
tacggcatct acaccaaggt gtccagatac gtgaactgga tcaaagaaaa gaccaagctc 1380
acctga 1386

<210> SEQ ID NO 20
<211> LENGTH: 1386
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20
atgcagcgcg tgaacatgat catggccgag agccccggcc tgatcaccat ctgcctgctg 60
ggctacctgc tgagcgccga gtgcaccgtg ttcctggacc acgagaacgc caacaagatc 120
ctgaaccgcc ccaagcgcta caacagcggc aagctggagg agttcgtgca gggcaacctg 180
gagcgcgagt gcatggagga gaagtgcagc ttcgaggagg cccgcgaggt gttcgagaac 240
accgagcgca ccaccgagtt ctggaagcag tacgtggacg gcgaccagtg cgagagcaac 300
ccctgcctga acggcggcag ctgcaaggac gacatcaaca gctacgagtg ctggtgcccc 360
ttcggcttcg agggcaagaa ctgcgagctg gacgtgacct gcaacatcaa gaacggccgc 420
tgcgagcagt tctgcaagaa cagcgccgac aacaaggtgg tgtgcagctg caccgagggc 480
taccgcctgg ccgagaacca gaagagctgc gagcccgccg tgcccttccc ctgcggccgc 540
gtgagcgtga gccagaccag caagctgacc cgcgccgaga ctgtgttccc cgacgtggac 600
tacgtgaaca gcaccgaggc cgaaacgatc ctggacaaca tcacccagag cacccagagc 660
ttcaacgact tcacccgcgt ggtgggcggc gaggacgcca agcccggcca gttcccctgg 720
caggtggtgc tgaacggcaa ggtggacgcc ttctgcggcg gcagcatcgt gaacgagaag 780
tggatcgtga ccgccgccca ctgcgtggaa accggcgtga agatcaccgt ggtggccggc 840
gagcacaaca tcgaggaaac cgagcacacc gagcagaagc gcaacgtgat ccgcatcatc 900
ccccaccaca actacaacgc cgccatcaac aagtacaacc acgacatcgc cctgctggag 960
ctggacgagc ccctggtgct gaacagctac gtgaccccca tctgcatcgc cgacaaggag 1020
tacaccaaca tcttcctgaa gttcggcagc ggctacgtga gcggctgggg ccgcgtgttc 1080
cacaagggcc gcagcgccct ggtgctgcag tacctgcgcg tgcccctggt ggaccgcgcc 1140
acctgcctgc tgagcaccaa gttcaccatc tacaacaaca tgttctgcgc cggcttccac 1200
gagggcggcc gcgacagctg ccagggcgac agcggcggcc cccacgtgac cgaggtggag 1260
ggcaccagct tcctgaccgg catcatcagc tggggcgagg agtgcgccat gaagggcaag 1320
tacggcatct acaccaaggt gagccgctac gtgaactgga tcaaggagaa aaccaagctg 1380
acctaa 1386

<210> SEQ ID NO 21
<211> LENGTH: 1386
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic polynucleotide"

<400> SEQUENCE: 21

```
atgcagcggg tgaacatgat catggccgag agccccgggc tgatcaccat ctgtctgctg     60

gggtacctgc tgtccgccga gtgcaccgtg ttcctggacc acgagaacgc caacaagatc    120

ctgaatcgcc ccaagagata caattccgga aagctggaag agtttgtgca gggcaacctg    180

gagagagagt gcatggaaga gaagtgctcc ttcgaggagg cccgggaggt gttcgagaat    240

actgaacgga caacagagtt ctggaagcag tatgtggacg gcgaccagtg tgagagcaac    300

ccctgtctga acggcgggag ctgcaaggac gacattaatt cctacgaatg ctggtgccca    360

ttcggcttcg agggcaagaa ctgcgagctg gacgtgacct gcaacatcaa gaacggccgc    420

tgcgagcagt tttgcaagaa ctccgccgac aacaaggtgg tgtgttcttg caccgagggc    480

taccgcctgg ccgaaaacca gaagagctgt gagcctgccg tgcccttccc ctgcggccgg    540

gtgtctgtgt cccagacctc caagctgacc agagccgaaa ccgtgtttcc agatgtggac    600

tacgtgaata gcaccgaggc cgagactatc ctcgacaaca tcacccagtc cacccagagc    660

tttaacgact tcacccgcgt ggtgggcggc gaggacgcca agcccggcca gttcccctgg    720

caggtggtgc tcaacggaaa ggtggacgcc ttctgcggag gcagcatcgt gaatgaaaag    780

tggatcgtga cagccgccca ctgcgtggaa acaggggtga agatcaccgt ggtggctgga    840

gagcacaaca tcgaggagac agagcacacc gaacagaaga ggaatgtgat caggatcatc    900

ccccaccaca actataatgc cgccatcaac aagtacaacc acgacatcgc cctgctggag    960

ctggatgagc ccctggtgct caacagctac gtgaccccca tctgcatcgc tgacaaggag   1020

tacaccaaca tcttcctgaa gttcggctcc ggctacgtgt ctggctgggg ccgcgtgttc   1080

cacaagggaa gaagcgccct cgtgctgcag tacctgcggg tgccactggt ggacagggcc   1140

acctgcctgc tgagcactaa gttcaccatt tacaacaaca tgttctgcgc cggcttccac   1200

gagggcggca gggactcctg ccagggcgac agcggcggcc cccatgtgac cgaggtggag   1260

ggcacctcct ttctgactgg cattatctcc tggggcgagg agtgcgccat gaaggggaag   1320

tatggcatct acaccaaggt gtcccgctac gtgaactgga ttaaggagaa aaccaagctg   1380

acctga                                                              1386
```

<210> SEQ ID NO 22
<211> LENGTH: 313
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
ttaaccctag aaagatagtc tgcgtaaaat tgacgcatgc attcttgaaa tattgctctc     60

tctttctaaa tagcgcgaat ccgtcgctgt gcatttagga catctcagtc gccgcttgga    120

gctcccgtga ggcgtgcttg tcaatgcggt aagtgtcact gattttgaac tataacgacc    180

gcgtgagtca aaatgacgca tgattatctt ttacgtgact tttaagattt aactcatacg    240

ataattatat tgttatttca tgttctactt acgtgataac ttattatata tatattttct    300

tgttatagat atc                                                       313
```

<210> SEQ ID NO 23
<211> LENGTH: 1733
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23
ctcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtcgagg tgagccccac gttctgcttc actctcccca 420 tctcccccc ctccccaccc ccaattttgt atttatttat tttttaatta ttttgtgcag 480
cgatgggggc gggggggggg gggggcgcg cgccaggcgg ggcggggcgg ggcgaggggc 540
ggggcggggc gaggcggaga ggtgcggcgg cagccaatca gagcggcgcg ctccgaaagt 600
ttccttttat ggcgaggcgg cggcggcggc ggccctataa aaagcgaagc gcgcggcggg 660
cgggagtcgc tgcgcgctgc cttcgccccg tgccccgctc cgccgccgcc tcgcgccgcc 720
cgccccggct ctgactgacc gcgttactcc cacaggtgag cgggcgggac ggcccttctc 780
ctccgggctg taattagcgc ttggtttaat gacggcttgt ttcttttctg tggctgcgtg 840
aaagccttga ggggctccgg gagggccctt tgtgcggggg gagcggctcg gggggtgcgt 900
gcgtgtgtgt gtgcgtgggg agcgccgcgt gcggctccgc gctgcccggc ggctgtgagc 960
gctgcgggcg cggcgcgggg ctttgtgcgc tccgcagtgt gcgcgagggg agcgcggccg 1020 gggcggtgc cccgcggtgc ggggggggct gcgaggggaa caaaggctgc gtgcggggtg 1080
tgtgcgtggg ggggtgagca gggggtgtgg gcgcgtcggt cgggctgcaa cccccccctgc 1140 acccccctcc ccgagttgct gagcacggcc cggcttcggg tgcggggctc cgtacggggc 1200
gtggcgcggg gctcgccgtg ccgggcgggg ggtggcggca ggtgggggtg ccgggcgggg 1260
cggggccgcc tcgggccggg gagggctcgg gggagggggcg cggcggcccc cggagcgccg 1320
gcggctgtcg aggcgcggcg agccgcagcc attgcctttt atggtaatcg tgcgagaggg 1380
cgcagggact tcctttgtcc caaatctgtg cggagccgaa atctgggagg cgccgccgca 1440
ccccctctag cgggcgcggg gcgaagcggt gcggcgccgg caggaaggaa atgggcgggg 1500
agggccttcg tgcgtcgccg cgccgccgtc cccttctccc tctccagcct cggggctgtc 1560
cgcgggggga cggctgcctt cggggggggac ggggcagggc ggggttcggc ttctggcgtg 1620
tgaccggcgg ctctagagcc tctgctaacc atgttcatgc cttcttcttt ttcctacagc 1680
tcctgggcaa cgtgctggtt attgtgctgt ctcatcattt tggcaaagaa ttg 1733

<210> SEQ ID NO 24
<211> LENGTH: 522
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24
tcctcaggtg caggctgcct atcagaaggt ggtggctggt gtggccaatg ccctggctca 60
caaataccac tgagatcttt ttccctctgc caaaaattat ggggacatca tgaagcccct 120
tgagcatctg acttctggct aataaaggaa atttattttc attgcaatag tgtgttggaa 180
ttttttgtgt ctctcactcg gaaggacata tgggagggca aatcatttaa aacatcagaa 240
tgagtatttg gtttagagtt tggcaacata tgcccatatg ctggctgcca tgaacaaagg 300
ttggctataa agaggtcatc agtatatgaa acagcccccct gctgtccatt ccttattcca 360
tagaaaagcc ttgacttgag gttagatttt ttttatattt tgttttgtgt tatttttttc 420
tttaacatcc ctaaaatttt ccttacatgt tttactagcc agatttttcc tcctctcctg 480
actactccca gtcatagctg tccctcttct cttatggaga tc 522

<210> SEQ ID NO 25
<211> LENGTH: 235
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25
ttaaccctag aaagataatc atattgtgac gtacgttaaa gataatcatg cgtaaaattg 60
acgcatgtgt tttatcggtc tgtatatcga ggtttattta ttaatttgaa tagatattaa 120
gttttattat atttacactt acatactaat aataaattca acaaacaatt tatttatgtt 180
tatttattta ttaaaaaaaa acaaaaactc aaaatttctt ctataaagta acaaa 235

<210> SEQ ID NO 26
<211> LENGTH: 6164
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26
ttaaccctag aaagatagtc tgcgtaaaat tgacgcatgc attcttgaaa tattgctctc 60
tctttctaaa tagcgcgaat ccgtcgctgt gcatttagga catctcagtc gccgcttgga 120
gctcccgtga ggcgtgcttg tcaatgcggt aagtgtcact gattttgaac tataacgacc 180
gcgtgagtca aaatgacgca tgattatctt ttacgtgact tttaagattt aactcatacg 240
ataattatat tgttatttca tgttctactt acgtgataac ttattatata tatattttct 300
tgttatagat atcatcaact ttgtatagaa aagttgctcg acattgatta ttgactagtt 360
attaatagta atcaattacg gggtcattag ttcatagccc atatatggag ttccgcgtta 420
cataacttac ggtaaatggc ccgcctggct gaccgcccaa cgacccccgc ccattgacgt 480
caataatgac gtatgttccc atagtaacgc caatagggac tttccattga cgtcaatggg 540
tggagtattt acggtaaact gcccacttgg cagtacatca agtgtatcat atgccaagta 600
cgccccctat tgacgtcaat gacggtaaat ggcccgcctg gcattatgcc cagtacatga 660
ccttatggga ctttcctact tggcagtaca tctacgtatt agtcatcgct attaccatgg 720
tcgaggtgag ccccacgttc tgcttcactc tccccatctc cccccccctcc ccacccccaa 780 ttttgtattt atttattttt taattatttt gtgcagcgat gggggcgggg gggggggggg 840

```
ggcgcgcgcc aggcggggcg gggcggggcg aggggcgggg cggggcgagg cggagaggtg    900
cggcggcagc caatcagagc ggcgcgctcc gaaagtttcc ttttatggcg aggcggcggc    960
ggcggcggcc ctataaaaag cgaagcgcgc ggcgggcggg agtcgctgcg cgctgccttc   1020
gccccgtgcc ccgctccgcc gccgcctcgc gccgcccgcc ccggctctga ctgaccgcgt   1080
tactcccaca ggtgagcggg cgggacggcc cttctcctcc gggctgtaat tagcgcttgg   1140
tttaatgacg gcttgtttct tttctgtggc tgcgtgaaag ccttgagggg ctccgggagg   1200
gccctttgtg cggggggagc ggctcggggg gtgcgtgcgt gtgtgtgtgc gtggggagcg   1260
ccgcgtgcgg ctccgcgctg cccggcggct gtgagcgctg cgggcgcggc gcggggcttt   1320
gtgcgctccg cagtgtgcgc gaggggagcg cggccggggg cggtgccccg cggtgcgggg   1380
ggggctgcga ggggaacaaa ggctgcgtgc ggggtgtgtg cgtgggggggg tgagcagggg   1440
gtgtgggcgc gtcggtcggg ctgcaacccc ccctgcaccc ccctccccga gttgctgagc   1500
acggcccggc ttcgggtgcg gggctccgta cggggcgtgg cgcggggctc gccgtgccgg   1560
gcgggggggtg gcggcaggtg gggtgccggg gcggggcggg gccgcctcgg gccggggagg   1620
gctcggggga ggggcgcggc ggcccccgga gcgccggcgg ctgtcgaggc gcggcgagcc   1680
gcagccattg ccttttatgg taatcgtgcg agagggcgca gggacttcct ttgtcccaaa   1740
tctgtgcgga gccgaaatct gggaggcgcc gccgcacccc ctctagcggg cgcggggcga   1800
agcggtgcgg cgccggcagg aaggaaatgg gcggggaggg ccttcgtgcg tcgccgcgcc   1860
gccgtcccct tctccctctc cagcctcggg gctgtccgcg gggggacggc tgccttcggg   1920
ggggacgggg cagggcgggg ttcggcttct ggcgtgtgac cggcggctct agagcctctg   1980
ctaaccatgt tcatgccttc ttcttttttcc tacagctcct gggcaacgtg ctggttattg   2040
tgctgtctca tcattttggc aaagaattgc aagtttgtac aaaaaagcag gctgccaccg   2100
aattcgcggc cgctaaaccc agctttcttg tacaaagtgg caactttatt atacatagtt   2160
gatcctcagg tgcaggctgc ctatcagaag gtggtggctg gtgtggccaa tgccctggct   2220
cacaaatacc actgagatct ttttccctct gccaaaaatt atggggacat catgaagccc   2280
cttgagcatc tgacttctgg ctaataaagg aaatttattt tcattgcaat agtgtgttgg   2340
aattttttgt gtctctcact cggaaggaca tatgggaggg caaatcattt aaaacatcag   2400
aatgagtatt tggtttagag tttggcaaca tatgcccata tgctggctgc catgaacaaa   2460
ggttggctat aaagaggtca tcagtatatg aaacagcccc ctgctgtcca ttccttattc   2520
catagaaaag ccttgacttg aggttagatt tttttttatat tttgttttgt gttatttttt   2580
tctttaacat ccctaaaatt ttccttacat gttttactag ccagattttt cctcctctcc   2640
tgactactcc cagtcatagc tgtccctctt ctcttatgga gatccctcga cctgcagccc   2700
aagcttggat ccctcgagtt aattaacgag agcataatat tgatatgtgc caaagttgtt   2760
tctgactgac taataagtat aatttgtttc tattatgtat aggttaagct aattacttat   2820
tttataatac aacatgactg tttttaaagt acaaaataag tttatttttg taaaagagag   2880
aatgtttaaa agttttgtta ctttatagaa gaaattttga gtttttgttt tttttttaata   2940
aataaataaa cataaataaa ttgtttgttg aatttattat tagtatgtaa gtgtaaatat   3000
aataaaactt aatatctatt caaattaata aataaacctc gatatacaga ccgataaaac   3060
acatgcgtca attttacgca tgattatctt taacgtacgt cacaatatga ttatctttct   3120
agggttaaat aatagtttct aattttttta ttattcagcc tgctgtcgtg aataccgagc   3180
```

-continued tccaattcgc cctatagtga gtcgtattac aattcactgg ccgtcgtttt acaacgtcgt 3240
gactgggaaa accctggcgt tacccaactt aatcgccttg cagcacatcc ccctttcgcc 3300
agctggcgta atagcgaaga ggcccgcacc gatcgccctt cccaacagtt gcgcagcctg 3360
aatggcgaat gggacgcgcc ctgtagcggc gcattaagcg cggcgggtgt ggtggttacg 3420
cgcagcgtga ccgctacact tgccagcgcc ctagcgcccg ctcctttcgc tttcttccct 3480
tcctttctcg ccacgttcgc cggctttccc cgtcaagctc taaatcgggg gctcccttta 3540
gggttccgat ttagtgcttt acggcacctc gaccccaaaa aacttgatta gggtgatggt 3600
tcacgtagtg ggccatcgcc ctgatagacg gtttttcgcc ctttgacgtt ggagtccacg 3660
ttctttaata gtggactctt gttccaaact ggaacaacac tcaaccctat ctcggtctat 3720
tcttttgatt tataagggat tttgccgatt tcggcctatt ggttaaaaaa tgagctgatt 3780
taacaaaaat ttaacgcgaa ttttaacaaa atattaacgc ttacaattta ggtggcactt 3840
ttcggggaaa tgtgcgcgga acccctattt gtttattttt ctaaatacat tcaaatatgt 3900
atccgctcat gagacaataa ccctgataaa tgcttcaata atattgaaaa aggaagagta 3960
tgagtattca acatttccgt gtcgccctta ttcccttttt tgcggcattt tgccttcctg 4020
tttttgctca cccagaaacg ctggtgaaag taaaagatgc tgaagatcag ttgggtgcac 4080
gagtgggtta catcgaactg gatctcaaca gcggtaagat ccttgagagt tttcgccccg 4140
aagaacgttt tccaatgatg agcactttta aagttctgct atgtggcgcg gtattatccc 4200
gtattgacgc cgggcaagag caactcggtc gccgcataca ctattctcag aatgacttgg 4260
ttgagtactc accagtcaca gaaaagcatc ttacggatgg catgacagta agagaattat 4320
gcagtgctgc cataaccatg agtgataaca ctgcggccaa cttacttctg acaacgatcg 4380
gaggaccgaa ggagctaacc gcttttttgc acaacatggg ggatcatgta actcgccttg 4440
atcgttggga accggagctg aatgaagcca taccaaacga cgagcgtgac accacgatgc 4500
ctgtagcaat ggcaacaacg ttgcgcaaac tattaactgg cgaactactt actctagctt 4560
cccggcaaca attaatagac tggatggagg cggataaagt tgcaggacca cttctgcgct 4620
cggcccttcc ggctggctgg tttattgctg ataaatctgg agccggtgag cgtgggtctc 4680
gcggtatcat tgcagcactg gggccagatg gtaagccctc ccgtatcgta gttatctaca 4740
cgacggggag tcaggcaact atggatgaac gaaatagaca gatcgctgag ataggtgcct 4800
cactgattaa gcattggtaa ctgtcagacc aagtttactc atatatactt tagattgatt 4860
taaaacttca tttttaattt aaaaggatct aggtgaagat cctttttgat aatctcatga 4920
ccaaaatccc ttaacgtgag ttttcgttcc actgagcgtc agaccccgta gaaaagatca 4980
aaggatcttc ttgagatcct ttttttctgc gcgtaatctg ctgcttgcaa acaaaaaaac 5040
caccgctacc agcggtggtt tgtttgccgg atcaagagct accaactctt tttccgaagg 5100
taactggctt cagcagagcg cagataccaa atactgttct tctagtgtag ccgtagttag 5160
gccaccactt caagaactct gtagcaccgc ctacatacct cgctctgcta atcctgttac 5220
cagtggctgc tgccagtggc gataagtcgt gtcttaccgg gttggactca agacgatagt 5280
taccggataa ggcgcagcgg tcgggctgaa cggggggttc gtgcacacag cccagcttgg 5340
agcgaacgac ctacaccgaa ctgagatacc tacagcgtga gctatgagaa agcgccacgc 5400
ttcccgaaga gagaaaggcg gacaggtatc cggtaagcgg cagggtcgga acaggagagc 5460
gcacgaggga gcttccaggg ggaaacgcct ggtatcttta tagtcctgtc gggtttcgcc 5520
acctctgact tgagcgtcga tttttgtgat gctcgtcagg ggggcggagc ctatggaaaa 5580

```
acgccagcaa cgcggccttt ttacggttcc tggccttttg ctggcctttt gctcacatgt   5640

tctttcctgc gttatcccct gattctgtgg ataaccgtat taccgccttt gagtgagctg   5700

ataccgctcg ccgcagccga acgaccgagc gcagcgagtc agtgagcgag gaagcggaag   5760

agcgcccaat acgcaaaccg cctctccccg cgcgttggcc gattcattaa tgcagctggc   5820

acgacaggtt tcccgactgg aaagcgggca gtgagcgcaa cgcaattaat gtgagttagc   5880

tcactcatta ggcaccccag gctttacact ttatgcttcc ggctcgtatg ttgtgtggaa   5940

ttgtgagcgg ataacaattt cacacaggaa acagctatga ccatgattac gccaagctcg   6000

aaattaaccc tcactaaagg gaacaaaagc tggtacctcg cgcgacttgg tttgccattc   6060

tttagcgcgc gtcgcgtcac acagcttggc cacaatgtgg tttttgtcaa acgaagattc   6120

tatgacgtgt ttaaagttta ggtcgagtaa agcgcaaatc tttt                   6164
```

<210> SEQ ID NO 27
<211> LENGTH: 6721
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
ctcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atggtcgagg tgagccccac gttctgcttc actctcccca    420

tctccccccc ctccccaccc ccaattttgt atttatttat tttttaatta ttttgtgcag    480

cgatgggggc gggggggggg ggggggcgcg cgccaggcgg ggcggggcgg ggcgaggggc    540

ggggcggggc gaggcggaga ggtgcggcgg cagccaatca gagcggcgcg ctccgaaagt    600

ttccttttat ggcgaggcgg cggcggcggc ggccctataa aaagcgaagc gcgcggcggg    660

cgggagtcgc tgcgcgctgc cttcgccccg tgccccgctc cgccgccgcc tcgcgccgcc    720

cgccccggct ctgactgacc gcgttactcc cacaggtgag cgggcgggac ggcccttctc    780

ctccgggctg taattagcgc ttggtttaat gacggcttgt ttcttttctg tggctgcgtg    840

aaagccttga ggggctccgg gagggccctt tgtgcggggg gagcggctcg gggggtgcgt    900

gcgtgtgtgt gtgcgtgggg agcgccgcgt gcggctccgc gctgcccggc ggctgtgagc    960

gctgcgggcg cggcgcgggg ctttgtgcgc tccgcagtgt gcgcgagggg agcgcggccg   1020

ggggcggtgc cccgcggtgc ggggggggct gcgaggggaa caaaggctgc gtgcggggtg   1080

tgtgcgtggg ggggtgagca gggggtgtgg gcgcgtcggt cgggctgcaa ccccccctgc   1140

acccccctcc ccgagttgct gagcacggcc cggcttcggg tgcggggctc cgtacggggc   1200

gtggcgcggg gctcgccgtg ccgggcgggg ggtggcggca ggtgggggtg ccgggcgggg   1260

cggggccgcc tcgggccggg gagggctcgg gggagggggcg cggcggcccc cggagcgccg   1320

gcggctgtcg aggcgcggcg agccgcagcc attgcctttt atggtaatcg tgcgagaggg   1380
```

-continued

```
cgcagggact tcctttgtcc caaatctgtg cggagccgaa atctgggagg cgccgccgca   1440
ccccctctag cgggcgcggg gcgaagcggt gcggcgccgg caggaaggaa atgggcgggg   1500
agggccttcg tgcgtcgccg cgccgccgtc cccttctccc tctccagcct cggggctgtc   1560
cgcgggggga cggctgcctt cgggggggac ggggcagggc ggggttcggc ttctggcgtg   1620
tgaccggcgg ctctagagcc tctgctaacc atgttcatgc cttcttcttt ttcctacagc   1680
tcctgggcaa cgtgctggtt attgtgctgt ctcatcattt tggcaaagaa ttgcaagttt   1740
gtacaaaaaa gcaggctgcc accatgcaga ttgagctgag cacctgtttc ttcctgtgcc   1800
tgctgagatt ttgcttctca gctacccgca ggtactacct gggagccgtt gagctgtcct   1860
gggattacat gcagtcagat ctgggggagc tgcctgtgga cgctcggttt ccccccagag   1920
tgccaaagtc ctttcccttc aacaccagcg tggtgtacaa aaagacactt tttgttgaat   1980
ttactgacca cttgttcaac atcgccaagc cacgaccccc atggatgggc ctgctggggc   2040
caaccattca ggcagaggtt tacgacacag tcgtgatcac actgaagaac atggcctccc   2100
atccagtgtc tctgcacgcc gtcggtgtgt cctactggaa agcatccgag ggcgccgagt   2160
atgacgacca gaccagccag agagagaaag aggacgacaa agtgttccct ggaggcagcc   2220
acacctacgt gtggcaggtg ttgaaggaaa atgggcccat ggccagtgac cctttgtgtc   2280
tgacttactc atacctgtct catgtggatc tagtcaagga cctgaattct ggactgattg   2340
ggcactgct tgtgtgccgc gaaggcagcc tggccaaaga aaagacacag acccttcaca   2400
agttcatcct gctgttcgcc gtgttcgacg aaggcaaatc ctggcactca gaaaccaaaa   2460
actcactgat gcaggaccgg gatgccgcct ctgcccgcgc atggccaaaa atgcacaccg   2520
tcaacggcta tgtcaataga agtttgcccg gcctcattgg atgtcacagg aaaagcgtct   2580
attggcatgt aatcgggatg ggaaccacac ctgaggtcca cagcatattt ctggaaggcc   2640
acacatttct ggtgagaaat catcgccagg cttccctgga aatttccccc atcaccttct   2700
tgaccgccca gacactgctc atggatcttg ggcagtttct gctgttttgt catatttctt   2760
ctcaccaaca cgacggaatg gaggcctacg ttaaggtcga tagttgccct gaagaacctc   2820
agctgaggat gaagaacaac gaggaagccg aggactacga tgacgatttg accgattccg   2880
aaatggacgt ggtgcgcttt gatgatgaca attctccatc cttcattcag attagatccg   2940
tcgccaagaa gcaccccaag acctgggtgc actacattgc agccgaggag gaggattggg   3000
actacgcccc cctggtgctg gcacccgacg accgaagcta caaatctcag tacctgaaca   3060
atggtccaca acggatcggc aggaagtaca agaaagtgcg gttcatggcc tatacagacg   3120
aaaccttcaa aaccagggag gctatccagc acgagtctgg gattctggga ccactcctgt   3180
acggcgaagt gggcgacacc ttgttaatta tcttcaagaa ccaggctagt agaccttata   3240
acatttatcc ccacggcatt accgatgtgc ggcctctcta ctctaggcgg cttccaaagg   3300
gggtgaaaca cctgaaggac tttcccatcc tccctggcga aatctttaag tataagtgga   3360
cagtgaccgt ggaggatgga ccaaccaaga gcgaccccag gtgcctgaca cgctattatt   3420
caagcttcgt gaatatggaa agggacctcg catctggctt gatcggccct ctgctgatat   3480
gttacaagga aagcgtcgat cagagaggaa atcagatcat gtcagacaaa aggaatgtga   3540
tcctgttctc cgtcttcgat gaaaacagga gctggtatct gacagagaac atccagagat   3600
tcctgccaaa tcccgccggc gtccagctgg aggacccgga gtttcaggca tctaacatca   3660
tgcattccat taatggttac gtgttcgact ccctgcagct gagcgtgtgc ctccacgagg   3720
tggcctactg gtacatcttg agcatcggcg cccagaccga ctttctgagc gtctttttct   3780
```

-continued

```
ccgggtatac tttcaaacat aagatggtgt acgaagatac tctgacgctg ttccctttct   3840
ctggggagac tgtgtttatg tctatggaga accctggact gtggattctc ggatgccaca   3900
acagtgactt tcgtaataga gggatgactg cactgctgaa ggtgtccagc tgtgataaaa   3960
atactggcga ctactacgaa gatagctatg aggatatctc agcatacctg ctgagcaaga   4020
ataacgccat cgagccccga agcttctcac agaatccccc tgtcctcaag gcccaccagg   4080
cggagatcac aaggaccaca ctccagtccg accaggagga gattgactac gatgacacga   4140
tttctgtgga gatgaaaaaa gaggactttg acatctacga tgaggatgaa aaccagagcc   4200
ctaggtcgtt ccagaagaaa acaaggcact acttcattgc cgccgtggag agactgtggg   4260
actacggaat gagtagttcc ccacacgtgt tgcggaacag agcccagagt gggtccgtcc   4320
cacagttcaa gaaggttgtt ttccaggagt tcacagatgg ctccttcact cagccactgt   4380
atcgcggcga gctgaatgag cacttgggct tattgggccc ctacattcgc gcagaagtcg   4440
aagataatat tatggtgacc ttccgcaacc aggccagccg gccttactca ttctactcct   4500
ctctcatctc ttatgaggag gatcagcgcc agggcgccga accccggaag aactttgtga   4560
agcccaatga aaccaaaact tacttttgga aggtgcagca ccatatggcg ccgacgaaag   4620
acgaatttga ctgcaaagcc tgggcctact tcagcgacgt cgacttggag aaggacgtcc   4680
acagcggcct gattggccct ttgttggtct gccataccaa tacactcaac cctgcccacg   4740
ggaggcaggt gaccgtgcag gagtttgcct tgttcttcac catcttcgac gaaaccaaga   4800
gctggtactt cacagagaac atggagagga actgcagagc accctgtaac atccagatgg   4860
aggaccctac tttcaaggaa aattacaggt tccatgccat taatggctac atcatggata   4920
ccctccccgg gcttgtgatg gctcaggacc agcgcatccg ctggtacctg ctctcaatgg   4980
gctccaacga gaacattcat agcatccact ttagtggcca cgtgtttacc gtgcgcaaga   5040
aggaggagta caagatggca ctgtacaacc tgtaccctgg cgtgtttgag acagtggaga   5100
tgctgccatc caaggccggc atctggcgcg tggagtgcct cattggggag cacctccatg   5160
ctggcatgtc tacactgttc ctggtgtaca gcaacaagtg tcagactcca ctcggaatgg   5220
cctccgggca tatccgcgat tttcagatca cggcctctgg ccagtatggc caatgggctc   5280
ccaagctggc caggctgcac tacagtggga gtatcaacgc ttggagcacc aaggagcctt   5340
tctcctggat caaggtggac ctgcttgccc ccatgattat tcacggcatt aagacacagg   5400
gggccaggca gaaattctcc tccctgtaca tctcccagtt catcatcatg tacagtctgg   5460
acggcaaaaa gtggcagacc taccgcggga acagtaccgg gacattgatg gtgttcttcg   5520
ggaacgtgga ctctagcggc attaaacaca acattttcaa ccccccccatc attgctaggt   5580
atatcaggct ccatcccacc cactatagca tcaggtccac tctgcggatg gagctgatgg   5640
gctgcgacct taattcatgc agcatgccgc tgggcatgga gtcaaaggcc atctccgacg   5700
cccaaatcac cgcctccagc tacttcacca atatgttcgc cacctggagc cccagcaagg   5760
cccggctgca cctgcagggc cgcagcaacg cctggcggcc tcaggtgaac aaccccaagg   5820
agtggctgca ggtggacttc cagaaaacca tgaaggtgac tggggtcacc acccagggag   5880
tcaagagcct gctgaccagc atgtatgtga aggagttctt gatcagctcg tcacaggatg   5940
gccaccagtg gactttgttc tttcagaacg gtaaggtgaa agtgttccag ggaaaccaag   6000
attcctttac accagtggtc aactctctgg atcctcccct gctgacacgg tacctgcgga   6060
tccatcccca gtcatgggtg caccagattg ctctgcgcat ggaggtgctt ggctgcgagg   6120
```

```
cccaggacct gtactgaaat tcgcggccgc taaacccagc tttcttgtac aaagtggcaa   6180

ctttattata catagttgat cctcaggtgc aggctgccta tcagaaggtg gtggctggtg   6240

tggccaatgc cctggctcac aaataccact gagatctttt tccctctgcc aaaaattatg   6300

gggacatcat gaagcccctt gagcatctga cttctggcta ataaaggaaa tttattttca   6360

ttgcaatagt gtgttggaat tttttgtgtc tctcactcgg aaggacatat gggagggcaa   6420

atcatttaaa acatcagaat gagtatttgg tttagagttt ggcaacatat gcccatatgc   6480

tggctgccat gaacaaaggt tggctataaa gaggtcatca gtatatgaaa cagccccctg   6540

ctgtccattc cttattccat agaaaagcct tgacttgagg ttagattttt tttatatttt   6600

gttttgtgtt atttttttct ttaacatccc taaaattttc cttacatgtt ttactagcca   6660

gatttttcct cctctcctga ctactcccag tcatagctgt ccctcttctc ttatggagat   6720

c                                                                   6721
```

<210> SEQ ID NO 28
<211> LENGTH: 3733
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
ctcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atggtcgagg tgagccccac gttctgcttc actctcccca    420

tctccccccc ctccccaccc ccaattttgt atttatttat tttttaatta ttttgtgcag    480

cgatgggggc gggggggggg ggggggcgcg cgccaggcgg ggcggggcgg ggcgaggggc    540

ggggcggggc gaggcggaga ggtgcggcgg cagccaatca gagcggcgcg ctccgaaagt    600

ttccttttat ggcgaggcgg cggcggcggc ggccctataa aaagcgaagc gcgcggcggg    660

cgggagtcgc tgcgcgctgc cttcgccccg tgccccgctc cgccgccgcc tcgcgccgcc    720

cgccccggct ctgactgacc gcgttactcc cacaggtgag cgggcgggac ggcccttctc    780

ctccgggctg taattagcgc ttggtttaat gacggcttgt ttcttttctg tggctgcgtg    840

aaagccttga ggggctccgg gagggccctt tgtgcggggg gagcggctcg gggggtgcgt    900

gcgtgtgtgt gtgcgtgggg agcgccgcgt gcggctccgc gctgcccggc ggctgtgagc    960

gctgcgggcg cggcgcgggg ctttgtgcgc tccgcagtgt gcgcgagggg agcgcggccg   1020

ggggcggtgc cccgcggtgc ggggggggct gcgaggggaa caaaggctgc gtgcggggtg   1080

tgtgcgtggg ggggtgagca gggggtgtgg gcgcgtcggt cgggctgcaa ccccccctgc   1140

acccccctcc ccgagttgct gagcacggcc cggcttcggg tgcggggctc cgtacggggc   1200

gtggcgcggg gctcgccgtg ccgggcgggg ggtggcggca ggtgggggtg ccgggcgggg   1260

cggggccgcc tcgggccggg gagggctcgg gggaggggcg cggcggcccc cggagcgccg   1320

gcggctgtcg aggcgcggcg agccgcagcc attgcctttt atggtaatcg tgcgagaggg   1380
```

```
cgcagggact tcctttgtcc caaatctgtg cggagccgaa atctgggagg cgccgccgca   1440
cccctctag cgggcgcggg gcgaagcggt gcggcgccgg caggaaggaa atgggcgggg   1500
agggccttcg tgcgtcgccg cgccgccgtc cccttctccc tctccagcct cggggctgtc   1560
cgcgggggga cggctgcctt cgggggggac ggggcagggc ggggttcggc ttctggcgtg   1620
tgaccggcgg ctctagagcc tctgctaacc atgttcatgc cttcttcttt ttcctacagc   1680
tcctgggcaa cgtgctggtt attgtgctgt ctcatcattt tggcaaagaa ttgcaagttt   1740
gtacaaaaaa gcaggctgcc accatgcagc gcgtgaacat gattatggcc gagtctcccg   1800
gcctgatcac catctgtctg ctgggctatc tgctgagcgc cgagtgcacc gtgtttctgg   1860
atcacgagaa cgccaacaag atcctgaaca gacccaagcg gtacaacagc ggcaagctgg   1920
aagagttcgt gcagggcaac ctggaacgcg agtgcatgga agagaagtgc agcttcgaag   1980
aggccagaga ggtgttcgag aacaccgaga gaaccaccga gttctggaag cagtacgtgg   2040
acggcgatca gtgcgagagc aacccttgtc tgaatggcgg cagctgcaag gacgacatca   2100
acagctacga gtgctggtgc cccttcggct tcgagggcaa gaattgcgag ctggacgtga   2160
cctgcaacat caagaacggc agatgcgagc agttctgcaa gaacagcgcc gacaacaagg   2220
tcgtgtgctc ctgcacagag ggctacagac tggccgagaa ccagaagtct tgcgagcccg   2280
ctgtgccctt tccatgtggc agagtgtctg tgtcccagac cagcaagctg accagagccg   2340
agacagtgtt ccccgacgtg gactacgtga acagcaccga ggccgagaca atcctggaca   2400
acatcaccca gagcacccag tccttcaacg acttcaccag agtcgtcggc ggcgaggatg   2460
ctaagcctgg acagtttcct tggcaagtgg tgctgaacgg caaggtggac gctttttgtg   2520
gcggctccat cgtgaacgag aagtggatcg tgaccgccgc tcactgtgtg gaaaccggcg   2580
tgaagattac agtggtggcc ggcgagcaca acatcgagga aacagagcac accgagcaga   2640
aacggaacgt gatcagaatc atccctcacc acaactacaa cgccgccatc aacaagtaca   2700
accacgatat cgccctgctg gaactggacg agcccctggt cctgaactct tacgtgaccc   2760
ctatctgtat cgccgacaaa gagtacacca acatctttct gaagttcggc agcggctacg   2820
tgtccggctg gggaagagtt ttccacaagg gcagatcagc cctggtgctg cagtacctga   2880
gagtgcccct ggtggataga gccacatgcc tgctgagcac caagttcacc atctacaaca   2940
acatgttctg cgccggcttc cacgaaggcg gcagagattc ttgtcaaggc gattctggcg   3000
gccctcacgt gacagaggtt gagggcacaa gctttctgac cggcatcatc agctggggcg   3060
aagagtgtgc catgaagggg aagtacggca tctacaccaa ggtgtccaga tacgtgaact   3120
ggatcaaaga aaagaccaag ctcacctgaa attcgcggcc gctaaaccca gctttcttgt   3180
acaaagtggc aactttatta tacatagttg atcctcaggt gcaggctgcc tatcagaagg   3240
tggtggctgg tgtggccaat gccctggctc acaaatacca ctgagatctt tttccctctg   3300
ccaaaaatta tggggacatc atgaagcccc ttgagcatct gacttctggc taataaagga   3360
aatttatttt cattgcaata gtgtgttgga atttttgtg tctctcactc ggaaggacat   3420
atgggagggc aaatcattta aaacatcaga atgagtattt ggtttagagt ttggcaacat   3480
atgcccatat gctggctgcc atgaacaaag gttggctata aagaggtcat cagtatatga   3540
aacagccccc tgctgtccat tccttattcc atagaaaagc cttgacttga ggttagattt   3600
tttttatatt ttgttttgtg ttattttttt ctttaacatc cctaaaattt tccttacatg   3660
ttttactagc cagatttttc ctcctctcct gactactccc agtcatagct gtccctcttc   3720
```

tcttatggag atc 3733

<210> SEQ ID NO 29
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 30
<211> LENGTH: 65
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60

Phe
65
```

<210> SEQ ID NO 31
<211> LENGTH: 115
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 31

Met Ile Pro Ala Lys Asp Met Ala Lys Val Met Ile Val Met Leu Ala
1               5                   10                  15

Ile Cys Phe Leu Thr Lys Ser Asp Gly Lys Ser Val Lys Lys Arg Ser
            20                  25                  30

Val Ser Glu Ile Gln Leu Met His Asn Leu Gly Lys His Leu Asn Ser
        35                  40                  45

Met Glu Arg Val Glu Trp Leu Arg Lys Lys Leu Gln Asp Val His Asn
    50                  55                  60

Phe Val Ala Leu Gly Ala Pro Leu Ala Pro Arg Asp Ala Gly Ser Gln
65                  70                  75                  80

Arg Pro Arg Lys Lys Glu Asp Asn Val Leu Val Glu Ser His Glu Lys
                85                  90                  95

Ser Leu Gly Glu Ala Asp Lys Ala Asp Val Asn Val Leu Thr Lys Ala
            100                 105                 110

Lys Ser Gln
        115


<210> SEQ ID NO 32
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190
```

```
Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro
            500                 505
```

<210> SEQ ID NO 33
<211> LENGTH: 1247
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 33

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30
```

-continued

```
Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445
```

```
Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860
```

-continued

```
Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro
    1235                1240                1245
```

<210> SEQ ID NO 34
<211> LENGTH: 232
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 34

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 35
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 35

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Cys Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

-continued

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585


<210> SEQ ID NO 36
<211> LENGTH: 461
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255
```

```
Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460


<210> SEQ ID NO 37
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Trp Glu Leu Tyr Tyr Pro Leu Arg Ala Asn Leu
1               5                   10


<210> SEQ ID NO 38
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

His Ala Val Asp Ile
1               5


<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 39

Asp Gly Glu Ala
1

<210> SEQ ID NO 40
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 40

Phe Tyr Phe Asp Leu Arg
1 5

<210> SEQ ID NO 41
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (3)..(3)
<223> OTHER INFORMATION: 4-hydroxyproline

<400> SEQUENCE: 41

Gly Phe Xaa Gly Glu Arg
1 5

<210> SEQ ID NO 42
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 42

Val Ala Pro Gly
1

<210> SEQ ID NO 43
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 43

Arg Gly Asp
1

<210> SEQ ID NO 44
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 44

Gly Pro Arg
1

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 45

Lys Gln Ala Gly Asp Val
1 5

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 46

Pro His Ser Arg Asn
1 5

<210> SEQ ID NO 47
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 47

Arg Glu Asp Val
1

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 48

Ile Lys Val Ala Val
1 5

<210> SEQ ID NO 49
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 49

Leu Arg Glu
1

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 50

Tyr Ile Gly Ser Arg
1 5

<210> SEQ ID NO 51
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 51

Ser Val Val Tyr Gly Leu Arg
1 5

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 52

Ala Glu Ile Asp Gly Ile Glu Leu
1 5

<210> SEQ ID NO 53
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 53

Val Thr Cys Gly
1

<210> SEQ ID NO 54
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:
<221> NAME/KEY: MOD_RES
<222> LOCATION: (19)..(19)
<223> OTHER INFORMATION: 4-hydroxyproline

```
<400> SEQUENCE: 54

Pro Gly Pro Pro Gly Pro Pro Gly Pro Pro Gly Pro Pro Gly Pro Pro
1               5                   10                  15

Gly Phe Xaa Gly Glu Arg Gly Pro Pro Gly Pro Pro Gly Pro Pro Gly
            20                  25                  30

Pro Pro Gly Pro Pro
        35


<210> SEQ ID NO 55
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Pro His Ser Arg Asn Gly Gly Gly Gly Gly Gly Arg Gly Asp Ser
1               5                   10                  15


<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ser Arg Ala Arg Lys Gln Ala Ala Ser Ile Lys Val Ala Val Ala Asp
1               5                   10                  15

Arg


<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Lys Gln Leu Arg Glu Gln
1               5


<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ser Val Thr Cys Gly
1               5


<210> SEQ ID NO 59
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 59

Arg Gly Asp Ser Pro
1               5


<210> SEQ ID NO 60
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Arg Gly Asp Ser Pro
1               5


<210> SEQ ID NO 61
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Gly Gly Gly
1


<210> SEQ ID NO 62
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Arg Gly Asp
1


<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(3)
<223> OTHER INFORMATION: /note="This region may encompass 1-3 residues"

<400> SEQUENCE: 63

Gly Gly Gly Arg Gly Asp
1               5


<210> SEQ ID NO 64
<211> LENGTH: 8
<212> TYPE: PRT
<213> ORGANISM: Artificial Sequence
```

-continued

<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may encompass 1-3 residues"

<400> SEQUENCE: 64

Gly Gly Gly Arg Gly Asp Ser Pro
1 5

<210> SEQ ID NO 65
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 65

Leu Lys Arg His Gln Arg
1 5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may encompass 1-3 residues"

<400> SEQUENCE: 66

Gly Gly Gly Asp Gly Glu Ala
1 5

<210> SEQ ID NO 67
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)
<223> OTHER INFORMATION: /note="This region may encompass 1-3 residues"

<400> SEQUENCE: 67

Gly Gly Gly Pro His Arg Ser Asn
1 5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: SITE
<222> LOCATION: (1)..(3)

-continued

<223> OTHER INFORMATION: /note="This region may encompass 1-3 residues"

<400> SEQUENCE: 68

Gly Gly Gly Arg Glu Asp Val
1 5

<210> SEQ ID NO 69
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 69

Gly Gly Gly Gly Gly Gly
1 5

<210> SEQ ID NO 70
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: SITE
<222> LOCATION: (1)..(4)
<223> OTHER INFORMATION: /note="This sequence may encompass 1-4 residues"

<400> SEQUENCE: 70

Gly Gly Gly Gly
1

IMPLANTABLE DEVICES FOR CELL THERAPY AND RELATED METHODS

CLAIM OF PRIORITY

This application is a U.S. National Phase Application under 35 U.S.C. § 371 of International Application No. PCT/US2019/053637, filed Sep. 27, 2019, which claims priority to U.S. Provisional Application No. 62/737,835, filed Sep. 27, 2018 and U.S. Provisional Application No. 62/824,768, filed Mar. 27, 2019. The disclosure of each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 20, 2019, is named S2225-7026WO_SL and is 213,209 bytes in size.

BACKGROUND

Treating chronic and genetic diseases by implanting cells engineered to produce a therapeutic substance capable of treating such diseases has exciting potential to improve the health of patients with such diseases. To fully achieve this potential, the implanted cells must be protected from the patient's immune response, so that they remain viable, and the implanted cells must also be capable of producing therapeutic levels of the desired therapeutic substance for several weeks, months or even longer. One exploratory approach for delivering such cellular therapies is to encapsulate the engineered cells into semi-permeable devices (e.g., hydrogel capsules), with the objective that the device structure isolates the cells from immune system cells, while allowing entry of nutrients for the cells and exit of the produced therapeutic substances. A need exists to improve upon this general approach to achieve increased viability and/or productivity of living cells contained in implantable devices.

SUMMARY

Described herein is a device comprising (i) at least one cell-containing compartment which comprises a polymer composition comprising a first cell-binding substance (CBS) and a plurality of cells. In an embodiment, the polymer composition comprises one or more additional cell-binding substances that are the same or different than the first CBS. In an embodiment, the amount of cell-binding substance(s) in the cell-containing compartment is an amount effective to increase viability of the cells and/or increase productivity of the cells in vitro (e.g., when the device is incubated in a cell culture medium) or in vivo (e.g., when the device is implanted in or otherwise administered to a test subject).

In an embodiment, the CBS is a cell-binding peptide (CBP) or cell-binding polypeptide (CBPP). In an embodiment, the CBS comprises a CBP covalently attached to a polymer molecule via a linker ("CBP-polymer"). In an embodiment, the CBS comprises a CBP covalently attached to a polymer molecule without a linker. In an embodiment, the polymer composition in the cell-containing compartment comprises one or more additional CBP-polymers which comprise different cell-binding peptides that are covalently attached to the same or different polymer type that is present in the first CBP-polymer. In an embodiment, cells encapsulated in a device described herein express at least a 1.25-fold, 1.5-fold, 2-fold, 5-fold, 8-fold, or 10-fold greater amount of the therapeutic agent at one or more time points after implant than when encapsulated in a substantially similar device lacking a cell-binding peptide, i.e., a CBS-null reference capsule or particle, as defined herein.

Various cell-binding peptides for use in the devices of the disclosure are described herein. In an embodiment, the cell-binding peptide is 40 amino acids or less (e.g., 35, 30 or less) or 25 amino acids or less (e.g., 20, 15, 10 or less) in length and comprises the cell binding sequence of a ligand for a cell-adhesion molecule (CAM). In an embodiment, the cell-binding peptide consists essentially of a cell binding sequence shown in Table 1 herein. In an embodiment, the cell binding sequence is RGD (SEQ ID NO: 43) or RGDSP (SEQ ID NO: 59). In an embodiment, the amino terminus of the cell-binding peptide is covalently attached to the polymer via an amino acid linker. In an embodiment, the amino acid in the linker is achiral. In an embodiment, the amino acid linker consists essentially of one to three glycine residues or one to three beta-alanine residues. In an embodiment, the cell-binding peptide consists essentially of RGD (SEQ ID NO: 43) or RGDSP (SEQ ID NO: 59) and the linker consists essentially of a single glycine residue or a single beta-alanine residue.

In one aspect, the polymer in the first CBP-polymer is a polysaccharide or other hydrogel-forming polymer. In an embodiment, the polymer in a second CBP-polymer and any other CBP-polymers that are present is also a hydrogel-forming polymer. In some embodiments, the hydrogel-forming polymer in each CBP-polymer in the cell-containing compartment is a polysaccharide. In some embodiments, the hydrogel-forming polymer in each CBP-polymer in the cell-containing compartment is an alginate. In some embodiments, the alginate in each CBP-polymer has a molecular weight of greater than 75 kDa (e.g., 75 kDa to 250 kDa) and a G:M ratio of greater than or equal to 1.5.

In an embodiment, each CBP-polymer present in the first compartment (e.g., in the polymer solution used to form the first compartment) has a cell-binding peptide density (% nitrogen as determined by combustion analysis, e.g., as described in Example 1 herein) of at least about 0.05% nitrogen (e.g., about 0.1%, 0.2% and 0.3% nitrogen) or within a range of between about any of 0.05%, 0.1%, 0.2% and 0.3% nitrogen as the lower value and any of 4%, 3%, 2% and 1% nitrogen as the upper value. In an embodiment, the CBP-polymer in the first compartment is an alginate with an approximate molecular weight of 75 kDa to 150 kD, a G:M ratio ≥1.5, that is covalently modified with GRGDSP (SEQ ID NO: 60).

In other embodiments, the density of a linker-RGD moiety (e.g., GRGDSP (SEQ ID NO: 60)) in each CBP-polymer (e.g., GRGDSP-alginate) in the first compartment (e.g., in the polymer solution used to form the first compartment) is determined by a quantitative peptide conjugation assay, e.g., by a quantitative peptide conjugation assay described herein. In an embodiment, the cells are engineered ARPE-19 cells, the linker-RGD moiety in the CBP-polymer is GRGDSP (SEQ ID NO: 60), the polymer is an alginate (e.g., sodium alginate) with an approximate molecular weight of 75 kDa to 150 kDa and a G:M ratio ≥1.5, and the determined conjugation density is expressed as micromoles of GRGDSP (SEQ ID NO: 60)/g of GRGDSP-alginate in solution (e.g., saline solution) with a viscosity of 80-120 cP. In an embodiment, the conjugation density for such a GRGDSP-alginate solution (MMW-Alg, G:M ratio ≥1.5) is about 0.1 to 1.0 micromoles/g or any of about 0.2 to about 0.8, about 0.3 to about 0.7 or about 0.3 to about 0.6 micromoles/g. In an embodiment, the engineered ARPE-19 cells comprise an exogenous coding sequence for a FVIII BDD protein, e.g., SEQ ID NO: 15. In an embodiment, the exogenous coding sequence is operably linked to a promoter sequence, e.g., nucleotides 337-2069 of SEQ ID NO:26.

In an embodiment, the cell-containing compartment also comprises an unmodified hydrogel-forming polymer which is the same or different than the polymer in the CBP-polymer. In an embodiment, both the CBP-polymer and the unmodified polymer are alginate with a molecular weight of 75 kDa (e.g., 75 kDa to 150 kDa) and a G:M ratio of greater than or equal to 1.5.

The plurality of cells (e.g., live cells) (e.g., viable cells) in the cell-containing compartment may be present as single cells, cell clusters (e.g., as spheroids), or attached to a microcarrier. In some embodiments, the plurality of live cells in the first compartment is at least 100, 250, 500, 750, 1,000, 2,500, 5,000, 10,000, 25,000, or 50,000 cells. In an embodiment, the plurality comprises cells derived from a cell line and engineered to express the therapeutic agent. In an embodiment, the cell line is an endothelial, epithelial, fibroblast, keratinocyte or mesenchymal cell line, e.g., a commercially available cell line listed in Table 5 herein. In an embodiment, the plurality of cells are engineered retinal pigment epithelial (RPE cells), e.g. cells engineered from the ARPE-19 cell line. In some embodiments, the plurality of cells is capable of expressing a therapeutic agent, for example, when the device is implanted into a subject.

In an aspect, the therapeutic agent expressed by the plurality of cells is a biological or chemical molecule (e.g., a nucleic acid, a polypeptide, a lipid, sugar or a small molecule) that is capable of directly or indirectly conferring a therapeutic benefit when the device implanted into a subject (e.g., a human). In an embodiment, the therapeutic agent is a protein that is secreted by the cells and which replaces or augments an endogenous protein that is missing or deficient in the subject, e.g., a blood clotting protein that improves blood clotting in a hemophilia patient or an enzyme that mediates the removal of a toxic metabolite which would otherwise build up in the body. In another embodiment, the therapeutic agent is a substance that is secreted by the cells and which performs or mediates a function that results in a therapeutic benefit to the subject, e.g., an inhibitory RNA molecule that inhibits the expression of one or more proteins by endogenous cells in the subject to generate a therapeutic benefit. In some embodiments, the therapeutic agent is a replacement therapy or a replacement protein, e.g., useful for the treatment of a blood clotting disorder or a lysosomal storage disease in a subject. In some embodiments, the therapeutic agent is a polypeptide useful for treating a blood clotting disorder, e.g., a Factor VIII protein or variant thereof, a Factor IX protein or variant thereof or a Factor VII protein or variant thereof.

In some embodiments, the device further comprises at least one means for mitigating the foreign body response (FBR), for example, mitigating the FBR when the device is implanted into or onto a subject. Various means for mitigating the FBR of the devices are described herein. In an embodiment, the means for mitigating the FBR comprises a combination of a spherical shape and a linear dimension, e.g., diameter, of at least 1 millimeter (mm), e.g., about 1.25 mm, about 1.5 mm, about 2.0 mm, about 2.5 mm, about 3.0 mm. In an embodiment, the means comprises a barrier compartment formed of a biocompatible polymer that surrounds the cell-containing compartment, and optionally a third compartment formed of a biocompatible polymer that surrounds the barrier compartment, to provide an additional biocompatible physical barrier between the cells in the first compartment and the subject's immune system. In an embodiment, the biocompatible polymer is an alginate.

In another embodiment, the means for mitigating the FBR comprises a compound that mitigates the FBR, e.g., an afibrotic compound as defined herein. In an embodiment, the afibrotic compound is disposed on an exterior surface of the device surface. In another embodiment, the means comprises a barrier compartment that surrounds the first compartment and comprises a polymer that is covalently modified with an afibrotic compound (an "afibrotic polymer", as defined herein). In some embodiments, an afibrotic compound is covalently attached to the exterior device surface and to a polymer within the barrier compartment, and optionally to a polymer within the cell-containing compartment. In an embodiment, the barrier compartment comprises an unmodified polymer which is the same or different than the polymer in the afibrotic polymer.

In an embodiment, the afibrotic compound is a compound of Formula (I):

(I)

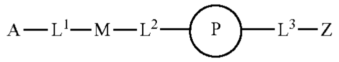

or a pharmaceutically acceptable salt thereof, wherein the variables A, $L^1$, M, $L^2$, P, $L^3$, and Z, as well as related subvariables, are defined herein. In some embodiments, the compound of Formula (I) or a pharmaceutically acceptable salt thereof (e.g., Formulas (I-a), (II), (II-a), (II-b), (III), (III-a), (III-b), (III-c), (III-d), or (III-e)) is a compound described herein, including for example, one of the compounds shown in Table 4 herein. In an embodiment, the afibrotic compound is Compound 100, Compound 101 or Compound 102 shown in Table 4.

In one aspect, a device of the disclosure is a 2-compartment hydrogel capsule (e.g., a microcapsule (less than 1 mm in diameter) or a millicapsule (at least 1 mm in diameter)) in which a cell-containing compartment (e.g., the inner compartment) comprising a plurality of cells (e.g., live cells) and one or more CBP-polymer(s) is surrounded by a barrier compartment (e.g., the outer compartment) comprising an afibrotic polymer. In an embodiment, the afibrotic compound is a compound of Formula (I). In an embodiment, the barrier compartment comprises two or more afibrotic polymers modified with different Formula (I) compounds and comprising the same or different hydrogel-forming polymers. In some embodiments, the inner cell-containing compartment comprises an afibrotic polymer comprising (i) a compound of Formula (I) which is the same or different than the afibrotic compound(s) in the outer barrier compartment and (ii) a polymer which is the same or different than in the CBP-polymer in the inner compartment or in the afibrotic-polymer(s) in the barrier compartment. In an embodiment, the barrier compartment comprises a mixture of the afibrotic polymer and an unmodified hydrogel-forming polymer. In an embodiment, the unmodified hydrogel-forming polymer is an alginate with a molecular weight of 150 kDa to 250 kDa and a G:M ratio of greater than or equal to 1.5.

In an embodiment, the compartments in a multi-compartment hydrogel capsule of the disclosure have approximately equal volumes, e.g., a variance of less than 20%, 10% or 5%. In an embodiment, the hydrogel capsule of the disclosure has two compartments and is spherical in shape, has a diameter of about 0.5 mm to about 1.5 mm, about 0.8 mm to about 1.2 mm, or about 1.0 mm to about 1.5 mm. In an embodiment, the thickness of the second compartment is about 10 to about 500 microns, 10 to about 300 microns, about 20 to about 150 microns, or about 40 to about 75 microns.

In another aspect, a device of the disclosure comprises a second plurality of cells which are encapsulated in the first cell-containing compartment or in a second cell-containing compartment. In an embodiment, the second plurality of cells are engineered from the same cell line as in the first plurality, but express a different therapeutic agent. In another embodiment, the second plurality of cells are engineered from a different cell line than in the first plurality, but express the same therapeutic agent as the first plurality.

In another aspect, the present disclosure features a preparation (e.g., a composition) comprising a plurality (at least any of 3, 6, 12, 25, 50 or more) of cell-containing devices described herein. In one embodiment, one or more of the devices in the plurality is a device comprising (i) a cell-containing compartment which comprises a plurality of cells (e.g., live cells) encapsulated in a polymer composition comprising a first polymer covalently modified with a first cell-binding peptide (first CBP-polymer), wherein the cells are capable of expressing a therapeutic agent when the device is implanted into a subject; and means for mitigating the foreign body response (FBR) when the device is implanted into the subject. In some embodiments, at least 75%, 80%, 85%, 90%, 95%, 99%, or more of the devices in the plurality are spherical hydrogel capsules. In some embodiments, the preparation is a pharmaceutically acceptable composition.

In another aspect, the present disclosure features a method of implanting into a subject a device or a device preparation described herein. In another aspect, the present disclosure features a method of providing a therapeutic agent to a subject comprising administering to the subject one or more of the devices described herein, wherein the plurality of cells in the administered device(s) has the ability to produce the therapeutic agent after administration. In another aspect, the present disclosure features a method of treating a subject in need of a therapeutic agent comprising administering to the subject one or more of the devices described herein, wherein the administered device(s) has the ability to produce the therapeutic agent. In some embodiments, the administering step comprises implanting in the subject a pharmaceutically acceptable preparation comprising a plurality of devices, each of which has the ability to produce the therapeutic agent. In some embodiments, the subject is a mammal (e.g., a human).

In another aspect, the present disclosure features a method of evaluating a device described herein. In some embodiments, the method comprises providing a device described herein and evaluating a structural or functional parameter of the device. In some embodiments, the method comprises evaluating the device or devices within a preparation described herein for one or more of a) cell viability and b) amount of the therapeutic agent produced. In some embodiments, the evaluation is performed at least 1, 5, 10, 20, 30, 60, 90 or 120 days after (i) formation of the device (or preparation of devices) or (ii) administration of the device (or preparation of devices) to a subject. In an embodiment, the evaluation further comprises assessing the amount of fibrosis and/or structural integrity of the device (or devices within a preparation) at least 10, 20, 30, 60, 90 or 120 days after implant into the subject. In some embodiments, the subject is a mammal (e.g., a mouse (e.g., an immune-competent mouse), a non-human primate, a human).

The details of one or more embodiments of the disclosure are set forth herein. Other features, objects, and advantages of the disclosure will be apparent from the Detailed Description, the Figures, the Examples, and the Claims.

BRIEF DESCRIPTION OF THE DRAWINGS

FIG. 1 discloses "GRGDSP" as SEQ ID NO: 60.

FIG. 22 discloses “RDGSP” as SEQ ID NO: 59.

FIGS. 24A-24DD show in Tables 7-11 exemplary amino acid sequences (SEQ ID NOs: 1, 3-7, 29-36) and coding sequences (SEQ ID NOs: 8-21) for therapeutic polypeptides and nucleotide sequences within an exemplary expression vector (SEQ ID NOs: 22-28) useful for engineering RPE cells.

DETAILED DESCRIPTION

Figure 1:
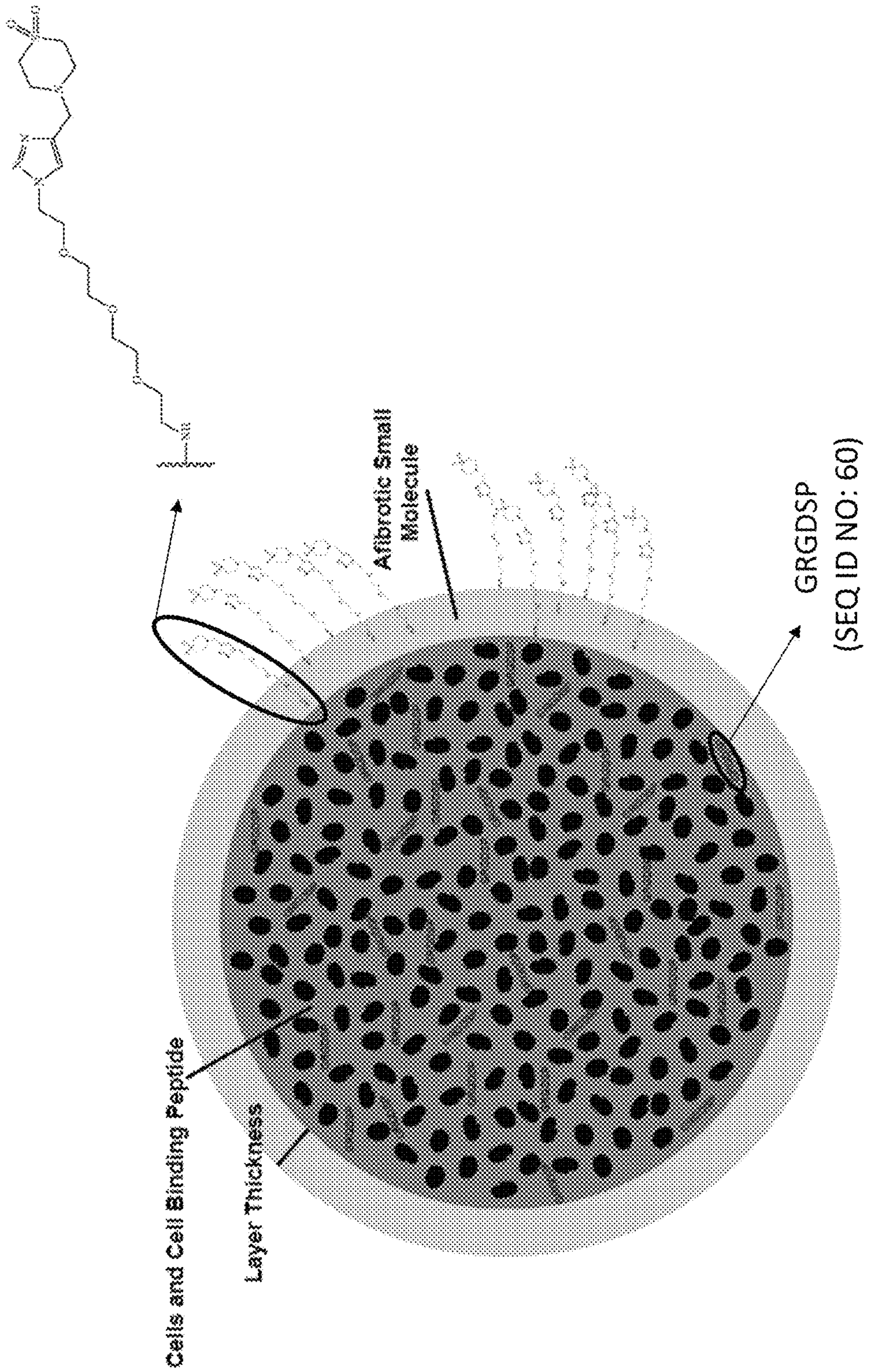
FIG. 1 illustrates an exemplary spherical hydrogel two-compartment capsule of the disclosure, with lines indicating: a first, inner compartment formed from a polymer covalently attached to a cell binding peptide and cells encapsulated therein; a second compartment; and an afibrotic compound disposed both within the second compartment and on the surface of the capsule.

The present disclosure features a device comprising at least one compartment comprising a plurality of cells (e.g., live cells) encapsulated by a polymer composition. The encapsulating polymer composition comprises at least one cell-binding substance (CBS), e.g., a cell-binding peptide (CBP) or cell-binding polypeptide (CBPP). The cells are capable of expressing a therapeutic agent when the device is implanted into a subject (e.g., a human) and the device further comprises means for mitigating the foreign body response (FBR) when the device is implanted into the subject. In an embodiment, the means for mitigating the FBR comprises a compound of Formula (I) disposed on the surface of the device. The present disclosure also provides a preparation comprising a plurality of devices described herein and methods of making and using the same. In some embodiments, the devices described herein and preparations or compositions thereof are useful for the prevention or treatment of a disease, disorder, or condition which can be prevented or treatment by in vivo expression of the therapeutic agent. In some embodiments, the devices and preparations have advantageous properties, e.g., the encapsulated cells have higher in vivo productivity and/or viability than substantially the same cells implanted in substantially the same device without the CBS, e.g. a CBS-null reference device.

Abbreviations and Definitions

Throughout the detailed description and examples of the disclosure the following abbreviations will be used.

CBP cell-binding peptide
CBPP cell-binding polypeptide
CBP-polymer polymer covalently modified with a CBP via a linker
CBS cell-binding substance
CM-Alg chemically modified alginate
CM-LMW-Alg chemically modified, low molecular weight alginate
CM-LMW-Alg-101 low molecular weight alginate, chemically modified with Compound 101 shown in Table 4
CM-HMW-Alg chemically modified, high molecular weight alginate
CM-HMW-Alg-101 high molecular weight alginate, chemically modified with Compound 101 shown in Table 4
CM-MMW-Alg chemically modified, medium molecular weight alginate
CM-MMW-Alg-101 medium molecular weight alginate, chemically modified with Compound 101 shown in Table 4
HMW-Alg high molecular weight alginate
MMW-Alg medium molecular weight alginate
RGD-alginate an alginate covalently modified with a peptide comprising the amino acid sequence RGD (SEQ ID NO: 43).
U-Alg unmodified alginate
U-HMW-Alg unmodified high molecular weight alginate
U-LMW-Alg unmodified low molecular weight alginate
U-MMW-Alg unmodified medium molecular weight alginate
70:30 CM-Alg:U-Alg 70:30 mixture (V:V) of a chemically modified alginate and an unmodified alginate, e.g., as described in Example 2

So that the disclosure may be more readily understood, certain technical and scientific terms used herein are specifically defined below. Unless specifically defined elsewhere in this document, all other technical and scientific terms used herein have the meaning commonly understood by one of ordinary skill in the art to which this disclosure belongs.

As used herein, including the appended claims, the singular forms of words such as "a," "an," and "the," include their corresponding plural references unless the context clearly dictates otherwise.

"About" or "approximately" means when used herein to modify a numerically defined parameter (e.g., a physical description of a hydrogel capsule such as diameter, sphericity, number of cells encapsulated therein, the number of capsules in a preparation), means that the recited numerical value is within an acceptable functional range for the defined parameter as determined by one of ordinary skill in the art, which will depend in part on how the numerical value is measured or determined, e.g., the limitations of the measurement system, including the acceptable error range for that measurement system. For example, "about" can mean a range of 20% above and below the recited numerical value. As a non-limiting example, a hydrogel capsule defined as having a diameter of about 1.5 millimeters (mm) and encapsulating about 5 million (M) cells may have a diameter of 1.2 to 1.8 mm and may encapsulate 4 M to 6 M cells. As another non-limiting example, a preparation of about 100 devices (e.g., hydrogel capsules) includes preparations having 80 to 120 devices. In some embodiments, the term "about" means that the modified parameter may vary by as much as 15%, 10% or 5% above and below the stated numerical value for that parameter. Alternatively, particularly with respect to certain properties of the devices described herein, such as cell productivity, or density of the CBP or the afibrotic compound, the term "about" can mean within an order of magnitude above and below the recited value, e.g., within 5-fold, 4-fold, 3-fold, 2-fold or 1-fold.

"Acquire" or "acquiring", as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., using a fluorescence microscope to acquire fluorescence microscopy data.

"Administer", "administering", or "administration", as used herein, refer to implanting, absorbing, ingesting, injecting or otherwise introducing into a subject, an entity described herein (e.g., a device or a preparation of devices), or providing such an entity to a subject for administration.

"Afibrotic", as used herein, means a compound or material that mitigates the foreign body response (FBR). For example, the amount of FBR in a biological tissue that is induced by implant into that tissue of a device (e.g., hydrogel capsule) comprising an afibrotic compound (e.g., a hydrogel capsule comprising a polymer covalently modified with a compound listed in Table 4) is lower than the FBR induced by implantation of an afibrotic-null reference device, i.e., a device that lacks any afibrotic compound, but is of substantially the same composition (e.g., same CBP-polymer, same cell type(s)) and structure (e.g., size, shape, no. of compartments). In an embodiment, the degree of the FBR is assessed by the immunological response in the tissue containing the implanted device (e.g., hydrogel capsule), which may include, for example, protein adsorption, macrophages, multinucleated foreign body giant cells, fibroblasts, and angiogenesis, using assays known in the art, e.g., as described in WO 2017/075630, or using one or more of the assays/methods described Vegas, A., et al., *Nature Biotechnol* (supra), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68 or F4/80), myofibroblasts (alpha-muscle actin, SMA) or general cellular deposition, quantification of 79 RNA sequences of known inflammation factors and immune cell markers, or FACS analysis for macrophage and neutrophil cells on retrieved devices (e.g., capsules) after 14 days in the intraperitoneal space of a suitable test subject, e.g., an immunocompetent mouse. In an embodiment, the FBR is assessed by measuring the levels in the tissue containing the implant of one or more biomarkers of immune response, e.g., cathepsin, TNF-α, IL-13, IL-6, G-CSF, GM-CSF, IL-4, CCL2, or CCL4. In some embodiments, the FBR induced by a device of the invention (e.g., a hydrogel capsule comprising an afibrotic compound disposed on its outer surface), is at least about 80%, about 85%, about 90%, about 95%, about 99%, or about 100% lower than the FBR induced by an FBR-null reference device, e.g., a device that is substantially identical to the test or claimed device except for lacking the means for mitigating the FBR (e.g., a hydrogel capsule that does not comprise an afibrotic compound but is otherwise substantially identical to the claimed capsule. In some embodiments, the FBR (e.g., level of a biomarker(s)) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Cell," as used herein, refers to an engineered cell or a cell that is not engineered. In an embodiment, a cell is an immortalized cell or an engineered cell derived from an immortalized cell. In an embodiment, the cell is a live cell, e.g., is viable as measured by any technique described herein or known in the art.

"Cell-binding peptide (CBP)", as used herein, means a linear or cyclic peptide that comprises an amino acid sequence that is derived from the cell binding domain of a ligand for a cell-adhesion molecule (CAM) (e.g., that mediates cell-matrix junctions or cell-cell junctions). The CBP is less than 50, 40 30, 25, 20, 15 or 10 amino acids in length. In an embodiment, the CBP is between 3 and 12 amino acids in length, 4 and 10 amino acids in length, or is 3, 4, 5, 6, 7 8, 9 or 10 amino acids in length. The CBP amino acid sequence may be identical to the naturally-occurring binding domain sequence or may be a conservatively substituted variant thereof. In an embodiment, the CAM ligand is a mammalian protein. In an embodiment, the CAM ligand is a human protein selected from the group of proteins listed in Table 1 below. In an embodiment, the CBP comprises a cell binding sequence listed in Table 1 below or a conservatively substituted variant thereof. In an embodiment, the CBP comprises at least one of the cell binding sequences listed in Table 1 below. In an embodiment, the CBP consists essentially of a cell binding sequence listed in Table 1 below. In an embodiment, the CBP is an RGD peptide, which means the peptide comprises the amino acid sequence RGD (SEQ ID NO: 43) and optionally comprises one or more additional amino acids located at one or both of the N-terminus and C-terminus. In an embodiment, the CBP is a cyclic peptide comprising RGD (SEQ ID NO: 43), e.g., one of the cyclic RGD peptides described in Vilaca, H. et al., *Tetrahedron* 70 (35):5420-5427 (2014). In an embodiment, the CBP is a linear peptide comprising RGD (SEQ ID NO: 43) and is less than 6 amino acids in length. In an embodiment, the CBP is a linear peptide that consists essentially of RGD (SEQ ID NO: 43) or RGDSP (SEQ ID NO: 59).

TABLE 1

Exemplary CAM Ligand Proteins and Cell Binding Sequences

| Protein | Cell Binding Sequence |
|---|---|
| E-cadherin | SWELYYPLRANL (SEQ ID NO: 37) |
| N-cadherin | HAVDI (SEQ ID NO: 38) |
| Collagen I | DGEA (SEQ ID NO: 39) |
| Collagen IV | FYFDLR (SEQ ID NO: 40)<br>GFOGER (SEQ ID NO: 41)<br>P(GPP)$_5$GFOGER(GPP)$_5$ (SEQ ID NO: 54)<br>(O in SEQ ID NO: 41 and 54 is 4-hydroxyproline) |
| Elastin | VAPG (SEQ ID NO: 42) |
| Fibrinogen | RGD (SEQ ID NO: 43)<br>GPR (SEQ ID NO: 44) |
| Fibronectin | RGD (SEQ ID NO: 43)<br>KQAGDV (SEQ ID NO: 45)<br>PHSRN (SEQ ID NO: 46)<br>PHSRNGGGGGGRGDS (SEQ ID NO: 55)<br>REDV (SEQ ID NO: 47) |
| Laminin | IKVAV (SEQ ID NO: 48)<br>SRARKQAASIKVAVADR (SEQ ID NO: 56)<br>LRE (SEQ ID NO: 49)<br>KQLREQ (SEQ ID NO: 57)<br>YIGSR (SEQ ID NO: 50) |
| Nidogen-1 | RGD (SEQ ID NO: 43) |
| Osteopontin | SVVYGLR (SEQ ID NO: 51) |
| Tenascin C (TN-C) | AEIDGIEL (SEQ ID NO: 52) |
| Tenascin-R | RGD (SEQ ID NO: 43) |
| Tenascin-X | RGD (SEQ ID NO: 43) |
| Thrombospondin | VTCG (SEQ ID NO: 53)<br>SVTCG (SEQ ID NO: 58) |
| Vitronectin | RGD (SEQ ID NO: 43) |
| Von Willebrand Factor | RGD (SEQ ID NO: 43) |

"CBP-polymer", as used herein, means a polymer comprising at least one cell-binding peptide molecule covalently attached to the polymer via a linker. In an embodiment, the polymer is not a peptide or a polypeptide. In an embodiment, the polymer in a CBP-polymer does not contain any amino acids. In an embodiment, the polymer in a CBP-polymer is a synthetic or naturally occurring polysaccharide, e.g., an alginate, e.g., a sodium alginate. In an embodiment, the linker is an amino acid linker (i.e., consists essentially of a single amino acid, or a peptide of several identical or different amino acids), which is joined via a peptide bond to the N-terminus or C-terminus of the CBP. In an embodiment, the C-terminus of an amino acid linker is joined to the N-terminus of the CBP and the N-terminus of the amino acid linker is joined to at least one pendant carboxyl group in the polysaccharide via an amide bond. In an embodiment, the structure of the linker-CBP is expressed as $G_{(1-4)}$-CBP, meaning that the linker has one, two, three or four glycine residues ("$G_{(1-4)}$" is disclosed as SEQ ID NO: 70). In an embodiment, one or more of the monosaccharide moieties in a CBP-polysaccharide, e.g., a CBP-alginate) is not modified with the CBP, e.g, the unmodified moiety has a free carboxyl group or lacks a modifiable pendant carboxyl group. In an embodiment, the number of polysaccharide moieties with a covalently attached CBP is less than any of the following values: 99%, 95%, 90%, 80%, 70%, 60%, 50%, 40% 30%, 20%, 10%, 5%, 1%.

In an embodiment, the density of CBP modification in the CBP-polymer is estimated by combustion analysis for percent nitrogen, e.g., as described in the Examples below. In an embodiment, the CBP-polymer is an RGD-polymer (e.g., an RGD-alginate), which is a polymer (e.g., an alginate) covalently modified with a linker-RGD molecule (e.g., a peptide consisting essentially of GRGD (SEQ ID NO: 62) or GRGDSP (SEQ ID NO: 60)) and the density of linker-RGD molecule modification (e.g., conjugation density) is about 0.05% nitrogen (N) to 1.00% N, about 0.10% N to about 0.75% N, about 0.20% N to about 0.50% N, or about 0.30% N to about 0.40% N, as determined using an assay described herein. In an embodiment, the conjugation density of the linker-RGD modification in an RGD-alginate (e.g., a MMW alginate covalently modified with GRGDSP (SEQ ID NO: 60)) is 0.1 to 1.0, 0.2 to 0.8, 0.3 to 0.7, 0.3 to 0.6, 0.4 to 0.6 micromoles of the linker-RGD moiety per g of the RGD-polymer in solution (e.g., saline solution) with a viscosity of 80-120 cP, as determined by any assay that is capable of quantitating the amount of a peptide conjugated to a polymer, e.g., a quantitative peptide conjugation assay described herein. Unless otherwise explicitly stated or readily apparent from the context, a specifically recited numerical concentration, concentration range, density or density range for a CBP in a CBP-polymer refers to the concentration or density of conjugated CBP molecules, i.e., it does not include any residual free (e.g., unconjugated) CBP that may be present in the CBP-polymer.

"Cell-binding polypeptide (CBPP)", as used herein, means a polypeptide of at least 50, at least 75, or at least 100 amino acids in length and comprising the amino acid sequence of a cell binding domain of a CAM ligand, or a conservatively substituted variant thereof. In an embodiment, the CAM ligand is a mammalian protein. In an embodiment, the CBPP amino acid comprises the naturally occurring amino acid sequence of a full-length CAM ligand, e.g., one of the proteins listed in Table 1, or a conservatively substituted variant thereof.

"CBP-density", as used herein, refers to the amount or concentration of a linker-CBP moiety in a CBP-polymer, e.g., an alginate modified with $G_{1-3}$RGD (SEQ ID NO: 63) or $G_{1-3}$RGDSP (SEQ ID NO: 64), unless otherwise explicitly stated herein.

"Cell-binding substance (CBS)", as used herein, means any chemical, biological or other type of substance (e.g., a small organic compound, a peptide, a polypeptide) that is capable of mimicking at least one activity of a ligand for a cell-adhesion molecule (CAM) or other cell-surface molecule that mediates cell-matrix junctions or cell-cell junctions or other receptor-mediated signaling. In an embodiment, when present in a polymer composition encapsulating cells, the CBS is capable of forming a transient or permanent bond or contact with one or more of the cells. In an embodiment, the CBS facilitates interactions between two or more live cells encapsulated in the polymer composition. In an embodiment, the presence of a CBS in a polymer composition encapsulating a plurality of cells, (e.g., live cells) is correlated with one or both of increased cell productivity (e.g., expression of a therapeutic agent) and increased cell viability when the encapsulated cells are implanted into a test subject, e.g., a mouse. In an embodiment, the CBS is physically attached to one or more polymer molecules in the polymer composition. In an embodiment, the CBS is a cell-binding peptide or cell-binding polypeptide, as defined herein.

"Conservatively modified variants" or conservative substitution", as used herein, refers to a variant of a reference peptide or polypeptide that is identical to the reference molecule, except for having one or more conservative amino acid substitutions in its amino acid sequence. In an embodiment, a conservatively modified variant consists of an amino acid sequence that is at least 70%, 80%, 85%, 90%, 95%, 97%, 98% or 99% identical to the reference amino acid sequence. A conservative amino acid substitution refers to substitution of an amino acid with an amino acid having similar characteristics (e.g., charge, side-chain size, hydrophobicity/hydrophilicity, backbone conformation and rigidity, etc.) and which has minimal impact on the biological activity of the resulting substituted peptide or polypeptide. Conservative substitution tables of functionally similar amino acids are well known in the art, and exemplary substitutions grouped by functional features are set forth in Table 2 below.

TABLE 2

Exemplary conservative amino acid substitution groups.

| Feature | Conservative Amino Group |
|---|---|
| Charge/Polarity | His, Arg, Lys |
| | Asp, Glu |
| | Cys, Thr, Ser, Gly, Asn, Gln, Tyr |
| | Ala, Pro, Met, Leu, Ile, Val, Phe, Trp |
| Hydrophobicity | Asp, Glu, Asn, Gln, Arg, Lys |
| | Cys, Ser, Thr, Pro, Gly, His, Tyr |
| | Ala, Met, Ile Leu, Val, Phe, Trp |
| Structural/Surface Exposure | Asp, Glu, Asn, Aln, His, Arg, Lys |
| | Cys, Ser, Tyr, Pro, Ala, Gly, Trp, Tyr |
| | Met, Ile, Leu, Val, Phe |
| Secondary Structure Propensity | Ala, Glu, Aln, His, Lys, Met, Leu, Arg |
| | Cys, Thr, Ile, Val, Phe, |

TABLE 2-continued

Exemplary conservative amino acid substitution groups.

| Feature | Conservative Amino Group |
|---|---|
| | Tyr, Trp |
| | Ser, Gly, Pro, Asp, Asn |
| Evolutionary Conservation | Asp, Glu |
| | His, Lys, Arg |
| | Asn, Gln |
| | Ser, Thr |
| | Leu, Ile, Val |
| | Phe, Tyr, Trp |
| | Ala, Gly |
| | Met, Cys |

"Consists essentially of", and variations such as "consist essentially of" or "consisting essentially of" as used throughout the specification and claims, indicate the inclusion of any recited elements or group of elements, and the optional inclusion of other elements, of similar or different nature than the recited elements, that do not materially change the basic or novel properties of the specified molecule, composition, device, or method. As a non-limiting example, a cell-binding peptide or a therapeutic protein that consists essentially of a recited amino acid sequence may also include one or more amino acids, including substitutions in the recited amino acid sequence, of one or more amino acid residues, which do not materially affect the relevant biological activity of the cell-binding peptide or the therapeutic protein, respectively. As another non-limiting example, a cell-binding peptide that consists essentially of a recited amino acid sequence may contain one or more covalently attached moieties (e.g., a radioactive or fluorescent label) that do not materially change the relevant biological activity of the cell-binding peptide, e.g., its ability to increase the viability or productivity of encapsulated cells as described herein.

"Derived from", as used herein with respect to cells, refers to cells obtained from tissue, cell lines, or cells, which optionally are then cultured, passaged, differentiated, induced, etc. to produce the derived cells. For example, mesenchymal stem cells can be derived from mesenchymal tissue and then differentiated into a variety of cell types.

"Device", as used herein, refers to any implantable object (e.g., a particle, a hydrogel capsule, an implant, a medical device), which contains cells (e.g., live cells) capable of expressing a therapeutic agent following implant of the device, and has a configuration that supports the viability of the cells by allowing cell nutrients to enter the device. In some embodiments, the device allows release from the device of metabolic byproducts and/or the therapeutic agent generated by the live cells.

"Differential volume," as used herein, refers to a volume of one compartment within a device described herein that excludes the space occupied by another compartment(s). For example, the differential volume of the second (e.g., outer) compartment in a 2-compartment device with inner and outer compartments, refers to a volume within the second compartment that excludes space occupied by the first (inner) compartment.

"Effective amount", as used herein, refers to an amount of a device, a device composition, or a component of the device or device composition, e.g, a plurality of hydrogel capsules comprising a cell, e.g., an engineered cell, or an agent, e.g., a therapeutic agent, produced by a cell, e.g., an engineered RPE cell, sufficient to elicit a biological response, e.g., to treat a disease, disorder, or condition. In some embodiments, the term "effective amount" refers to the amount of a component of the device, e.g., number of cells in the device, the density of an afibrotic compound disposed on the surface and/or in a barrier compartment of the device, the density of a CBS in the cell-containing compartment. As will be appreciated by those of ordinary skill in this art, the effective amount may vary depending on such factors as the desired biological endpoint, the pharmacokinetics of the therapeutic agent, composition or device (e.g., capsule, particle), the condition being treated, the mode of administration, and the age and health of the subject. An effective amount encompasses therapeutic and prophylactic treatment. For example, to mitigate the FBR, an effective amount of a compound of Formula (I) may reduce the fibrosis or stop the growth or spread of fibrotic tissue on or near the implanted device. As another example, an effective amount of a CBS may enhance the viability of the cells in the device (e.g., number of live cells) and/or increase the level of a therapeutic agent expressed and/or secreted by the cells. An effective amount of a device, composition or component, e.g., afibrotic compound or CBS, may be determined by any technique known in the art or described herein.

An "endogenous nucleic acid" as used herein, is a nucleic acid that occurs naturally in a subject cell.

An "endogenous polypeptide," as used herein, is a polypeptide that occurs naturally in a subject cell.

"Engineered cell," as used herein, is a cell (e.g., an RPE cell) having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide. In an embodiment, an engineered cell comprises an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a chromosomal or extra-chromosomal nucleic acid sequence, which comprises a sequence that encodes a polypeptide, or which is expressed as a polypeptide. In an embodiment, the exogenous nucleic acid sequence comprises a first chromosomal or extra-chromosomal exogenous nucleic acid sequence that modulates the conformation or expression of a second nucleic acid sequence, wherein the second amino acid sequence can be exogenous or endogenous. For example, an engineered cell can comprise an exogenous nucleic acid that controls the expression of an endogenous sequence. In an embodiment, an engineered cell comprises a polypeptide present at a level or distribution which differs from the level found in a similar cell that has not been engineered. In an embodiment, an engineered cell comprises an RPE engineered to produce an RNA or a polypeptide. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell (e.g., an RPE cell) comprises an exogenous nucleic acid sequence that comprises a chromosomal or extra-chromosomal nucleic acid sequence comprising a sequence that encodes a polypeptide, or which is expressed as a polypeptide. In an embodiment, the polypeptide is encoded by a codon optimized sequence to achieve higher expression of the polypeptide than a naturally-occurring coding sequence. The codon optimized sequence may be generated using a commercially available algorithm, e.g., GeneOptimizer (ThermoFisher Scientific), OptimumGene™ (GenScript, Piscataway, NJ USA), GeneGPS® (ATUM, Newark, CA USA), or Java Codon Adaptation Tool (JCat, www.jcat.de, Grote, A. et al., Nucleic Acids Research, Vol 33, Issue suppl_2, pp. W526-W531 (2005). In an embodiment, an engineered cell (e.g., an RPE cell) comprises an exogenous nucleic acid sequence that modulates the conformation or expression of an endogenous sequence. In an embodiment, an engineered cell (e.g., RPE cell) is cultured from a population of stably-transfected cells, or from a monoclonal cell line.

An "exogenous nucleic acid," as used herein, is a nucleic acid that does not occur naturally in a subject cell.

An "exogenous polypeptide," as used herein, is a polypeptide that does not occur naturally in a subject cell, e.g., engineered cell. Reference to an amino acid position of a specific sequence means the position of said amino acid in a reference amino acid sequence, e.g., sequence of a full-length mature (after signal peptide cleavage) wild-type protein (unless otherwise stated), and does not exclude the presence of variations, e.g., deletions, insertions and/or substitutions at other positions in the reference amino acid sequence.

"Factor VII protein" or "FVII protein" as used herein, means a polypeptide that comprises the amino acid sequence of a naturally occurring factor VII protein or variant thereof that has a FVII biological activity, e.g., promoting blood clotting, as determined by an art-recognized assay, unless otherwise specified. Naturally occurring FVII exists as a single chain zymogen, a zymogen-like two-chain polypeptide and a fully activated two-chain form (FVIIa). In some embodiments, reference to FVII includes single-chain and two-chain forms thereof, including zymogen-like and FVIIa. FVII proteins that may be produced by a device described herein, e.g., a device containing engineered RPE cells, include wild-type primate (e.g., human), porcine, canine, and murine proteins, as well as variants of such wild-type proteins, including fragments, mutants, variants with one or more amino acid substitutions and/or deletions. In some embodiments, a variant FVII protein is capable of being activated to the fully activated two-chain form (Factor Vila) that has at least 50%, 75%, 90% or more (including >100%) of the activity of wild-type Factor Vila. Variants of FVII and FVIIa are known, e.g., marzeptacog alfa (activated) (MarzAA) and the variants described in European Patent No. 1373493, U.S. Pat. Nos. 7,771,996, 9,476,037 and US published application No. US20080058255.

Factor VII biological activity may be quantified by an art recognized assay, unless otherwise specified. For example, FVII biological activity in a sample of a biological fluid, e.g., plasma, may be quantified by (i) measuring the amount of Factor Xa produced in a system comprising tissue factor (TF) embedded in a lipid membrane and Factor X (Persson et al., *J. Biol. Chem.* 272:19919-19924, 1997); (ii) measuring Factor X hydrolysis in an aqueous system; (iii) measuring its physical binding to TF using an instrument based on surface plasmon resonance (Persson, *FEBS Letts.* 413:359-363, 1997); or (iv) measuring hydrolysis of a synthetic substrate; and/or (v) measuring generation of thrombin in a TF-independent in vitro system. In an embodiment, FVII activity is assessed by a commercially available chromogenic assay (BIOPHEN FVII, HYPHEN BioMed Neuville sur Oise, France), in which the biological sample containing FVII is mixed with thromboplastin calcium, Factor X and SXa-11 (a chromogenic substrate specific for Factor Xa.

"Factor VIII protein" or "FVIII protein" as used herein, means a polypeptide that comprises the amino acid sequence of a naturally occurring factor VIII polypeptide or variant thereof that has an FVIII biological activity, e.g., coagulation activity, as determined by an art-recognized assay, unless otherwise specified. FVIII proteins that may be expressed by a device described herein, e.g., a device containing engineered RPE cells, include wild-type primate (e.g., human), porcine, canine, and murine proteins, as well as variants of such wild-type proteins, including fragments, mutants, variants with one or more amino acid substitutions and/or deletions, B-domain deletion (BDD) variants, single chain variants and fusions of any of the foregoing wild-type or variants with a half-life extending polypeptide. In an embodiment, the cells are engineered to encode a precursor factor VIII polypeptide (e.g., with the signal sequence) with a full or partial deletion of the B domain. In an embodiment, the cells are engineered to encode a single chain factor VIII polypeptide which contains a variant FVIII protein preferably has at least 50%, 75%, 90% or more (including >100%) of the coagulation activity of the corresponding wild-type factor VIII. Assays for measuring the coagulation activity of FVIII proteins include the one stage or two stage coagulation assay (Rizza et al., 1982, Coagulation assay of FVIII:C and FIXa in Bloom ed. The Hemophelias. NY Churchill Livingston 1992) or the chromogenic substrate FVIII:C assay (Rosen, S. 1984. *Scand J Haematol* 33:139-145, suppl.).

A number of FVIII-BDD variants are known, and include, e.g., variants with the full or partial B-domain deletions disclosed in any of the following U.S. Pat. No. 4,868,112 (e.g., col. 2, line 2 to col. 19, line 21 and table 2); U.S. Pat. No. 5,112,950 (e.g., col. 2, lines 55-68, FIG. 2, and example 1); U.S. Pat. No. 5,171,844 (e.g., col. 4, line 22 to col. 5, line 36); U.S. Pat. No. 5,543,502 (e.g., col. 2, lines 17-46); U.S. Pat. Nos. 5,595,886; 5,610,278; 5,789,203 (e.g., col. 2, lines 26-51 and examples 5-8); U.S. Pat. No. 5,972,885 (e.g., col. 1, lines 25 to col. 2, line 40); U.S. Pat. No. 6,048,720 (e.g., col. 6, lines 1-22 and example 1); U.S. Pat. Nos. 6,060,447; 6,228,620; 6,316,226 (e.g., col. 4, line 4 to col. 5, line 28 and examples 1-5); U.S. Pat. Nos. 6,346,513; 6,458,563 (e.g., col. 4, lines 25-53) and 7,041,635 (e.g., col. 2, line 1 to col. 3, line 19, col. 3, line 40 to col. 4, line 67, col. 7, line 43 to col. 8, line 26, and col. 11, line 5 to col. 13, line 39).

In some embodiments, a FVIII-BDD protein produced by a device described herein (e.g., expressed by engineered cells contained in the device) has one or more of the following deletions of amino acids in the B-domain: (i) most of the B domain except for amino-terminal B-domain sequences essential for intracellular processing of the primary translation product into two polypeptide chains (WO 91/09122); (ii) a deletion of amino acids 747-1638 (Hoeben R. C., et al. *J. Biol. Chem.* 265 (13): 7318-7323 (1990)); amino acids 771-1666 or amino acids 868-1562 (Meulien P., et al. *Protein Eng.* 2(4):301-6 (1988); amino acids 982-1562 or 760-1639 (Toole et al., *Proc. Natl. Acad. Sci. U.S.A.* 83:5939-5942 (1986)); amino acids 797-1562 (Eaton et al., *Biochemistry* 25:8343-8347 (1986)); 741-1646 (Kaufman, WO 87/04187)), 747-1560 (Sarver et al., DNA 6:553-564 (1987)); amino acids 741-1648 (Pasek, WO 88/00831)), amino acids 816-1598 or 741-1689 (Lagner (Behring Inst. Mitt. (1988) No 82:16-25, EP 295597); a deletion that includes one or more residues in a furin protease recognition sequence, e.g., LKRHQR (SEQ ID NO: 65) at amino acids 1643-1648, including any of the specific deletions recited in U.S. Pat. No. 9,956,269 at col. 10, line 65 to col. 11, line 36.

In other embodiments, a FVIII-BDD protein retains any of the following B-domain amino acids or amino acid sequences: (i) one or more N-linked glycosylation sites in the B-domain, e.g., residues 757, 784, 828, 900, 963, or optionally 943, first 226 amino acids or first 163 amino acids (Miao, H. Z., et al., *Blood* 103(a): 3412-3419 (2004), Kasuda, A., et al., *J. Thromb. Haemost.* 6: 1352-1359 (2008), and Pipe, S. W., et al., *J. Thromb. Haemost.* 9: 2235-2242 (2011).

In some embodiments, the FVIII-BDD protein is a single-chain variant generated by substitution of one or more amino acids in the furin protease recognition sequence (LKRHQR (SEQ ID NO: 65) at amino acids 1643-1648) that prevents proteolytic cleavage at this site, including any of the substitutions at the R1645 and/or R1648 positions described in U.S. Pat. Nos. 10,023,628, 9,394,353 and 9,670,267.

In some embodiments, any of the above FVIII-BDD proteins may further comprise one or more of the following variations: a F309S substitution to improve expression of the FVIII-BDD protein (Miao, H. Z., et al., Blood 103(a): 3412-3419 (2004); albumin fusions (WO 2011/020866); and Fc fusions (WO 04/101740).

All FVIII-BDD amino acid positions referenced herein refer to the positions in full-length human FVIII, unless otherwise specified.

"Factor IX protein" or "FIX protein", as used herein, means a polypeptide that comprises the amino acid sequence of a naturally occurring factor IX protein or variant thereof that has a FIX biological activity, e.g., coagulation activity, as determined by an art-recognized assay, unless otherwise specified. FIX is produced as an inactive zymogen, which is converted to an active form by factor XIa excision of the activation peptide to produce a heavy chain and a light chain held together by one or more disulfide bonds. FIX proteins that may be produced by devices described herein (e.g., a device containing engineered RPE cells) include wild-type primate (e.g., human), porcine, canine, and murine proteins, as well as variants of such wild-type proteins, including fragments, mutants, variants with one or more amino acid substitutions and/or deletions and fusions of any of the foregoing wild-type or variant proteins with a half-life extending polypeptide. In an embodiment, cells are engineered to encode a full-length wild-type human factor IX polypeptide (e.g., with the signal sequence) or a functional variant thereof. A variant FIX protein preferably has at least 50%, 75%, 90% or more (including >100%) of the coagulation activity of wild-type factor VIX. Assays for measuring the coagulation activity of FIX proteins include the Biophen Factor IX assay (Hyphen BioMed) and the one stage clotting assay (activated partial thromboplastin time (aPTT), e.g., as described in EP 2 032 607, thrombin generation time assay (TGA) and rotational thromboelastometry, e.g., as described in WO 2012/006624.

A number of functional FIX variants are known and may be expressed by engineered cells encapsulated in a device described herein, including any of the functional FIX variants described in the following international patent publications: WO 02/040544 at page 4, lines 9-30 and page 15, lines 6-31; WO 03/020764 in Tables 2 and 3 at pages 14-24, and at page 12, lines 1-27; WO 2007/149406 at page 4, line 1 to page 19, line 11; WO 2007/149406 A2 at page 19, line 12 to page 20, line 9; WO 08/118507 at page 5, line 14 to page 6, line 5; WO 09/051717 at page 9, line 11 to page 20, line 2; WO 09/137254 at page 2, paragraph [006] to page 5, paragraph [011] and page 16, paragraph [044] to page 24, paragraph [057]; WO 09/130198 A2 at page 4, line 26 to page 12, line 6; WO 09/140015 at page 11, paragraph [0043] to page 13, paragraph [0053]; WO 2012/006624; WO 2015/086406.

In certain embodiments, the FIX polypeptide comprises a wild-type or variant sequence fused to a heterologous polypeptide or non-polypeptide moiety extending the half-life of the FIX protein. Exemplary half-life extending moieties include Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. An exemplary FIX polypeptide is the rFIXFc protein described in WO 2012/006624, which is an FIXFc single chain (FIXFc-sc) and an Fc single chain (Fc-sc) bound together through two disulfide bonds in the hinge region of Fc.

FIX variants also include gain and loss of function variants. An example of a gain of function variant is the "Padua" variant of human FIX, which has a L (leucine) at position 338 of the mature protein instead of an R (arginine) (corresponding to amino acid position 384 of SEQ ID NO:2), and has greater catalytic and coagulant activity compared to wild-type human FIX (Chang et al., J. Biol. Chem., 273:12089-94 (1998)). An example of a loss of function variant is an alanine substituted for lysine in the fifth amino acid position from the beginning of the mature protein, which results in a protein with reduced binding to collagen IV (e.g., loss of function).

"Interleukin-2 protein" or "IL-2 protein", as used herein means a polypeptide comprising the amino acid sequence of a naturally-occurring IL-2 protein or variant thereof that has an IL-2 biological activity, e.g., activate IL-2 receptor signaling in Treg cells, as determined by an art-recognized assay, unless otherwise specified. IL-2 proteins that may be produced by a device described herein, e.g., a device containing engineered RPE cells, include wild-type primate (e.g., human), porcine, canine, and murine proteins, as well as variants of such wild-type proteins. A variant IL-2 protein preferably has at least 50%, 75%, 90% or more (including >100%) of the biological activity of the corresponding wild-type IL-2. Biological activity assays for IL-2 proteins are described in U.S. Pat. No. 10,035,836, and include, e.g., measuring the levels of phosphorylated STAT5 protein in Treg cells compared to CD4+CD25−/low T cells or NK cells. Variant IL-2 proteins that may be produced by a device of the present disclosure (e.g., a device containing engineered RPE cells) include proteins with one or more of the following amino acid substitutions: N88R, N88I, N88G, D20H, Q126L, Q126F, and C125S or C125A.

"Islet cell" as used herein means a cell that comprises any naturally occurring or any synthetically created, or modified, cell that is intended to recapitulate, mimic or otherwise express, in part or in whole, the functions, in part or in whole, of the cells of the pancreatic islets of Langerhans. The term "islet cells" includes glucose-responsive, insulin producing cells derived from stem cells, e.g., from an induced pluripotent stem cell line.

"Mannitol", as used herein, refers to D-mannitol unless otherwise explicitly stated.

"Medium molecular weight alginate," or "MMW-Alg" as used herein means an alginate with an approximate molecular weight of 75 kDa to 150 kDa.

"Mesenchymal stem function cell" or "MSFC," as those terms are used herein, refers to a cell derived from, or having at least one characteristic specific to a cell of, mesodermal lineage, and wherein the MSFC is i) not in a terminal state of differentiation and ii) can terminally differentiate into one or more cell types. An MSFC does not comprise a cell of endodermal origin, e.g., a gut cell, or of ectodermal origin, e.g., a cell derived from skin, CNS, or a neural cell. In an embodiment, the MSFC is multipotent. In an embodiment, the MSFC is not totipotent. In an embodiment, an MSFC comprises one or more of the following characteristics:

a) it comprises a mesenchymal stem cell (MSC) or a cell derived therefrom, including a cell derived from a primary cell culture of MSCs, a cell isolated directly (without long term culturing, e.g., less than 5 or 10 passages or rounds of cell division since isolation) from naturally occurring MSCs, e.g., from a human or other mammal, a cell derived from a transformed, a pluripotent, an immortalized, or a long term (e.g., more than 5 or 10 passages or rounds of cell division) MSC culture.

b) it comprises a cell that has been obtained from a less differentiated cell, e.g., a cell developed, programmed, or reprogramed (e.g., in vitro) into an MSC or a cell that is, except for any genetic engineering, substantially similar to one or more of a naturally occurring MSC or a cell from a primary or long term culture of MSCs, or a cell described in a) above. Examples of less differentiated cells from which MSFC can be derived include IPS cells, embryonic stem cells, or other totipotent or pluripotent cells; see, e.g., Chen, Y. S. et al (2012) *Stem Cells Transl Med* 1(83-95); Frobel, J et al (2014) *Stem Cell Reports* 3(3):414-422; Zou, L et al (2013) Sci Rep 3:2243;

c) it is multipotent, e.g., as measured by any assay capable of providing information about cell multipotency, e.g., microscopy;

d) it exhibits a characteristic mononuclear ovoid, stellate shape or spindle shape, with a round to oval nucleus. The oval elongate nucleus may have prominent nucleoli and a mix of heterochromatin and euchromatin. An MSFC (e.g., an MSC) may have little cytoplasm, but many thin processes that appear to extend from the nucleus;

e) it is capable of cell division, e.g., as measured any assay capable of providing information about cell division, e.g., microscopy. In an embodiment, an MSFC is capable of cell division in culture (e.g., prior to being encapsulated or incorporated into a device). In an embodiment, it is capable of cell division after being encapsulated, e.g., encapsulated as described herein, or incorporated into a device (e.g., a device described herein). In an embodiment, it is incapable of cell division after reaching confluence;

f) it is capable of differentiating into a mesenchymal cell lineage, e.g., an osteoblast, a chrondoblast, an adipocyte, or a fibroblast;

g) it expresses a mesenchymal cell marker, e.g., one, two, three, four, five or all of CD105, CD106, CD73, CD90, Stro-1, CD49a, CD29, CD44, CD146, CD166, TNAP+, THY-1+, Stro-2, Stro-4, and alkaline phosphatase;

h) it does not express significant levels of one, two, three, or any of CD34, CD31, VE-cadherin, CD45, HLA-DR, CD lib and a glycophorin or leukocyte differentiation antigen, e,g, CD14, CD33, CD3 and CD19;

i) it expresses one, two, or all of CD75, CD90, and CD105 and does not express one, two, or any of CD45, CD34, and CD14;

j) it is anti-inflammatory or immune dampening, e.g., as measured by any method capable of providing information regarding inflammation, e.g., in vivo inhibition of T cell proliferation;

k) it is capable of being adherent, e.g., plastic adherent, e.g., as determined by, e.g., visual inspection; or l) can grow in three dimensions, e.g., as determined by, e.g., visual inspection.

"Parathyroid hormone" or "PTH" as used herein means a polypeptide or peptide that comprises the amino acid sequence of a naturally occurring parathyroid hormone polypeptide or peptide or variant thereof that has a PTH biological activity, e.g., as determined by an art recognized assay. PTH polypeptides and peptides that may be expressed by encapsulated cells described herein include wild-type primate (e.g., human), porcine, canine, and murine proteins, as well as variants of such wild-type proteins. Such PTH polypeptides and peptides may consist essentially of the wild-type human sequence for pre-pro-PTH polypeptide (115 amino acids), pro-PTH polypeptide (90 amino acids), the mature 84-amino acid peptide (PTH(1-84)), and biologically active variants thereof, such as the truncated variant peptide PTH(1-34). PTH peptide variants with one or more amino acid substitutions in the human wild-type sequence have been described, e.g., in U.S. Pat. Nos. 7,410,948 and 8,563,513 and in US Patent Application Publication No. 20130217630. A PTH variant preferably has at least 50%, 75%, 90% or more (including >100%) of a biological activity of the corresponding wild-type PTH. An assay to detect certain PTH variants by tandem mass spectrometry is described in U.S. Pat. No. 8,383,417. A biological activity assay for PTH peptide variants—stimulation of adenylate cyclase as determined by measuring cAMP levels—is described in U.S. Pat. No. 7,410,948.

"Poloxamer", as used herein, refers to the standard generic term for a class of nonionic triblock linear copolymers composed of a central hydrophobic chain of polyoxypropylene (polypropylene oxide)) flanked by two polyoxyethylene (poly(ethylene oxide)) moieties.

"Poloxamer 188" or "P 188", as used herein, refers to a poloxamer with an approximate molecular mass of 1800 g/mole for the polyoxypropylene core and an oxyethylene content of about 80% weight percent, e.g., 79.0 to 83.7 percent. In an embodiment, poloxamer 188 has an average molecular weight of 8350 g/mole. In an embodiment, poloxamer 188 has an average molecular weight of 7680 g/mole to 9510 g/mole, e.g., as determined by size exclusion chromatography, and an oxyethylene content of 81.8±1.9% weight percent. In an embodiment, each polyoxyethylene chain in poloxamer 188 has 75-85 (e.g., 80) ethylene oxide monomers and the polyoxypropylene core has 25-30 (e.g., 27) propylene oxide monomers. In an embodiment, poloxamer 188 used in a process described herein substantially meets the specifications set forth in a poloxamer monograph published by the United States Pharmacopeia-National Formulary (USP-NF) or the European Pharmacopoeia (Ph. Eur.) that is official at the time the process is performed.

"Polymer composition", as used herein, is a composition (e.g., a solution, mixture) comprising one or more polymers. As a class, "polymers' includes homopolymers, heteropolymers, co-polymers, block polymers, block co-polymers and can be both natural and synthetic. Homopolymers contain one type of building block, or monomer, whereas co-polymers contain more than one type of monomer.

"Polypeptide", as used herein, refers to a polymer comprising amino acid residues linked through peptide bonds and having at least two, and in some embodiments, at least 10, 50, 75, 100, 150 or 200 amino acid residues.

"Prevention," "prevent," and "preventing" as used herein refers to a treatment that comprises administering or applying a therapy, e.g., administering a composition of devices encapsulating cells (e.g., as described herein), prior to the onset of a disease, disorder, or condition to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

A "replacement therapy" or "replacement protein" is a therapeutic protein or functional fragment thereof that replaces or augments a beneficial function of a protein that is diminished, present in insufficient quantity, altered (e.g., mutated) or lacking in a subject having a disease or condition related to the diminished, altered or lacking protein. Examples are certain blood clotting factors in certain blood clotting disorders or certain lysosomal enzymes in certain lysosomal storage diseases. In an embodiment, a replacement therapy or replacement protein provides the function of an endogenous protein. In an embodiment, a replacement therapy or replacement protein has the same amino acid sequence of a naturally occurring variant of the replaced protein, e.g., a wild type allele or an allele not associated with a disorder. In an embodiment, or replacement therapy or a replacement protein differs in amino acid sequence from a naturally occurring variant, e.g., a wild type allele or an allele not associated with a disorder, e.g., the allele carried by a subject, at no more than about 1, 2, 3, 4, 5, 10, 15 or 20% of the amino acid residues.

"Reference device", as used herein with respect to a claimed device (e.g., hydrogel capsule), means a device (e.g., hydrogel capsule) that: (i) lacks a particular feature, e.g., FBR-mitigating means (e.g., a barrier compartment comprising an afibrotic compound (as defined herein) or a CBS (as defined herein) (e.g., an RGD polymer), (ii) encapsulates in the cell-containing compartment about the same quantity of cells of the same cell type(s) as in the claimed device, and (iii) has a substantially similar polymer composition and structure as in the claimed device other than lacking the particular feature (e.g., the afibrotic compound or CBS). In an embodiment, the number of live cells in the cell-containing compartment of a reference device is within 80% to 120%, or within 90% to 110%, of the number of live cells in the cell-containing compartment of the claimed device. In an embodiment, the cells in the reference and claimed devices are obtained from the same cell culture. In an embodiment, a substantially similar polymer composition means all polymers in the reference and claimed device, including the polymer component of any CBP-polymer and afibrotic polymer, as applicable, are of the same chemical and molecular weight class (e.g., an alginate with high G content and the same molecular weight range). For example, in an embodiment, the cell-containing compartment of a CBP-null reference device is formed from the unmodified version of the polymer (e.g., alginate) in the CBP-polymer used to form the cell-containing compartment of the claimed device. In some embodiments in which a claimed two-compartment hydrogel millicapsule has (i) an inner compartment formed from a CBP-polymer encapsulating the plurality of cells and (ii) an outer compartment formed from a mixture of a chemically-modified polymer (e.g., a CM-LMW-alginate as described herein) and an unmodified polymer (e.g., an U-HMW-alginate as described herein), then the outer compartments of the reference and claimed capsules are formed from the same polymer mixture, while the inner compartment of the reference capsule is formed from a suspension of cells in the same polymer mixture used for the outer compartment. In an embodiment, a substantially similar structure means the reference and claimed devices have the same number of compartments (e.g., one, two, three, etc.) and about the same size and shape.

"RPE cell" as used herein refers to a cell having one or more of the following characteristics: a) it comprises a retinal pigment epithelial cell (RPE) (e.g., cultured using the ARPE-19 cell line (ATCC® CRL-2302™)) or a cell derived therefrom, e.g., by stably transfecting cells cultured from the ARPE-19 cell line with an exogenous sequence that encodes a therapeutic protein or otherwise engineering such cultured ARPE-19 cells to express an exogenous protein or other exogenous substance, a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogramed (e.g., in vitro) into an RPE cell or a cell that is, except for any genetic engineering, substantially similar to one or more of a naturally occurring RPE cell or a cell from a primary or long term culture of RPE cells (e.g., the cell can be derived from an IPS cell); or c) a cell that has one or more of the following properties: i) it expresses one or more of the biomarkers CRALBP, RPE-65, RLBP, BEST1, or αB-crystallin; ii) it does not express one or more of the biomarkers CRALBP, RPE-65, RLBP, BEST1, or αB-crystallin; iii) it is naturally found in the retina and forms a monolayer above the choroidal blood vessels in the Bruch's membrane; iv) it is responsible for epithelial transport, light absorption, secretion, and immune modulation in the retina; or v) it has been created synthetically, or modified from a naturally occurring cell, to have the same or substantially the same genetic content, and optionally the same or substantially the same epigenetic content, as an immortalized RPE cell line (e.g., the ARPE-19 cell line (ATCC® CRL-2302™)). In an embodiment, an RPE cell described herein is engineered, e.g., to have a new property, e.g., the cell is engineered to express the therapeutic agent when encapsulated in the polymer composition comprising a CBP or CBS. In other embodiments, an RPE cell is not engineered.

"Saline solution" as used herein, means normal saline, i.e., water containing 0.9% NaCl, unless otherwise specified.

"Sequence identity" or "percent identical", when used herein to refer to two nucleotide sequences or two amino acid sequences, means the two sequences are the same within a specified region, or have the same nucleotides or amino acids at a specified percentage of nucleotide or amino acid positions within the specified when the two sequences are compared and aligned for maximum correspondence over a comparison window or designated region. Sequence identity may be determined using standard techniques known in the art including, but not limited to, any of the algorithms described in US Patent Application Publication No. 2017/02334455. In an embodiment, the specified percentage of identical nucleotide or amino acid positions is at least about 80%, 85%, 90%, 91%, 92%, 93%, 94%, 95%, 96%, 97%, 98%, 99% or higher.

"Spherical" as used herein, means a device (e.g., a hydrogel capsule or other particle) having a curved surface that forms a sphere (e.g., a completely round ball) or sphere-like shape, which may have waves and undulations, e.g., on the surface. Spheres and sphere-like objects can be mathematically defined by rotation of circles, ellipses, or a combination around each of the three perpendicular axes, a, b, and c. For a sphere, the three axes are the same length. Generally, a sphere-like shape is an ellipsoid (for its averaged surface) with semi-principal axes within 10%, or 5%, or 2.5% of each other. The diameter of a sphere or sphere-like shape is the average diameter, such as the average of the semi-principal axes.

"Spheroid", as that term is used herein to refer to a device (e.g., a hydrogel capsule or other particle), means the device has (i) a perfect or classical oblate spheroid or prolate spheroid shape or (ii) has a surface that roughly forms a spheroid, e.g., may have waves and undulations and/or may be an ellipsoid (for its averaged surface) with semi-principal axes within 100% of each other.

"Subject" as used herein refers to a human or non-human animal. In an embodiment, the subject is a human (i.e., a male or female), e.g., of any age group, a pediatric subject (e.g., infant, child, adolescent) or adult subject (e.g., young adult, middle-aged adult, or senior adult). In an embodiment, the subject is a non-human animal, for example, a mammal (e.g., a mouse, a dog, a primate (e.g., a cynomolgus monkey or a rhesus monkey)). In an embodiment, the subject is a commercially relevant mammal (e.g., a cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Total volume," as used herein, refers to a volume within one compartment of a multi-compartment device that includes the space occupied by another compartment. For example, the total volume of the second (e.g., outer) compartment of a two-compartment device refers to a volume within the second compartment that includes space occupied by the first compartment.

"Treatment," "treat," and "treating" as used herein refers to one or more of reducing, reversing, alleviating, delaying the onset of, or inhibiting the progress of one or more of a symptom, manifestation, or underlying cause, of a disease, disorder, or condition. In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., considering a history of symptoms and/or in light of genetic or other susceptibility factors). Treatment may also be continued after symptoms have resolved, for example, to delay or prevent recurrence. In some embodiments, treatment comprises prevention and in other embodiments it does not.

"Von Willebrand factor protein" or "VWF protein", as used herein, means a polypeptide that comprises the amino acid sequence of a naturally occurring VWF polypeptide or variant thereof that has VWF biological activity, e.g., FVIII binding activity, as determined by an art-recognized assay, unless otherwise specified. VWF proteins that may be produced by a device described herein (e.g., expressed by engineered cells contained in the device) include wild-type primate (e.g., human), porcine, canine, and murine proteins, as well as variants of such wild-type proteins. The encapsulated cells may be engineered to encode any of the following VWF polypeptides: precursor VWF of 2813 amino acids, a VWF lacking the signal peptide of 22 amino acids and optionally the prepropeptide of 741 amino acids, mature VWF protein of 2050 amino acids, and truncated variants thereof, such as a VWF fragment sufficient to stabilize endogenous FVIII levels in VWF-deficient mice, e.g, a truncated variant containing the D'D3 region (amino acids 764-1247) or the D1D2D'D3 region; and VWF variants with one or more amino acid substitutions, e.g., in the D' region as described in U.S. Pat. No. 9,458,223. A variant VWF protein preferably has at least 50%, 75%, 90% or more (including >100%) of a biological activity of the corresponding wild-type VWF protein. Art-recognized assays for determining the biological activity of a VWF include ristocetin co-factor activity (Federici A B et al. 2004. *Haematologica* 89:77-85), binding of VWF to GP Iba of the platelet glycoprotein complex Ib-V-IX (Sucker et al. 2006. *Clin Appl Thromb Hemost.* 12:305-310), and collagen binding (Kallas & Talpsep. 2001. *Annals of Hematology* 80:466-471).

In some embodiments, the VWF protein produced by a device of the disclosure comprises a naturally-occurring or variant VWF amino acid sequence fused to a heterologous polypeptide or non-polypeptide moiety extending the half-life of the VWF protein. Exemplary half-life extending moieties include Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof.

Selected Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry, University Science Books, Sausalito,* 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 10 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_8$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH═CH—O—CH_3$, $—Si(CH_3)_3$, $—CH_2—CH═N—OCH_3$, $—CH═CH—N(CH_3)—CH_3$, $—O—CH_3$, and $—O—CH_2—CH_3$. Up to two or three heteroatoms may be consecutive, such as, for example, $—CH_2—NH—OCH_3$ and $—CH_2—O—Si(CH_3)_3$. Where "heteroalkyl" is recited, followed by recitations of specific heteroalkyl groups, such as $—CH_2O$, $—NR^CR^D$, or the like, it will be understood that the terms heteroalkyl and $—CH_2O$ or $—NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as $—CH_2O$, $—NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_2$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ may represent both $—C(O)_2R'—$ and $—R'C(O)_2—$.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5] decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings.

"Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom.

As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein. When compounds of Formula (I) used to prepare devices of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the devices of the present disclosure (e.g., a particle, a hydrogel capsule) contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

Devices of the present disclosure may contain a compound of Formula (I) in a prodrug form. Prodrugs are those compounds that readily undergo chemical changes under physiological conditions to provide the compounds useful for preparing devices in the present disclosure. Additionally, prodrugs can be converted to useful compounds of Formula (I) by chemical or biochemical methods in an ex vivo environment.

Certain compounds of Formula (I) described herein can exist in unsolvated forms as well as solvated forms, including hydrated forms. In general, the solvated forms are equivalent to unsolvated forms and are encompassed within the scope of the present disclosure. Certain compounds of Formula (I) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of $\pi$ electrons and an atom (usually H). For example, ends and ketones are tautomers because they are rapidly interconverted by treatment with either acid or base. Tautomeric forms may be relevant to the attainment of the optimal chemical reactivity and biological activity of a compound of interest.

The symbol "〰" as used herein refers to a connection to an entity, e.g., a polymer (e.g., hydrogel-forming polymer such as alginate) or surface of an implantable device, e.g., a particle, a hydrogel capsule. The connection represented by "〰" may refer to direct attachment to the entity, e.g., a polymer or an implantable element, may refer to linkage to the entity through an attachment group. An "attachment group," as described herein, refers to a moiety for linkage of a compound of Formula (I) to an entity (e.g., a polymer or an implantable element (e.g., a device) as described herein), and may comprise any attachment chemistry known in the art. A listing of exemplary attachment groups is outlined in *Bioconjugate Techniques* ($3^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$)—, or a metal, wherein each of $R^A$, $R^C$, $R^D$, $R^F$, $R^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)($C_1$-$C_6$-alkylene)-, wherein alkylene is substituted with $R^1$, and $R^1$ is as described herein. In some embodiments, the attachment group is —C(O)($C_1$-$C_6$-alkylene)-, wherein alkylene is substituted with 1-2 alkyl groups (e.g., 1-2 methyl groups). In some embodiments, the attachment group is —C(O)C($CH_3$)$_2$—. In some embodiments, the attachment group is —C(O)(methylene)-, wherein alkylene is substituted with 1-2 alkyl groups (e.g., 1-2 methyl groups). In some embodiments, the attachment group is —C(O)CH($CH_3$)—. In some embodiments, the attachment group is —C(O)C($CH_3$)—.

Features of Devices

The present disclosure features an implantable device comprising a plurality of cells (e.g., live cells) which are encapsulated in a first cell-containing compartment by a polymer composition that comprises at least one cell binding substance (CBS) (as defined herein). The cells are capable of expressing a therapeutic agent upon implant of the device into a subject, e.g., a human or other mammalian subject. In addition, the device comprises at least one means for mitigating the FBR (as defined herein).

In an embodiment, the CBS in the cell-containing compartment is present in an amount effective to increase viability of the cells and/or increase productivity of the cells at a timepoint after the device is implanted into an immune-compromised or immune-competent animal, e.g., immune-competent mice (e.g., the C57BL/6J mouse strain available from the Jackson Laboratory, Bar Harbor, ME USA) as compared to a CBS-null reference device, as defined above herein. In an embodiment, the increase in cell viability and/or productivity is detectable at a desired timepoint after implant, e.g., at one or more of 1 day, 3 days, 5 days, 1 week, 2 weeks, 4 weeks, 8 weeks, 12 weeks, 24 weeks, 36 weeks and 48 weeks. In an embodiment, the effective amount of the CBS results in an increase in one or both of (i) cell viability by at least 10%, 25%, 50% or 100% when measured at 1 week, 2 weeks, 4 weeks or 12 weeks after implant and (ii) increases cell productivity by at least 1.25-fold, 1.5-fold, 2-fold, 5-fold, 8-fold or 10-fold when measured at 1 week, 2 weeks, 4 weeks or 12 weeks after implant. In an embodiment, the effective amount of the CBS in the cell-containing compartment falls within a range between the minimally effective amount and a higher amount at which the cell viability and/or productivity are reduced compared to a CBS-null reference device or compared to the a device containing a maximally-effective amount, e.g., the optimal amount, of the CBS in the cell-containing compartment. In an embodiment, the amount of the CBS in the cell-containing compartment is no more than 50%, 25%, 10% or 5% above or below the optimal amount, e.g., the amount that results in the greatest increase in cell viability and/or productivity as compared to the CBS-null reference device. In an embodiment, the effective amount of a CBP to achieve improved productivity after implant is determined for the desired combination of cells, CBS, therapeutic protein expressed by the cells, e.g., engineered ARPE-19 cells, specific polypeptide (e.g., Factor VIII, Factor IX, Factor VII) and optionally including the particular coding sequence for the therapeutic protein.

The number of viable (and optionally dead) cells in a device described herein may be estimated using any technique known in the art, including an assay that differentially labels live and dead cells with two fluorescent dyes followed by detection, and optionally quantification, of labeled cells using fluorescent microscopy. Cell viability may also be evaluated by assessing other cell viability indicators, including measuring esterase activity, or quantitating the amount of ATP in the cells.

In an embodiment, the post-implant increase in cell productivity is detected by assaying for the level of the therapeutic agent expressed by the cells in vivo or ex vivo (e.g., cell expression after the device has been retrieved from the animal. Depending on the nature of the therapeutic agent, its expression may be measured intracellularly, extracellularly but inside the device, and/or outside of the device, e.g., in a tissue sample removed from an animal (e.g., a non-human animal) treated with a device or device preparation described herein. In an embodiment, the cell productivity is expressed as the measured amount of the therapeutic agent or agent activity divided by the number of administered devices (e.g., number of capsules placed in the animal) and/or by the number of administered cells (e.g., approximate number of cells per capsule in the administered capsule preparation, e.g., determined as described in the Examples herein below). In an embodiment, the increase in cell productivity is further normalized by dividing the determined amount (e.g., of therapeutic agent or amount of activity) by the time between two time points of interest, e.g., between administration and measurement, e.g., number of hours, days or weeks. In an embodiment, the therapeutic agent is a protein, and the increase in productivity is determined by measuring the amount and/or activity of the protein in a tissue sample removed from the animal (e.g., plasma separated from a blood sample collected from the animal), dividing the measured amount and/or activity by the number of administered devices (e.g, number of implanted 2-compartment capsules), and optionally further dividing the result by the number of days between administration and tissue sample removal.

The CBS may comprise a polypeptide polymer (e.g., a CBPP such as fibronectin or laminin) that is within the encapsulating polymer composition or it may be a CBP that is covalently attached to an unrelated amino acid polymer (e.g., a silk polymer), or to a naturally occurring polymer (e.g., an alginate, chitin, cotton) or to a synthetic polymer (e.g., a polymer in any of the following classes: acrylic, polyester, polyethylene, polypropylene polyacetonitrile, polyethylene teraphthalate, nylon, polyamide, polyurethane, polybutester). In addition to the CBS, the polymer composition in the cell-containing compartment may contain one or more unmodified naturally-occurring or synthetic polymers of any of the above-recited polymer classes to help provide structural integrity to the compartment and/or help provide a scaffold for supporting the cells.

In some embodiments, the CBS comprises an alginate covalently modified with one or more CBPs, e.g., RGD (SEQ ID NO: 43), RGDSP (SEQ ID NO: 59), DGEA (SEQ ID NO: 39), FYFDLR (SEQ ID NO: 40), PHSRN (SEQ ID NO: 46), YIGSR (SEQ ID NO: 50), a peptide comprising or consisting essentially of any of the cell binding sequences listed in Table 1 herein, or a mixture of 2, 3 or more of these CBPs (e.g., RGD+DGEA (SEQ ID NOs: 43 and 39, respectively), RGD+PHSRN (SEQ ID NOs: 43 and 46, respectively), RGD+DGEA+PHSRN (SEQ ID NOs: 43, 39, and 46, respectively)). Alginate is a polysaccharide made up of P-D-mannuronic acid (M) and α-L-guluronic acid (G). In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the ratio of G:M is at least 1.3, 1.5 or greater than 1.5. In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1.

In an embodiment, each CBP is attached to the alginate via an amino acid linker (e.g., consisting essentially of one, two or three glycine residues). In an embodiment, the linker is a single glycine residue attached to the N-terminus of the CBP. In an embodiment, the first CBS is a polymer covalently modified with an RGD peptide. In an embodiment, the first CBS is an alginate with a molecular weight of 75-150 kDa and a G:M ratio of greater than or equal to 1.5 and is covalently modified with a linker-CBP that consists essentially of GRGD (SEQ ID NO: 62) or GRGDSP (SEQ ID NO: 60).

In an embodiment, each CBP may further comprise a terminal capping group or protecting group on the free terminus of the CBP, e.g, the non-linker terminus of the CBP. A terminal capping group or protecting group may prevent the terminal amino acid residue from unwanted or unnecessary reactions and/or reduce or prevent degradation or modification of the CBP. Exemplary capping groups include alkyl groups, ethers, amides, and the like. In an embodiment, the linker-CBP comprises GRGD or GRGDSP and a terminal capping group. In an embodiment, the linker-CBP comprises GRGD or GRGDSP and does not comprise a terminal capping group.

In an embodiment, the encapsulating polymer composition in the cell-containing compartment may comprise one or more additional cell-binding substances, which may be a CBPP or a polymer covalently modified with a CBP. In an embodiment, the polymer composition also comprises a second CBP-alginate, e.g., an alginate covalently modified with a linker-CBP selected from the group consisting of $G_{(1-3)}$DGEA (SEQ ID NO: 66), $G_{(1-3)}$PHRSN (SEQ ID NO: 67), or $G_{(1-3)}$REDV (SEQ ID NO: 68). In an embodiment, the alginate in the second CBP-alginate also has a molecular weight of 75-150 kDa and a G:M ratio of greater than or equal to 1.5.

As described in the Examples herein below, it has been surprisingly discovered that when an RGD-modified alginate is used to encapsulate engineered RPE cells in the inner compartment of a two-compartment hydrogel capsule, the productivity of the encapsulated cells can be significantly impacted by the density of the RGD peptide in the modified alginate. Thus, in some embodiments, the density of a cell-binding peptide (e.g., RGD (SEQ ID NO: 43) or RGDSP (SEQ ID NO: 59)) in the CBP-polymer used to form the cell-containing compartment is (a) 0.10% nitrogen (N) to 1.00% N, about 0.20% N to about 0.80% N, about 0.30% N to about 0.60% N, about 0.30% to about 0.50%, or 0.33% N to 0.46% N, or (b) about 0.1 to about 1.0 micromoles of the CBP per g of the CBP-polymer (e.g., a MMW-alginate covalently modified with RGD (SEQ ID NO: 43) or RGDSP (SEQ ID NO: 59)) in solution as determined by a quantitative peptide conjugation assay, e.g., an assay described herein. In an embodiment, the encapsulated cells are engineered ARPE-19 cells. In an embodiment, the engineered ARPE-19 cells are stably-transfected cells or a monoclonal cell line derived from ATCC (CRL-2302). In an embodiment, the engineered ARPE-19 cells express a Factor VIII or a Factor IX protein. In some embodiments, in which the device comprises a mixture of different CBP-polymers in a cell-containing compartment, the total density of cell-binding peptide in the cell-containing compartment is 0.1% nitrogen (N) to 1.00% N, about 0.20% N to about 0.80% N, about 0.30% N to about 0.60% N or about 0.30% N to about 0.50% N or about 0.1 to about 1.0 micromoles of the CBP per g of the CBP-polymer in solution as determined by a quantitative peptide conjugation assay, e.g., an assay described herein.

In an embodiment, the quantitative peptide conjugation assay includes subjecting a sample of a CPB-polymer to acid hydrolysis to generate individual amino acids from the conjugated peptide (and any residual unconjugated peptide in the CBP-polymer), quantitating the individual amino acids, averaging the molar concentration of each amino acid, and calculating the total peptide concentration in the sample. In an embodiment, the quantitative peptide conjugation assay is performed substantially similar to the process described in Example 25 herein. In an embodiment, the quantitative peptide conjugation assay also includes subtracting the concentration of any residual unconjugated peptide in the sample from the total peptide concentration. The concentration of unconjugated peptide in a CBP-polymer composition may be determined using any suitable assay known in the art, e.g., by LC-MS as described in Example 26 herein. Typically, the quantitative peptide conjugation assay is performed on a sample of a saline solution of the CBP-polymer that is used to prepare the device, but may also be performed on a lyophilized sample of the CBP-polymer.

Polymers may be covalently modified with a CBP using any of a variety of methods known in the art, see, e.g., Jeon O, et al., Biodegradable, photocrosslinked alginate hydrogels with independently tailorable physical properties and cell adhesivity. *Tissue Eng. Part A* 16:2915-2925 (2010); Rowley, J. A. et al., *Biomaterials* 20:45-53 (1999). For example, when the polymer to be modified is an alginate, the N-terminus of a peptide that consists essentially of an amino acid linker sequence (of one to several amino acids) and a cell binding amino acid sequence can be covalently attached to the alginate using an approach similar to that described in Example 1B herein below.

In addition to the polymer composition in the cell-containing compartment, the device (e.g., macrodevice, particle, hydrogel capsule) may comprise or be formed from materials such as metals, metallic alloys, ceramics, polymers, fibers, inert materials, and combinations thereof. A device may be completely made up of one type of material, or may comprise other materials within the cell-containing compartment and any other compartments.

The means for mitigating the FBR in the devices of the disclosure may comprise one or more of a variety of approaches known in the art.

For example, the means for mitigating the FBR in devices disclosed herein can comprise surrounding the cells with a semi-permeable biocompatible membrane having a pore size that is selected to allow oxygen and other molecules important to cell survival and function to move through the semi-permeable membrane while preventing immune cells from traversing through the pores. In an embodiment, the semi-permeable membrane has a molecular weight cutoff of less than 1000 kD or between 50-700 kD, 70-300 kD, or between 70-150 kD, or between 70 and 130 kD.

Another FBR-mitigating means comprises surrounding the cell-containing compartment with a barrier compartment formed from a cell-free biocompatible material, such as the core-shell microcapsules described in Ma, M et al., *Adv. Healthc Mater.,* 2(5):667-672 (2012). Such a barrier compartment could be used with or without the semi-permeable member means. FBR-mitigating means can comprise disposing on or within the device an anti-inflammatory drug that is released from the implanted device to inhibit FBR, e.g., as described in U.S. Pat. No. 9,867,781. Other FBR-mitigating means employ a CSF-1R inhibitor that is disposed on the device surface or encapsulated within the device, as described in WO 2017/176792 and WO 2017/176804. Other FBR-mitigating means employ configuring the device in a spherical shape with a diameter of greater than 1 mm, as described in Veiseh, O., et al., Nature Materials 14:643-652 (2015). In some embodiments, the means for mitigating the FBR comprises disposing an afibrotic compound on the exterior surface of the device and/or within a barrier compartment surrounding the cell-containing compartment. Exemplary afibrotic compounds are described herein below. In some embodiments, the device can comprise combinations of two or more of the above FBR-mitigating means.

The device (e.g., particle) can have any configuration and shape appropriate for supporting the viability and productivity of the encapsulated cells after implant into the intended target location. As non-limiting examples, device shapes may be cylinders, rectangles, disks, ovoids, stellates, or spherical. The device can be comprised of a mesh-like or nested structure. In some embodiments, a device is capable of preventing materials over a certain size from passing through a pore or opening. In some embodiments, a device (e.g., particle) is capable of preventing materials greater than 50 kD, 75 kD, 100 kD, 125 kD, 150 kD, 175 kD, 200 kD, 250 kD, 300 kD, 400 kD, 500 kD, 750 kD, or 1,000 kD from passing through.

In an embodiment, the device is a macroencapsulation device. Nonlimiting examples of macrodevices are described in: U.S. Pat. Nos. 9,526,880, 9,724,430 and 8,278,106; European Patent No. EP742818B1, and Sang, S. and Roy, S., *Biotechnol. Bioeng.* 113(7): 1381-1402 (2016).

In some embodiments, a device (e.g., particle) has a largest linear dimension (LLD), e.g., mean diameter, or size that is at least about 0.5 millimeter (mm), preferably about 1.0 mm, about 1.5 mm or greater. In some embodiments, a device can be as large as 10 mm in diameter or size. For example, a device or particle described herein is in a size range of 0.5 mm to 10 mm, 1 mm to 10 mm, 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm.

The device may form part of a plurality of substantially the same devices in a preparation (e.g., composition). In some embodiments, the devices (e.g. particles, hydrogel capsules) in the preparation have a mean diameter or size between about 0.5 mm to about 8 mm. In some embodiments, the mean diameter or size of devices in the preparation is between about 0.5 mm to about 4 mm or between about 0.5 mm to about 2 mm. In some embodiments, the devices in the preparation are two-compartment hydrogel capsules and have a mean diameter or size of about 0.7 mm to about 1.3 mm or about 1.2 mm to about 1.8 mm.

In some embodiments, the device has two hydrogel compartments, in which the inner, cell-containing compartment is completely surrounded by the second, outer (e.g., barrier) compartment. In an embodiment, the inner boundary of the second compartment forms an interface with the outer boundary of the first compartment, e.g., as illustrated in FIG. 1. In such embodiments, the thickness of the second (outer) compartment means the average distance between the outer boundary of the second compartment and the interface between the two compartments, e.g., the average of the distances measured at each of the thinnest and thickest points visually observed in the outer compartment. In some embodiments (e.g., the device is about 1.5 mm in diameter), the thinnest and thickest distances for the outer compartment are between 25 and 110 micrometers (μm) and between 270 and 480 μm, respectively. In some embodiments, the thickness of the outer compartment is greater than about 10 nanometers (nm), preferably 100 nm or greater and can be as large as 1 millimeter (mm). For example, the thickness (e.g., average distance) of the outer compartment in a hydrogel capsule device described herein may be 10 nm to 1 mm, 100 nm to 1 mm, 500 nm to 1 millimeter, 1 micrometer (μm) to 1 mm, 1 μm to 1 mm, 1 μm to 500 μm, 1 μm to 250 μm, 1 μm to 1 mm, 5 μm to 500 μm, 5 μm to 250 μm, 10 μm to 1 mm, 10 μm to 500 μm, or 10 μm to 250 μm. In some embodiments, the thickness (e.g., average distance) of the outer compartment is 100 nm to 1 mm, between 1 μm and 1 mm, between 1 μm and 500 μm or between 5 μm and 1 mm. In some embodiments, the thickness (e.g., average distance) of the outer compartment is between about 50 μm and about 100 μm. In some embodiments (e.g., the device is about 1.5 mm in diameter), the thickness of the outer compartment (e.g., average distance) is between about 180 μm and 260 μm or between about 310 μm and 440 μm.

In some embodiments, a device of the disclosure (e.g., particle, capsule) comprises at least one pore or opening, e.g., to allow for the free flow of materials. In some embodiments, the mean pore size of a device is between about 0.1 μm to about 10 μm. For example, the mean pore size may be between 0.1 μm to 10 μm, 0.1 μm to 5 μm, 0.1 μm to 2 μm, 0.15 μm to 10 μm, 0.15 μm to 5 μm, 0.15 μm to 2 μm, 0.2 μm to 10 μm, 0.2 μm to 5 μm, 0.25 μm to 10 μm, 0.25 μm to 5 μm, 0.5 μm to 10 μm, 0.75 μm to 10 μm, 1 μm to 10 μm, 1 μm to 5 μm, 1 μm to 2 μm, 2 μm to 10 μm, 2 μm to 5 μm, or 5 μm to 10 μm. In some embodiments, the mean pore size of a device is between about 0.1 μm to 10 μm. In some embodiments, the mean pore size of a device is between about 0.1 μm to 5 μm. In some embodiments, the mean pore size of a device is between about 0.1 μm to 1 μm. In some embodiments of a two-compartment hydrogel capsule device, the mean pore size of the cell-containing inner compartment and the outer compartment is substantially the same. In some embodiments, the mean pore size of the inner compartment and the second compartment differ by about 1.5%, 2%, 5%, 7.5%, 10%, 15%, 20%, 25%, 30%, 35%, 40%, 45%, 50%, 55%, 60%, 65%, 70%, 75%, or more. In some embodiments, the mean pore size of the device (e.g., mean pore size of the first compartment and/or mean pore size of the second compartment) is dependent on a number of factors, such as the material(s) within each compartment and the presence and density of a compound of Formula (I).

In some embodiments, the device comprises a metal or a metallic alloy. In an embodiment, one or more of the compartments in the device (e.g., the first compartment, the second compartment, or all compartments) comprises a metal or a metallic alloy. Exemplary metallic or metallic alloys include comprising titanium and titanium group alloys (e.g., nitinol, nickel titanium alloys, thermo-memory alloy materials), platinum, platinum group alloys, stainless steel, tantalum, palladium, zirconium, niobium, molybdenum, nickel-chrome, chromium molybdenum alloys, or certain cobalt alloys (e.g., cobalt-chromium and cobalt-chromium-nickel alloys, e.g., ELGILOY® and PHYNOX®). For example, a metallic material may be stainless steel grade 316 (SS 316L) (comprised of Fe, <0.3% C, 16-18.5% Cr, 10-14% Ni, 2-3% Mo, <2% Mn, <1% Si, <0.45% P, and <0.03% S). In metal-containing devices, the amount of metal (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, the device comprises a ceramic. In an embodiment, one or more of the compartments in the device (e.g., the first compartment, the second compartment, or all compartments) comprises a ceramic. Exemplary ceramic materials include oxides, carbides, or nitrides of the transition elements, such as titanium oxides, hafnium oxides, iridium oxides, chromium oxides, aluminum oxides, and zirconium oxides. Silicon based materials, such as silica, may also be used. In ceramic-containing devices, the amount of ceramic (e.g., by % weight, actual weight) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, one or more compartments in a device comprises an afibrotic polymer, e.g., an afibrotic compound of Formula (I) covalently attached to a polymer that is the same or different than the polymer in the CBP-polymer. In an embodiment, some or all the monomers in the afibrotic polymer are modified with the same compound of Formula (I). In some embodiments, some or all the monomers in the afibrotic polymer are modified with different compounds of Formula (I). In some embodiments in which the device is a 2-compartment hydrogel capsule, the afibrotic polymer is present only in the outer, barrier compartment.

One or more compartments in a device may comprise an unmodified polymer that is the same or different than the polymer in the CBP-polymer and in any afibrotic polymer that is present in the device. In an embodiment, the first compartment, second compartment or all compartments in the device comprises the unmodified polymer.

Each of the modified and unmodified polymers in the device may be a linear, branched, or cross-linked polymer, or a polymer of selected molecular weight ranges, degree of polymerization, viscosity or melt flow rate. Branched polymers can include one or more of the following types: star polymers, comb polymers, brush polymers, dendronized polymers, ladders, and dendrimers. A polymer may be a thermoresponsive polymer, e.g., gel (e.g., becomes a solid or liquid upon exposure to heat or a certain temperature) or a photocrosslinkable polymer. Exemplary polymers include polystyrene, polyethylene, polypropylene, polyacetylene, poly(vinyl chloride) (PVC), polyolefin copolymers, poly(urethane)s, polyacrylates and polymethacrylates, polyacrylamides and polymethacrylamides, poly(methyl methacrylate), poly(2-hydroxyethyl methacrylate), polyesters, polysiloxanes, polydimethylsiloxane (PDMS), polyethers, poly(orthoester), poly(carbonates), poly(hydroxyalkanoate)s, polyfluorocarbons, PEEK®, Teflon® (polytetrafluoroethylene, PTFE), PEEK, silicones, epoxy resins, Kevlar®, Dacron® (a condensation polymer obtained from ethylene glycol and terephthalic acid), polyethylene glycol, nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polyethylene glycol and 2-hydroxyethyl methacrylate (HEMA), polysaccharides, poly(glycolic acid), poly(L-lactic acid) (PLLA), poly(lactic glycolic acid) (PLGA), a polydioxanone (PDA), or racemic poly(lactic acid), polycarbonates, (e.g., polyamides (e.g., nylon)), fluoroplastics, carbon fiber, agarose, alginate, chitosan, and blends or copolymers thereof. In polymer-containing devices, the amount of a polymer (e.g., by % weight of the device, actual weight of the polymer) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

In some embodiments, one or more of the modified and unmodified polymers in the device comprises a polyethylene. Exemplary polyethylenes include ultra-low-density polyethylene (ULDPE) (e.g., with polymers with densities ranging from 0.890 to 0.905 g/cm$^3$, containing comonomer); very-low-density polyethylene (VLDPE) (e.g., with polymers with densities ranging from 0.905 to 0.915 g/cm$^3$, containing comonomer); linear low-density polyethylene (LLDPE) (e.g., with polymers with densities ranging from 0.915 to 0.935 g/cm$^3$, contains comonomer); low-density polyethylene (LDPE) (e.g., with polymers with densities ranging from about 0.915 to 0.935 g/m$^3$); medium density polyethylene (MDPE) (e.g., with polymers with densities ranging from 0.926 to 0.940 g/cm$^3$, may or may not contain comonomer); high-density polyethylene (HDPE) (e.g., with polymers with densities ranging from 0.940 to 0.970 g/cm$^3$, may or may not contain comonomer) and polyethylene glycol.

In some embodiments, one or more of the modified and unmodified polymers in the device comprises a polypropylene. Exemplary polypropylenes include homopolymers, random copolymers (homophasic copolymers), and impact copolymers (heterophasic copolymers), e.g., as described in McKeen, *Handbook of Polymer Applications in Medicine and Medical Devices,* 3-Plastics Used in Medical Devices, (2014):21-53, which is incorporated herein by reference in its entirety.

In some embodiments, one or more of the modified and unmodified polymers in the device comprises a polypropylene. Exemplary polystyrenes include general purpose or crystal (PS or GPPS), high impact (HIPS), and syndiotactic (SPS) polystyrene.

In some embodiments, one or more of the modified and unmodified polymers comprises a comprises a thermoplastic elastomer (TPE). Exemplary TPEs include (i) TPA—polyamide TPE, comprising a block copolymer of alternating hard and soft segments with amide chemical linkages in the hard blocks and ether and/or ester linkages in the soft blocks; (ii) TPC—co-polyester TPE, consisting of a block copolymer of alternating hard segments and soft segments, the chemical linkages in the main chain being ester and/or ether; (iii) TPO—olefinic TPE, consisting of a blend of a polyolefin and a conventional rubber, the rubber phase in the blend having little or no cross-linking; (iv) TPS—styrenic TPE, consisting of at least a triblock copolymer of styrene and a specific diene, where the two end blocks (hard blocks) are polystyrene and the internal block (soft block or blocks) is a polydiene or hydrogenated polydiene; (v) TPU—urethane TPE, consisting of a block copolymer of alternating hard and soft segments with urethane chemical linkages in the hard blocks and ether, ester or carbonate linkages or mixtures of them in the soft blocks; (vi) TPV—thermoplastic rubber vulcanizate consisting of a blend of a thermoplastic material and a conventional rubber in which the rubber has been cross-linked by the process of dynamic vulcanization during the blending and mixing step; and (vii) TPZ—unclassified TPE comprising any composition or structure other than those grouped in TPA, TPC, TPO, TPS, TPU, and TPV.

In some embodiments, the unmodified polymer is an unmodified alginate. In some embodiments, the alginate is a high guluronic acid (G) alginate, and comprises greater than about 50%, 55%, 60%, 65%, 70%, 75%, 80%, 85%, 90%, or more guluronic acid (G). In some embodiments, the alginate is a high mannuronic acid (M) alginate, and comprises greater than about 50%, 55%, 60%, 65%, 70%, 75%, 80%, 85%, 90%, or more mannuronic acid (M). In some embodiments, the ratio of M:G is about 1. In some embodiments, the ratio of M:G is less than 1. In some embodiments, the ratio of M:G is greater than 1. In an embodiment, the unmodified alginate has a molecular weight of 150 kDa-250 kDa and a G:M ratio of ≥1.5.

In some embodiments, the afibrotic polymer comprises an alginate chemically modified with a Compound of Formula (I). The alginate in the afibrotic polymer may be the same or different than any unmodified alginate that is present in the device. In an embodiment, the density of the Compound of Formula (I) in the afibrotic alginate (e.g., amount of conjugation) is between about 4.0% and about 8.0%, between about 5.0% and about 7.0%, or between about 6.0% and about 7.0% nitrogen (e.g., as determined by combustion analysis for percent nitrogen). In an embodiment, the amount of Compound 101 produces an increase in % N (as compared with the unmodified alginate) of about 0.5% to 2% 2% to 4% N, about 4% to 6% N, about 6% to 8%, or about 8% to 10% N), where % N is determined by combustion analysis and corresponds to the amount of Compound 101 in the modified alginate.

In other embodiments, the density (e.g., concentration) of the Compound of Formula (I) (e.g., Compound 101) in the afibrotic alginate is defined as the % w/w, e.g., % of weight of amine/weight of afibrotic alginate in solution (e.g., saline) as determined by a suitable quantitative amine conjugation assay (e.g. by an assay described herein), and in certain embodiments, the density of a Compound of Formula (I) (e.g., Compound 101) is between about 1.0% w/w and about 3.0% w/w, between about 1.3% w/w and about 2.5% w/w or between about 1.5% w/w and 2.2% w/w. In an embodiment, the quantitative amine conjugation assay includes subjecting a sample of a chemically-modified polymer (e.g., an alginate modified with a Compound of Formula (I), e.g., CM-FMW-Alg-101) to acid hydrolysis to generate free amine and quantitating the total free amine in the sample. In an embodiment, the quantitative amine conjugation assay also includes subtracting the concentration of unconjugated amine (e.g., Compound of Formula (I)) in an unhydrolyzed sample from the total amine concentration. The quantitative amine conjugation assay is typically performed on a sample of a saline solution of the chemically-modified alginate used to prepare the device, but may also be performed on a lyophilized sample of the chemically-modified alginate. In an embodiment, the quantitative amine conjugation assay is performed substantially similar to the process described in Example 27 herein. In an embodiment, the Compound of Formula (I) is Compound 101 shown in Table 4.

In alginate-containing devices, the amount of modified and unmodified alginates (e.g., by % weight of the device, actual weight of the alginate) can be at least 5%, e.g., at least 5%, 10%, 20%, 30%, 40%, 50%, 60%, 70%, 80%, 90%, 95%, 99%, or more, e.g., w/w; less than 20%, e.g., less than 20%, 15%, 10%, 5%, 1%, 0.5%, 0.1%, or less.

The alginate in an afibrotic polymer can be chemically modified with a compound of Formula (I) using any suitable method known in the art. For example, the alginate carboxylic acid moiety can be activated for coupling to one or more amine-functionalized compounds to achieve an alginate modified with a compound of Formula (I). The alginate polymer may be dissolved in water (30 mL/gram polymer) and treated with 2-chloro-4,6-dimethoxy-1,3,5-triazine (0.5 eq) and N-methylmorpholine (1 eq). To this mixture may be added a solution of the compound of Formula (I) in acetonitrile (0.3M). The reaction may be warmed to 55° C. for 16 h, then cooled to room temperature and gently concentrated via rotary evaporation, then the residue may be dissolved, e.g., in water. The mixture may then be filtered, e.g., through a bed of cyano-modified silica gel (Silicycle) and the filter cake washed with water. The resulting solution may then be dialyzed (10,000 MWCO membrane) against water for 24 hours, e.g., replacing the water twice. The resulting solution can be concentrated, e.g., via lyophilization, to afford the desired chemically modified alginate.

Each device described herein comprises at least one cell-containing compartment. In an embodiment, the device contains two, three, four or more cell-containing compartments. Each cell-containing compartment comprises a plurality of cells (e.g., live cells) and the cells in at least one of the compartments are capable of expressing a therapeutic agent when the device is implanted into a subject. In some embodiments, the therapeutic agent is a protein or polypeptide, e.g., an antibody, protein, enzyme, or growth factor).

In an embodiment, all the cells in a cell-containing compartment are derived from a single parental cell-type or a mixture of at least two different parental cell types. In an embodiment, all of the cells in a cell-containing compartment are derived from the same parental cell type, but a first plurality of the derived cells are engineered to express a first therapeutic agent, and a second plurality of the derived cells are engineered to express a second therapeutic agent. In devices with two or more cell-containing compartments, the cells and the therapeutic agent produced thereby may be the same or different in each cell-containing compartment. In some embodiments, all of the cell-containing compartments are surrounded by a single barrier compartment. In some embodiments, the barrier compartment is substantially cell-free.

In addition to therapeutic agent(s) expressed by the encapsulated cells, a device (e.g., capsule, particle) may comprise one or more exogenous agents that are not expressed by the cells, and may include, e.g., a nucleic acid (e.g., an RNA or DNA molecule), a protein (e.g., a hormone, an enzyme (e.g., glucose oxidase, kinase, phosphatase, oxygenase, hydrogenase, reductase) antibody, antibody fragment, antigen, or epitope)), small molecule, lipid, drug, vaccine, or any derivative thereof, a small-molecule, an active or inactive fragment of a protein or polypeptide. In an embodiment, the device is configured to release such an exogenous agent.

A device described herein may be provided as a preparation or composition for implantation or administration to a subject, i.e., a device preparation or device composition. In some embodiments, a device preparation or device composition comprises at least 2, 4, 8, 16, 32, 64 or more devices, and at least 20%, 30%, 35%, 40%, 45%, 50%, 55%, 60%, 65%, 70%, 75%, 80%, 85%, 90%, 95% or 100% of the devices in the preparation or composition have a characteristic as described herein, e.g., mean diameter or mean pore size or cell density.

In some embodiments, a device, device preparation or device composition targets or is designed for a certain system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, a device, preparation or composition is targeted to the CNS. In some embodiments, a device, device preparation or device composition targets or is designed for a certain part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

A device, device preparation or device composition may be configured for implantation, or implanted or disposed into or onto any site of the body. In some embodiments, a device, device preparation or device composition is configured for implantation, implanted or disposed into the omentum of a subject, into the subcutaneous fat of a subject, or into the muscle tissue of a subject. A device, device composition or device preparation can be configured for implantation, or implanted, or disposed on or in the skin; a mucosal surface, a body cavity, the peritoneal cavity (e.g., the lesser sac); the central nervous system, e.g., the brain or spinal cord; an organ, e.g., the heart, liver, kidney, spleen, lung, lymphatic system, vasculature, the oral cavity, the nasal cavity, the teeth, the gums, the GI tract; bone; hip; fat tissue; muscle tissue; circulating blood; the eye (e.g., intraocular); breast, vagina; uterus, a joint, e.g., the knee or hip joint, or the spine.

In some embodiments, the device, device preparation or device composition is configured for implantation or implanted or disposed into the peritoneal cavity (e.g., the omentum). In some embodiments, the device is configured for implantation or implanted or disposed into or onto the lesser sac, also known as the omental bursa or bursalis omentum. The lesser sac refers to a cavity located in the abdomen formed by the omentum, and is in close proximity to, for example, the greater omentum, lesser omentum, stomach, small intestine, large intestine, liver, spleen, gastrosplenic ligament, adrenal glands, and pancreas. Typically, the lesser sac is connected to the greater sac via the omental foramen (i.e., the Foramen of Winslow). In some embodiments, the lesser sac comprises a high concentration of adipose tissue. A device, device preparation or device composition may be implanted in the peritoneal cavity (e.g., the omentum, e.g., the lesser sac) or disposed on a surface within the peritoneal cavity (e.g., omentum, e.g., lesser sac) via injection or catheter. Additional considerations for implantation or disposition of a device, device preparation or device composition into the omentum (e.g., the lesser sac) are provided in M. Pellicciaro et al. (2017) *CellR4* 5(3): e2410, which is incorporated herein by reference in its entirety.

In some embodiments, the device, device preparation or device composition is configured for implantation or implanted or disposed into the central nervous system (CNS), e.g., the brain or spinal cord and their corresponding tissues and cavities. In vertebrates, the CNS is contained within the dorsal body cavity, including the cranial cavity and the spinal canal. In some embodiments, the device, device composition or device preparation is configured for implantation or implanted or disposed into an intracerebral space, e.g., the intraparenchymal space, the intraventricular space, or the subdural space. A device, device composition or device preparation may be implanted in the CNS or disposed on a surface within the CNS through a hole made in the skull and delivered via injection or catheter.

In some embodiments, a device, device composition or device preparation is configured for implantation or implanted in or disposed into the eye. Exemplary regions suitable for implantation or disposition of the device include any surface or cavity within the eye, such as the retina, cornea, epithelium, aqueous humor, or vitreal space. In some embodiments, the device, device composition or device preparation is configured for implantation or implanted or disposed into the vitreal space. A device, device composition or devise preparation may be implanted in the eye or disposed on a surface within the eye through incision and/or injection.

In some embodiments, a device or device preparation is easily retrievable from a subject, e.g., without causing injury to the subject or without causing significant disruption of the surrounding tissue. In an embodiment, the device or device preparation can be retrieved with minimal or no surgical separation of the device(s) from surrounding tissue, e.g., via minimally invasive surgical approach, extraction, or resection.

A device, device composition or device preparation can be configured for a variety of exposures after implant into a mammalian recipient, including: limited exposure (e.g., less than 2 days, e.g., less than 2 days, 1 day, 24 hours, 20 hours, 16 hours, 12 hours, 10 hours, 8 hours, 6 hours, 5 hours, 4 hours, 3 hours, 2 hours, 1 hour or less); prolonged exposure (e.g., at least 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more) and permanent exposure (e.g., at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 1.5 years, 2 years, 2.5 years, 3 years, 3.5 years, 4 years or more).

In some embodiments, the device is not any capsule, device, implant or other object disclosed in any of WO2012/112982, WO2012/167223, WO2014/153126, WO2016/019391, WO2016/187225, US2012-0213708, US 2016-0030359, and US 2016-0030360.

Small Molecule Compounds

In some embodiments, the devices described herein comprise at least one compound of Formula (I):

(I)

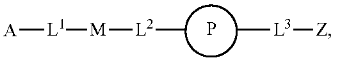

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^a$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, $S(O)_xR^{E1}$, —$OS(O)_xR^{E1}$, —N($R^{C1}$)$S(O)_xR^{E1}$, —$S(O)_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

(I-a)

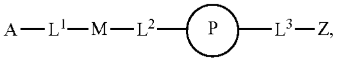

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, N($R^C$)C(O)($C_1$-$C_6$-alkylene)-, —N($R^C$)C(O)($C_1$-$C_6$-alkenylene)-, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, $S(O)_xR^{E1}$, —$OS(O)_xR^{E1}$, —N($R^{C1}$)$S(O)_xR^{E1}$, —$S(O)_x$N($R^{C1}$)($R^{D1}$), —P($R^{E1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) and (I-a), A is alkyl, alkenyl, alkynyl, heteroalkyl, cycloalkyl, heterocyclyl, aryl, heteroaryl, —O—, —C(O)O—, —C(O)—, —OC(O)—, —$N(R^C)C(O)$—, —$N(R^C)C(O)(C_1$-$C_6$-alkylene)-, —$N(R^C)C(O)(C_1$-$C_6$-alkenylene)-, or —$N(R^C)$—. In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —$N(R^C)$—. In some embodiments, A is alkyl, alkenyl, alkynyl, heteroalkyl, —O—, —C(O)O—, —C(O)—, —OC(O)—, or —$N(R^C)$—. In some embodiments, A is alkyl, —O—, —C(O)O—, —C(O)—, —OC(O), or —$N(R^C)$—. In some embodiments, A is —$N(R^C)C(O)$—, —$N(R^C)C(O)(C_1$-$C_6$-alkylene)-, or —$N(R^C)C(O)(C_1$-$C_6$-alkenylene)-. In some embodiments, A is —$N(R^C)$—. In some embodiments, A is —$N(R^C)$—, and $R^C$ an $R^D$ is independently hydrogen or alkyl. In some embodiments, A is —NH—. In some embodiments, A is —$N(R^C)C(O)(C_1$-$C_6$-alkylene)-, wherein alkylene is substituted with $R^1$. In some embodiments, A is —$N(R^C)C(O)$($C_1$-$C_6$-alkylene)-, and $R^1$ is alkyl (e.g., methyl). In some embodiments, A is —$NHC(O)C(CH_3)_2$—. In some embodiments, A is —$N(R^C)C(O)$(methylene)-, and $R^1$ is alkyl (e.g., methyl). In some embodiments, A is —$NHC(O)CH(CH_3)$—. In some embodiments, A is —$NHC(O)C(CH_3)$—.

In some embodiments, for Formulas (I) and (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —$CH_2$—, —$CH(CH_3)$—, —$CH_2CH_2CH_2$, or —$CH_2CH_2$—. In some embodiments, $L^1$ is —$CH_2$— or —$CH_2CH_2$—.

In some embodiments, for Formulas (I) and (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —$C(O)OCH_2$—, —$CH_2(OCH_2CH_2)_2$—, —$CH_2(OCH_2CH_2)_3$—, $CH_2CH_2O$—, or —$CH_2O$—. In some embodiments, $L^3$ is —$CH_2O$—.

In some embodiments, for Formulas (I) and (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is (—$OCH_2CH_2$—)z, wherein z is an integer selected from 1 to 10. In some embodiments, z is an integer selected from 1 to 5. In some embodiments, M is —$OCH_2CH_2$—, (—$OCH_2CH_2$—$)_2$, (—$OCH_2CH_2$—$)_3$, (—$OCH_2CH_2$—$)_4$, or (—$OCH_2CH_2$—$)_5$. In some embodiments, M is —$OCH_2CH_2$—, (—$OCH_2CH_2$—$)_2$, (—$OCH_2CH_2$—$)_3$, or (—$OCH_2CH_2$—$)_4$. In some embodiments, M is (—$OCH_2CH_2$—$)_3$. In some embodiments, M is aryl. In some embodiments, M is phenyl. In some embodiments, M is unsubstituted phenyl. In some embodiments, M is

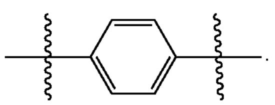 [SMILES: *c1ccc(*)cc1]

In some embodiments, M is phenyl substituted with $R^7$ (e.g., 1 $R^7$). In some embodiments, M is

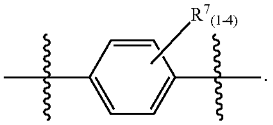

In some embodiments, $R^7$ is $CF_3$.

In some embodiments, for Formulas (I) and (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

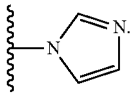

In some embodiments, P is triazolyl. In some embodiments, P is 1,2,3-triazolyl. In some embodiments, P is

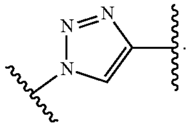 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

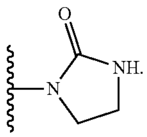 [SMILES: *N1CCNC1=O]

In some embodiments, P is thiomorpholinyl-1,1-dioxidyl. In some embodiments, P is

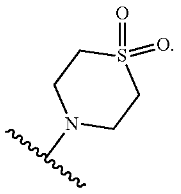 [SMILES: *N1CCS(=O)(=O)CC1]

In some embodiments, for Formulas (I) and (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

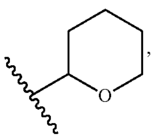, 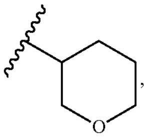, or 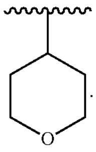.

In some embodiments, Z is a 4-membered oxygen-containing heterocyclyl. In some embodiments, Z is

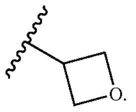 [SMILES: *C1COC1]

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1, 1-dioxidyl. In some embodiments, Z is

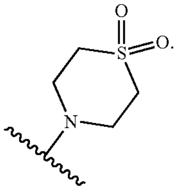 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is b

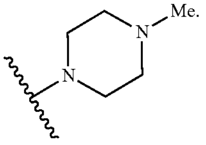 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

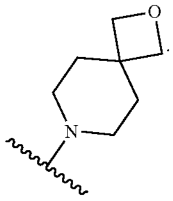 [SMILES: *N1CCC2(CC1)COC2]

In some embodiments, Z is 1-oxa-3,8-diazaspiro[4.5]decan-2-one. In some embodiments, Z is

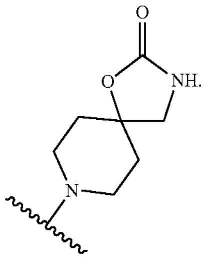 [SMILES: *N1CCC2(CC1)CNC(=O)O2]

In some embodiments, for Formulas (I) and (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) and (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —C(O)OH. In some embodiments, Z is —$CH_3$.

In some embodiments, for Formulas (I) and (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —C(O)$OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

(I-b)

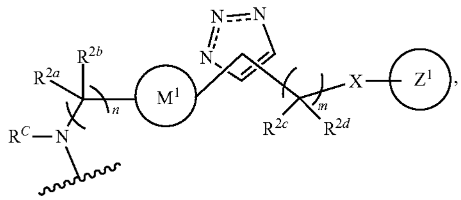

or a pharmaceutically acceptable salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —$N(R^{C1})(R^{D1})$, —$N(R^{C1})C(O)R^{B1}$, —C(O)$N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —C(O)$OR^{A1}$, —C(O)$R^{B1}$, —OC(O)$R^{B1}$, —C(O)$N(R^{C1})$, cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and ∿∿∿ refers to a connection to an attachment group or a polymer described herein. In some embodiments, for each $R^3$ and $R^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

(I-b-i)

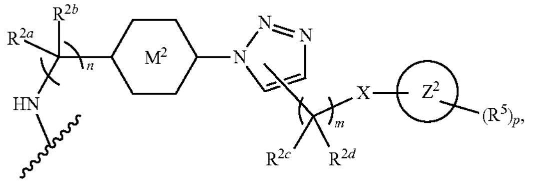

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; each $R^3$ and $R^5$ is independently alkyl, heteroalkyl, halogen, oxo, —$OR^{A1}$, —C(O)$OR^{A1}$, or —C(O)$R^{B1}$, wherein each alkyl and heteroalkyl is optionally substituted with halogen; or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and "∿∿∿" refers to a connection to an attachment group or a polymer described herein.

In some embodiments, the compound of Formula (I-b-i) is a compound of Formula (I-b-ii):

(I-b-ii)

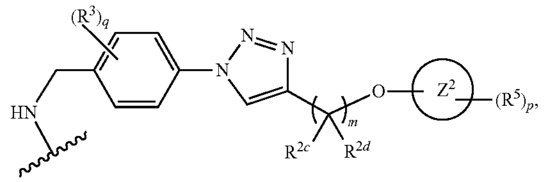

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ and taken together to form an oxo group; each $R^3$ and $R^5$ is independently alkyl, heteroalkyl, halogen, oxo, —$OR^{A1}$, —C(O)$OR^{A1}$, or —C(O)$R^{B1}$, wherein each alkyl and heteroalkyl is optionally substituted with halogen; each $R^{A1}$ and $R^{B1}$ is independently hydrogen, alkyl, or heteroalkyl; each of p and q is independently 0, 1, 2, 3, 4, 5, or 6; and "∿∿∿" refers to a connection to an attachment group or a polymer described herein.

In some embodiments, the compound of Formula (I) is a compound of Formula (I-c):

(I-c)

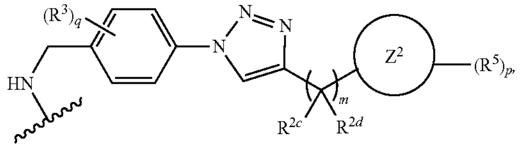

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ is taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; each of p and q is independently 0, 1, 2, 3, 4, 5, or 6; and “ ∿∿∿ ” refers to a connection to an attachment group or a polymer described herein.

In some embodiments, the compound of Formula (I) is a compound of Formula (I-d):

(I-d)

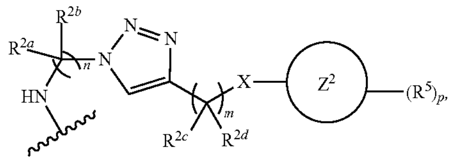

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and “ ∿∿∿ ” refers to a connection to an attachment group or a polymer described herein.

In some embodiments, the compound of Formula (I) is a compound of Formula (I-e):

(I-e)

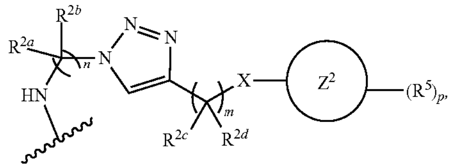

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and “ ∿∿∿ ” refers to a connection to an attachment group or a polymer described herein.

In some embodiments, the compound of Formula (I) is a compound of Formula (I-f):

(I-f)

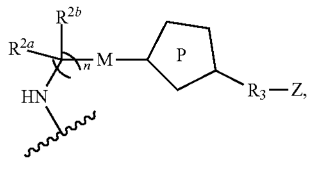

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and “ ∿∿∿ ” refers to a connection to an attachment group or a polymer described herein.

In some embodiments, the compound of Formula (I) is a compound of Formula (II):

(II)

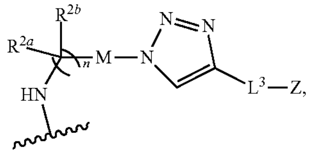

or a pharmaceutically acceptable salt thereof, wherein M is a bond, alkyl or aryl, wherein alkyl and aryl is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl or —$OR^A$, wherein alkyl, heteroalkyl, cycloalkyl, heterocyclyl, aryl, and heteroaryl is optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and “ ∿∿∿ ” refers to a connection to an attachment group or a polymer described herein.

In some embodiments, the compound of Formula (II) is a compound of Formula (II-a):

(II-a)

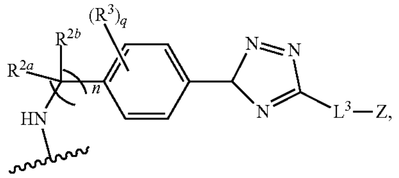

or a pharmaceutically acceptable salt thereof, wherein $L^3$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; $R^A$ is hydrogen; each $R^{A1}$ and $R^{B1}$ is independently hydrogen, alkyl, or heteroalkyl; n is independently 1, 2, 3, 4, 5, or 6; and “ ∿∿∿ ” refers to a connection to an attachment group or a polymer described herein.

In some embodiments, the compound of Formula (I) is a compound of Formula (III):

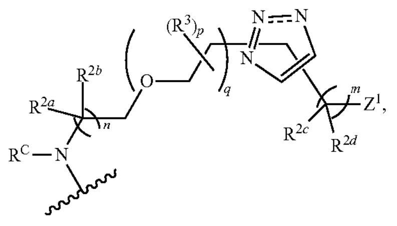

(III)

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and “ ” refers to a connection to an attachment group or a polymer described herein.

In some embodiments, the compound of Formula (III) is a compound of Formula (III-a):

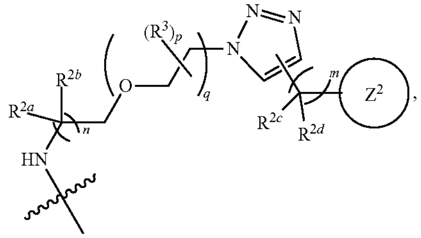

(III-a)

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and “ ” refers to a connection to an attachment group or a polymer described herein.

In some embodiments, the compound of Formula (III-a) is a compound of Formula (III-b):

(III-b)

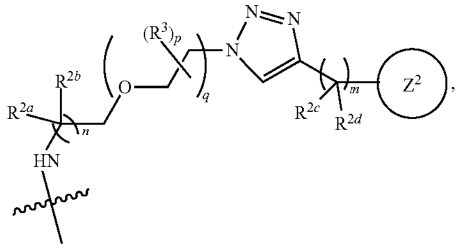

or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and “ ” refers to a connection to an attachment group or a polymer described herein.

In some embodiments, the compound of Formula (III-a) is a compound of Formula (III-c):

(III-c)

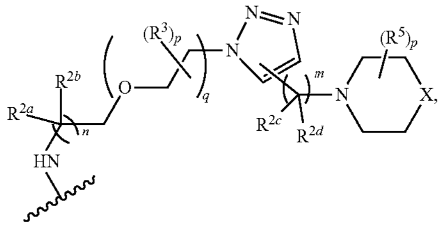

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and “ ” refers to a connection to an attachment group or a polymer described herein.

In some embodiments, the compound of Formula (III-c) is a compound of Formula (III-d):

(III-d)

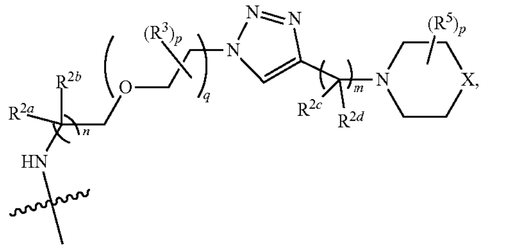

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and " ∿∿∿ " refers to a connection to an attachment group or a polymer described herein.

In some embodiments, the compound is a compound of Formula (I). In some embodiments, $L^2$ is a bond and P and $L^3$ are independently absent.

In some embodiments, the compound is a compound of Formula (I-a). In some embodiments of Formula (II-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (I-b). In some embodiments, P is absent, $L^1$ is —$NHCH_2$, $L^2$ is a bond, M is aryl (e.g., phenyl), $L^3$ is —$CH_2O$, and Z is heterocyclyl (e.g., a nitrogen-containing heterocyclyl, e.g., thiomorpholinyl-1,1-dioxide). In some embodiments, the compound of Formula (I-b) is Compound 116.

In some embodiments of Formula (I-b), P is absent, $L^1$ is —$NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-b) is Compound 105.

In some embodiments, the compound is a compound of Formula (I-b-i). In some embodiments of Formula (I-b-i), each of $R^{2a}$ and $R^{2b}$ is independently hydrogen or $CH_3$, each of $R^{2c}$ and $R^{2d}$ is independently hydrogen, m is 1 or 2, n is 1, X is O, p is 0, $M^2$ is phenyl optionally substituted with one or more $R^3$, $R^3$ is —$CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, the compound of Formula (I-b-i) is Compound 100, Compound 106, Compound 107, Compound 108, Compound 109, or Compound 111.

In some embodiments, the compound is a compound of Formula (I-b-ii). In some embodiments of Formula (I-b-ii), each of $R^{2a}$, $R^{2b}$, $R^{2c}$, and $R^{2d}$ is independently hydrogen, q is 0, p is 0, m is 1, and $Z^2$ is heterocyclyl (e.g., an oxygen-containing heterocyclyl, e.g., tetrahydropyranyl). In some embodiments, the compound of Formula (I-b-ii) is Compound 100.

In some embodiments, the compound is a compound of Formula (I-c). In some embodiments of Formula (I-c), each of $R^{2c}$ and $R^{2d}$ is independently hydrogen, m is 1, p is 1, q is 0, $R^5$ is —$CH_3$, and Z is heterocyclyl (e.g., a nitrogen-containing heterocyclyl, e.g., piperazinyl). In some embodiments, the compound of Formula (I-c) is Compound 113.

In some embodiments, the compound is a compound of Formula (I-d). In some embodiments of Formula (I-d), each of $R^{2a}$, $R^{2b}$, $R^{2c}$, and $R^{2d}$ is independently hydrogen, m is 1, n is 3, X is O, p is 0, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-d) is Compound 110 or Compound 114.

In some embodiments, the compound is a compound of Formula (I-f). In some embodiments of Formula (I-f), each of $R^{2a}$ and $R^{2b}$ is independently hydrogen, n is 1, M is —$CH_2$—, P is a nitrogen-containing heteroaryl (e.g., imidazolyl), $L^3$ is —$C(O)OCH_2$—, and Z is $CH_3$. In some embodiments, the compound of Formula (I-f) is Compound 115.

In some embodiments, the compound is a compound of Formula (II-a). In some embodiments of Formula (II-a), each of $R^{2a}$ and $R^{2b}$ is independently hydrogen, n is 1, q is 0, $L^3$ is —$CH_2(OCH_2CH_2)_2$, and Z is —$OCH_3$. In some embodiments, the compound of Formula (II-a) is Compound 112.

In some embodiments of Formula (II-a), each of $R^{2a}$ and $R^{2b}$ is independently hydrogen, n is 1, $L^3$ is a bond or —$CH_2$, and Z is hydrogen or —OH. In some embodiments, the compound of Formula (II-a) is Compound 103 or Compound 104.

In some embodiments, the compound is a compound of Formula (III). In some embodiments of Formula (III), each of $R^{2a}$, $R^{2b}$, $R^{2c}$, and $R^{2d}$ is independently hydrogen, m is 1, n is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, the compound of Formula (III) is Compound 120.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 0, n is 2, q is 3, p is 0, and $Z^2$ is aryl (e.g., phenyl) substituted with 1 $R^5$ (e.g., —$NH_2$). In some embodiments, the compound of Formula (III-b) is Compound 102.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.g., 2-oxa-7-azaspiro[3.5]nonanyl). In some embodiments, the compound of Formula (III-b) is Compound 121.

In some embodiments, the compound is a compound of Formula (III-d). In some embodiments of Formula (III-d), each of $R^{2a}$, $R^{2b}$, $R^{2c}$, and $R^{2d}$ is independently hydrogen, m is 1, n is 2, q is 1, 2, 3, or 4, p is 0, and X is $S(O)_2$. In some embodiments of Formula (III-d), each of $R^{2a}$ and $R^{2b}$ is independently hydrogen, m is 1, n is 2, q is 1, 2, 3, or 4, p is 0, and X is $S(O)_2$. In some embodiments, the compound of Formula (III-d) is Compound 101, Compound 117, Compound 118, or Compound 119.

In some embodiments, the compound is a compound of Formula (I-b), (I-d), or (I-e). In some embodiments, the compound is a compound of Formula (I-b), (I-d), or (II). In some embodiments, the compound is a compound of Formula (I-b), (I-d), or (I-f). In some embodiments, the compound is a compound of Formula (I-b), (I-d), or (III).

In some embodiments, the compound of Formula (I) is not a compound disclosed in WO2012/112982, WO2012/167223, WO2014/153126, WO2016/019391, WO 2017/075630, US2012-0213708, US 2016-0030359 or US 2016-0030360.

In some embodiments, the compound of Formula (I) comprises a compound shown in Table 4, or a pharmaceutically acceptable salt thereof. In some embodiments, the exterior surface and/or one or more compartments within a device described herein comprises a small molecule compound shown in Table 4, or a pharmaceutically acceptable salt thereof.

TABLE 4

| Exemplary small molecule compounds | |
|---|---|
| Compound No. | Structure |
| 100 | 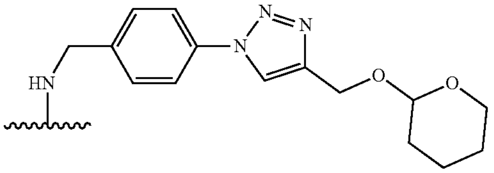 [SMILES: *NCc1ccc(-n2cc(COC3CCCCO3)nn2)cc1] |
| 101 | 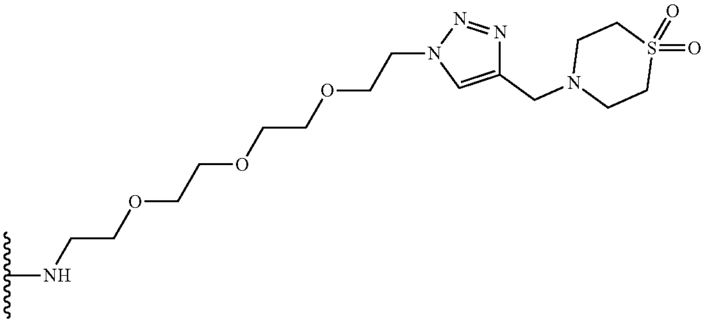 [SMILES: *NCCOCCOCCOCCn1cc(CN2CCS(=O)(=O)CC2)nn1] |
| 102 | 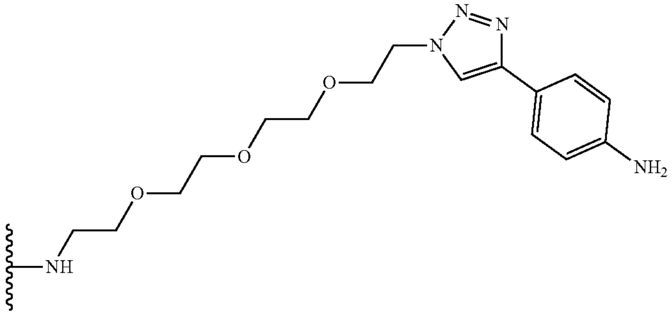 [SMILES: *NCCOCCOCCOCCn1cc(-c2ccc(N)cc2)nn1] |
| 103 | 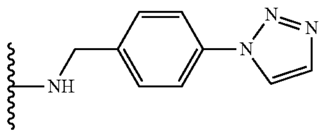 [SMILES: *NCc1ccc(-n2ccnn2)cc1] |
| 104 | 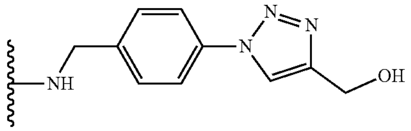 [SMILES: *NCc1ccc(-n2cc(CO)nn2)cc1] |
| 105 | 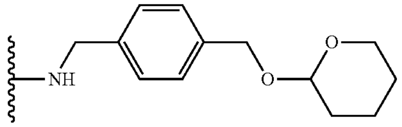 [SMILES: *NCc1ccc(COC2CCCCO2)cc1] |

TABLE 4-continued
| Exemplary small molecule compounds | |
|---|---|
| Compound No. | Structure |
| 106 | 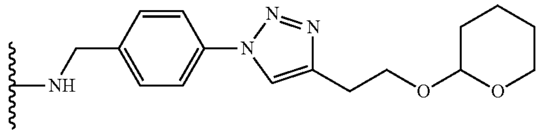 [SMILES: *NCc1ccc(-n2cc(CCOC3CCCCO3)nn2)cc1] |
| 107 | 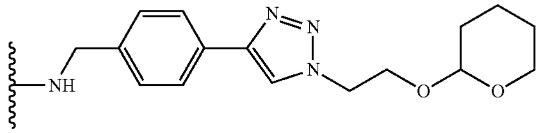 [SMILES: *NCc1ccc(-c2cn(CCOC3CCCCO3)nn2)cc1] |
| 108 | 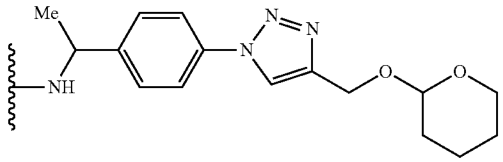 [SMILES: *NC(C)c1ccc(-n2cc(COC3CCCCO3)nn2)cc1] |
| 109 | 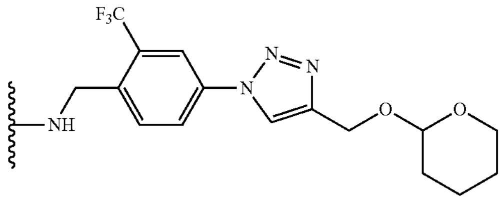 [SMILES: *NCc1ccc(-n2cc(COC3CCCCO3)nn2)cc1C(F)(F)F] |
| 110 | 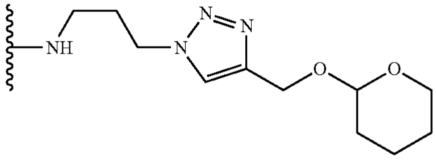 [SMILES: *NCCCn1cc(COC2CCCCO2)nn1] |
| 111 | 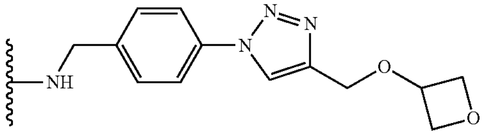 |
| 112 | 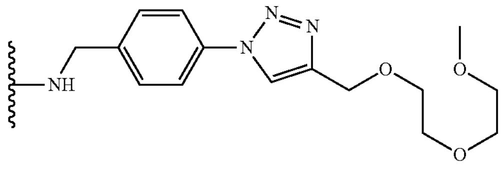 [SMILES: *NCc1ccc(-n2cc(COCCOCCOC)nn2)cc1] |
| 113 | 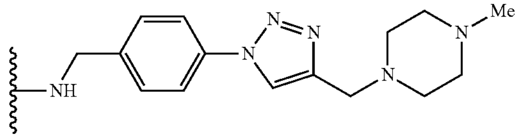 [SMILES: *NCc1ccc(-n2cc(CN3CCN(C)CC3)nn2)cc1] |
| 114 | 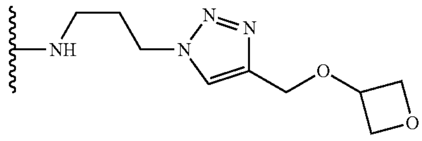 [SMILES: *NCCCn1cc(COC2COC2)nn1] |

TABLE 4-continued
Exemplary small molecule compounds
| Compound No. | Structure |
| --- | --- |
| 115 | 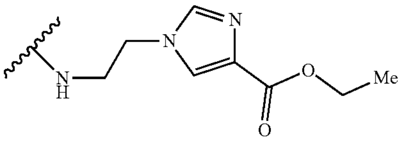 [SMILES: *NCCn1cnc(C(=O)OCC)c1] |
| 116 | 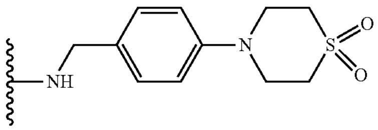 [SMILES: *NCc1ccc(N2CCS(=O)(=O)CC2)cc1] |
| 117 | 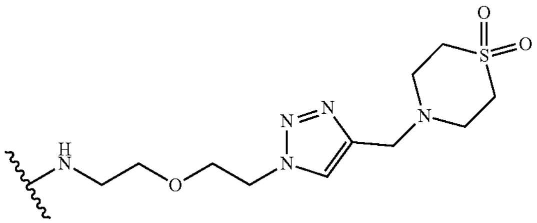 [SMILES: *NCCOCCn1cc(CN2CCS(=O)(=O)CC2)nn1] |
| 118 | 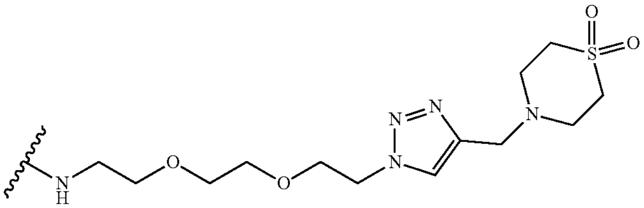 [SMILES: *NCCOCCOCCn1cc(CN2CCS(=O)(=O)CC2)nn1] |
| 119 | 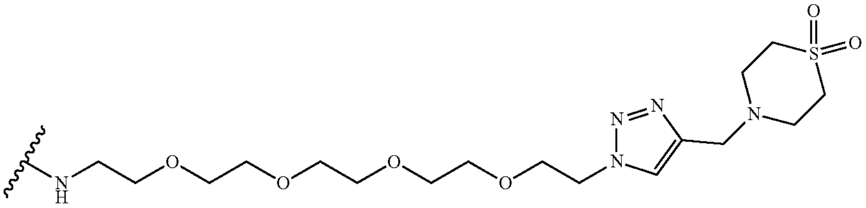 [SMILES: *NCCOCCOCCOCCOCCn1cc(CN2CCS(=O)(=O)CC2)nn1] |
| 120 | 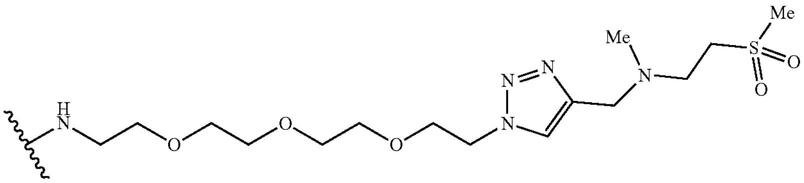 [SMILES: *NCCOCCOCCOCCn1cc(CN(C)CCS(C)(=O)=O)nn1] |
| 121 | 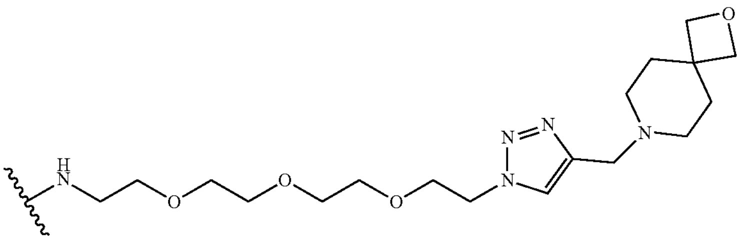 [SMILES: *NCCOCCOCCOCCn1cc(CN2CCC3(CC2)COC3)nn1] |

In some embodiments, the compound is a compound of Formula (I) (e.g., Formulas (I-a), (I-b), (I-c), (I-d), (I-e), (I-f), (II), (II-a), (III), (III-a), (III-b), (III-c), or (III-d)), or a pharmaceutically acceptable salt thereof and is selected from:

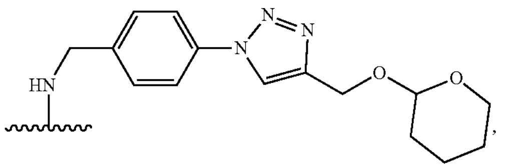

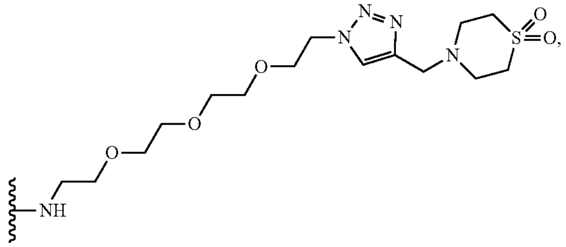

and

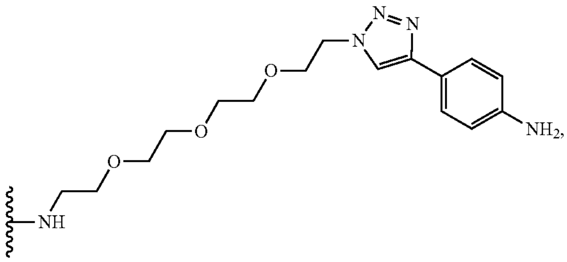

or a pharmaceutically acceptable salt thereof.

In some embodiments, the device described herein comprises the compound of

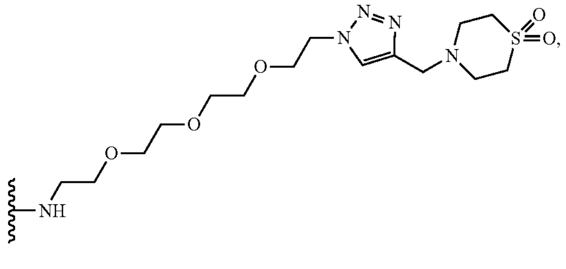

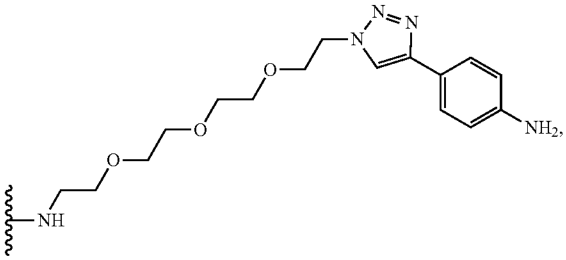

pharmaceutically acceptable salt of either compound.

In some embodiments, a compound of Formula (I) (e.g., Compound 101 in Table 4) is covalently attached to an alginate (e.g., an alginate with approximate MW <75 kDa, G:M ratio ≥1.5) at a conjugation density of at least 2.0% and less than 9.0%, or 3.0% to 8.0%, 4.0-7.0, 5.0 to 7.0, or 6.0 to 7.0 or about 6.8 as determined by combustion analysis for percent nitrogen as described in the Examples below.

Cells

The devices of the present disclosure comprise at least one cell-containing compartment that comprises a plurality of cells (e.g., live cells). The cells may be a variety of different cell types (e.g., human cells), including epithelial cells, endothelial cells, fibroblast cells, mesenchymal stem cells, keratinocyte cells and islet cells. Exemplary cell types include the cell types recited in WO 2017/075631. In some embodiments, the cells are derived from a cell-line shown in Table 5 below.

TABLE 5

| Exemplary cell lines | | | |
|---|---|---|---|
| Cell Line | Cell Type | Germ Layer | Commercial Source |
| ARPE-19 | Epithelial (Retinal) | Ectoderm | ATCC (CRL-2302) |
| BJ | Fibroblast (Foreskin) | Ectoderm | ATCC (CRL-2522) |
| CCD-841-CoN | Epithelial (Colon) | Endoderm | ATCC (CRL-1790) |
| HaCat | Keratinocyte | Ectoderm | Addexbio (T0020001) |
| HHSEC | Endothelial (Hepatic Sinusoidal) | Endoderm | Sciencellonline.com (#5000) |
| Huv-EC-C | Endothelial (Embryonic umbilical) | Mesoderm | ATCC (CRL-1730) |
| MCF-10A | Epithelial (Mammary Gland) | Ectoderm | ATCC (CRL-10317) |
| MRC-5 | Fibroblast (Lung) | Mesoderm | ATCC (CCL-171) |
| MSC, human | Mesenchyme (Bone Marrow) | Mesoderm | ATCC (PCS-500-012) |
| MSC, mouse | Mesenchyme (Bone Marrow) | Mesoderm | Cyagen (MU BMX-01001) |
| WS-1 | Fibroblast (Skin) | Ectoderm | ATCC (CRL-1502) |
| 293F | Epithelial (Embryonic Kidney) | Mesoderm | Thermo Fisher (R790007) |

In some embodiments, the device does not comprise any islet cells, as defined herein. In an embodiment, cells contained in a device of the disclosure, e.g., RPE cells, MSFCs, including engineered RPE cells and MSFCs, have one or more of the following characteristics: (i) are not capable of producing insulin (e.g., insulin A-chain, insulin B-chain, or proinsulin) in an amount effective to treat diabetes or another disease or condition that may be treated with insulin; (ii) not capable of producing insulin in a glucose-responsive manner; or (iii) not derived from an induced pluripotent stem cell that was engineered or differentiated into insulin-producing pancreatic beta cells.

In an embodiment, the plurality of cells is in the form of a cell suspension prior to being encapsulated within a device described herein, e.g., a hydrogel capsule. The cells in the suspension may take the form of single cells (e.g., from a monolayer cell culture), or provided in another form, e.g., disposed on a microcarrier (e.g., a bead or matrix) or as a three-dimensional aggregate of cells (e.g., a cell cluster or spheroid). The cell suspension can comprise multiple cell clusters (e.g., as spheroids) or microcarriers.

In some embodiments, the cells in the plurality have been engineered to produce a therapeutic agent. In an embodiment, the therapeutic agent is for the prevention or treatment of a disease, disorder, or condition, e.g., those described in WO 2017/075631. The therapeutic agent may be any biological substance, such as a nucleic acid (e.g., a nucleotide, DNA, or RNA), a polypeptide, a lipid, a sugar (e.g., a monosaccharide, disaccharide, oligosaccharide, or polysaccharide), or a small molecule. Exemplary therapeutic agents include the agents listed in WO 2017/075631.

In some embodiments, the therapeutic agent is a peptide or polypeptide (e.g., a protein), such as a hormone, enzyme, cytokine (e.g., a pro-inflammatory cytokine or an anti-inflammatory cytokine), growth factor, clotting factor, or lipoprotein. A peptide or polypeptide (e.g., a protein, e.g., a hormone, growth factor, clotting factor or coagulation factor, antibody molecule, enzyme, cytokine, cytokine receptor, or a chimeric protein including cytokines or a cytokine receptor) produced by an engineered cell can have a naturally occurring amino acid sequence, or may contain a variant of the naturally occurring sequence. The variant can be a naturally occurring or non-naturally occurring amino acid substitution, mutation, deletion or addition relative to the reference sequence, e.g., a naturally occurring sequence. The naturally occurring amino acid sequence may be a polymorphic variant. The naturally occurring amino acid sequence can be a human or a non-human amino acid sequence. In some embodiments, the naturally occurring amino acid sequence or naturally occurring variant thereof is a human sequence. In addition, a peptide or polypeptide (e.g., a protein) for use with the present disclosure may be modified in some way, e.g., via chemical or enzymatic modification (e.g., glycosylation, phosphorylation). In some embodiments, the peptide has about 2, 3, 4, 5, 6, 7, 8, 9, 10, 12, 14, 16, 18, 20, 25, 30, 35, 40, 45, or less than 50 amino acids. In some embodiments, the protein has an average molecular weight of 5 kD, 10 kD, kD, 50 kD, 100 kD, 150 kD, 200 kD, 250 kD, 500 kD, or more.

In some embodiments, the protein is a hormone. Exemplary hormones include anti-diuretic hormone (ADH), oxytocin, growth hormone (GH), prolactin, growth hormone-releasing hormone (GHRH), thyroid stimulating hormone (TSH), thyrotropin-release hormone (TRH), adrenocorticotropic hormone (ACTH), follicle-stimulating hormone (FSH), luteinizing hormone (LH), luteinizing hormone-releasing hormone (LHRH), thyroxine, calcitonin, parathyroid hormone (PTH), aldosterone, cortisol, epinephrine, glucagon, insulin, estrogen, progesterone, and testosterone. In some embodiments, the protein is insulin (e.g., insulin A-chain, insulin B-chain, or proinsulin). In some embodiments, the protein is a growth hormone, such as human growth hormone (hGH), recombinant human growth hormone (rhGH), bovine growth hormone, methionine-human growth hormone, des-phenylalanine human growth hormone, and porcine growth hormone.

In some embodiments, the protein is a growth factor, e.g., vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

In some embodiments, the protein is a clotting factor or a coagulation factor, e.g., a blood clotting factor or a blood coagulation factor. In some embodiments, the protein is a protein involved in coagulation, i.e., the process by which blood is converted from a liquid to solid or gel. Exemplary clotting factors and coagulation factors include Factor I (e.g., fibrinogen), Factor II (e.g., prothrombin), Factor III (e.g., tissue factor), Factor V (e.g., proaccelerin, labile factor), Factor VI, Factor VII (e.g., stable factor, proconvertin), Factor VIII (e.g., antihemophilic factor A), Factor VIIIC, Factor IX (e.g., antihemophilic factor B), Factor X (e.g., Stuart-Prower factor), Factor XI (e.g., plasma thromboplastin antecedent), Factor XII (e.g., Hagerman factor), Factor XIII (e.g., fibrin-stabilizing factor), von Willebrand factor (vWF), prekallikrein, heparin cofactor II, high molecular weight kininogen (e.g., Fitzgerald factor), antithrombin III, and fibronectin. In some embodiments, the protein is an anti-clotting factor, such as Protein C.

In some embodiments, the protein is an antibody molecule. As used herein, the term “antibody molecule” refers to a protein, e.g., an immunoglobulin chain or fragment thereof, comprising at least one immunoglobulin variable domain sequence. The term “antibody molecule” includes, for example, a monoclonal antibody (including a full-length antibody which has an immunoglobulin Fc region). In an embodiment, an antibody molecule comprises a full-length antibody, or a full-length immunoglobulin chain. In an embodiment, an antibody molecule comprises an antigen binding or functional fragment of a full-length antibody, or a full-length immunoglobulin chain. In an embodiment, an antibody molecule is a monospecific antibody molecule and binds a single epitope, e.g., a monospecific antibody molecule having a plurality of immunoglobulin variable domain sequences, each of which binds the same epitope. In an embodiment, an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

Various types of antibody molecules may be produced by the encapsulated engineered cells, including whole immunoglobulins of any class, fragments thereof, and synthetic proteins containing at least the antigen binding variable domain of an antibody. The antibody molecule can be an antibody, e.g., an IgG antibody, such as $IgG_1$, $IgG_2$, $IgG_3$, or $IgG_4$. An antibody molecule can be in the form of an antigen binding fragment including a Fab fragment, F(ab')2 fragment, a single chain variable region, and the like. Antibodies can be polyclonal or monoclonal (mAb). Monoclonal antibodies may include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity. In some embodiments, the antibody molecule is a single-domain antibody (e.g., a nanobody). The described antibodies can also be modified by recombinant means, for example by deletions, additions or substitutions of amino acids, to increase efficacy of the antibody in mediating the desired function. Exemplary antibodies include anti-beta-galactosidase, anti-collagen, anti-CD14, anti-CD20, anti-CD40, anti-HER2, anti-IL-1, anti-IL-4, anti-IL6, anti-IL-13, anti-IL17, anti-IL18, anti-IL-23, anti-IL-28, anti-IL-29, anti-IL-33, anti-EGFR, anti-VEGF, anti-CDF, anti-flagellin, anti-IFN-α, anti-IFN-β, anti-IFN-γ, anti-mannose receptor, anti-VEGF-A, anti-TLR1, anti-TLR2, anti-TLR3, anti-TLR4, anti-TLR5, anti-TLR6, anti-TLR9, anti-PDF, anti-PD1 (also known as anti-PD-1), anti-PD-L1, or anti-nerve growth factor antibody. In some embodiments, the antibody is an anti-nerve growth factor antibody (e.g., fulranumab, fasinumab, tanezumab).

In some embodiments, the protein is a cytokine or a cytokine receptor, or a chimeric protein including cytokines or their receptors, including, for example tumor necrosis factor alpha and beta, their receptors and their derivatives, renin; lipoproteins; colchicine; corticotrophin; vasopressin; somatostatin; lypressin; pancreozymin; leuprolide; alpha-1-antitrypsin; atrial natriuretic factor; lung surfactant; a plasminogen activator other than a tissue-type plasminogen activator (t-PA), for example a urokinase; bombesin; thrombin; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1, IL-2 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. Suitable proteins or peptides may be native or recombinant and include, e.g., fusion proteins.

Examples of a polypeptide (e.g., a protein) produced by devices described herein also include CCL1, CCL2 (MCP-1), CCL3 (MIP-1α), CCL4 (MIP-1β), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, IL5, IL6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A (IL1F1), IL1B (IL1F2), IL1Ra (IL1F3), IL1F5 (IL36RN), IL1F6 (IL36A), IL1F7 (IL37), IL1F8 (IL36B), IL1F9 (IL36G), IL1F10 (IL38), IL33 (IL1F11), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, C1qtnf4, Ccl21a, Ccl27a, Cd70, Cer1, Cklf, Clcf1, Cmtm2a, Cmtm2b, Cmtm3, Cmtm4, Cmtm5, Cmtm6, Cmtm7, Cmtm8, Crlf1, Ctf2, Ebi3, Edn1, Fam3b, Fasl, Fgf2, Flt31, Gdf10, Gdf11, Gdf15, Gdf2, Gdf3, Gdf5, Gdf6, Gdf7, Gdf9, Gm12597, Gm13271, Gm13275, Gm13276, Gm13280, Gm13283, Gm2564, Gpi1, Grem1, Grem2, Grn, Hmgb1, Ifna11, Ifna12, Ifna9, Ifnab, Ifne, Il17a, Il23a, Il25, Il31, Iltifb, Inhba, Lefty1, Lefty2, Mstn, Nampt, Ndp, Nodal, Pf4, Pglyrp1, Prl7d1, Scg2, Scgb3a1, Slurp1, Spp1, Thpo, Tnfsf10, Tnfsf11, Tnfsf12, Tnfsf13, Tnfsf13b, Tnfsf14, Tnfsf15, Tnfsf18, Tnfsf4, Tnfsf8, Tnfsf9, Tslp, Vegfa, Wnt1, Wnt2, Wnt5a, Wnt7a, Xcl1, epinephrine, melatonin, triiodothyronine, a prostaglandin, a leukotriene, prostacyclin, thromboxane, islet amyloid polypeptide, müllerian inhibiting factor or hormone, adiponectin, corticotropin, angiotensin, vasopressin, arginine vasopressin, atriopeptin, brain natriuretic peptide, calcitonin, cholecystokinin, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, hepcidin, human chorionic gonadotropin, human placental lactogen, inhibin, somatomedin, leptin, lipotropin, melanocyte stimulating hormone, motilin, orexin, oxytocin, pancreatic polypeptide, pituitary adenylate cyclase-activating peptide, relaxin, renin, secretin, somatostatin, thrombopoietin, thyrotropin, thyrotropin-releasing hormone, vasoactive intestinal peptide, androgen, alpha-glucosidase (also known as acid maltase), glycogen phosphorylase, glycogen debrancher enzyme, phosphofructokinase, phosphoglycerate kinase, phosphoglycerate mutase, lactate dehydrogenase, carnitine palymityl transferase, carnitine, and myoadenylate deaminase.

In some embodiments, the protein is a replacement therapy or a replacement protein. In some embodiments, the replacement therapy or replacement protein is a clotting factor or a coagulation factor, e.g., Factor VIII (e.g., comprises a naturally occurring human Factor VIII amino acid sequence or a variant thereof) or Factor IX (e.g., comprises a naturally occurring human Factor IX amino acid sequence or a variant thereof).

Figure 20:
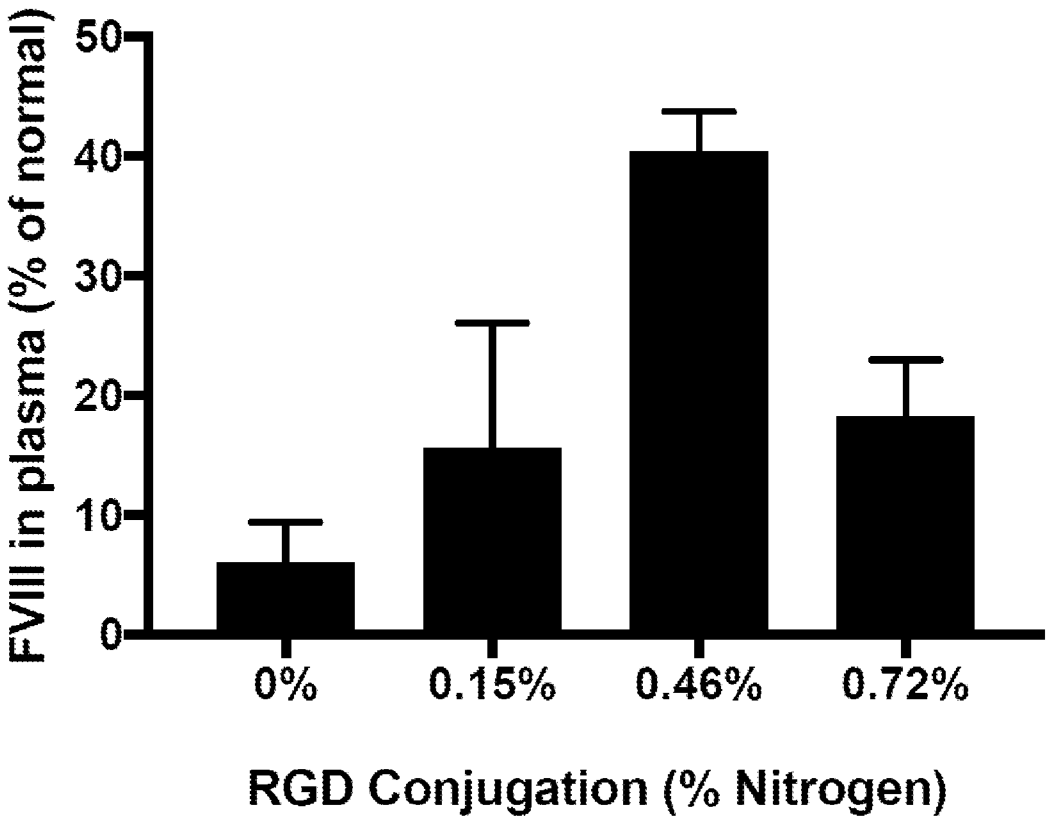
FIG. 20 is a bar graph showing the plasma levels of FVIII-BDD in nude mice (5 mice per group) after 11 days implantation of 2-compartment hydrogel capsules containing RPE cells engineered to express the FVIII protein (SEQ ID NOT encoded by SEQ ID NO:8).
Figure 21:
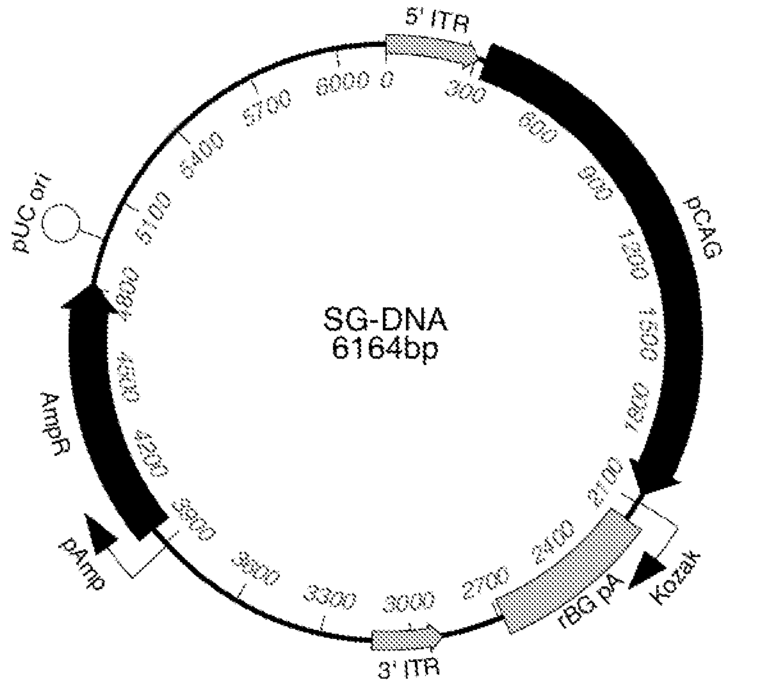
FIG. 21 illustrates a PiggyBac transposon expression vector useful for generating engineered RPE cells.

In some embodiments, the plurality of cells are engineered to express a human Factor VIII protein, e.g., a recombinant Factor VIII. In some embodiments, the recombinant Factor VIII is a B-domain-deleted recombinant Factor VIII (FVIII-BDD). In some embodiments, the FVIII-BDD protein is a FVIII-BDD protein shown in FIG. 20. In an embodiment, the FVIII-BDD protein comprises, consists essentially of, or consists of SEQ ID NO:1.

In some embodiments, the cells are engineered to express a Factor IX, e.g., a human Factor IX (FIX) protein. In some embodiments, the FIX protein is a FIX-padua protein and comprises, consists essentially of, or consists of SEQ ID NO:36.

In some embodiments, the encapsulated cells are derived from a human RPE cell line and comprise an exogenous nucleic acid sequence which comprises a promoter sequence (e.g., nucleotides 337-2069 of SEQ ID NO:26 or SEQ ID NO:23) operably linked to a coding sequence for a polypeptide. In an embodiment, the coding sequence is a codon-optimized FVIII-BDD coding sequence shown in FIG. 24 (SEQ ID NO: 9, 10, 11, 12, 13, 14, 15, 16 or 17) or a codon-optimized FIX-padua coding sequence shown in FIG. 24 (SEQ ID NO: 19, 20 or 21).

In some embodiments, the replacement therapy or replacement protein is an enzyme, e.g., alpha-galactosidase A (GLA), alpha-L-iduronidase (IDUA), glucocerebrosidase, N-sulfoglucosamine sulfohydrolase (SGSH), N-acetyl-alpha-d-glucosaminidase, N-acetylglucosamine 4-sulphatase, urate oxidase, phenyalanine hydroxylase, or phenylalanine ammonia lyase. In some embodiments, the replacement therapy or replacement protein is a cytokine or an antibody.

In some embodiments, the therapeutic agent is a sugar, e.g., monosaccharide, disaccharide, oligosaccharide, or polysaccharide. In some embodiments, a sugar comprises a triose, tetrose, pentose, hexose, or heptose moiety. In some embodiments, the sugar comprises a linear monosaccharide or a cyclized monosaccharide. In some embodiments, the sugar comprises a glucose, galactose, fructose, rhamnose, mannose, arabinose, glucosamine, galactosamine, sialic acid, mannosamine, glucuronic acid, galactosuronic acid, mannuronic acid, or guluronic acid moiety. In some embodiments, the sugar is attached to a protein (e.g., an N-linked glycan or an O-linked glycan). Exemplary sugars include glucose, galactose, fructose, mannose, rhamnose, sucrose, ribose, xylose, sialic acid, maltose, amylose, inulin, a fructooligosaccharide, galactooligosaccharide, a mannan, a lectin, a pectin, a starch, cellulose, heparin, hyaluronic acid, chitin, amylopectin, or glycogen. In some embodiments, the therapeutic agent is a sugar alcohol.

In some embodiments, the therapeutic agent is a lipid. A lipid may be hydrophobic or amphiphilic, and may form a tertiary structure such as a liposome, vesicle, or membrane or insert into a liposome, vesicle, or membrane. A lipid may comprise a fatty acid, glycerolipid, glycerophospholipid, sterol lipid, prenol lipid, sphingolipid, saccharolipid, polyketide, or sphingolipid. Examples of lipids produced by the encapsulated cells include anandamide, docosahexaenoic acid, a prostaglandin, a leukotriene, a thromboxane, an eicosanoid, a triglyceride, a cannabinoid, phosphatidylcholine, phosphatidylethanolamine, a phosphatidylinositol, a phosohatidic acid, a ceramide, a sphingomyelin, a cerebroside, a ganglioside, estrogen, androsterone, testosterone, cholesterol, a carotenoid, a quinone, a hydroquinone, or a ubiquinone.

In some embodiments, the therapeutic agent is a small molecule. A small molecule may include a natural product produced by a cell. In some embodiments, the small molecule has poor availability or does not comply with the Lipinski rule of five (a set of guidelines used to estimate whether a small molecule will likely be an orally active drug in a human; see, e.g., Lipinski, C. A. et al (2001) *Adv Drug Deliv* 46:2-36). Exemplary small molecule natural products include an anti-bacterial drug (e.g., carumonam, daptomycin, fidaxomicin, fosfomycin, ispamicin, micronomicin sulfate, miocamycin, mupiocin, netilmicin sulfate, teicoplanin, thienamycin, rifamycin, erythromycin, vancomycin), an anti-parasitic drug (e.g., artemisinin, ivermectin), an anti-cancer drug (e.g., doxorubicin, aclarubicin, aminolaevulinic acid, arglabin, omacetaxine mepesuccinate, paclitaxel, pentostatin, peplomycin, romidepsin, trabectdin, actinomycin D, bleomycin, chromomycin A, daunorubicin, leucovorin, neocarzinostatin, streptozocin, trabectedin, vinblastine, vincristine), anti-diabetic drug (e.g., voglibose), a central nervous system drug (e.g., L-dopa, galantamine, zicontide), a statin (e.g., mevastatin), an anti-fungal drug (e.g., fumagillin, cyclosporin), 1-deoxynojirimycin, and theophylline, sterols (cholesterol, estrogen, testerone). Additional small molecule natural products are described in Newman, D. J. and Cragg, M. (2016) *J Nat Prod* 79:629-661 and Butler, M. S. et al (2014) *Nat Prod Rep* 31:1612-1661, which are incorporated herein by reference in their entirety.

In some embodiments, the cells are engineered to synthesize a non-protein or non-peptide small molecule. For example, in an embodiment an engineered cell can produce a statin (e.g., taurostatin, pravastatin, fluvastatin, or atorvastatin).

In some embodiments, the therapeutic agent is an antigen (e.g., a viral antigen, a bacterial antigen, a fungal antigen, a plant antigen, an environmental antigen, or a tumor antigen). An antigen is recognized by those skilled in the art as being immunostimulatory, i.e., capable of stimulating an immune response or providing effective immunity to the organism or molecule from which it derives. An antigen may be a nucleic acid, peptide, protein, sugar, lipid, or a combination thereof.

The cells in the devices described herein may produce a single therapeutic agent or a plurality of therapeutic agents. The plurality of therapeutic agents may be related or may form a complex. In some embodiments, the therapeutic agent secreted or released from a device is in an active form. In some embodiments, the therapeutic agent is secreted or released from a device in an inactive form, e.g., as a prodrug. In the latter instance, the therapeutic agent may be activated by a downstream agent, such as an enzyme.

Methods of Treatment

Described herein are methods for preventing or treating a disease, disorder, or condition in a subject through administration or implantation of a device or preparation of devices described herein that produces a therapeutic agent that treats the disease, disorder or condition. The methods comprise administering or implanting a device or device preparation comprising a plurality of the device, wherein the device comprises (i) at least one cell-containing compartment which comprises a polymer composition comprising a first cell-binding substance (CBS) and encapsulating a plurality of cells (e.g., live cells) capable of expressing the therapeutic agent when the device or device preparation is implanted into the subject, and (ii) means for mitigating the FBR when the device or device preparation is implanted in the subject. In an embodiment, the means comprises a barrier compartment surrounding the cell-containing compartment and comprising a compound of Formula (I) (e.g., as described herein). In some embodiments, the methods described herein directly or indirectly reduce or alleviate at least one symptom of the disease, disorder, or condition. In some embodiments, the methods described herein prevent or slow the onset of the disease, disorder, or condition. In some embodiments, the subject is a human.

In some embodiments, the disease, disorder, or condition affects a system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, the disease, disorder, or condition affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

In some embodiments, the disease, disorder or condition is a neurodegenerative disease, diabetes, a heart disease, an autoimmune disease, a cancer, a liver disease, a lysosomal storage disease, a blood clotting disorder or a coagulation disorder, an orthopedic condition, an amino acid metabolism disorder.

In some embodiments, the disease, disorder or condition is a neurodegenerative disease. Exemplary neurodegenerative diseases include Alzheimer's disease, Huntington's disease, Parkinson's disease (PD) amyotrophic lateral sclerosis (ALS), multiple sclerosis (MS) and cerebral palsy (CP), dentatorubro-pallidoluysian atrophy (DRPLA), neuronal intranuclear hyaline inclusion disease (NIHID), dementia with Lewy bodies, Down's syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Jakob-Creutzfeldt disease, Niemann-Pick disease type 3, progressive supranuclear palsy, subacute sclerosing panencephalitis, spinocerebellar ataxias, Pick's disease, and dentatorubral-pallidoluysian atrophy.

In some embodiments, the disease, disorder, or condition is an autoimmune disease, e.g., scleroderma, multiple sclerosis, lupus, or allergies.

In some embodiments, the disease is a liver disease, e.g., hepatitis B, hepatitis C, cirrhosis, NASH.

In some embodiments, the disease, disorder, or condition is cancer. Exemplary cancers include leukemia, lymphoma, melanoma, lung cancer, brain cancer (e.g., glioblastoma), sarcoma, pancreatic cancer, renal cancer, liver cancer, testicular cancer, prostate cancer, or uterine cancer.

In some embodiments, the disease, disorder, or condition is an orthopedic condition. Exemplary orthopedic conditions include osteoporosis, osteonecrosis, Paget's disease, or a fracture.

In some embodiments, the disease, disorder or condition is a lysosomal storage disease. Exemplary lysosomal storage diseases include Gaucher disease (e.g., Type I, Type II, Type III), Tay-Sachs disease, Fabry disease, Farber disease, Hurler syndrome (also known as mucopolysaccharidosis type I (MPS I)), Hunter syndrome, lysosomal acid lipase deficiency, Niemann-Pick disease, Salla disease, Sanfilippo syndrome (also known as mucopolysaccharidosis type IIIA (MPS3A)), multiple sulfatase deficiency, Maroteaux-Lamy syndrome, metachromatic leukodystrophy, Krabbe disease, Scheie syndrome, Hurler-Scheie syndrome, Sly syndrome, hyaluronidase deficiency, Pompe disease, Danon disease, gangliosidosis, or Morquio syndrome.

In some embodiments, the disease, disorder, or condition is a blood clotting disorder or a coagulation disorder. Exemplary blood clotting disorders or coagulation disorders include hemophilia (e.g., hemophilia A or hemophilia B), Von Willebrand disease, thrombocytopenia, uremia, Bernard-Soulier syndrome, Factor XII deficiency, vitamin K deficiency, or congenital afibrinogenimia.

In some embodiments, the disease, disorder, or condition is an amino acid metabolism disorder, e.g., phenylketonuria, tyrosinemia (e.g., Type 1 or Type 2), alkaptonuria, homocystinuria, hyperhomocysteinemia, maple syrup urine disease.

In some embodiments, the disease, disorder, or condition is a fatty acid metabolism disorder, e.g., hyperlipidemia, hypercholesterolemia, galactosemia.

In some embodiments, the disease, disorder, or condition is a purine or pyrimidine metabolism disorder, e.g., Lesch-Nyhan syndrome.

In some embodiments, the disease, disorder, or condition is diabetes (e.g., Type I or Type II diabetes).

The present disclosure further comprises methods for identifying a subject having or suspected of having a disease, disorder, or condition described herein, and upon such identification, administering to the subject a device comprising an inner compartment comprising an alginate covalently modified with a cell-binding peptide and an outer compartment comprising a compound of Formula (I) (e.g., as described herein), or a composition comprising such a plurality of such a device. In an embodiment, the subject is a human.

Pharmaceutical Compositions, Kits, and Administration

The present disclosure further comprises pharmaceutical compositions comprising the devices described herein, as well as kits thereof.

In some embodiments, a pharmaceutical composition comprises a device, or a plurality of the device, wherein the device comprises at least one cell-containing compartment which comprises a polymer composition comprising a cell-binding substance and encapsulating a plurality of cells (e.g., live cells), means for mitigating the foreign body response (FBR), and a pharmaceutically acceptable excipient. The live cells express a therapeutic agent when the composition is administered to (e.g., implanted into) a subject. In some embodiments, the pharmaceutical composition comprises an effective amount of the device (e.g., a quantity of hydrogel capsules, e.g., 100, 200, 400, 800, 2,000 or more capsules. In some embodiments, the effective amount is a therapeutically effective amount. In some embodiments, the effective amount is a prophylactic ally effective amount.

Pharmaceutical compositions described herein can be prepared by any method known in the art of pharmacology. In general, such preparatory methods include the steps of bringing the devices as the "active ingredient" (e.g., hydrogel capsules, particles) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient (i.e., number of hydrogel capsules, particles). The predetermined amount is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

The term "pharmaceutically acceptable excipient" refers to a non-toxic carrier, adjuvant, diluent, or vehicle that does not destroy the pharmacological activity of the device with which it is formulated. Pharmaceutically acceptable excipients useful in the manufacture of the pharmaceutical compositions of the disclosure are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The devices and related compositions described herein may be administered orally, parenterally (including subcutaneous, intramuscular, and intradermal), topically, rectally, nasally, intratumorally, intrathecally, intraocularlly, intravitreally, buccally, vaginally or via an implanted reservoir. In some embodiments, provided devices or compositions are administrable subcutaneously or by implant.

In some embodiments, the devices and related compositions described herein may be administered to or implanted in or on a certain region of the body, such as a mucosal surface or a body cavity. Exemplary sites of administration or implantation include the peritoneal cavity (e.g., lesser sac), adipose tissue, heart, eye (e.g., retina), muscle, spleen, lymph node, esophagus, nose, sinus, teeth, gums, tongue, mouth, throat, small intestine, large intestine, thyroid, bone (e.g. hip or a joint), breast, cartilage, vagina, uterus, fallopian tube, ovary, penis, testicles, blood vessel, liver, kidney, central nervous system (e.g., brain, spinal cord, nerve), or ear (e.g., cochlea).

In some embodiments, the devices and related compositions described herein are administered to or implanted at a site other than the central nervous system, e.g., the brain, spinal cord, nerve. In some embodiments, the devices and related compositions described herein are administered or implanted at a site other than the eye.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For ophthalmic use, provided pharmaceutically acceptable compositions may be formulated as micronized suspensions or in an ointment such as petrolatum.

Although the descriptions of pharmaceutical compositions provided herein are principally directed to pharmaceutical compositions which are suitable for administration to humans, it will be understood by the skilled artisan that such compositions are generally suitable for administration to subjects of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The devices and related compositions described herein may be formulated in dosage unit form, e.g., single unit dosage form, for ease of administration and uniformity of dosage. It will be understood, however, that the total dosage and usage regimens of the compositions of the present disclosure will be decided by the attending physician within the scope of sound medical judgment. The specific therapeutically effective dose level for any particular subject or organism will depend upon a variety of factors including the disease being treated and the severity of the disorder; the productivity of the specific devices employed and the activity of the therapeutic agent produced by the devices; the specific composition employed; the age, body weight, general health, sex and diet of the subject; the time of administration, route of administration, and half-life of the specific therapeutic agent secreted by the administered device(s); the duration of the treatment; drugs used in combination or coincidental with the specific therapeutic agent expressed by the device; and like factors well known in the medical arts.

The exact amount of a treatment required to achieve an effective amount will vary from subject to subject, depending, for example, on species, age, and general condition of a subject, severity of the side effects or disorder, identity of the particular device(s), mode of administration, and the like. The desired dosage can be delivered three times a day, two times a day, once a day, every other day, every third day, every week, every two weeks, every three weeks, every four weeks. In some embodiments, the desired dosage is delivered once every two, three, four, six, nine or twelve months or once every one, two, three or more years. In certain embodiments, the desired dosage can be delivered using multiple administrations (e.g., two, three, four, five, six, seven, eight, nine, ten, eleven, twelve, thirteen, fourteen, or more administrations). In some embodiments, each succeeding administration or implant of devices or related composition is performed following removal of the preceding administration or implant.

It will be appreciated that the devices and related compositions described herein can be administered in combination with one or more additional pharmaceutical agents. Such pharmaceutical agents may improve bioavailability or the therapeutic agent, reduce and/or modify metabolism of the therapeutic agent, inhibit the FBR of the implanted devices, and/or modify distribution of the therapeutic agent within the body. It will also be appreciated that the therapy employed may achieve a desired effect for the same disorder, and/or it may achieve different effects.

Also encompassed by the disclosure are kits (e.g., pharmaceutical packs). The inventive kits may be useful for preventing and/or treating any of the diseases, disorders or conditions described herein. The kits provided may comprise a pharmaceutical composition (e.g., composition of devices) or a device as described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or device described herein. In some embodiments, the pharmaceutical composition or device provided in the container and the second container are combined to form one unit dosage form.

Methods of Making Devices

The present disclosure further comprises methods for making a device described herein, e.g., a cell-containing compartment comprising a plurality of cells encapsulated in a polymer composition comprising a cell-binding substance and means for mitigating the FBR.

In embodiments where the device comprises a preparation of single compartment hydrogel capsules, the device may be made as follows. Briefly, a volume of hydrogel-forming polymer solution that comprises an afibrotic polymer (e.g., an alginate modified with a Compound of Formula (I)) may be loaded into a syringe, e.g., a syringe that is then capped with a blunt tipped needle. The syringe may then be placed into a syringe pump oriented vertically above a vessel containing an aqueous cross-linking solution which comprises a cross-linking agent, a buffer, an osmolarity-adjusting agent. A high voltage power generator may then be connected to the needle. The syringe pump and power generator can then be used to extrude the polymer solution through the syringe with settings determined to achieve a desired droplet rate of polymer solution into a cross-linking solution. After exhausting the volume of polymer solution, the droplets are allowed to cross-link in the cross-linking solution for several minutes, e.g., about five minutes. In an embodiment, the number of non-capsule debris on the surface of the cross-linking solution is determined. Hydrogel capsules that have fallen to the bottom of the cross-linking vessel may then be collected, e.g., by transferring cross-linking solution containing the hydrogel capsules to a separate container, leaving behind any non-capsular debris on the solution surface in the original cross-linking vessel. The removed hydrogel capsules may then be allowed to settle, the cross-linking solution can be removed, and the capsules may then be washed one or more times with a buffer (e.g., a HEPES buffer). In an embodiment, one or more aliquots of the resulting hydrogel capsule composition is inspected by microscopy to assess the quality of the composition, e.g., the number of capsule defects and satellite capsules.

In some embodiments where the device comprises a hydrogel capsule with two hydrogel compartments or a preparation of two-compartment hydrogel capsules, the method of making the device comprises contacting a plurality of droplets comprising first and second polymer solutions (e.g., each solution comprising a hydrogel-forming polymer) with an aqueous cross-linking solution. The droplets can be formed using any technique known in the art.

Briefly, in performing a method of making a composition of two-compartment hydrogel capsules, a volume of a first polymer solution (e.g., comprising a plurality of cells (e.g., live cells) suspended in a polymer modified with a cell-binding peptide and optionally blended with an unmodified polymer) is loaded into a first syringe connected to the inner lumen of a coaxial needle. The first syringe may then be connected to a syringe pump oriented vertically above a vessel containing an aqueous cross-linking solution which comprises a cross-linking agent, a buffer, and an osmolarity-adjusting agent. A volume of the second polymer solution (e.g., comprising an unmodified polymer, a polymer modified with a compound of Formula (I), or a blend thereof) is loaded into a second syringe connected to the outer lumen of the coaxial needle. The second syringe may then be connected to a syringe pump oriented horizontally with respect to the vessel containing the cross-linking solution. A high voltage power generator may then be connected to the needle. The syringe pumps and power generator can then be used to extrude the first and second polymer solutions through the syringes with settings determined to achieve a desired droplet rate of polymer solution into the cross-linking solution. After exhausting the first and second volumes of polymer solution, the droplets may be allowed to cross-link in the cross-linking solution for certain amount of time, e.g., about five minutes. In an embodiment, the number of non-capsular debris on the surface of the cross-linking solution is determined. Capsules that have fallen to the bottom of the cross-linking vessel may then be collected, e.g., by transferring cross-linking solution containing the capsules to a separate container, leaving behind any non-capsular debris on the solution surface in the original cross-linking vessel. The removed capsules may then be allowed to settle, the cross-linking solution can be removed, and the capsules may then be washed one or more times with a buffer (e.g., a HEPES buffer). In an embodiment, one or more aliquots of the resulting device composition is inspected by microscopy to assess the quality of the composition, e.g., the number of capsule defects and capsules.

In some embodiments, the cross-linking solution used in a process for making a single-compartment or two-compartment capsules further comprises a process additive (e.g., a hydrophilic, non-ionic surfactant). The process additive may reduce surface tension of the cross-linking solution. Agents useful as the process additive in the present disclosure include polysorbate-type surfactants, copolymer of polyethyleneoxide (PEO) and polypropyleneoxide (PPO), poly(ethylene oxide)-poly(propylene oxide)-poly(ethylene oxide) (PEO—PPO-PEO) triblock copolymers, and non-ionic surfactants, such as Tween® 20, Tween® 80, Triton™ X-100, IGEPAL® CA-630, poloxamer 188, or poloxamer 407. In some embodiments, the process additive is a non-ionic surfactant. In an embodiment, the process additive comprises more than one surfactant, e.g., more than one hydrophilic surfactant. In some embodiments, the process additive does not contain Tween® 20 or Triton™ X-100. In an embodiment, the process additive is IGEPAL® CA-630. In some embodiments, the process additive is poloxamer 188.

In some embodiments, the process additive (e.g., surfactant) is present in the cross-linking solution at a concentration of at least 0.0001% or more. In some embodiments, the cross-linking solution comprises at least 0.001%, 0.01%, or 0.1% of the process additive. In some embodiments, the process additive is present at a concentration selected from about 0.001% to about 0.1%, about 0.005% to about 0.05%, about 0.005% to about 0.01%, and about 0.01% to about 0.5%. In an embodiment, the process additive is a surfactant and is present at a concentration that is below the critical micelle concentration for the surfactant.

In some embodiments, the cross-linking agent comprises divalent cations of a single type or a mixture of different types, e.g., one or more of $Ba^{2+}$, $Ca^{2+}$, $Sr^{2+}$. In some embodiments, the cross-linking agent is $BaCl_2$, e.g., at a concentration of 1 mM to 100 mM, 2.5 mM to 75 mM, 5 mM to 50 mM or 7.5 mM to 25 mM, or about 20 mM. In some embodiments, the cross-linking agent is $CaCl_2$, e.g., at a concentration of 50 mM to 150 mM or about 100 mM. In some embodiments, the cross-linking agent is $SrCl_2$, e.g., at a concentration of 37.5 mM to 100 mM. In some embodiments, the cross-linking agent is a mixture of $BaCl_2$ (e.g., 5 mM to 20 mM) and $CaCl_2$ (e.g., 37.5 mM to 12.5 mM) or a mixture of $BaCl_2$ (e.g., 5 mM to 20 mM) and $SrCl_2$ (e.g., 37.5 mM to 12.5 mM).

The type and concentration of buffer in the aqueous cross-linking solution is selected to be compatible with the cells to be encapsulated and to maintain the solution pH at approximately neutral, e.g., from about 6.5 to about 7.5, about 7.0 to about 7.5, or about 7.0. In some embodiments, the buffer in the aqueous cross-linking solution comprises HEPES (4-(2-hydroxyethyl)-1-piperazineethanesulfonic acid).

The osmolarity-adjusting agent in the aqueous cross-linking solution is selected to maintain the solution osmolarity at a value similar to the osmolarity of the first polymer solution comprising a suspension of cells (e.g., live cells), e.g., an osmolarity that has a higher or lower variance of up to 20%, 10% or 5%. In some embodiments, the osmolarity agent is mannitol at a concentration of 0.1 M to 0.3 M.

In an embodiment, the process additive is poloxamer 188. In an embodiment, the poloxamer 188 is present in the capsule composition in a detectable amount after the wash steps. Poloxamer 188 may be detected by any technique known in the art, e.g., by removing an aliquot of the capsules, adding a sodium sulfate solution to partially or completely dissolve the capsules in the aliquot, and analyzing the resulting solution by LC/MS.

Reduction in the surface tension of the cross-linking solution may be assessed by any method known in the art, for example, through the use of a contact angle goniometer or a tensiometer, e.g., via the du Nouy ring method (see, e.g., Davarci et al (2017) *Food Hydrocolloids* 62:119-127).

Enumerated Exemplary Embodiments

1. A device comprising:
   (a) at least one cell-containing compartment which comprises a polymer composition comprising a first cell-binding substance (CBS) and encapsulating a plurality of cells capable of expressing a therapeutic agent when the device is implanted into a subject; and
   (b) means for mitigating the foreign body response (FBR) when the device is implanted into the subject.
2. A device comprising:
   (a) a polymer composition, e.g., a polymer matrix, e.g., a hydrogel matrix, comprising:
   (i) a first cell-binding substance (CBS); and
   (ii) a plurality of cells capable of providing, e.g., producing, expressing, or releasing, a therapeutic agent,
   wherein the device comprises one of the following properties:
   (b) it comprises a combination of a spherical shape and a linear dimension, e.g., diameter, of at least 1.0 mm, 1.3 mm, 1.5 mm, 2.0 mm, 2.5 mm, or 3.0 mm;
   (c) the polymer composition is disposed within a compartment, e.g., a compartment or matrix comprising a biocompatible polymer that surrounds the polymer composition;
   (d) it comprises an entity, e.g., a compound that mitigates the FBR, e.g., an afibrotic compound as defined herein, which in some embodiments is disposed on an exterior surface of the device; or
   (e) the device comprises an afibrotic compound, e.g., an afibrotic compound as described herein, e.g., an afibrotic compound disposed on the exterior of the device.
3. The device of embodiment 2, comprising property (b).
4. The device of any one of embodiments 2 or 3, comprising property (c).
5. The device of any one of embodiments 2 to 4, comprising property (d).
6. The device of any one of embodiments 2-5, comprising property (e).
7. The device of embodiment 2, comprising two of properties (b) to (e).
8. The device of embodiment 2, comprising three of properties (b) to (e).
9. The device of embodiment 2, comprising all of properties (b) to (e).
10. The device of any one of embodiments 2 to 9, comprising a compound that mitigates the FBR covalently coupled to another element of the device, e.g., to a polymer.
11. The device of any one of embodiments 2 to 9, comprising an afibrotic compound, e.g., an afibrotic compound as described herein, covalently coupled to another element of the device, e.g., to a polymer.
12. The device of any one of embodiments 1 to 11, wherein the first CBS comprises a cell-binding peptide (CBP) or a cell-binding polypeptide (CBPP).
13. The device of any one of embodiments 1 to 12, wherein the polymer composition comprises a second CBS that is different than the first CBS.
14. The device of embodiment 13, wherein one or both of the first CBS and second CBS comprises a cell-binding peptide (CBP) or a cell-binding polypeptide (CBPP).
15. The device of any one of embodiments 1 to 14, wherein the first CBS comprises a first CBP covalently attached to a first polymer via a first linker ("first CBP-polymer").
16. The device of any one of embodiments 12 to 15, wherein the second CBS comprises a second CBP covalently attached to a second polymer via a second linker ("second CBP-polymer"), wherein the chemical composition of at least one of the second CBP, second linker and second polymer is different than the corresponding component in the first CBP-polymer.
17. The device of any one of embodiments 12 to 16, wherein the polymer composition further comprises a third CBS.
18. The device of embodiment 17, wherein the third CBS comprises a third CBP covalently attached to a third polymer via a third linker ("third CBP-polymer), wherein the chemical composition of at least one of the third CBP, third linker and third polymer is different than the corresponding component in the first and second CBP-polymers.
19. The device of any one of embodiments 1 to 18, wherein the first CBS is a first CBP-polymer comprising an amino acid sequence selected from the group consisting of DGEA (SEQ ID NO: 39), FYFDLR (SEQ ID NO: 40), HAVDI (SEQ ID NO: 38), PHSRN (SEQ ID NO: 46), REDV (SEQ ID NO: 47), RGD (SEQ ID NO: 43), RGDSP (SEQ ID NO: 59), and YIGSR (SEQ ID NO: 50), or a conservatively substituted variant of any of said sequences.
20. The device of any one of embodiments 12 to 19, wherein the first CBP is a linear or cyclic peptide of less than 10 amino acids in length.

21. The device of any one of embodiments 14 to 20, wherein the second CBP is a linear or cyclic peptide of less than 10 amino acids in length.

22. The device of any one of embodiments 12 to 21, wherein the polymer composition comprises a first CBP-polymer, a second CBP-polymer and optionally a third CBP-polymer, wherein the first CBP-polymer is an RGD polymer and at least one of the second CBP-polymer and third CBP-polymer, if present, comprises an amino acid sequence selected from the group consisting of DGEA (SEQ ID NO:39), FYFDLR (SEQ ID NO:40), HAVDI (SEQ ID NO:38), PHSRN (SEQ ID NO:46), PHSRNGGGGG-GRGDS (SEQ ID NO:55), REDV (SEQ ID NO:47), GFO-GER (SEQ ID NO:41), P(GPP)$_5$GFOGER(GPP)$_5$ (SEQ ID NO:54) and YIGSR (SEQ ID NO:50), or a conservatively substituted variant of any of said sequences.

23. The device of any one of embodiments 1 to 22, wherein the first CBS is a linear CBP of less than 10 amino acids in length which comprises RGD (SEQ ID NO: 43) or RGDSP (SEQ ID NO: 59).

24. The device of any one of embodiments 1 to 22, wherein the first CBS is a linear CBP that consists essentially of RGD (SEQ ID NO: 43) or RGDSP (SEQ ID NO: 59).

25. The device of any one of embodiments 1 to 24, wherein the polymer composition comprises a second CBS comprising a second CBP-polymer, wherein the CBP in the first CBP-polymer is different than the CBP in the second CBP-polymer and the polymer in the first CBP-polymer is the same or different than the polymer in the second CBP-polymer.

26. The device of any one of embodiments 1 to 25, wherein the polymer composition comprises a first CBP-polymer and optionally a second CBP-polymer and optionally a third CBP-polymer, wherein the linker in each CBP-polymer in the polymer composition is selected from the group consisting of:

(a) a linear amino acid linker consisting essentially of one to ten, one to six, or one to four residues of glycine and/or of beta-alanine;

(b) a linear amino acid linker consisting essentially of one, two or three glycine residues;

(c) ethylene oxide or an oligomer of two to four ethylene oxide monomers; and (d) an amino carboxylate.

27. The device of embodiment 26, wherein the first CBP consists essentially of RGD (SEQ ID NO: 43) or RGDSP (SEQ ID NO: 59) and the linker consists essentially of a single glycine residue.

28. The device of any one of embodiments 1 to 27, wherein the polymer composition comprises a first CBP-polymer and optionally a second CBP-polymer and optionally a third CBP-polymer, wherein the polymer in each CBP-polymer in the polymer composition is an alginate, chitosan, hyaluronate, a polyethylene glycol (PEG), a polyacrylamide, gelatin, poly(L-lactic acid) (PLLA), poly(lactic glycolic acid) (PLGA), carboxymethylcellulose or carboxymethylchitosan.

29. The device of embodiment 28, wherein the polymer in the first CBP-polymer is an alginate.

30. The device of any one of embodiments 28 or 29, wherein an alginate is the polymer in one or both of the second CBP-polymer and the third CBP-polymer.

31. The device of any one of embodiments 28 to 30, wherein the alginate has a molecular weight of 75-150 kDa and a G:M ratio of greater than or equal to 1.5.

32. The device of any one of embodiments 1 or 12-31, wherein the cell-containing compartment further comprises an unmodified polymer that is the same or different than the first polymer.

33. The device of embodiment 32, wherein the unmodified polymer in the cell-containing compartment is an alginate, chitosan, hyaluronate, a polyethylene glycol (PEG), a polyacrylamide, gelatin, poly(L-lactic acid) (PLLA), poly(lactic glycolic acid) (PLGA), carboxymethylcellulose or carboxymethylchito s an.

34. The device of any one of the above embodiments, wherein the means for mitigating the FBR comprises a barrier compartment which surrounds the cell-containing compartment.

35. The device of any one of embodiments 1 to 34, wherein the means for mitigating the FBR comprises a first afibrotic compound disposed on the exterior surface of the device.

36. The device of any one of embodiments 1 to 35, wherein the means for mitigating the FBR comprises a barrier compartment that surrounds the cell-containing compartment and the barrier compartment comprises an afibrotic compound covalently attached to a polymer (afibrotic-polymer), wherein the polymer in the afibrotic polymer is the same or different than each polymer present in the cell-containing compartment.

37. The device of embodiment 35, wherein the means for mitigating the FBR further comprises a barrier compartment that surrounds the cell-containing compartment and the barrier compartment comprises a second afibrotic compound covalently attached to a polymer (afibrotic-polymer), wherein the polymer in the afibrotic polymer is the same or different than each polymer present in the cell-containing compartment, and the second afibrotic compound is the same or different than the first afibrotic compound.

38. The device of embodiment 36 or 37, wherein the barrier compartment further comprises an unmodified polymer that is the same or different than the polymer in the afibrotic polymer in the barrier compartment and each polymer present in the cell-containing compartment.

39. The device of embodiment 38, wherein the barrier compartment is formed using a mixture of the unmodified polymer and the afibrotic-polymer, and optionally wherein the conjugation density of the afibrotic compound in the afibrotic polymer is determined by combustion analysis for percent nitrogen (e.g. as described in Example 1A hereinbelow), wherein the determined percent nitrogen is at least 2.0% and less than 9.0%, or is 3.0% to 8.0%, 4.0% to 7.0%, 5.0% to 7.0%, or 6.0% to 7.0% or about 6.8%.

40. The device of any one of embodiments 36 to 39, wherein one of both of the first and second afibrotic compounds is a compound of Formula (I-a):

(I-a)

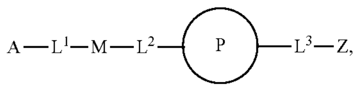

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —N($R^C$)C(O)($C_1$-$C_6$-alkylene)-, —N($R^C$)C(O)($C_1$-$C_6$-alkenylene)-, —NCN—, —C(=N($R^C$)($R^D$))O—, —S—, —S(O)$_x$—, —OS(O)$_x$—, —N($R^C$)S(O)$_x$—, —S(O)$_x$N $(R^C)$—, —$P(R^F)_y$—, —$Si(OR^A)_2$—$Si(R^G)(OR^A)$—, —$B(OR^A)$—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, —$S(O)_xN(R^{C1})(R^{D1})$, —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

41. The device of any one of embodiments 1-39, wherein the compound of Formula (I) is a compound of any one of Formulas (I-b), (I-c), (I-d), (I-e), (I-f), (II), (II-a), (III), (III-a), (III-b), (III-c), or (III-d), or a pharmaceutically acceptable salt thereof.

42. The device of any one of embodiments 35 to 41, wherein the first afibrotic compound is Compound 100, Compound 101, Compound 110, Compound 112, Compound 113 or Compound 114 shown in Table 4, and optionally wherein the conjugation density of the first afibrotic compound in the afibrotic polymer is determined by (a) combustion analysis for percent nitrogen, e.g., as described in Example 1A hereinbelow, wherein the determined percent nitrogen is at least 2.0% and less than 9.0%, or is 3.0% to 8.0%, 4.0% to 7.0%, 5.0% to 7.0%, or 6.0% to 7.0% or about 6.8%; or (b) quantitative free amine analysis, e.g., as described in Example 26 hereinbelow, wherein the determined conjugation density is 1.0% w/w to 3.0% w/w, 1.3% w/w to 2.8% ww, 1.3% w/w to 2.6% w/w, 1.5% w/w to 2.4% w/w, 1.5% w/w to 2.2% w/w, or 1.7% w/w to 2.2% w/w.

43. The device of any one of embodiments 37 to 42, wherein the second afibrotic compound is Compound 100, Compound 101, Compound 110, Compound 112, Compound 113 or Compound 114 shown in Table 4.

44. The device of any one of embodiments 35 to 43, wherein the first afibrotic compound is Compound 100 shown in Table 4.

45. The device of any one of embodiments 35 to 43, wherein the first afibrotic compound is not Compound 100 shown in Table 4.

46. The device of any one of embodiments 37 to 43, wherein each of the first and second afibrotic compounds is Compound 101 shown in Table 4.

47. The device of any one of embodiments 37 to 46, wherein each polymer present in the barrier compartment is an alginate, chitosan, hyaluronate, a polyethylene glycol (PEG), a polyacrylamide, gelatin, poly(L-lactic acid) (PLLA), or poly(lactic glycolic acid) (PLGA), carboxymethylcellulose, carboxymethylchitosan.

48. The device of any one of embodiments 36 to 47, wherein the polymer in each afibrotic polymer in the barrier compartment is an alginate with a molecular weight of <75 kDa and a G:M ratio of greater than or equal to 1.5.

49. The device of any one of embodiments 38 to 48, wherein the unmodified polymer in the barrier compartment is an alginate with a molecular weight of 150 kDa to 250 kDa and a G:M ratio of greater than or equal to 1.5.

50. The device of any one of embodiments 1 or 11 to 49, wherein the cell-containing compartment is formed from a CBP-polymer which consists essentially of $G_{1-3}$RGD (SEQ ID NO: 63) or $G_{1-3}$RGDSP (SEQ ID NO: 64) covalently conjugated to an alginate having a molecular weight of 75 kDa to 150 kDa and a G:M ratio of greater than or equal to 1.5, and has a CBP-conjugation density that is at least one of the following:

(a) an amount sufficient to increase the viability of the cells, e.g., as determined by an assay described herein, optionally the amount is an optimal amount;

(b) an amount sufficient to increase the productivity of the cells, e.g., as determined by an assay described herein, optionally the amount is an optimal amount;

(c) 0.10% nitrogen (N) to 1.00% N, about 0.20% N to about 0.80% N, about 0.30% N to about 0.60% N, about 0.30% to about 0.50%, or 0.33% N to 0.46% N, as determined by combustion analysis of the CBP-polymer that has been lyophilized to a constant weight, e.g., as described in Example 1B herein below;

(d) 0.1 to 1.0, 0.2 to 0.8, 0.3 to 0.7 or 0.3 to 0.6 micromoles of $G_{1-3}$RGD (SEQ ID NO: 63) or $G_{1-3}$RGDSP (SEQ ID NO: 64) per gram of the CBP-polymer in solution; or (e) any combination of two or more of (a), (b), (c) and (d).

51. The device of any one of embodiments 34 to 49, wherein the cell-containing compartment and barrier compartment form a two-compartment hydrogel capsule.

52. The device of embodiment 50 or 51, wherein the cell-containing- and barrier compartments have approximately equal volumes.

53. The device of any one of embodiments 34 to 51, wherein the thickness of the barrier compartment is within a range selected from the group consisting of:

(a) 1 nanometer and 1 millimeter;

(b) 100 nanometers and 1 millimeter; and (c) 500 nanometers and 500 micrometers.

54. The device of any one of embodiments 1 to 53, wherein the device has a largest linear dimension (LLD), e.g., diameter, of between 500 nanometers to 5 millimeters.

55. The device of any one of embodiments 1 to 54, wherein the device has a spherical shape and has a largest linear dimension (LLD), e.g., diameter, of 0.5 millimeter to 5 millimeters, e.g., between 0.75 millimeter to 4 millimeters, 1 millimeter to 3 millimeters, 1 millimeter to 2 millimeters, about 1.5 millimeters to 2 millimeters, or about 1.5 millimeters.

56. The device of any one of embodiments 35 to 55, which comprises one or more properties selected from the following:

a) the plurality of cells (e.g., live cells) in the cell-containing compartment is at least 100; 250; 500; 750; 1,000; 2,500; 5,000; 10,000; 25,000; or 50,000 cells;

b) the barrier compartment is substantially free of the CBS and of the cells; and c) the cell-containing compartment is substantially free of any afibrotic compound.

57. The device of any one of embodiments 36 to 56, wherein (a) the cell-containing compartment and the barrier compartment form a two-compartment hydrogel capsule;

(b) the first CBP polymer in the cell-containing compartment consists essentially of an alginate with a molecular weight of 150 to 250 kDa and a G:M ratio of greater than or equal to 1.5 as the first polymer, a single glycine residue as the linker and a linear peptide consisting of RGDSP (SEQ ID NO: 59) as the first CBP;

(c) the polymer in the afibrotic polymer in the barrier compartment is an alginate with a molecular weight of less than 75 kDa and a G:M ratio of greater than or equal to 1.5 and the afibrotic compound is Compound 101 shown in Table 4; and (d) the barrier compartment further comprises an unmodified alginate with a molecular weight of 150 kDa-250 kDa and a G:M ratio of greater than or equal to 1.5.

58. The device of embodiment 56, wherein the barrier compartment is formed from an alginate solution consisting essentially of a 70:30 ratio of (i) the afibrotic-alginate dissolved at 5% weight to volume in 0.9% saline and (ii) the unmodified alginate dissolved at 3% weight to volume in 0.9% saline.

59. The device of any one of embodiments 1 to 58, wherein the plurality of cells are engineered from a cell line to express the therapeutic agent, wherein the cell line is an endothelial, epithelial, fibroblast, keratinocyte or mesenchyme cell line.

60. The device of embodiment 46, wherein the cell line is selected from the cell lines listed in Table 5.

61. The device of any one of embodiments 1 to 58, wherein the plurality of cells are engineered RPE cells.

62. The device of any one of embodiments 1 to 58, wherein the plurality of cells are engineered ARPE-19 cells.

63. The device of any one of embodiments 1 to 62, wherein the therapeutic agent is a Factor VIII protein or a variant thereof or a Factor IX protein or a variant thereof.

64. The device of any one of embodiments 1 to 63, wherein the device comprises two or more cell-containing compartments.

65. The device of any one of embodiments 1 to 64, wherein the amount of the therapeutic agent expressed by the cells at a first time point after implant (e.g., at least 7 days, two weeks, four weeks, eight weeks, or 16 weeks) is at least 1.25-fold, 1.5-fold, 2-fold (4-fold, 6-fold, 8-fold, or 10-fold) greater than expressed at that time point by a CBC-null reference device capable of expressing the same therapeutic agent.

66. A hydrogel capsule comprising:

(a) a cell-containing compartment which comprises a plurality of cells (e.g., live cells), encapsulated in a first polymer composition comprising a first RGD-polymer, wherein the encapsulated cells express an exogenous polypeptide and optionally wherein the concentration of the plurality of cells is 40 million cells per ml of the first polymer composition; and (b) a barrier compartment surrounding the cell-binding compartment and comprising a second polymer composition which comprises a mixture of an unmodified alginate and an alginate covalently modified with at least one compound selected from the group consisting of Compound 100, Compound 101, Compound 110, Compound 112, Compound 113 and Compound 114 shown in Table 4, wherein the hydrogel capsule has a spherical shape and has a diameter of 0.5 millimeter to millimeters, and optionally the average thickness of the barrier compartment is about 10 to about 300 microns, about 20 to about 150 microns, or about 40 to about 75 microns.

67. The hydrogel capsule of embodiment 66, which comprises an effective amount of the first RGD-polymer for increased expression of the exogenous polypeptide and wherein the first RGD-polymer consists essentially of an alginate covalently modified with an RGD peptide via a linker, the cell-containing compartment is substantially free of any afibrotic compound and the barrier compartment is substantially free of cells and the RGD peptide, and optionally wherein the effective amount of the RGD-polymer is an optimal amount.

68. The hydrogel capsule of embodiment 66 or 67, wherein the RGD peptide consists essentially of an amino acid sequence of RGD (SEQ ID NO: 43) or RGDSP (SEQ ID NO: 59) and the linker is a single glycine residue or a single beta-alanine residue attached to the N-terminus of the RGD peptide.

69. The hydrogel capsule of any one of embodiments 67 to 68, wherein:

(a) the polymer in the first RGD-polymer is an alginate and has a molecular weight of 150 to 250 kDa and a G:M ratio of greater than or equal to 1.5, and optionally the cell-containing compartment is formed from an alginate solution with a viscosity of between about 90 cP and about 230 cP to about 300, 350 or 400 cP, or between about 80 cP to about 120 cP;

(b) the alginate in the covalently-modified alginate in the barrier compartment has a molecular weight of <75 kDa and a G:M ratio of greater than or equal to 1.5;

(c) the unmodified alginate in the barrier compartment has a molecular weight of 150 kDa to 250 kDa and a G:M ratio of greater than or equal to 1.5; and (d) optionally, the barrier compartment is formed from an alginate solution comprising a mixture of the covalently modified alginate and unmodified alginate and having a viscosity of 250-350 cP.

70. The hydrogel capsule of embodiment 69, wherein:

(a) the capsule has a diameter of between 1.0 millimeters and 2.0 millimeters;

(b) the conjugation density of the RGD peptide on the alginate is the percent nitrogen determined by combustion analysis of the RGD-polymer that has been lyophilized to a constant weight (e.g., as described in Example 1B herein), wherein the determined percent nitrogen is about 0.10% nitrogen (N) to 1.00% N, about 0.20% N to about 0.80% N, about 0.30% N to about 0.60% N, about 0.30% to about 0.50%, or 0.33% N to 0.46% N; and (c) the covalently modified alginate in the barrier compartment is modified only with Compound 101 and the density of Compound 101 in the covalently modified alginate is the percent nitrogen determined by combustion analysis of the covalently modified alginate that has been lyophilized to a constant weight, e.g., as described in Example 1A herein, wherein the determined percent nitrogen is between about nitrogen is at least 2.0% and less than 9.0%, or is 3.0% to 8.0%, 4.0% to 7.0%, 5.0% to 7.0%, or 6.0% to 7.0% or about 6.8%.

71. The hydrogel capsule of embodiment 70, wherein:

(a) the plurality of cells are engineered RPE cells, e.g., engineered ARPE-19 cells;

(b) the capsule has a diameter of about 1.5 millimeters;

(c) the RGD peptide consists essentially of an amino acid sequence of RGDSP (SEQ ID NO: 59) and the linker is a single glycine residue;

(d) the conjugation density of the RGD peptide on the alginate is selected from the group consisting of:

(i) an amount effective to increase the viability of the cells, e.g., as determined by an assay described herein, (ii) an amount effective to increase the productivity of the cells, e.g., as determined by an assay described herein, (iii) the percent nitrogen determined by combustion analysis of the RGD-polymer that has been lyophilized to a constant weight (e.g., as described in Example 1B herein), wherein the determined percent nitrogen is about 0.10% nitrogen (N) to 1.00% N, about 0.20% N to about 0.80% N, about 0.30% N to about 0.60% N, about 0.30% to about 0.50%, or 0.33% N to 0.46% N;

(iv) 0.1 to 1.0, 0.2 to 0.8, 0.3 to 0.7 or 0.3 to 0.6 micromoles of GRGDSP per gram of RGD-polymer in solution, e.g., as described in Example 25 herein; and (v) any combination of two or more of d(i), d(ii), d(iii) and d(iv);

(e) the covalently modified alginate in the barrier compartment is modified only with Compound 101 and the density of Compound 101 in the covalently modified alginate is:

(i) the percent nitrogen determined by combustion analysis of the covalently modified alginate that has been lyophilized to a constant weight, e.g., as described in Example 1A herein, wherein the determined percent nitrogen is between about nitrogen is at least 2.0% and less than 9.0%, or is 3.0% to 8.0%, 4.0% to 7.0%, 5.0% to 7.0%, or 6.0% to 7.0% or about 6.8%; or (ii) the % amine on a weight/weight basis as determined by quantitative free amine analysis, e.g., as described in Example 27 herein, wherein the determined density is 1.0% w/w to 3.0% w/w, 1.3% w/w to 2.8% ww, 1.3% w/w to 2.6% w/w, 1.5% w/w to 2.4% w/w, 1.5% w/w to 2.2% w/w, or 1.7% w/w to 2.2% w/w.

72. The hydrogel capsule of embodiment 71, wherein the plurality of cells are ARPE-19 cells engineered to express a FVIII-BDD protein, e.g., SEQ ID NO:1.

73. The hydrogel capsule of embodiment 72, wherein the ARPE-19 cells comprise SEQ ID NO: 15, which optionally is operably linked to a CAG promoter nucleotide sequence, e.g., nucleotides 337-2069 of SEQ ID NO:26.

74. The hydrogel capsule of 72 or 73, wherein the conjugation density of the RGD peptide on the alginate in the RGD-polymer is 0.3 to 0.6 micromoles of GRGDSP per gram of RGD-polymer in solution.

75. The hydrogel capsule of any one of embodiments 66 to 74, wherein the plurality of cells is at least 1,000, 2,500, 5,000, 10,000, 25,000, or 50,000 RPE cells.

76. A preparation of devices, wherein each device in the preparation is a device of any one embodiments 1 to 65 or a hydrogel capsule of any one of embodiments 66 to 75.

77. The preparation of embodiment 76, wherein each device in the preparation is a spherical hydrogel capsule with a diameter selected from the group consisting of: 0.5 millimeter to 2 millimeters; 0.7 millimeter to 1.8 millimeters, 1.0 millimeter to 1.8 millimeters; 1.2 millimeters to 1.7 millimeters; 1.3 millimeters to 1.7 millimeters; and 1.4 to 1.6 millimeters.

78. The preparation of embodiment 76 or 77, wherein the preparation is a pharmaceutically acceptable composition.

79. A method of implanting a device in a subject comprising:

providing a device or preparation of devices described herein, e.g., the device in any one of embodiments 1 to 65, the hydrogel capsule in any one of embodiments 66 to 75 or the preparation of any one of embodiments 76 to 78; and disposing the device or preparation in the body of the subject.

80. A method of providing a therapeutic agent to a subject comprising:

providing a device or preparation of devices described herein, e.g., the device in any one of embodiments 1 to 65, the hydrogel capsule in any one of embodiments 66 to 75, or the preparation of any one of embodiments 76 to 78; and disposing the device or preparation in the body of the subject.

81. A method of evaluating a device, e.g., in a subject comprising:

providing a device described herein, e.g., the device in any one of embodiments 1 to 65 or the hydrogel capsule in any one of embodiments 66 to 75; and disposing the device or preparation in the body of the subject.

82. A method of treating a subject in need of a therapeutic agent comprising:

providing a device or preparation of devices described herein, e.g., the device in any one of embodiments 1 to 65, the hydrogel capsule in any one of embodiments 66 to 75, or the preparation of any one of embodiments 76 to 78; and disposing the device or preparation in the body of the subject.

83. A method of manufacturing a device or hydrogel capsule disclosed herein comprising:

combining a first element of the device or hydrogel capsule with a second element of the device or hydrogel capsule, thereby manufacturing a device or hydrogel capsule disclosed herein.

84. A method of manufacturing a preparation of a device or hydrogel capsule disclosed herein comprising:

combining a device or hydrogel capsule with a second component, e.g., a buffer, carrier, or excipient, thereby manufacturing a device or hydrogel capsule disclosed herein.

85. A method of manufacturing a device or hydrogel capsule, or preparation thereof, disclosed herein comprising:

supplying a device or hydrogel capsule or preparation thereof, described herein;

acquiring, e.g., by measuring, a value for a parameter associated with an element of or property of the device or hydrogel capsule, or preparation thereof, e.g., size, the presence or amount of a component, a biological property, the viability of a component, thereby manufacturing a device or hydrogel capsule disclosed herein.

86. A method of evaluating a device or hydrogel capsule, or preparation thereof, disclosed herein comprising:

supplying a device or hydrogel capsule, or preparation thereof, described herein;

acquiring, e.g., by measuring, a value for a parameter associated with an element of or property of the device or hydrogel capsule, e.g., size, the presence or amount of a component, a biological property, the viability of a component, thereby evaluating a device or hydrogel capsule, or preparation thereof, disclosed herein.

EXAMPLES

In order that the disclosure described herein may be more fully understood, the following examples are set forth. The examples described in this application are offered to illustrate the devices (e.g., capsules, particles, chemical modifications, compositions and methods provided herein and are not to be construed in any way as limiting their scope.

Example 1: Preparation of Exemplary Modified Polymers

1A. Chemically-modified Polymer. A polymeric material may be chemically modified with a compound of Formula (I) (or pharmaceutically acceptable salt thereof) prior to formation of a device described herein (e.g., a hydrogel capsule described herein) using methods known in the art.

For example, in the case of alginate, the alginate carboxylic acid is activated for coupling to one or more amine-functionalized compounds to achieve an alginate modified with an afibrotic compound, e.g., a compound of Formula (I). The alginate polymer is dissolved in water (30 mL/gram polymer) and treated with 2-chloro-4,6-dimethoxy-1,3,5-triazine (0.5 eq) and N-methylmorpholine (1 eq). To this mixture is added a solution of the compound of interest (e.g., Compound 101 shown in Table 4) in acetonitrile (0.3M). A compound of interest may be prepared using methods known in the art, for example, as described in WO2018/067615, which is incorporated herein by reference in its entirety.

The amounts of the compound and coupling reagent added depends on the desired concentration of the compound bound to the alginate, e.g., conjugation density. To prepare a CM-LMW-Alg-101-Medium polymer solution, the dissolved unmodified low molecular weight alginate (approximate MW <75 kDa, G:M ratio ≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate). To prepare a CM-LMW-Alg-101-High polymer solution, the dissolved unmodified low-molecular weight alginate (approximate MW<75 kDa, G:M ratio ≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate).

The reaction is warmed to 55° C. for 16 h, then cooled to room temperature and gently concentrated via rotary evaporation, then the residue is dissolved in water. The mixture is filtered through a bed of cyano-modified silica gel (Silicycle) and the filter cake is washed with water. The resulting solution is then extensively dialyzed (10,000 MWCO membrane) and the alginate solution is concentrated via lyophilization to provide the desired chemically-modified alginate as a solid or is concentrated using any technique suitable to produce a chemically modified alginate solution with a viscosity of 25 cP to 35 cP.

In an embodiment, the conjugation density of a chemically modified alginate is measured by combustion analysis for percent nitrogen. The sample is prepared by dialyzing a solution of the chemically modified alginate against water (10,000 MWCO membrane) for 24 hours, replacing the water twice followed by lyophilization to a constant weight.

In another embodiment, the conjugation density of a chemically modified alginate is determined using a quantitative amine assay as described in Example 27 below.

For use in generating the hydrogel capsules described in the Examples below, chemically modified alginate polymers were prepared with Compound 101 (shown in Table 4) conjugated to a low molecular weight alginate (approximate MW <75 kDa, G:M ratio ≥1.5) at medium (2% to 5% N) or high (5.1% to 8% N) densities, as determined by combustion analysis for percent nitrogen, and are referred to herein as CM-LMW-Alg-101-Medium and CM-LMW-Alg-101-High. Unless otherwise specified, the chemically modified alginate in the capsules made in the Examples below is CM-LMW-Alg-101-Medium.

1B. CBP-Alginates. A polymeric material may be covalently modified with a peptide prior to formation of a device described herein (e.g., a hydrogel capsule described herein) using methods known in the art, see, e.g., Jeon O, et al., *Tissue Eng Part A.* 16:2915-2925 (2010) and Rowley, J. A. et al., *Biomaterials* 20:45-53 (1999).

For example, in the case of alginate, an alginate solution (1%, w/v) is prepared with 50 mM of 2-(N-morpholino)-ethanesulfonic acid hydrate buffer solution containing 0.5M NaCl at pH 6.5, and sequentially mixed with N-hydroxysuccinimide and 1-ethyl-3-[3-(dimethylamino)propyl]carbodiimide (EDC). The molar ratio of N-hydroxysuccinimide to EDC is 0.5:1.0. The peptide of interest is added to the alginate solution. The amounts of peptide and coupling reagent added depends on the desired concentration of the peptide bound to the alginate, e.g., peptide conjugation density. By increasing the amount of peptide and coupling reagent, higher conjugation density can be obtained. After reacting for 24 h, the reaction is purified by dialysis against ultrapure deionized water (diH2O) (MWCO 3500) for 3 days, treated with activated charcoal for 30 min, filtered (0.22 mm filter), and concentrated to the desired viscosity.

In an embodiment, the conjugation density of a peptide-modified alginate is measured by combustion analysis for percent nitrogen. The sample is prepared by dialyzing a solution of the peptide-modified alginate against water (10,000 MWCO membrane) for 24 hours, replacing the water twice followed by lyophilization to a constant weight.

In another embodiment, the conjugation density of a peptide-modified alginate is measured using a quantitative peptide-conjugation assay as described in Examples 25 and optionally 26.

Example 2: Preparation of Exemplary Alginate Solutions for Making Hydrogel Capsules 70:30 mixture of chemically-modified and unmodified alginate. A low molecular weight alginate (PRONOVA™ VLVG alginate, NovaMatrix® Cat. #4200506, approximate MW <75 kDa, G:M ratio ≥1.5) was chemically modified with Compound 101 in Table 4 to produce a chemically modified low molecular weight alginate solution with a viscosity of 25 cP to 35 cP (CM-LMW-Alg-101). A solution of high molecular weight unmodified alginate (U-HMW-Alg) was prepared by dissolving unmodified alginate (PRONOVA™ SLG100, NovaMatrix, Sandvika, Norway, cat. #4202106, approximate MW of 150 kDa-250 kDa, G:M ratio ≥1.5) at 3% weight to volume in 0.9% saline. The CM-LMW-Alg solution was blended with the U-HMW-Alg solution at a volume ratio of 70% CM-LMW-Alg to 30% U-HMW-Alg (referred to herein as a 70:30 CM-LMW-Alg:U-HMW-Alg solution).

60:40 mixture of chemically-modified and unmodified alginate. This solution was prepared using the same procedure as for the above 70:30 mixture, except that the CM-LMW-Alg-101 solution was blended with the U-HMW-Alg solution at a volume ratio of 60% CM-LMW-Alg-101 to 40% U-HMW-Alg (referred to herein as a 60:40 CM-LMW-Alg-101:U-HMW-Alg solution).

Unmodified alginate solution. An unmodified medium molecular weight alginate (SLG20, NovaMatrix, Sandvika, Norway, cat. #4202006, approximate molecular weight of 75-150 kDa), was dissolved at 1.4% weight to volume in 0.9% saline to prepare a U-MMW-Alg solution.

Alginate Solutions Comprising Cell Binding Sites. Various alginate solutions containing a CBP-alginate or a mixture of a cell-binding protein and an unmodified alginate were prepared as summarized in Table 6 below.

TABLE 6

Experimental Alginate Solutions Containing Cell-Binding Sites Used To Form Cell-Containing Compartments

| Solution Name* | % N | Cell Binding Peptide (CBP) | Linker | Modified Alginate Source Alginate MW; G:M Ratio | Solution Composition** |
|---|---|---|---|---|---|
| VLVG-4GRGDSP | 0.7 | RGDSP (SEQ ID NO: 59) | GGGG (SEQ ID NO: 61) | NovaMatrix 4270519 MW = <75 kDa; G:M ≥ 1.5 | 5 w/v % of CBP-alginate blended at 70:30 volume ratio with 3% SLG100 in saline |
| MVG-GRGDSP | 0.95 | RGDSP (SEQ ID NO: 59) | G | NovaMatrix 4270129 MW = >200 kDa; G:M ≥ 1.5 | 1.4 w/v % of CBP-alginate in saline |
| 1G-MVG: 0.71, 143 cP<br>1G-MVG: 0.71, 79 cP<br>1G-MVG: 0.71, 97 cP<br>1G-MVG: 0.71, 202 cP | 0.71 | RGDSP (SEQ ID NO: 59) | G | Prepared in Examples 1, 2 | Viscosity = 143 cP<br>Viscosity = 79 cP<br>Viscosity = 97 cP<br>Viscosity = 202 cP |
| 1G-SLG100: 0.65 | 0.65 | RGDSP (SEQ ID NO: 59) | G | Prepared in Examples 1, 2 | Viscosity = 98 cP |
| 1G-RGD: 0.22<br>1G-RGD: 0.41<br>1G-RGD: 0.33<br>1G-RGD: 0.72<br>1G-RGD: 1.47<br>4G-RGD: 0.53<br>4G-RGD: 0.96<br>4G-RGD: 1.77<br>4G-RGD: 2.95 | 0.22<br>0.41<br>0.33<br>0.72<br>1.47<br>0.53<br>0.96<br>1.77<br>2.95 | RGDSP (SEQ ID NO: 59) | G or GGGG (SEQ ID NO: 61) | Prepared in Examples 1, 2 | Viscosity = 118 cP<br>Viscosity = 57 cP<br>Viscosity = 113 cP<br>Viscosity = 133 cP<br>Viscosity = 141 cP<br>Viscosity = 70 cP<br>Viscosity = 58 cP<br>Viscosity = 102 cP<br>Viscosity = 123 cP |
| 1G-RGD: 6.04<br>1G-RGD: 6.04, 1:55<br>1G-RGD: 6.04, 1:30<br>1G-RGD: 6.04, 1:15 | 6.04<br>0.11<br>0.20<br>0.40 | RGDSP (SEQ ID NO: 59) | G | Prepared in Examples 1, 2 | Viscosity = 102 cP<br>Blended 1:55 with 1.4 w/v % SLG20<br>Blended 1:30 with 1.4 w/v % SLG20<br>Blended 1:15 with 1.4 w/v % SLG20 |
| 4G-DGEA: 0.15 | 0.15 | DGEA (SEQ ID NO: 39) | GGGG (SEQ ID NO: 61) | Prepared in Examples 1, 2 | Viscosity = 133 cP |
| 4G-PHSRN: 0.68 | 0.68 | PHSRN (SEQ ID NO: 46) | GGGG (SEQ ID NO: 61) | Prepared in Examples 1, 2 | Viscosity = 133 cP |

TABLE 6-continued

Experimental Alginate Solutions Containing Cell-Binding Sites Used To Form Cell-Containing Compartments

| Solution Name* | % N | Cell Binding Peptide (CBP) | Linker | Modified Alginate Source Alginate MW; G:M Ratio | Solution Composition** |
|---|---|---|---|---|---|
| G-PHSRN: 0.83 | 0.83 | PHSRN (SEQ ID NO: 46) | G | Prepared in Examples 1, 2 | Viscosity = 108 cP |
| PHSRN/RGD, same polymer | 0.87 | RGDSP (SEQ ID NO: 59) and PHSRN (SEQ ID NO: 46) | G | Prepared in Examples 1, 2 | Viscosity = 98 cP |
| G-HAVDI: 0.38 | 0.38 | HAVDI (SEQ ID NO: 38) | G | Prepared in Examples 1, 2 | Viscosity = 132 cP |
| Collagen I | N/A | Full-length protein | None | Not Applicable | 0.36 mg/ml Collagen I in 1.4 w/v % SLG20 in saline |
| Hyaluronic Acid (HA) | N/A | Full-length glycosamino-glycan | None | Not Applicable saline | 0.15 w/v % HA in 1.4 w/v % SLG20 |

*Where known, the solution names incorporate the peptide conjugation density as percent nitrogen determined by combustion analysis as described in Example 1B.
**When present, the type and concentration of cells are noted in the Examples below.

All unmodified and peptide-modified alginates were purchased from NovaMatrix®, Sandvika Norway unless otherwise stated. Collagen I was purchased from Corning Life Sciences, Cat No. 354236 (Collagen Type I, Rat Tail), Oneonta, NY HA was purchased from Lifecore Biomedical, Cat. No. HA700K (MW=500 kDa-749 kDa), Chaska MN).

Example 3: Preparation of Exemplary Cells for Encapsulation in One-Compartment or Two-Compartment Hydrogel Millicapsules 3A. Engineered ARPE-19 Cells for Encapsulation as Single Cells.

ARPE-19 cells engineered to express a therapeutic agent, e.g., a blood clotting factor (e.g., a FVIII or FIX protein) may be cultured according to any method known in the art, such as according to the following protocol.

Engineered ARPE-19 cells in a 75 $cm^2$ culture flask were aspirated to remove culture medium, and the cell layer was briefly rinsed with 0.05% (w/v) trypsin/0.53 mM EDTA solution ("TrypsinEDTA") to remove all traces of serum containing a trypsin inhibitor. Two to three mL of Trypsin/EDTA solution was added to the flask, and the cells were observed under an inverted microscope until the cell layer was dispersed, usually between 5-15 minutes. To avoid clumping, cells were handled with care and hitting or shaking the flask during the dispersion period was minimized. If the cells did not detach, the flasks were placed at 37° C. to facilitate dispersal. Once the cells dispersed, 6-8 mL complete growth medium was added and the cells were aspirated by gentle pipetting. The cell suspension was transferred to a centrifuge tube and spun down at approximately 125×g for 5-10 minutes to remove TrypsinEDTA. The supernatant was discarded, and the cells were re-suspended in fresh growth medium. Appropriate aliquots of cell suspension was added to new culture vessels, which were incubated at 37° C. The medium was renewed 2-3 times weekly.

3B. ARPE-19 Cells for Encapsulation as Clusters

Spheroid clusters of exemplary cells (e.g., engineered ARPE-19 cells) are prepared using AggreWell™ spheroid plates (STEMCELL Technologies) and the protocol outlined herein. On Day 1, rinsing solution (4 mL) is added to each plate, and the plates is spun down for 5 minutes at 3,000 RPM in a large centrifuge. The rinsing solution is removed by pipet, and 4 mL of the complete growth medium is added. The engineered ARPE-19 cells are seeded into the plates at the desired cell density and pipetted immediately to prevent aggregation, with the general rule of thumb that 3.9 million cells per well will generate 150 μm diameter clusters. The plate is spun down for 3 minutes at 800 RPM, and the plate is placed into an incubator overnight at 37° C.

On Day 2, the plate is removed from incubation. Using wide bore pipet tips, the cells are gently pipetted to dislodge the spheroid clusters. The clusters are filtered through a 40 μm or 80 μm cell strainer to remove extraneous detached single cells and then spun down in a centrifuge for 2×1 minute. The clusters are resuspended gently using wide bore pipet tips and are gently stirred to distribute them throughout the medium or another material (e.g., alginate).

Alternatively, ARPE-19 spheroids are prepared using the following protocol. On Day 1, AggreWell™ plates are removed from the packaging in a sterile tissue culture hood. 2 mL of Aggrewell™ Rinsing solution is added to each well. The plate is centrifuged at 2,000 g for 5 minutes to remove air bubbles, and the AggreWell™ Rinsing Solution is removed from the wells. Each well is rinsed with 2 mL of the complete growth medium, and 2 million engineered ARPE-19 cells in 3.9 mL of the complete growth medium is added to each well. The plate is centrifuged at 100 g for 3 minutes, then the cells are incubated the cells at 37° C. for 48 hours. On Day 3, the same protocol described above is used to dislodge the spheroid clusters.

Alternatively, ARPE19 spheroids are prepared using a PBS MINI bioreactor (PBS Biotec, Inc., Camarillo CA, USA) with the following protocol. Cell culture media and 220 million ARPE19 cells are added into a PBS 0.1 L or PBS 0.5 L vessel which is then inserted into the base unit which is placed in an incubator. The PBS MINI speed adjust dial is set at 40 rpm and the vessel is incubated at 37° C. for at least 48 hours prior to collection of spheroids as described above.

Example 4: Preparation of Hydrogel Capsules Used in the Examples Below

Capsules encapsulating RPE cells as single cells. Immediately before encapsulation, single ARPE-19 cells, engineered to express a therapeutic protein were centrifuged at 1,400 r.p.m. for 1 min and washed with calcium-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH≈7.4, ≈290 mOsm). After washing, the cells were centrifuged again and all of the supernatant was aspirated. In some experiments, the cell pellet was then resuspended in the 70:30 CM-LMW-Alg:U-HMW-Alg solution described in Example 2 (control capsules) or one of the modified alginate solutions described in Table 6 of Example 2 at the desired density of suspended single cells per ml alginate solution.

Prior to fabrication of one-compartment and two-compartment hydrogel capsules, buffers and alginate solutions were sterilized by filtration through a 0.2-μm filter using aseptic processes.

For fabrication of one-compartment hydrogel capsules of about 1.5 mm diameter encapsulating cells, the desired number of cells were suspended in the desired alginate solution (e.g., the 70:30 CM-LMW-Alg:U-HMW-Alg solution used in Control capsules or one of the experimental alginate solutions described in Example 2 and Table 6) the resulting cell suspension was loaded into a syringe and capped with an 18-gauge blunt tipped needle (SAI Infusion Technologies). The syringe was placed onto a syringe pump oriented vertically above a dish containing a cross-linking solution. A high voltage power generator was connected to the needle and grounded to the biosafety cabinet. The syringe pump and power generator were turned on to extrude the alginate solution through the needle with a flow-rate of 0.16 mL/min or 10 mL/hr and adjusting the voltage in a range of 5-9 kV until there was a droplet rate of 12 droplets per 10 seconds.

To prepare devices configured as two-compartment hydrogel millicapsules of about 1.5 mm diameter, an electrostatic droplet generator was set up as follows: an ES series 0-100-kV, 20-watt high-voltage power generator (EQ series, Matsusada, NC, USA) was connected to the top and bottom of a coaxial needle (inner lumen of 22G, outer lumen of 18G, Ramé-Hart Instrument Co., Succasunna, NJ, USA). The inner lumen was attached to a first BD disposable 5-ml syringe with BD Luer-Lok™ tip (BD (Cat. No. 309646), Franklin Lakes, NJ, USA), which was connected to a syringe pump (Pump 11 Pico Plus, Harvard Apparatus, Holliston, MA, USA) that was oriented vertically. The outer lumen was connected via a luer coupling to a second 5-ml Luer-lock syringe which was connected to a second syringe pump (Pump 11 Pico Plus) that was oriented horizontally. To encapsulate cells only in the first (inner) compartment, a first alginate solution (70:30 CM-Alg-101:UM-Alg solution (as a control) or one of the experimental alginate solutions described in Example 2 and Table 6) comprising the cells (as single cell suspension) was placed in the first syringe and a second cell-free alginate solution comprising an afibrotic compound (e.g., a mixture of CM-LMW-Alg-101 and an U-HMW-Alg) was placed in the second syringe. For control 2-compartment hydrogel capsules in the Examples below, the second (outer) compartment was formed using the 70:30 CM-LMW-Alg-101:U-HMW-Alg solution. The two syringe pumps move the first and second alginate solutions from the syringes through both lumens of the coaxial needle and single droplets containing both alginate solutions are extruded from the needle into a glass dish containing a cross-linking solution. The settings of each Pico Plus syringe pump were 12.06 mm diameter and the flow rates of each pump were adjusted to achieve a flow rate ratio of 1:1 for the two alginate solutions. Thus, with the total flow rate set at 10 ml/h, the flow rate for each alginate solution was about 5 mL/h.

For fabrication of both the two-compartment and one-compartment millicapsules, after extrusion of the desired volumes of alginate solutions, the alginate droplets were crosslinked for five minutes in a cross-linking solution which contained 25 mM HEPES, 20 mM $BaCl_2$, 0.2M mannitol, and poloxamer 188. Capsules that had fallen to the bottom of the crosslinking vessel were collected by pipetting into a conical tube. After the capsules settled in the tube, the crosslinking buffer was removed, and capsules were washed. Capsules without cells were washed four times with HEPES buffer (NaCl 15.428 g, KCl 0.70 g, $MgCl_2.6H_2O$ 0.488 g, 50 ml of HEPES (1 M) buffer solution (Gibco, Life Technologies, California, USA) in 2 liters of deionized water) and stored at 4° C. until use. Capsules encapsulating cells were washed four times in HEPES buffer, two times in 0.9% saline, and two times in culture media and stored in an incubator at 37° C.

Example 5: Effect of Incorporating Cell Binding Sites Within a Single Compartment Alginate Capsule Encapsulating Cells on In Vitro Cell Productivity and Viability Compositions containing single-compartment hydrogel millicapsules (about 1.5 mm in diameter) were prepared essentially as described in Example 4, using alginate solutions described in Example 2, which lacked or contained cell binding sites.

ARPE-19 cells engineered to express a FVIII-BDD protein (SEQ ID NO:1) (ARPE-19:FVIII-BDD cells) were suspended at 3.3 million cells/ml alginate in the control alginate solution (70:30 CM-LMW-Alg-101:U-HMW-Alg) or one of the experimental alginate solutions described in Example 2 and Table 6. After preparation, one capsule per well of each capsule composition was placed into a 96-well plate. The supernatants were collected 24 h later and the concentration of FVIII in each supernatant was measured by ELISA. Also, at this time, the number of viable cells present in two aliquots of one capsule per well for each capsule composition was measured by a CellTiter Glo® viability assay (Promega Corporation, Madison, WI USA), Productivity (pg/cell/day) was calculated by dividing the pg of protein in the supernatant by the cell number in each aliquot. The results of this analyses are shown in FIG. 2.

Figure 2:
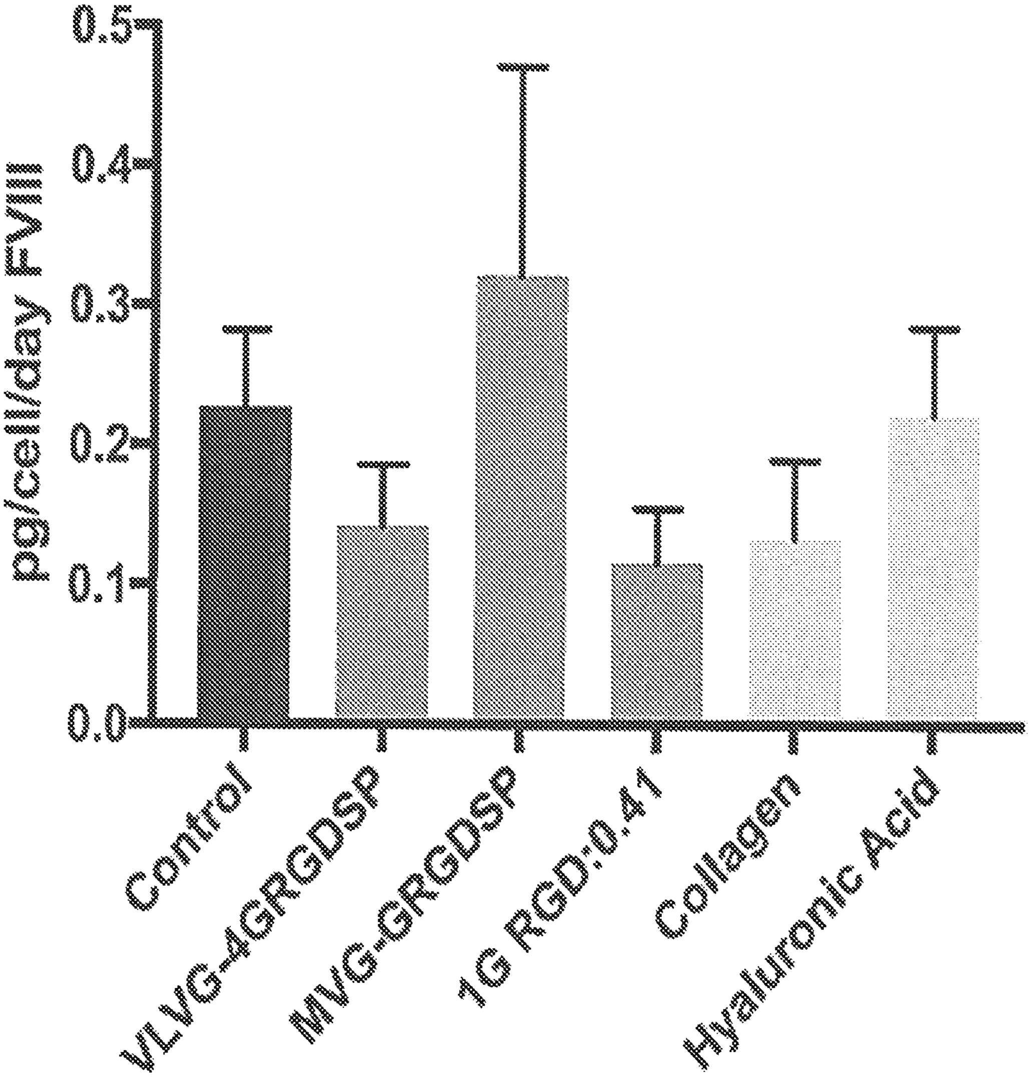
FIG. 2 is a bar graph showing the in vitro productivity of ARPE19 cells engineered to express a FVIII-BDD protein (ARPE-19:FVIII-BDD cells) and then encapsulated in single-compartment hydrogel capsules formed from alginate solutions comprising no cell-binding site (control) or a cell-binding site as described in Example 2 below.

As shown in FIG. 2, cells encapsulated in an alginate solution covalently modified with a cell-binding peptide (e.g., a CBP-alginate) did not show increased productivity compared to the control (e.g., alginate lacking a CBP). Additionally, alginate blends with Collagen I and HA also did not improve productivity of the encapsulated cells. These results demonstrate that the in vitro productivity of encapsulated cells is not affected by the presence of cell binding sites in the encapsulating alginate polymer.

Example 6: Encapsulating ARPE19:FVIII-BDD Cells in an RGD-Modified Alginate in the Inner Capsule Compartment Increases FVIII-BDD Plasma Levels After Capsule Implant Compositions of control and RGD-modified two-compartment hydrogel millicapsules encapsulating ARPE19:FVIII-BDD cells were prepared by extruding first and second alginate solutions through a coaxial needle as described in Example 4. The solution for the second (outer) compartment was the cell-free 70:30 CM-LMW-Alg-101:U-HMW-Alg solution and the solution for the first (inner) compartment was a suspension of ARPE19:FVIII-BDD cells in the 70:30 CM-LMW-Alg-101:U-HMW-Alg solution (control) or in one of the RGD-modified alginate solutions described in Example 2 (VLVG-4GRGD and 1G-RGD:0.41). ARPE19:FVIII-BDD cells were suspended at 100 million cells/ml in the first alginate solution (inner compartment solution).

Figure 3:
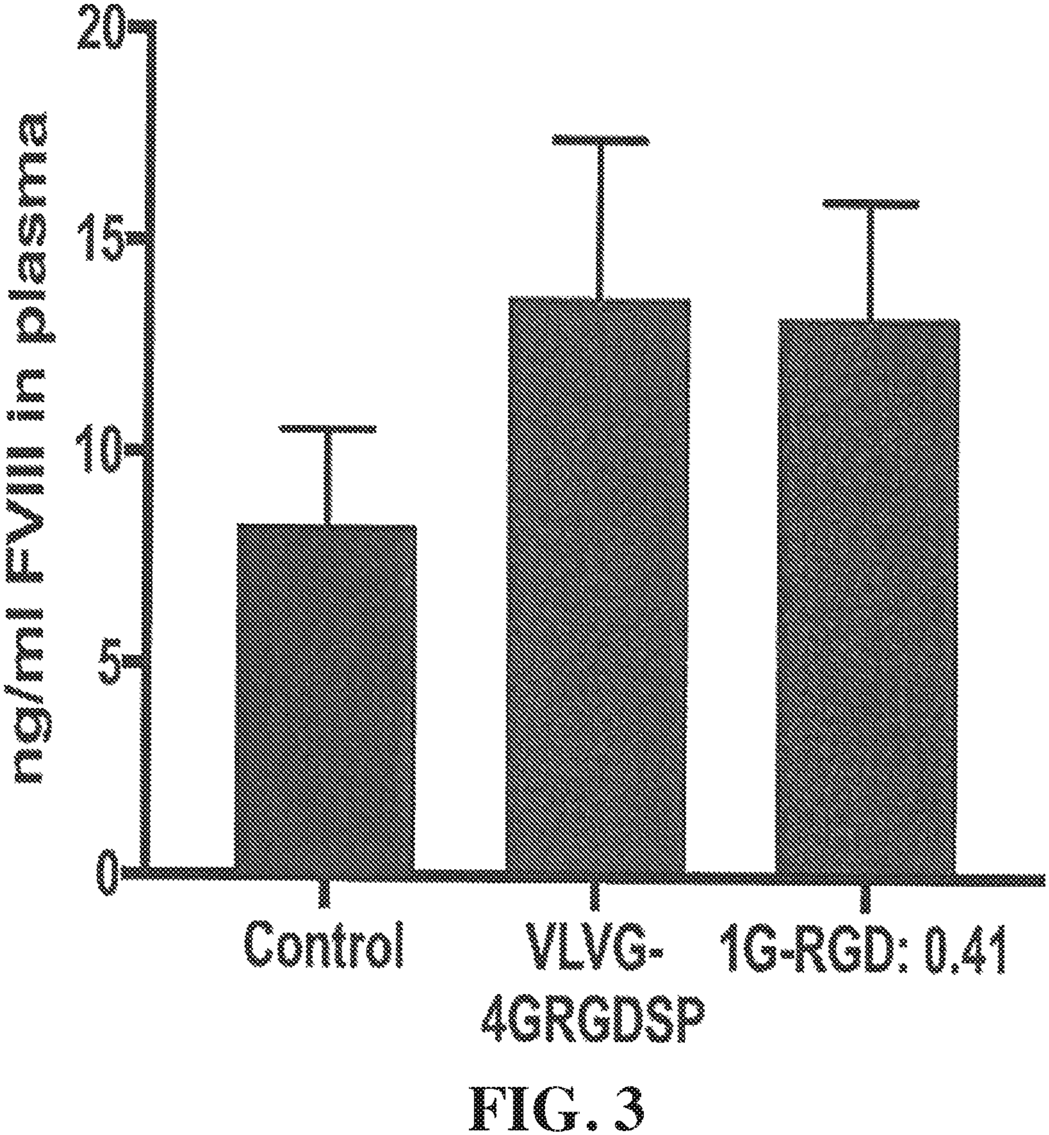
FIG. 3 is a bar graph showing plasma FVIIII-BDD levels at 2 weeks after implantation into nude mice of two-compartment hydrogel capsules in which the second compartment was formed from a mixture of an afibrotic alginate and an unmodified alginate and the first compartment was formed from a suspension of ARPE-19:FVIII-BDD cells in a test CBP-alginate solution described in the Examples herein (VLVG-4GRGDSP, 1G-RGD: 0.41) or the afibrotic alginate+unmodified alginate mixture (Control).

A 0.5 mL aliquot of each capsule composition was implanted into the intraperitoneal (IP) space of nude mice (4 mice per composition). At 2 weeks post-implantation, blood samples were collected from each mouse via an interim bleed. Plasma levels of FVIII-BDD in these samples were measured by ELISA and the results are shown in FIG. 3.

Plasma FVIII-BDD levels were higher for both RGD-modified alginate capsules compared to the control, indicating that the presence of an RGD-alginate within the first compartment can increase FVIII-BDD plasma levels in vivo.

Example 7: Encapsulating Cells in a Polymer Comprising Cell Binding Sites in the Inner Capsule Compartment does not Affect In Vivo Cell Proliferation or Ex Vivo Capsule Mechanical Properties Compositions of two-compartment control and capsules containing a CBP and encapsulating ARPE19:FVIII-BDD cells in the first (inner) compartment were prepared as described in Example 6. Similar two-compartment capsules were also prepared in which the outer compartment was the same, but the inner compartments were formed from the Collagen I or HA alginate solutions described in Example 2 and Table 6 above. For all control and test capsules, the concentration of suspended cells in the solution used to form the inner compartment was 100 million cells/ml.

Figure 4A:
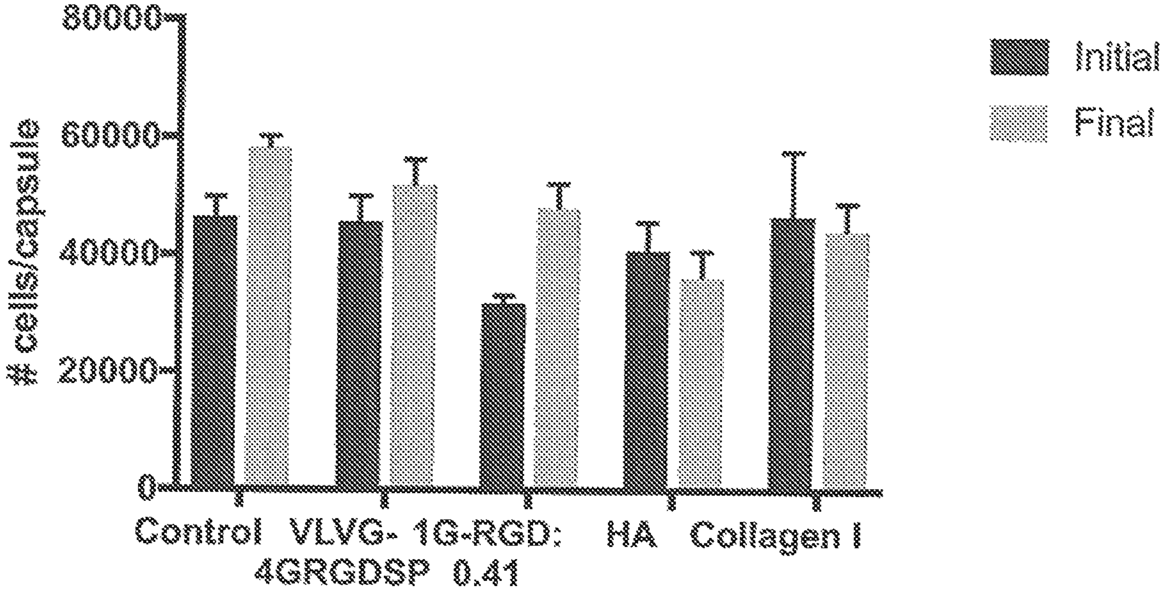
FIGS. 4A and 4B are bar graphs showing the number of cells/capsule (FIG. 4A) and mechanical strength (FIG. 4B) before implantation (Initial) and 1 month after IP implantation into mice (Final) of two-compartment hydrogel capsules in which the second compartment was formed from a mixture of an afibrotic alginate and an unmodified alginate and the first compartment was formed from a suspension of ARPE-19:FVIII-BDD cells in a test alginate solution comprising a CBP-alginate (VLVG-4GRGDSP, 1G-RGD: 0.41), HA, or Collagen I or the afibrotic alginate+unmodified alginate mixture (Control).
Figure 4B:
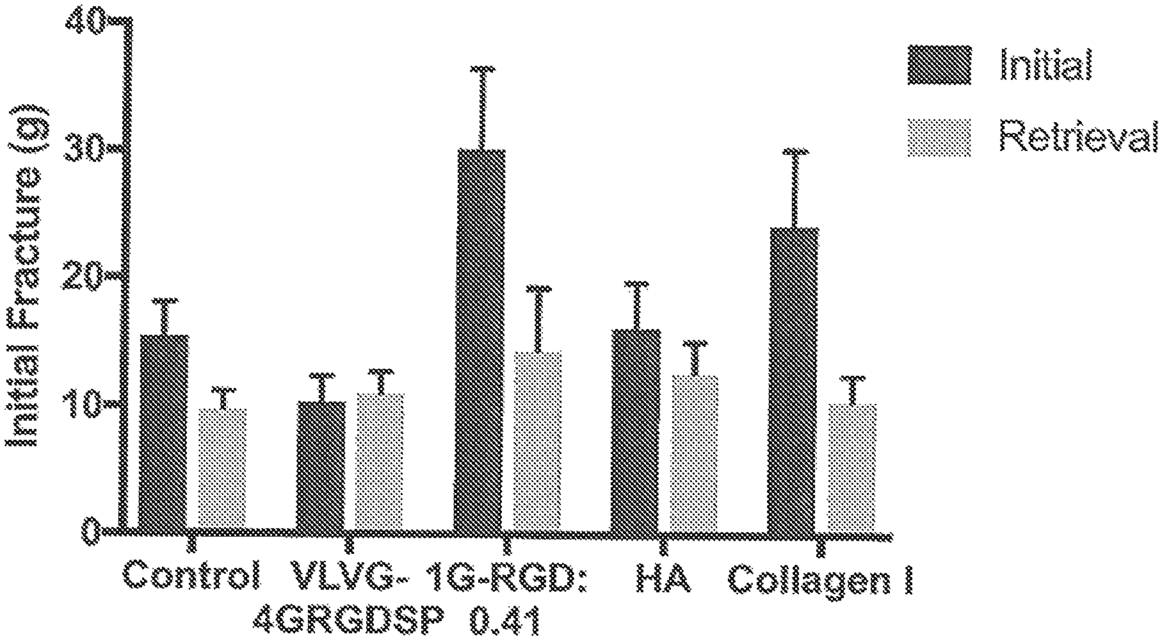

A 0.5 mL aliquot of each capsule composition was implanted into the IP space of nude mice (4 mice per composition). At 4 weeks post-implantation, the large majority of the capsules were retrieved from the mice and capsule cell numbers (one capsule in duplicate for each mouse) was measured using a CellTiter Glo® 3D Cell Viability Assay (Promega Corporation, Madison, WI USA). Briefly, one capsule per well was analyzed in duplicate and compared to a standard curve of plated cells. 100 μl of the CellTiter Glo® 3D reagent was added to the each well containing 100 μl of medium, the plate was placed onto a shaker at 400 rpm for 15 minutes and then luminescence was read on a plate reader. Also, a texture analyzer was used to measure the mechanical strength (initial fracture) of the capsules in aliquots of each composition at pre-implantation and upon retrieval after the 1-month implantation period. The cell number and capsule strength results are shown in FIG. 4A and FIG. 4B, respectively. There was some variability observed due to experimental error.

In the control and CBP capsules, some cell growth during the one-month implantation period was observed, but the cell number in the retrieved capsules was similar for the control and CBP-alginate groups. Cell numbers in the Collagen and HA capsules did not significantly change during the one month implantation period. Although the magnitude of the proliferation varies across groups, other data (not shown) suggests that cell numbers plateau around ~50,000 cells/capsule, as shown in FIG. 4A, regardless of starting cell concentration. Thus, the data in FIG. 4A suggest that the GRGDSP (SEQ ID NO: 60) peptide is not stimulating significant proliferation in vivo beyond what is observed in control capsules.

The initial fracture measured at pre-implantation varied across the capsule compositions: a first (inner) compartment comprised of SFG20 (i.e., 1G-RGD, HA, Collagen I) created a stronger capsule compared to the Control and VFVG-4GRGD capsules. However, the initial fracture strength determined at retrieval after the one-month implantation was similar for capsules in the Control and all test capsule compositions. These data suggest that the presence of cell binding domains within the capsule does not affect mechanical integrity of the capsules.

Example 8: Encapsulating ARPE19-FVIII-BDD Cells in a G-RGD-Alginate in the Inner Capsule Compartment Increases FVIII-BDD Plasma Levels After Capsule Implant Compositions of two-compartment hydrogel millicapsules encapsulating ARPE19:FVIII-BDD cells were prepared by extruding first and second alginate solutions through a coaxial needle as described in Example 4. The second (outer) compartment was prepared using the 70:30 CM-LMW-Alg-101:U-LMW-Alg solution and the inner compartment contained the 70:30 CM-LMW-Alg-101:U-LMW-Alg solution (Control) or one of the following CBP-modified alginate solutions described in Example 2 and Table 6: MVG-GRGDSP, 1G-RGD:0.41, 4G-RGD:0.53. For all control and test capsules, the concentration of cells in the alginate solution used to form the inner compartment was 100 million cells/ml.

Figure 5:
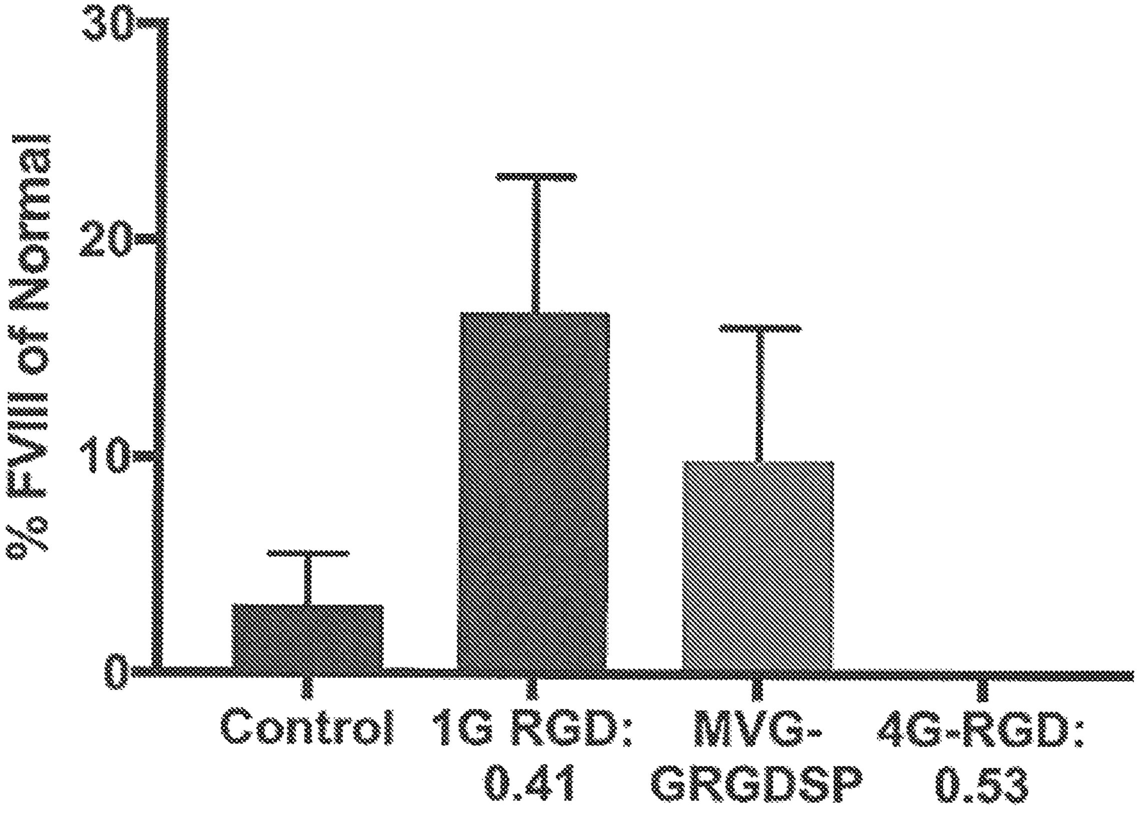
FIG. 5 is a bar graph showing the plasma FVIIII-BDD levels at 2 weeks after implantation into nude mice of two-compartment hydrogel capsules in which the second compartment was formed from a mixture of an afibrotic alginate and an unmodified alginate and the first compartment was formed from a suspension of ARPE-19:FVIII-BDD cells in a test CBP-alginate solutions described in the Examples herein (1G RGD: 0.41, MVG-GRGDSP, 4G-RGD: 0.53) or the afibrotic alginate+unmodified alginate mixture (Control).

A 0.5 mL aliquot of each of capsule composition was implanted into the IP space of nude mice (4 mice per composition). At 14 days post-implantation, animals were sacrificed and blood samples were collected from each mouse. Plasma levels of FVIII-BDD in these samples was measured by ELISA; the results are shown in FIG. 5.

Plasma FVIII-BDD levels were higher in mice implanted with capsules containing an alginate covalently modified with an RGD peptide via a single G linker than in mice implanted with control capsules or capsules containing an alginate covalently modified with the same RGD peptide via a 4 G linker. There was no significant difference between two RGD alginates with the same RGD peptide, but different MW alginates (MVG-GRGDSP and 1G-RGD:0.41) or between a mixture of the MVG-GRGDSP alginate and M REDV alginate. Surprisingly, the 4G-RGD:0.53 alginate, which was modified with the same RGD peptide (RGDSP (SEQ ID NO: 59)) as in the 1G-RGD:0.41 alginate, but with a 4 G linker instead of a single G linker, appeared to have a negative impact on cell productivity: plasma FVIII-BDD was undetectable in mice implanted with the 4G-RGD:0.53 capsules. These data indicate that plasma levels of a therapeutic protein expressed by implanted engineered RPE cells in an animal model can be increased by implanting the cells via a device (e.g., a hydrogel millicapsule) that encapsulates the engineered RPE cells in a polymer (e.g., alginate) conjugated to an RGD cell binding peptide via a single G linker.

Example 9: Presence of an RGD-Alginate in the Inner Capsule Compartment does not Impact Fibrosis of Implanted Capsules This experiment examined whether the presence of a cell-binding peptide in the inner compartment and medium or high density of an afibrotic compound in the outer compartment affected the level of fibrosis after capsule implant into an animal model. The capsule compositions used in this experiment had the 2-compartment capsule configurations described below.

(1) Control: inner compartment formed from a solution comprising a suspension of ARPE19-FVIII-BDD cells in the 70:30 CM-LMW-Alg-101-Medium:U-HMW-Alg mixture, outer compartment formed from 70:30 CM-LMW-Alg-101-Medium:U-HMW-Alg mixture;

(2) RGD Inner/Medium Outer: inner compartment formed from a solution comprising a suspension of ARPE19-FVIII-BDD cells in 1G-RGD:0.41 (Table 6), outer compartment formed from 70:30 CM-LMW-Alg-101-Medium:U-HMW-Alg mixture;

(3) RGD Inner/High Outer: inner compartment formed from a solution comprising a suspension of ARPE19-FVIII-BDD cells in 1G-RGD:0.41 (Table 6), outer compartment formed from 70:30 CM-LMW-Alg-101-High:U-HMW-Alg mixture;

(4) RGD Inner/High (60:40) Outer: inner compartment formed from a solution comprising a suspension of ARPE19-FVIII-BDD cells in 1G-RGD:0.41 (Table 6), outer compartment formed from 60:40 CM-LMW-Alg-101-High: U-HMW-Alg mixture; and (5) RGD, Empty: Inner/Medium Outer: inner compartment formed from 1G-RGD:0.41 (Table 6), outer compartment formed from 70:30 CM-LMW-Alg-101-Medium:U-HMW-Alg mixture, but no cells were encapsulated.

Figure 6:
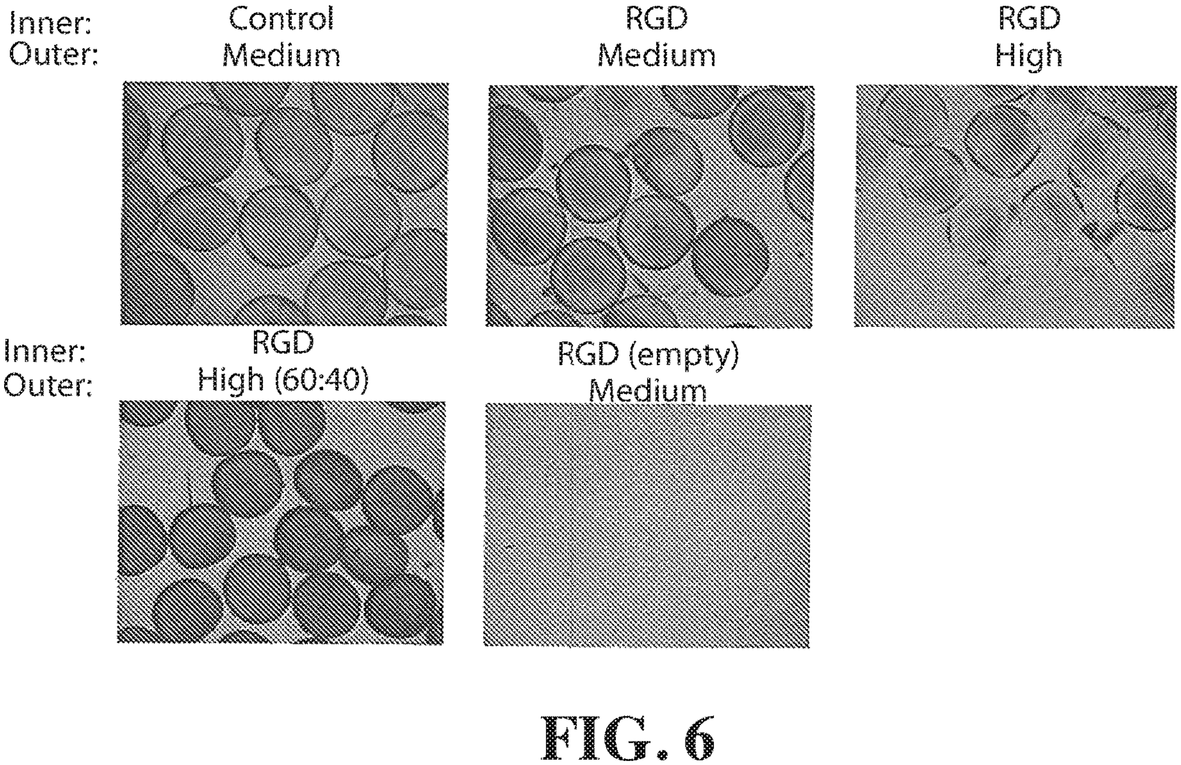
FIG. 6 shows brightfield images of two-compartment hydrogel millicapsules with a 50:50 volume ratio of inner:outer compartments. Second (outer) compartments comprise a medium or high conjugation afibrotic alginate. Inner compartments contain either a medium conjugation afibrotic alginate (Control) or a CBP-alginate (RGD) with or without (RGD, Empty) exemplary RPE cells engineered to express an exogenous protein. The capsules were imaged after 11 day implantation in C57/BL6 mice for the presence of fibrosis.

A 0.5 mL aliquot of each capsule composition was implanted into the IP space of C57/BL6 mice (4 mice per composition), and retrieved after 11 days. The retrieved capsules were imaged by brightfield microscopy, and the results are shown in FIG. 6.

There was no difference in fibrosis for capsules that had medium density afibrotic compound in the second (outer) compartment and a first compartment encapsulating cells in an afibrotic alginate:unmodified alginate mixture (Control) or an RGD-alginate. As expected, implanted capsules without cells (RGD (empty)) exhibited less fibrosis in mice than capsules containing the xenogenic RPE cells. Varying the density of the afibrotic compound in the second (outer) compartment by using high density CM-LMW Alginate decreased fibrosis, while changing the CM-LMW:U-HMW blend ratio from 70:30 to 60:40 increased fibrosis, as expected. Therefore, the presence of a cell binding peptide within the first (inner) compartment does not impact the afibrotic property of the capsules.

Example 10: Encapsulating ARPE19:FIX-Padua Cells in a G-RGD-Alginate in Inner Capsule Compartment Increases Plasma FIXpadua Levels After Implant Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from one of the following alginate solutions, each of which contained 100 million ARPE19: FIX-Padua cells/ml:

(1) Control: 70:30 CM-LMW-Alg-101-Medium:U-HMW-Alg mixture;

(2) 1G-RGD: 0.41

(3) 4G-RGD: 0.53

(4) 4G-RGD: 0.96

(5) 4G-RGD: 1.77

(6) RGD-4G: 2.95

A 0.5 mL aliquot of each capsule composition was implanted into the IP space of nude mice (4 mice per composition). At 12 days post-implantation, animals were sacrificed and blood samples were collected from each mouse. Plasma levels of FIX in these samples was measured by ELISA.

Figure 7:
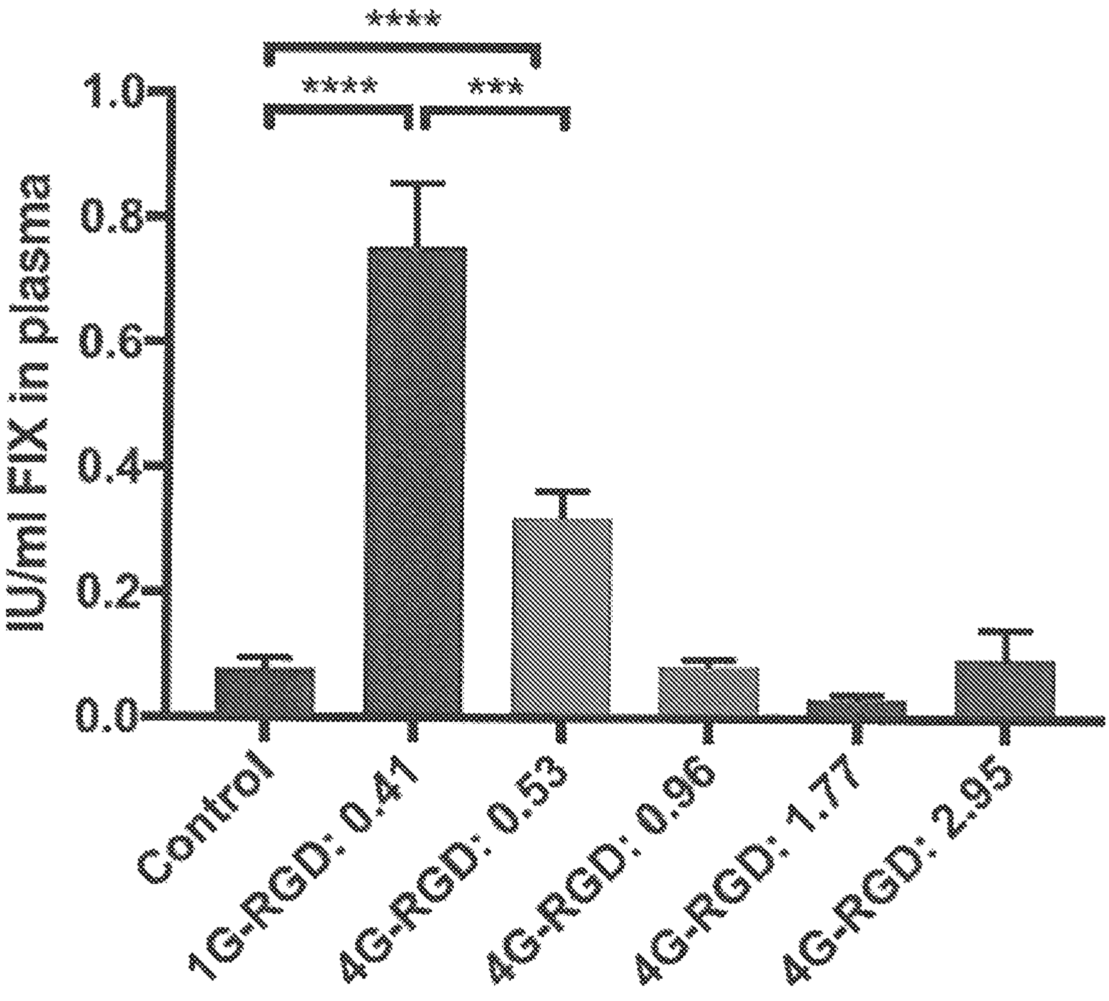
FIG. 7 is a bar graph showing the plasma levels of FIX in nude mice after 2 week implantation of 2-compartment hydrogel capsules containing RPE cells engineered to express a FIX protein. The RPE cells were encapsulated in the first compartment with varying alginate compositions: no cell binding peptide (control), alginate modified with varying densities of an RGD peptide via a linker with a single glycine residue (1G-RGD: 0.41 or a 4G linker (SEQ ID NO: 61) (4G-RGD: 0.53, 0.96, 1.77 and 2.95).

As shown in FIG. 7, post-implant plasma FIX levels were significantly higher for capsules containing the 1G-RGD: 0.41 alginate or the 4G-RGD:0.53 alginate in the inner compartment compared to the control and capsules with the higher density 4G-RGD alginate in the inner compartment. Surprisingly, implant of the 1G-RGD:0.41 capsules resulted in significantly higher plasma FIX levels than implant of the 4G-RGD:0.53 capsules, demonstrating that the composition of the RGD linker can affect cell productivity with respect to the amount of therapeutic protein secreted from the capsules. Finally, capsules prepared using the alginate polymers with higher concentrations of the 4G linker peptide (SEQ ID NO: 61) all had similar FIX levels to the control. Together, these data demonstrate that implanting 2-compartment hydrogel capsules comprising RPE cells engineered to express a FIX protein and encapsulated in an RGD-alginate within the first (inner) compartment can significantly increase plasma FIX levels in an animal model, and suggest that some combinations of RGD density and linker size may not work as well as an alginate modified with 1G-RGDSP at about 0.41% N.

Example 11. Post-Implant Plasma FIX Levels are Higher Using a Blend of an RGD-Alginate and a Second CBP-Alginate to Encapsulate ARPE19:FIX-Padua Cells in the Inner Capsule Compartment Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from one of the following alginate solutions, each of which contained 100 million ARPE19: FIX-Padua cells/ml.

(1) Control: 70:30 CM-LMW-Alg-101-Medium:U-HMW-Alg mixture;

(2) 1G-RGD: 0.41 (Table 6)

(3) 4G-DGEA (Table 6)

(4) 1G-RGD/4G-DGEA: a 1:1 blend of the 1G-RGD: 0.41 solution and the 4G-DGEA solution (5) 1G-RGD/4G-PHSRN: a 1:1 blend of the 1G-RGD: 0.41 solution and the 4G-PHSRN solution (6) 1G-RGD/4G-DGEA/4G-PHSRN: a 1:1:1 blend of the 1G-RGD: 0.41, 4G-DGEA and PHSRN solutions.

A 0.5 mL aliquot of each capsule composition was implanted into the IP space of nude mice (4 mice per composition). At 2 weeks post-implantation, animals were sacrificed and blood samples were collected from each mouse. Plasma levels of FIX in these samples was measured by EFISA.

Figure 8:
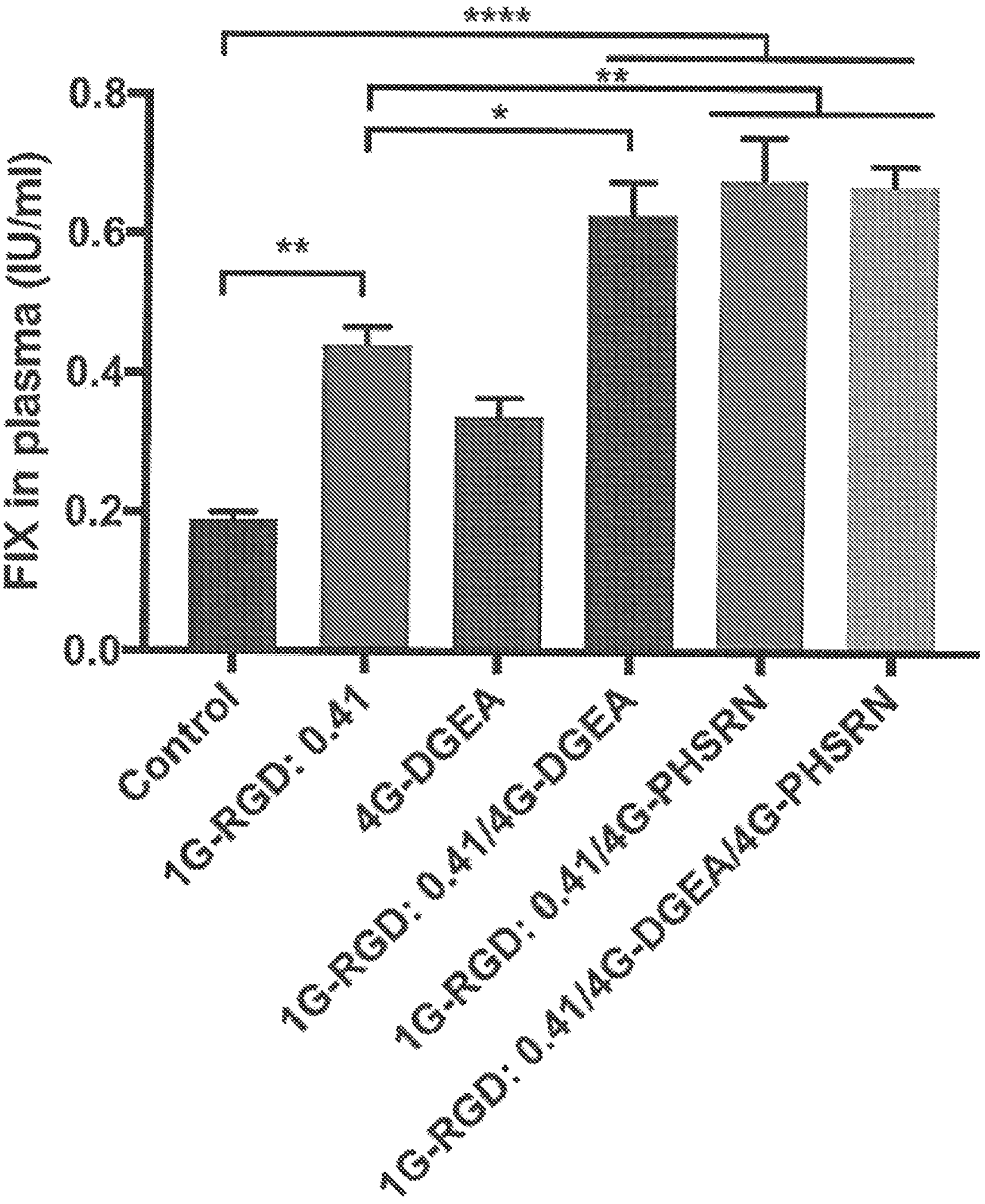
FIG. 8 is a bar graph showing the plasma levels of FIX in nude mice after 2 week implantation of 2-compartment hydrogel capsules containing RPE cells engineered to express a FIX protein. The RPE cells were encapsulated in the first compartment with varying alginate compositions: no cell binding peptide (control), alginate modified with 1G-RGD, 4G-DGEA or 4G-PHSRN or combinations of 1G-RGD blended with other CBP alginates. (1G-RGD: 0.41, 4G-DGEA, 1:1 1G-RGD: 0.41/4G-DGEA, 1:1 1G-RGD: 0.41/4G-PHSRN, 1:1:1 1G-RGD: 0.41/4G-DGEA/4G-PHSRN).

As shown in FIG. 8, the plasma levels of FIX were higher for the capsules containing the 1G-RGD-alginate or DGEA-alginate compared to the control, with the higher levels in the RGD capsules reaching statistical significance with a one-way ANOVA. Although it did not reach statistical significance, the 1G-RGD alginate was still substantially higher than the 4G-DGEA capsules. The FIX plasma levels were highest for the three groups of capsules containing the RGD alginate blended with another CBP-alginate. These data demonstrates that capsules containing ARPE19-FIX-Padua cells and combinations of multiple CBP-alginates can improve the FIX levels compared to capsules created with a single CBP-alginate (RGDSP (SEQ ID NO: 59) or DGEA (SEQ ID NO: 39)).

Example 12. Density of an RGD Peptide in the Inner Compartment Encapsulating ARPE19:FIX-Padua Cells Affects FIX Plasma Levels Produced by Implanted Hydrogel Capsules Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from one of the following alginate solutions described in Table 6, each of which contained 100 million ARPE19:FIX-Padua cells/ml:

(1) Control: 70:30 CM-LMW-Alg-101-Medium:U-HMW-Alg mixture;

(2) 1G-RGD: 0.22

(3) 1G-RGD: 0.33

(4) 1G-RGD: 0.72

(5) 1G-RGD: 1.47

A 0.5 mL aliquot of each capsule composition was implanted into the IP space of nude mice. At 2 weeks post-implantation, animals were sacrificed and blood samples were collected from each mouse. Plasma levels of FIX in these samples was measured by ELISA.

Figure 9:
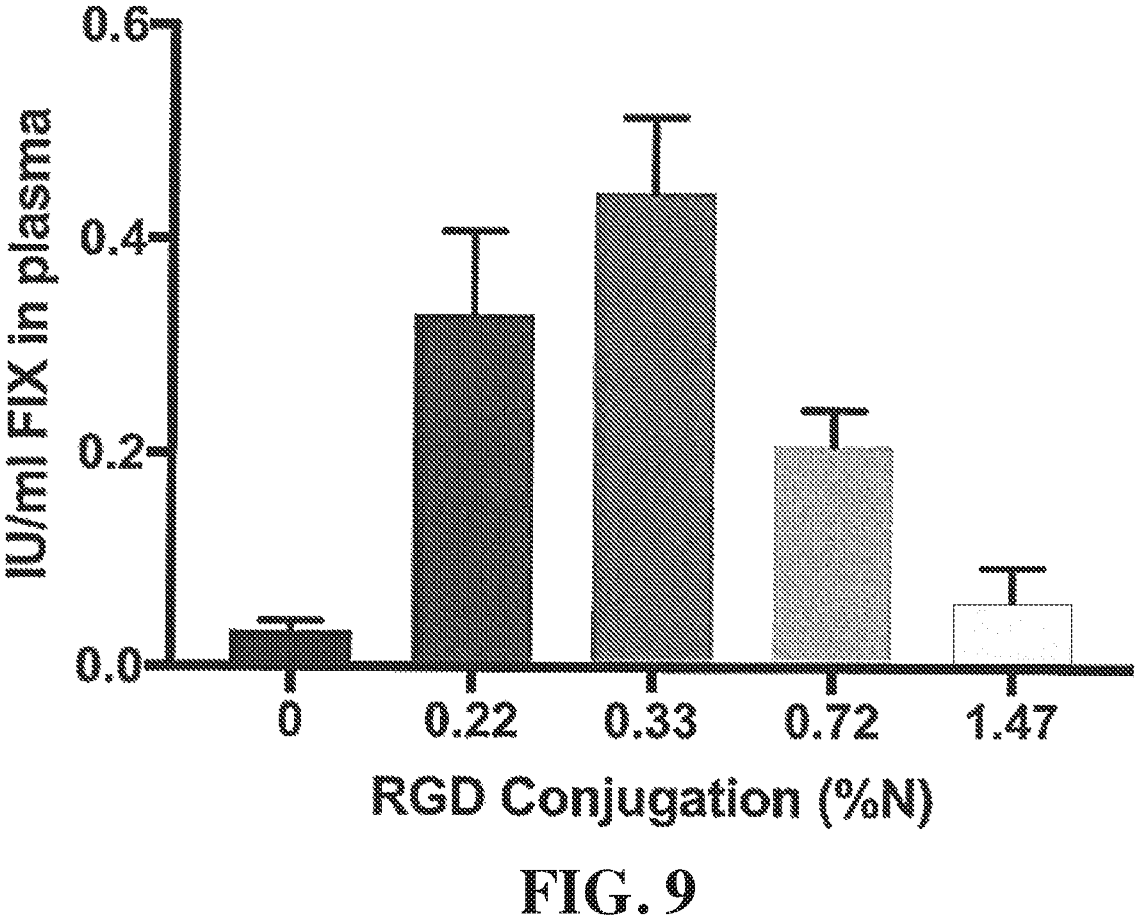
FIG. 9 is a bar graph showing the plasma levels of FIX in nude mice after 2 week implantation of 2-compartment hydrogel capsules containing RPE cells engineered to express a FIX protein. The RPE cells were encapsulated in the first compartment with varying 1G-RGD density (0, 0.22, 0.33, 0.72 and 1.47% N).

As shown in FIG. 9, the amount of RGD conjugation to the first (inner) compartment polymer affected the levels of FIX detected in the plasma. FIX levels increased as the RGD density increased from 0 to 1G-RGD: 53 but, surprisingly, the FIX levels were successively lower following implant of the 1G-RGD: 0.72 and 1G-RGD: 1.47 capsules. Together, these data demonstrate that the conjugation density of the RGD peptide can have a significant effect on FIX levels produced by hydrogel capsules, and that further, for capsules configured as described in this Example, capsules prepared with 1G-RGD: 0.33 in the inner compartment may be optimal for achieving the highest plasma FIX-Padua levels.

Example 13. Encapsulating ARPE19:PTH Cells in a 1G-RGD-Alginate in Inner Capsule Compartment Increases Plasma PTH Levels After Implant Compositions of control and RGD-modified two-compartment hydrogel millicapsules encapsulating ARPE19:PTH cells were prepared by extruding first and second alginate solutions through a coaxial needle as described in Example 4. The alginate solution for the second (outer) compartment was the cell-free 70:30 CM-LMW-Alg-101:U-HMW-Alg solution and the alginate solution for the first (inner) compartment was a suspension of ARPE19:FVIII-PTH cells at 100 million cells/ml in the 70:30 CM-LMW-Alg-101:U-HMW-Alg solution (control) or an RGD-modified alginate solution (1G-RGD: 0.72%) described in Table 6.

Figure 10:
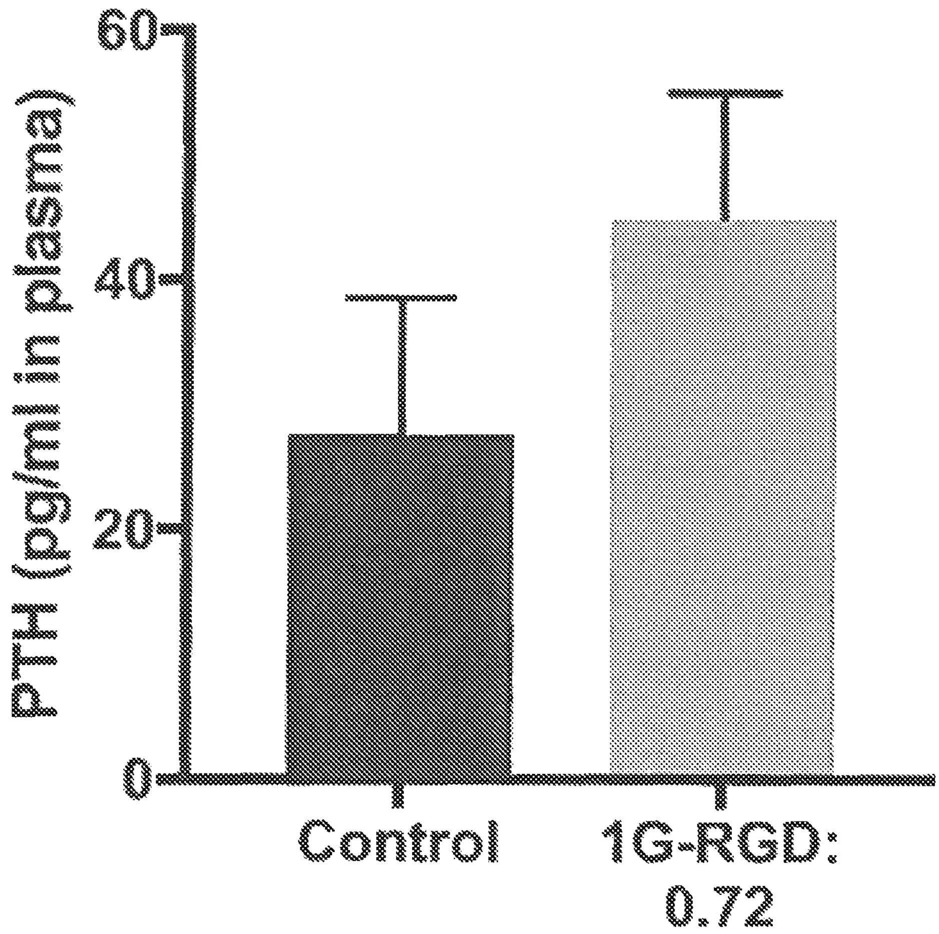
FIG. 10 is a bar graph showing the plasma levels of PTH in nude mice after 2 week implantation of 2-compartment hydrogel capsules containing RPE cells engineered to express a PTH protein. The RPE cells were encapsulated in the first compartment with varying either control or 1G-RGD: 0.72 polymer.

An aliquot of 0.5 mL of each capsule composition was implanted into the intraperitoneal (IP) space of nude mice (4 mice per composition). At 1 week post-implantation, animals were sacrificed and blood samples were collected from each mouse. Plasma levels of PTH in these samples were measured by ELISA and the results are shown in FIG. 10.

Plasma PTH levels were approximately two-times higher for the RGD-modified alginate capsules compared to the control, indicating that the presence of an RGD-alginate within the first compartment can increase PTH plasma levels in vivo.

Figure 11:
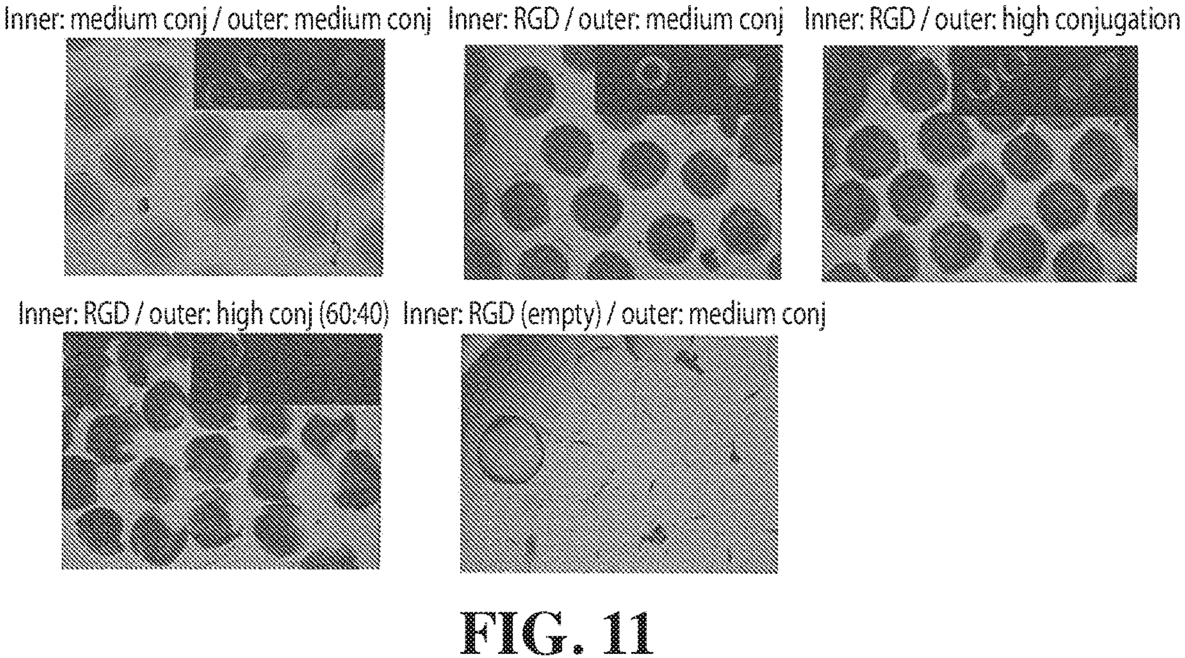
FIG. 11 shows brightfield images of two-compartment hydrogel millicapsules where second (outer) compartments comprise a medium or high conjugation afibrotic alginate. Inner compartments contain either a medium conjugation afibrotic alginate (Control) or a CBP-alginate (RGD) with or without (RGD, Empty) exemplary RPE cells engineered to express an exogenous protein.

Example 14: Capsules Containing ARPE19:FVIII Cells Within a G-RGD-Alginate in Inner Capsule Compartment have Stability Comparable to a No RGD Control Compositions of two-compartment hydrogel millicapsules encapsulating ARPE19:FVIII cells were prepared by extruding first and second alginate solutions through a coaxial needle as described in Example 4. Compositions of capsules were prepared with the following combinations of first and second compartment solutions: (1) first and second: CM-LMW-Alg-101-Medium:U-HMW-Alg solution (the control condition), (2) first: 1G-RGD: 0.41, second: CM-LMW-Alg-101-Medium:U-HMW-Alg solution, (3) first: 1G-RGD: 0.41, second: CM-LMW-Alg-101-High:U-HMW-Alg solution, (4) first: 1G-RGD: 0.41, second: CM-LMW-Alg-101-High:U-HMW-Alg solution prepared at a 60:40 volume ratio of CM-LMW-ALG-101 to High:U-HMW, and (5) first: 1G-RGD: 0.41, second: CM-LMW-Alg-101-Medium:U-HMW-Alg solution. The ARPE19:FIX cells were encapsulated in the first (inner) compartment at 100 million cells/ml for conditions (1-4) above. A 0.5 mL aliquot of each capsule composition was implanted into the IP space of nude mice. At 2 months post-implantation, animals were sacrificed and the capsules were collected from each mouse. Capsules were imaged and a live/dead stain was performed. The data are shown in FIG. 11.

All capsules were retrieved intact and viable cells were detected. There were visible differences in densities of cells within the first compartment for control compared to GRGDSP-containing capsules (SEQ ID NO: 60), but the total number of viable cells was similar (data not shown). Together, these data demonstrate that the incorporation of RGD within the first compartment does not negatively affect capsule integrity.

Example 15: Capsules Containing Balb/3T3 Cells Within a G-RGD-Alginate in Inner Capsule Compartment are Equally Afibrotic to No RGD Control Through 2 Month Implantation in C57/BL6

Compositions of two-compartment hydrogel millicapsules encapsulating ARPE19:FVIII cells were prepared by extruding first and second alginate solutions through a coaxial needle as described in Example 4. Compositions of capsules were prepared with the following combinations of first and second compartment solutions as described in Example 14. The Balb/3T3 cells were encapsulated in the first (inner) compartment at 20 million cells/ml for conditions (1-4) above. A 0.5 mL aliquot of each capsule composition was implanted into the IP space of C57/BL6 mice. At 2 months post-implantation, capsules were retrieved and imaged by brightfield microscopy for the presence of fibrosis.

Figure 12:
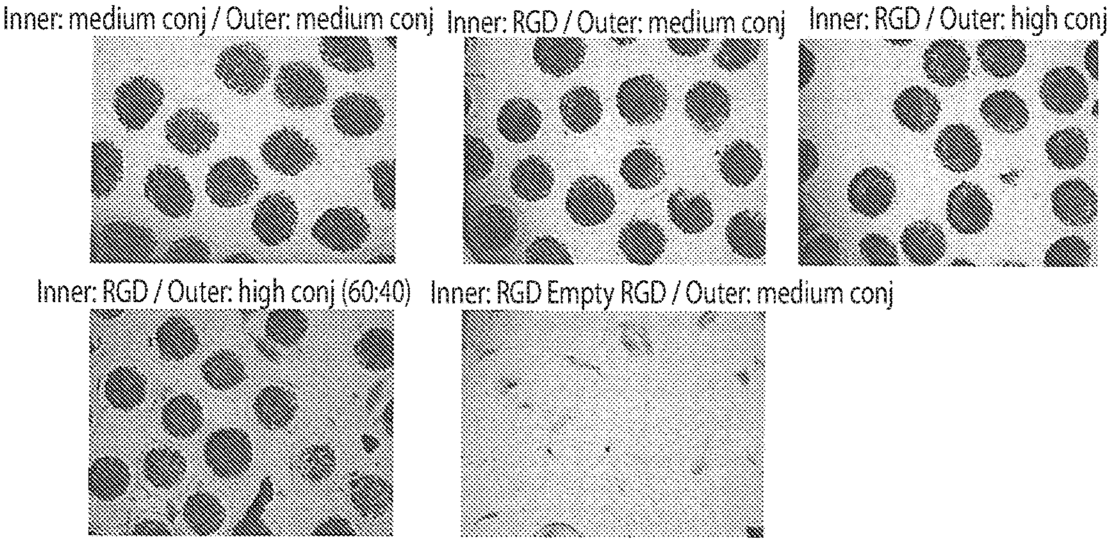
FIG. 12 shows brightfield images of two-compartment hydrogel millicapsules where second (outer) compartments comprise a medium or high conjugation afibrotic alginate. Inner compartments contain either a medium conjugation afibrotic alginate (Control) or a CBP-alginate (RGD) with or without (RGD, Empty) mouse-derived Balb/3T3 cells.

All capsules were retrieved intact and were largely lacking fibrosis, as shown in FIG. 12 where the empty, clear outer layer is not covered in opaque, fibrotic deposition. More fibrosis was observed on the capsules prepared with the 60:40 blend of CM-LMW-Alg-101-High:U-HMW-Alg compared to the 70:30 blend, as expected. Together, these data demonstrate that the incorporation of RGD within the first compartment does impact the afibrotic nature of the capsules within an allogeneic context.

Example 16: Identity of a G-RGD-Modified Polymer in the Inner Compartment Encapsulating ARPE19:FIX-Padua Cells Affects FIX Plasma Levels Produced by Implanted Hydrogel Capsules Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from one of the following alginate solutions using different initial polymers as described in Table 6, each of which contained 100 million ARPE19:FIX-Padua cells/ml:

(1) 1G-RGD: 0.72
(2) 1G-MVG: 0.71, 79 cP
(3) 1G-MVG: 0.71, 97 cP
(4) 1G-MVG: 0.71, 143 cP
(5) 1G-MVG: 0.71, 202 cP
(6) 1G-SLG100: 0.65

A 0.5 mL aliquot of each capsule composition was implanted into the IP space of nude mice. At 4 weeks post-implantation, animals were sacrificed and capsules and blood samples were collected from each mouse. Plasma levels of FIX in these samples was measured by ELISA. The initial fracture of the capsules at pre-implantation and ex-vivo retrieval were measured using a texture analyzer.

Figure 13A:
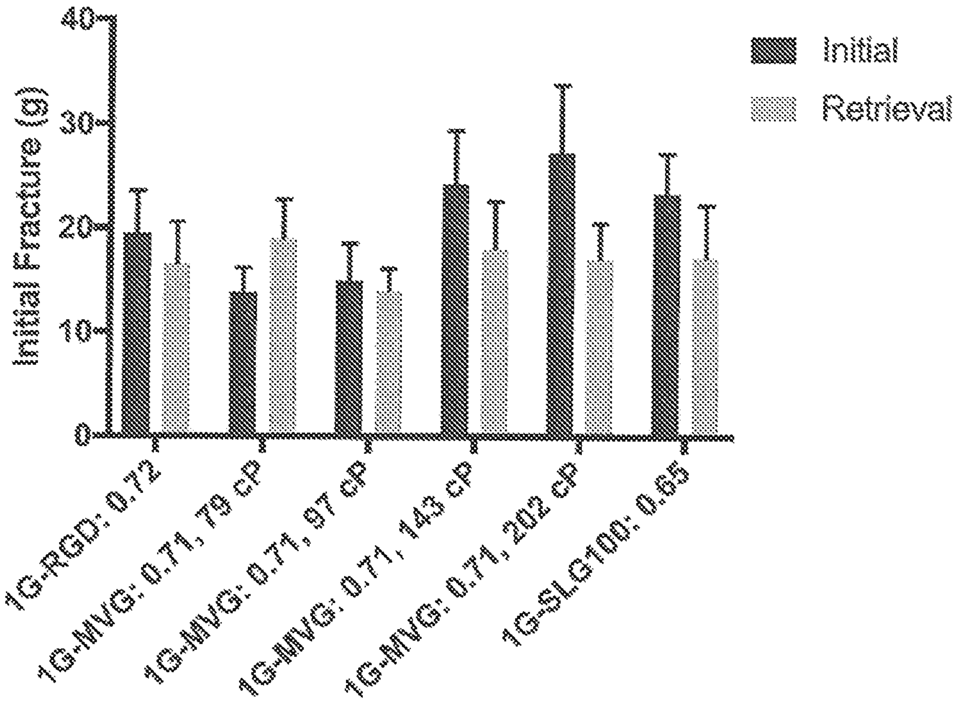
FIGS. 13A and 13B are bar graphs showing the initial fracture (FIG. 13A) and FIX levels in the plasma (FIG. 13B) for capsules prepared with 1G-RGD polymers with varying polymer identity and solution viscosity.
Figure 13B:
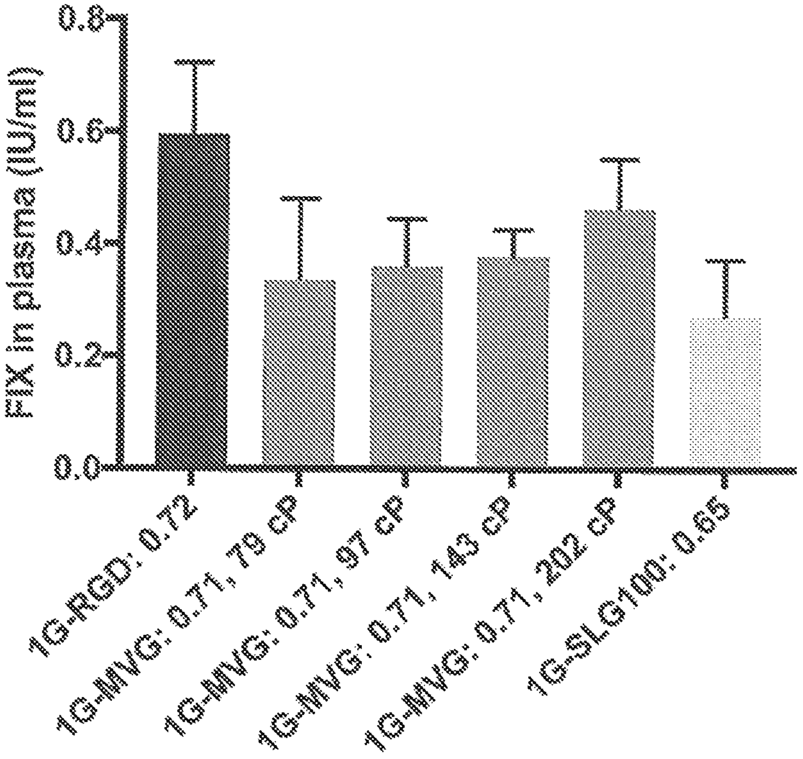

The initial fracture of capsules varied with polymer identity and solution viscosity prior to implantation. All capsules were retrieved intact with similar ex vivo mechanical strength as shown in FIG. 13A. As shown in FIG. 13B, the plasma levels of FIX-padua were highest for the capsules containing the G-RGD: 0.72 compared to the G-SLG100: 0.65 or the G-MVG: 0.71 at any of the four viscosities (79, 97, 143, 202 cP). Together, these data demonstrate that the identity of the polymer with conjugated RGD peptide can have a significant effect on FIX levels produced by hydrogel capsules, and that further, for capsules configured as described in this Example, the SLG20 polymer may be optimal for achieving the highest plasma FIX levels.

Example 17: Encapsulating ARPE19:FIX Cells in a 1G-HAVDI-Alginate in Inner Capsule Compartment Increases Plasma FIX Levels After Implant Compositions of control and HAVDI-modified (SEQ ID NO: 38) two-compartment hydrogel millicapsules encapsulating ARPE19:FIX cells were prepared by extruding first and second alginate solutions through a coaxial needle as described in Example 4. The alginate solution for the second (outer) compartment was the cell-free 70:30 CM-LMW-Alg-101:U-HMW-Alg solution and the alginate solution for the first (inner) compartment was a suspension of ARPE19:FIX cells at 100 million cells/ml in the 70:30 CM-LMW-Alg-101:U-HMW-Alg solution (control) or an HAVDI-modified alginate solution (G-HAVDI: 0.38%) described in Table 6.

Figure 14:
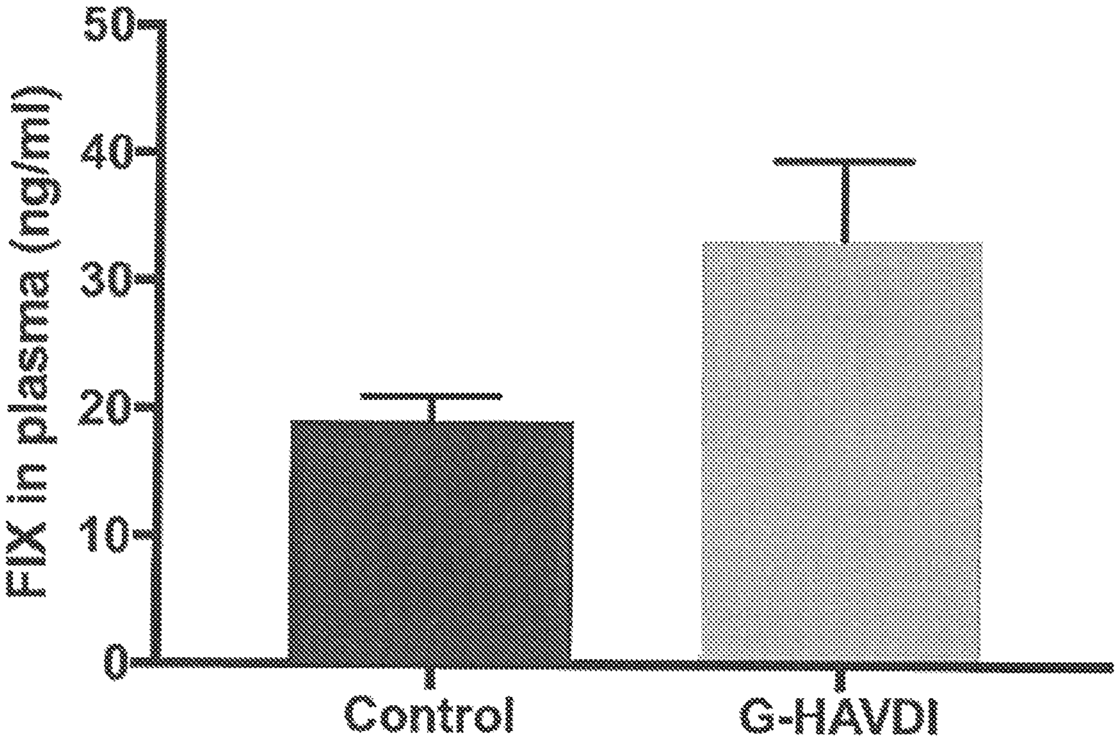
FIG. 14 is a bar graph showing the plasma levels of FIX in nude mice after 2 week implantation of 2-compartment hydrogel capsules containing RPE cells engineered to express a FIX protein. The RPE cells were encapsulated in the first compartment with varying either control or 1G-HAVDI polymer.

An aliquot of 0.5 mL of each capsule composition was implanted into the intraperitoneal (IP) space of nude mice (4 mice per composition). At 2 week post-implantation, samples were collected from an interim bleed on each mouse. Plasma levels of FIX in these samples were measured by ELISA and the results are shown in FIG. 14.

Plasma FIX levels were approximately two-times higher for the HAVDI-modified alginate capsules compared to the control, indicating that the presence of an alginate modified with a CBP derived from a cadherin (e.g., G-HAVDI) within the first compartment can increase FIX plasma levels in vivo.

Example 18: A G-RGD-Modified Polymer in the Inner Compartment Encapsulating ARPE19:FIX-Padua Cells Increases FIX Levels in Plasma from IP and SubQ Sites Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from G-RGD: 0.33 as described in Table 6, each of which contained 100 million ARPE19:FIX-Padua cells/ml.

Capsules were implanted into IP and SubQ sites of nude mice at 0.2 mL capsules/animal. Animals were sacrificed after 10 days when plasma samples and capsules were collected. FIX levels in the plasma were determined by ELISA and number of viable cells per capsule was determined by Cell Titer Glo.

Figure 15A:
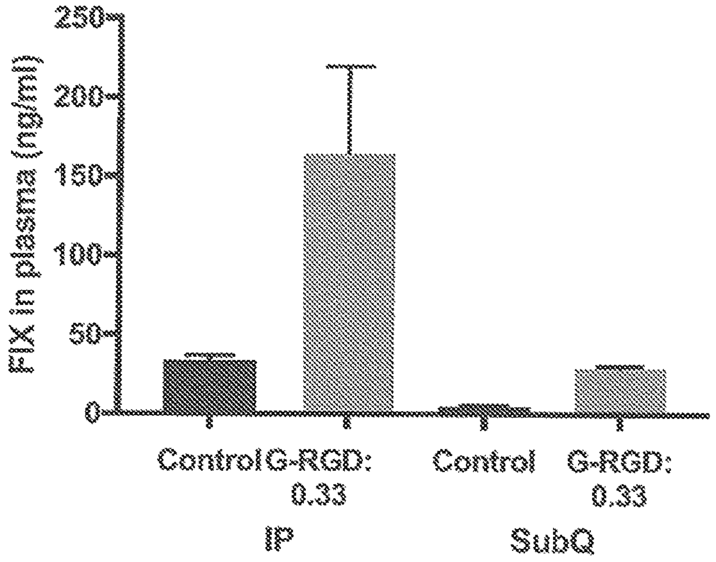
FIGS. 15A and 15B are bar graphs showing the FIX-padua levels and number of viable cells per capsule for capsules prepared with control or 1G-RGD polymers in the first compartment implanted into either the IP or SubQ site.
Figure 15B:
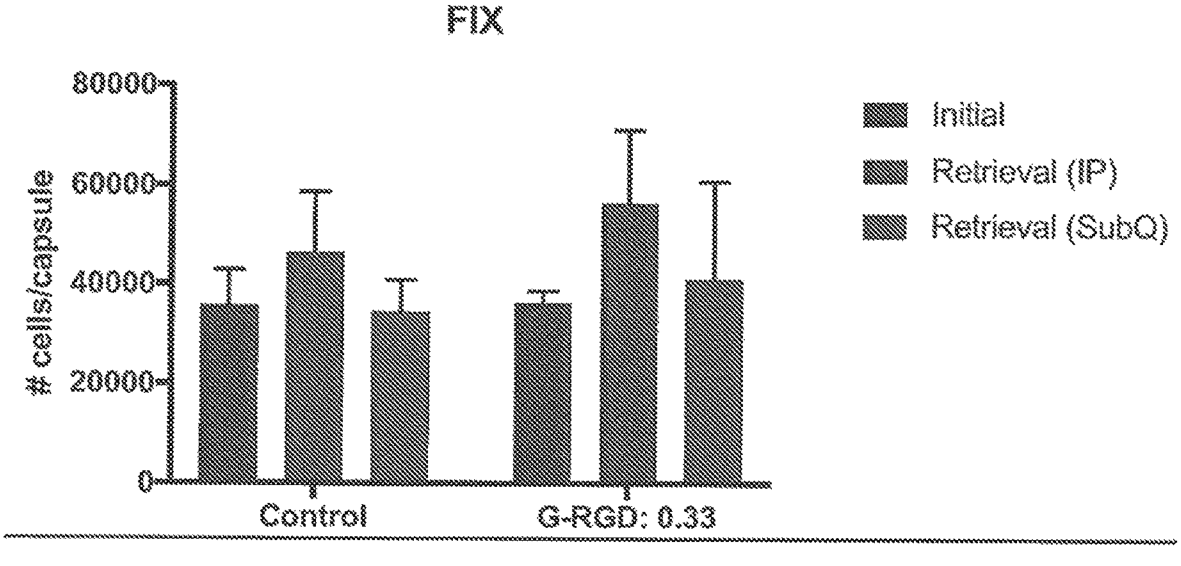

As shown in FIG. 15A, FIX was detected in the plasma from all conditions, but levels were higher for the animals with capsules implanted IP rather than SubQ. The FIX levels were higher for the G-RGD containing capsules compared to the control for both the IP and SubQ site. The number of viable cells per capsule was slightly higher for capsules retrieved from IP compared to SubQ, as shown in FIG. 15B. Together, this demonstrates that CBP-containing capsules can increase serum levels of a therapeutic protein from multiple routes of administration.

Figure 16:
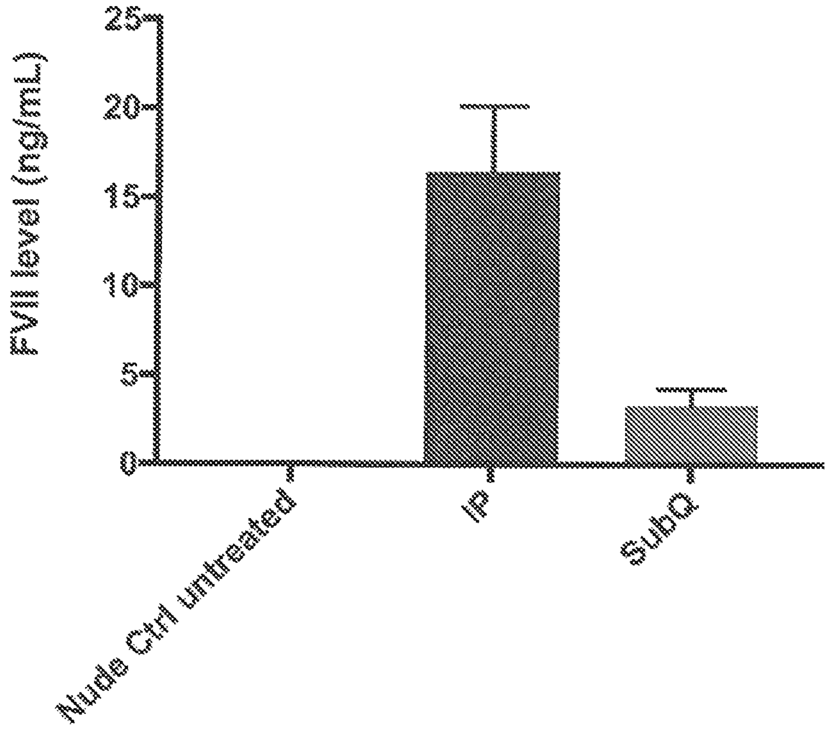
FIG. 16 is a bar graph showing the plasma levels of FVII-padua for untreated nude mice, or mice with capsules containing ARPE19:FVII with 1G-RGD: 0.33 in the first compartment.

Example 19: A G-RGD-Modified Polymer in the Inner Compartment Encapsulating ARPE19:FVII Cells Causes Detectable FVII from the IP and SubQ Sites Capsules encapsulating ARPE19:FVII cells were prepared with 1G-RGD: 0.33 and implanted as described in Example 18. FIG. 16 shows that FVII was detectable in the plasma from both the IP and SubQ sites, demonstrating that capsules containing 1 G-RGD: 0.33 can be used for delivery of FVII and that capsules can be implanted either IP or SubQ.

Example 20: Capsules Prepared with a Blend of Highly Conjugated G-RGD Alginate with Unmodified Alginate Achieves FIX Similar Levels to the 1G-RGD: 0.33 Alginate Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from one of the following alginate solutions using different initial polymers as described in Table 6, each of which contained 100 million ARPE19:FIX-Padua cells/ml:

(1) 1 G-RGD: 0.33
(2) 1 G-RGD: 6.04, 1:55
(3) 1 G-RGD: 6.04, 1:30
(4) 1 G-RGD: 6.04, 1:15

A 0.5 mL aliquot of each capsule composition was implanted into the IP space of nude mice. At 2 weeks post-implantation, animals were sacrificed and capsules and blood samples were collected from each mouse. Plasma levels of FIX in these samples was measured by EFISA.

Figure 17:
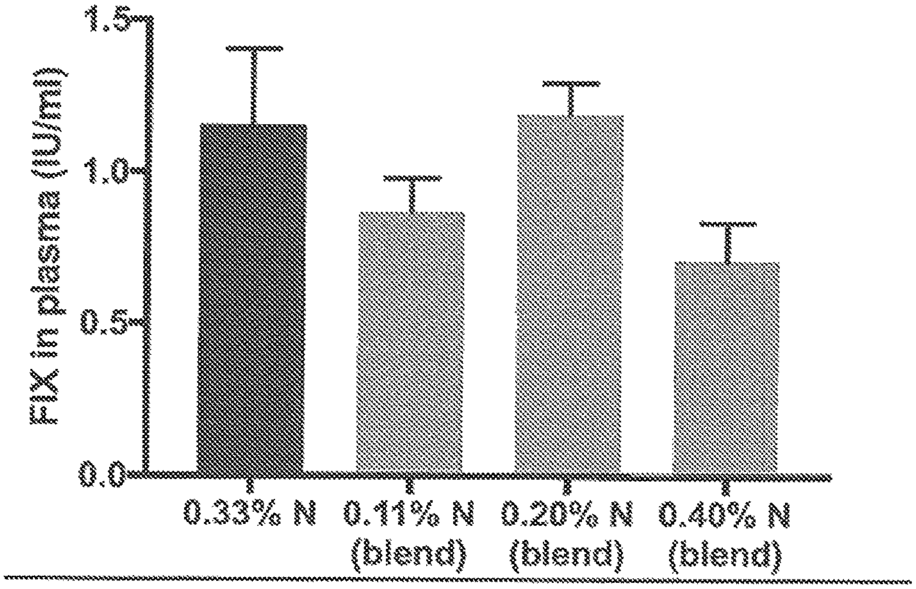
FIG. 17 is a bar graph showing the plasma levels of FIX in nude mice after 2 week implantation of 2-compartment hydrogel capsules containing RPE cells engineered to express a FIX protein. The RPE cells were encapsulated in the first compartment with varying either 1G-RGD: 0.33 or 1:55, 1:30 or 1:50 blends of 1G-RGD: 6.04 with unmodified SLG20 polymer.

As shown in FIG. 17, the plasma levels of FIX-padua were highest for the capsules containing the 1G-RGD: 0.33 and the G-RGD: 6.04, 1:30 (0.20% N) compared to the G-RGD: 6.04, 1:55 and G-RGD: 6.04: 1:15. Together, these data demonstrate that the optimal RGD conjugation levels can be mimicked by blending a highly conjugated polymer with an unconjugated polymer to the approximately the same levels. Additionally, with the blended solutions described in this Example, there is a maximum FIX level at an intermediate conjugation level similar to that described in Example 12.

Example 21: 1G-RGD Must be Contained Within the First Compartment to Prevent Fibrosis Compositions of two-compartment hydrogel millicapsules encapsulating ARPE19:FIX-Padua were prepared by extruding first and second alginate solutions through a coaxial needle as described in Example 4. Compositions of capsules were prepared with the following combinations of first and second compartment solutions and encapsulated 20 million ARPE19:FIX cells/ml in the first compartment: (1) first: unmodified 1.4 w/v % SFG20, second: CM-FMW-Alg-101-High:U-HMW-Alg, (2): first: 1 G-RGD: 0.33, second: CM-FMW-Alg-101-High:U-HMW-Alg, and (3): first: unmodified 1.4 w/v % SFG20 blended with unconjugated G-RGD peptide to achieve 0.33% N in the solution, and (4): first: unmodified 1.4 w/v % SLG20, second: 1G-RGD: 0.33.

Capsules were implanted at 0.5 mL/animal into the IP space of C57/BL6 mice for 2 weeks. At sacrifice, the capsules were collected. Retrieved capsules were stained for mouse macrophages with anti-F4/80 and imaged by fluorescent microscopy for the presence of fibrosis.

Figure 18:
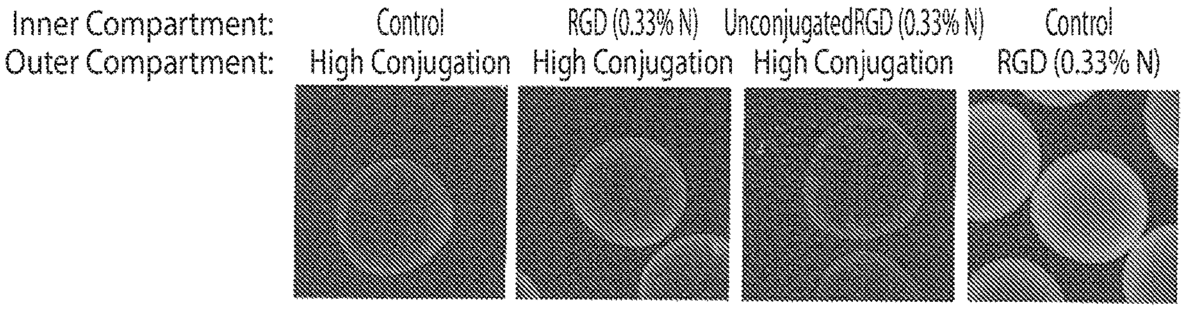
FIG. 18 are black and white photocopies of fluorescent images of two-compartment capsules with either control or RGD-conjugated alginate on the first or second compartment. The capsules are stained for F4/80 to identify mouse macrophages adhered to the capsule surface, which normally appear as green fluorescence, but shown in white in these photocopies.

As shown in FIG. 18, similar macrophage adhesion was observed for capsules with a control, conjugated 1G-RGD: 0.33 or unconjugated 0.33% N G-RGD peptide in the first compartment. Notably, the capsules containing the unconjugated 0.33% N G-RGD within the first compartment did not have increased macrophage adhesion compared to the control, demonstrating that unconjugated G-RGD does not drive a fibrotic response. Importantly, there was increased macrophage adhesion for the capsules where the G-RGD: 0.33 alginate was used for the second (outer) compartment, demonstrating that the CBP-alginate must be contained within the first (inner) compartment of the capsule to prevent fibrosis.

Example 22: Encapsulating ARPE19:FIX Cells with G-RGD and G-PHSRN Either on Two Polymers Blended Together or as Conjugated to the Same Polymer Result in Similar Plasma FIX Levels After Implant Compositions of two-compartment hydrogel millicapsules encapsulating ARPE19:FIX-Padua cells were prepared by extruding first and second alginate solutions through a coaxial needle as described in Example 4. The second (outer) compartment was formed from the 70:30 CM-LMW-Alg-101-Medium:U-HMW-Alg solution and the inner compartment was formed from one of the following alginate solutions, using different initial polymers as described in Table 6, each of which contained 100 million ARPE19:FIX-Padua cells/ml:

(1) 1:1 blend of 1 G-RGD: 0.72 with G-PHSRN: 0.83; and
(2) PHSRN/RGD, same polymer (0.87% N overall).

A 0.5 mL aliquot of each capsule composition was implanted into the IP space of nude mice. At 2 weeks post-implantation, animals were sacrificed and capsules and blood samples were collected from each mouse. Plasma levels of FIX in these samples was measured by ELISA.

Figure 19:
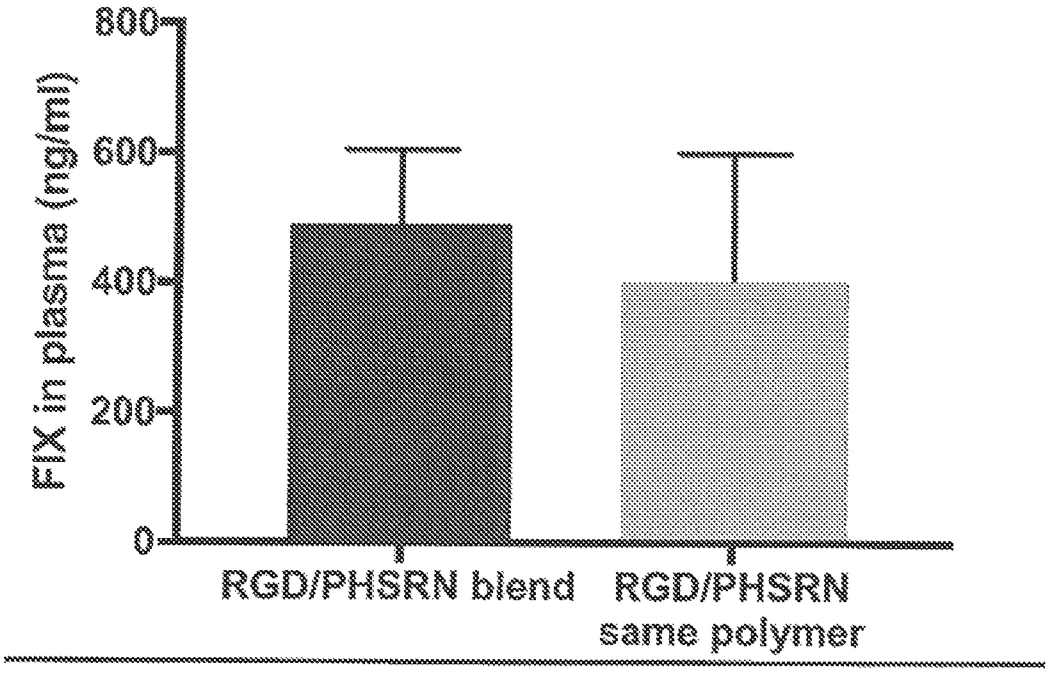
FIG. 19 is a bar graph showing the plasma levels of FIX-padua in nude mice after 2 week implantation of 2-compartment hydrogel capsules containing RPE cells engineered to express a FIX protein. The RPE cells were encapsulated in the first compartment that contains both 1G-RGD and G-PHSRN peptides either on different polymers that were blended together or both conjugated to the same polymer.

As shown in FIG. 19, the plasma levels of FIX were similar for both compositions of capsules containing both G-RGD and G-PHSRN.

Example 23: Evaluation of Linker Composition on Productivity of ARPE19-FIX Cells Encapsulated in RGDSP-Conjugated Alginate Compositions of two-compartment hydrogel millicapsules encapsulating ARPE19:FIX cells were prepared by extruding first and second alginate solutions through a coaxial needle as described in Example 4. The second (outer) compartment was formed from the 70:30 CM-LMW-Alg-101-High:U-HMW-Alg solution and the inner compartment was formed from RGD-alginate solutions with the RGDSP peptide (SEQ ID NO: 59) conjugated to the alginate with no linker or with a linker consisting of 1, 2, 3, 4 or 6 glycine residues (1G, 2G, 3G, 4G (SEQ ID NO: 61), 6G (SEQ ID NO: 69)), or a linker consisting of one β-alanine residue. The peptide conjugation level was determined by elemental analysis after lyophilization for percent nitrogen content to afford: 0.19% N for no linker, 0.30% N for a 1G linker, 0.32% N for a 2G linker, 0.29% N for a 3G linker, 0.48% N for a 4G linker (SEQ ID NO: 61), 0.43% N for a 6G linker, and 0.28% N for the 1 13-alanine linked RGDSP peptide (SEQ ID NO: 59). The ARPE19:FIX cells were encapsulated in the first (inner) compartment at 100 million cells/mL. A 0.25 mL aliquot of each capsule composition was implanted into the IP space of nude mice (n=3/group). At 12 days post-implantation, animals were sacrificed and plasma collected from each mouse. Plasma levels of FIX in these samples was measured by ELISA.

Figure 22:
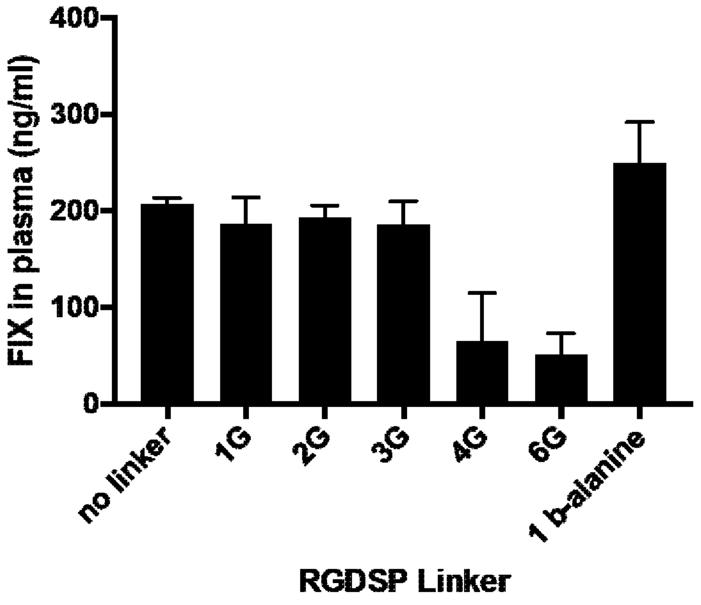
FIG. 22 is a bar graph depicting the plasma levels of FIX protein in nude mice (3 mice per group) after 12 days implantation of 2-compartment hydrogel capsules containing exemplary RPE cells engineered to express the FIX protein. The engineered RPE cells were encapsulated in the first compartment of capsules modified with CBP-polymers comprising various linker lengths and sequences.

As shown in FIG. 22, the choice of linker used to conjugate the RGDSP peptide (SEQ ID NO: 59) to the first (inner) compartment polymer affected the levels of FIX detected in the plasma. Plasma FIX levels produced by the capsules dropped significantly as the number of glycine linker residues in the peptide-modified alginate increased from 3 to 4, and from 4 to 6. In contrast, similar levels of plasma FIX levels were produced by capsules with alginate in which the peptide RGDSP (SEQ ID NO: 59) was attached via no linker, or via any of the 1G, 2G, 3G or 1-β-alanine linkers.

Example 24: Low to Moderate Viscosity of GRDGSP-Conjugated Alginate Maximizes FIX Levels Compositions of two-compartment hydrogel millicapsules encapsulating ARPE19:FIX cells were prepared by extruding first and second alginate solutions through a coaxial needle as described in Example 4. The second (outer) compartment was formed from the 70:30 CM-LMW-Alg-101-High:U-HMW-Alg solution and the inner compartment was formed from RGD-alginate solutions with the GRGDSP peptide (SEQ ID NO: 60) conjugated to the alginate. The RGD-alginate solution was formulated to different solution viscosities: 91, 112, 142, 228, 366, 453 cP. The peptide conjugation level was determined by elemental analysis after lyophilization for percent nitrogen content to afford: 0.38% N for the 91 cP, 142 cP, 228 cP samples and 0.32% N for the 112 cP, 366 cP, and 453 cP samples, respectively. These RGD-alginate solutions were used to encapsulate ARPE19:FIX cells in the first (inner) compartment at 100 million cells/mL. A 0.25 mL aliquot of each capsule composition was implanted into the IP space of nude mice (n=4/group). At 18 days post-implantation, animals were sacrificed and plasma collected from each mouse. Plasma levels of FIX in these samples was measured by EFIS A.

Figure 23:
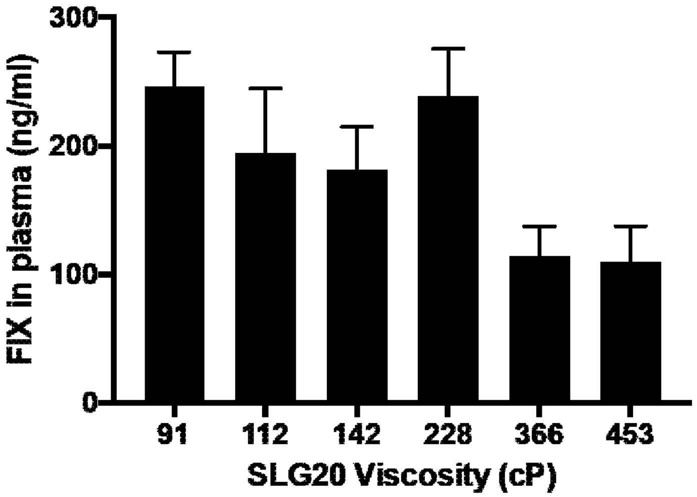
FIG. 23 is a bar graph depicting the plasma levels of FIX protein in nude mice (4 mice per group) after 18 days implantation of 2-compartment hydrogel capsules containing exemplary RPE cells engineered to express the FIX protein. The engineered RPE cells were encapsulated in the first compartment of capsules prepared with CBP-modified alginate of different solution viscosities.

As shown in FIG. 23, the viscosity of the first (inner) compartment polymer solution affected the levels of FIX detected in the plasma. ARPE19:FX cells produced higher plasma FIX levels when encapsulated in the low to intermediate viscosity solutions (91 cP to 228 cP) than when encapsulated in the higher viscosity solutions (366 cP and 453 cP).

Example 25: Exemplary Quantitative Peptide Conjugation Assay

This assay determines the amount of peptide in a CBP-polymer by subjecting a sample of the CBP-polymer to acid hydrolysis, which cleaves off the CBP as individual amino acids. The individual amino acids in the hydrolyzed sample are separated and quantitated using amino acid references by pre-column on-line derivatization and reverse-phase liquid chromatograpy-Ultra-Violet-Fluoscense (LC-UV-FFR) (adapted from Agilent Biocolumns Amino Acid Analysis "How-To" Guide, Agilent Technologies, Inc., 5991-7694EN, published Mar. 1, 2018). Primary AAs (e.g., all but proline of the 20 standard F-alpha amino acids) are derivatized with Ortho-phthaladehyde (OPA) and secondary AAs (e.g., proline) are derivatized with 9-Fluorenylmethyl chloroformate (FMOC). The molar concentration of each amino acid is then averaged to calculate the concentration of the total peptide in the sample. This concentration can be corrected for the presence of any residual unconjugated CBP in the CBP-polymer by determining the amount of peptide in an unhydrolyzed sample of the CBP-polymer using any suitable analytical technique, e.g., as described in Example 26, and subtracting that amount from the total peptide amount.

The assay is further described below as applied to determining peptide conjugation density in a GRGDSP-alginate; however, the skilled artisan can readily modify the assay to determine peptide concentration in a GRGDSP-alginate or other peptide-modified polymers, provided the unmodified polymer does not contain any amino acids. Also, the skilled person can readily substitute any equipment, material or chemical specified below with a different equipment, material or chemical that can perform or provide substantially the same function or role in the assay.

Definitions

| Abbreviation | Definition |
|---|---|
| LC-UV-FLR | Liquid Chromatography-Ultra-Violet-Fluorescence |
| LCMS | Liquid Chromatography-Mass Spectroscopy |
| SLG20 | Pronova Ultrapure SLG20 sterile sodium alginate |
| RT | Retention Time |
| ACN | Acetonitrile |
| MeOH | Methanol |
| SST | System Suitability |
| RSD | Relative Standard Deviation |
| TBD | To Be Determined |
| NMT | No More Than |
| NLT | No Less Than |
| RSQ | Coefficient of Determination |
| AA | Amino acid |
| OPA | Ortho-phthaladehyde |
| FMOC | 9-Fluorenylmethyl chloroformate |
| G | Glycine |
| R | Arginine |
| D | Aspartic acid |
| S | Serine |
| P | Proline |
| iSTD | Internal standard |
| PPE | Personal Protective Equipment |
| SDS | Safety Data Sheet |
| MW | Molecular Weight |
| PTFE | Polytetrafluoroethylene |
| RPM | Revolutions per Minute |
| min | Minutes |
| s | Seconds |
| mL | Millilitre |
| μL | Microlitre |
| nm | Nanometre |

Equipment, Materials and Chemicals

Equipment

- Agilent 1260 LC system
- Agilent diode array detector (G1315D): 13 μL/10 mm flow cell
- Agilent Fluorescence detector (G1321B)
- ChemStation software
- Hot/stir plate with heating blocks, IKA RCT BS001
- Analytical balance, Mettler Toledo XPE105
- pH meter, Mettler Toledo S220 SevenCompact
- Centrifuge, Beckman Coulter Allegra 25R
- Vortex mixer, VWR 97043-562
- Nitrogen evaporator with heating (acid resistant), Organomation 1156Y80

Materials

- AdvanceBio AA LC column, 2.7 μm, 4.6×100 mm, Agilent 655950-80
- AdvanceBio AAA guard column, 2.7 μm, 4.6×5 mm, Agilent 820750-931
- Microwave reaction vials with PTFE lined caps, Chemglass CG-4920-02
- 50 mL Centrifuge tubes, VWR 10160-140
- Crimper, Chemglass CG-4930-20
- Decapper, VWR 10806-372
- Graduated cylinders, class A
- Volumetric transfer pipets (to deliver) class A
- Volumetric flasks, class A
- Transfer pipette (200 μL variable volume), Eppendorf 3123000055
- Transfer pipette (1000 μL variable volume), Eppendorf 3123000063
- Transfer pipette (10 mL variable volume), Eppendorf 3123000080
- Disposable transfer pipet, VWR 16001-180
- Stir bar, VWR 58948-078
- LC vial (2 mL), Agilent 5182-0716
- LC vial cap (non-preslit), Agilent 5182-0721
- LC vial insert (250 μL), Agilent 5183-2085
- Various lab glassware Chemicals

| Name | CAS # | Supplier & PN | Storage |
|---|---|---|---|
| Sodium monophosphate ($Na_2HPO_4 \cdot 7H_2O$) | 7782-85-6 | BDH 92960 | ambient |
| Sodium tetraborate ($Na_2B_4O_7$) | 1330-43-4 | Acros Organics 206291000 | ambient |
| AA standard (17 AA): 25 pmol/μL | n/a | Agilent 5061-3333 | 2-8° C. |
| AA standard (17 AA): 100 pmol/μL | n/a | Agilent 5061-3332 | 2-8° C. |
| AA standard (17 AA): 250 pmol/μL | n/a | Agilent 5061-3331 | 2-8° C. |
| L-Norvaline | 6600-40-4 | Sigma Aldrich N7627 | ambient |
| Sarcosine | 107-97-1 | TCI M0332 | ambient |
| Glycine | 56-40-6 | (L-amino acids kit) | 2-8° C. |
| L-Arginine HCl | 1119-34-2 | Sigma-Aldrich | 2-8° C. |
| L-Aspartic acid | 56-84-8 | LAA21-1KT | 2-8° C. |
| L-Serine | 56-45-1 | | 2-8° C. |
| L-Proline | 147-85-3 | | 2-8° C. |
| Borate buffer | n/a | Agilent 5061-3339 | 2-8° C. |
| FMOC reagent | n/a | Agilent 5061-3337 | 2-8° C. |
| OPA reagent | n/a | Agilent 5061-3335 | 2-8° C. |
| 6N HCl | n/a | Ricca 3750-32 | ambient |
| 0.1N HCl | n/a | Ricca 3600-16 | ambient |
| Phosphoric acid 85% | n/a | BDH 153155E | ambient |
| Acetonitrile (LCMS grade) | 75-05-8 | Fisher Chemical A955-4 | ambient |

-continued

| Name | CAS # | Supplier & PN | Storage |
|---|---|---|---|
| Methanol (LCMS grade) | 67-56-1 | Fisher Chemical A454-4 | ambient |
| Water (LCMS grade) | 7732-18-5 | Fisher Chemical W6-4 | ambient |
| Nitrogen (high purity > 99.99%) | 7727-37-9 | Airgas NI HP200 | ambient |

Procedure

Reagent Preparation

NOTE: the volumes can be scaled proportionally to make a smaller or larger batch 10 mM $Na_2HPO_4$/$Na_2B_4O_7$/pH 8.2 (aqueous mobile phase)

- Using a 1-L graduated cylinder, measure and transfer 1 L of LCMS grade water to a mobile phase bottle
- Weigh 2.64±0.10 g of $Na_2HPO_4$-$7H_2O$
- Weigh 2.00±0.10 g of $Na_2B_4O_7$
- Add both salts in the same bottle containing 1 L of water
- Pipet 2.4 mL of 6N HCl into the same bottle
- Stir on the stir plate at ambient temperature until the solid completely dissolves
- Adjust the final pH to 8.20±0.05 with 6N HCl Expiration date/storage condition (1 week at ambient; 1 month at 2-8° C.)

45/45/10 ACN/MeOH/Water (Organic Mobile Phase)

- Using a 500-mL graduated cylinder, measure and transfer 450 mL of LCMS grade ACN to a mobile phase bottle.
- Using a 500-mL graduated cylinder, measure and transfer 450 mL of LCMS grade MeOH to the same bottle.
- Using a 100-mL graduated cylinder, measure and transfer 100 mL of LCMS grade water to the same bottle.
- Mix well by inverting and shaking manually.
- Expiration date/storage condition (1 month at ambient)

Injection Diluent

- Using a 100-mL graduated cylinder, measure and transfer 100 mL of the aqueous mobile phase to a mobile phase bottle
- Pipet 0.4 mL of concentrated phosphoric acid into the same bottle
- Mix well by inverting and shaking manually
- Expiration date/storage condition (1 month at 2-8° C.)
- Transfer 1.5 mL of the injection diluent to an LC vial and place the vial at location “4” in the Agilent LC system for instrument analysis Derivatization Reagent: Borate Buffer

- Transfer 1.5 mL to an LC vial and place at location “1” in the Agilent LC system for instrument analysis Derivatization Reagents: OPA and FMOC

- Break open an ampoule of each of the OPA reagent and the FMOC reagent
- Aliquot (NLT) 100 μL of the OPA reagent or the FMOC reagent into an LC vial with an LC vial insert and place the LC vial containing the OPA reagent in location “2” and place the LC vial containing the FMOC reagent into location “3” (FMOC) in the Agilent LC system for instrument analysis Acid Hydrolysis of a Sample of a Lyophilized Peptide-Alginate Conjugate

- Weigh 12~16 mg of the lyophilized conjugate into a microwave reaction vial, make sure the sample stays on the bottom
- Hydrolyze according to steps 3.3.2-3.3.19 below Acid Hydrolysis of a Sample of a Peptide-Alginate Conjugate in Saline Solution

- Weigh 1000±50 mg of the conjugate solution in saline into a microwave reaction vial Add 10.0 mL of 6N HCl to the sample using a 10-mL transfer pipet or volumetric pipet Add one stir bar Seal the PTFE lined cap with a crimper Place each sample vial in the matching heat block on a hot/stir plate Heat at 120° C., stir at 400 rpm, for 6 hours Remove from heat and let cool to ambient temperature Remove cap and transfer the entire solution from the reaction vial to a 20-mL volumetric flask with a disposable transfer pipet Pipet 2 mL of LCMS grade water into the empty reaction vial, rinse the inner wall thoroughly with the same disposable transfer pipet, and transfer the rinseate completely to the same 20-mL volumetric flask Repeat the above step twice Bring to mark of the volumetric flask with LCMS grade water Cap and invert the flask multiple times to mix well Transfer completely to a 50-mL centrifuge tube Centrifuge at 5000 rpm for 10 minutes Pipet accurately 1 mL of the supernatant to an LC vial and store at 2-8° C. until drying (e.g., the next day) (store the remaining supernatant at 2-8° C. for any repeat testing if needed)

Dry the 1 mL supernatant completely under nitrogen at 60° C., make sure the needle does not touch the sample but is low enough for fast drying of the sample Into the vial with the dried sample, pipet 0.25 mL of 0.1 µmol/mL internal standard mixture Vortex thoroughly Transfer with a pipet to an LC vial with a LC vial insert Store at 2-8° C. until HPLC analysis (step 3.6)

Standard Preparation

AA Standard Stock Solutions: 10 µMol/mL

For each AA, calculate the weight needed to prepare a 10 µmol/mL stock solution based on the MW See an example below:

| Letter name | Full name | MW (g/mol) | Actual weight (mg) | Volume (mL) | Purity (%) | Actual Concentration (µmol/mL) |
|---|---|---|---|---|---|---|
| D | Aspartic acid | 133.10 | 66.38 | 50 | 100 | 9.97 |
| S | Serine | 105.09 | 52.55 | 50 | 100 | 10.00 |
| G | Glycine | 75.07 | 38.56 | 50 | 100 | 10.27 |
| R | Arginine HCl | 210.66 | 102.67 | 50 | 100 | 9.75 |
| N-iSTD | Norvaline | 117.15 | 58.76 | 50 | 100 | 10.03 |
| S-iSTD | Sarcosine | 89.09 | 44.00 | 50 | 98.4 | 9.72 |
| P | Proline | 115.13 | 57.74 | 50 | 100 | 10.03 |

Weigh the calculated weight into a 50-mL volumetric flask

Dissolve and bring to mark with 0.1N HCl

Mix well by capping and inverting or vortexing

Store at 2-8° C. until HPLC analysis (step 3.6)

Internal Standard Mixture: 1 µMol/mL

Into the same 10-mL volumetric flask, pipet accurately 1.0 mL of Norvaline stock (10 µmol/mL) and 1.0 mL of Sarcosine stock (10 µmol/mL) solutions Bring to mark with 0.1N HCl Mix well by capping and inverting or vortexing Store at 2-8° C. until HPLC analysis (step 3.6)

Internal Standard Mixture: 0.1 µMol/mL

NOTE: this solution is for reconstituting samples after drying

Into a 10-mL volumetric flask, pipet accurately 1.0 mL of the internal standard mixture (1 µmol/mL)

Bring to mark with 0.1N HCl

Mix well by capping and inverting or vortexing

Store at 2-8° C. until HPLC analysis (step 3.6)

5 AA mixture (+iSTD 0.1): 0.025/0.1/0.25 µmol/mL

Into the same 10-mL volumetric flask, pipet accurately xx µL (see table below) of D, S, G, R, N-iSTD, S-iSTD, and P (10 µmol/mL) solutions Bring to mark with 0.1N HCl Mix well by capping and inverting or vortexing Store at 2-8° C. until HPLC analysis (step 3.6)

| D/S/G/R/P STD (µmol/mL) | AA STD (xx µL) | N-iSTD or S-iSTD (µmol/mL) | N-iSTD or S-iSTD (xx µL) | Total (mL) | Final µmol/mL (D/S/G/R/P) | Final µmol/mL (iSTD) |
|---|---|---|---|---|---|---|
| 10 | 25 | 10 | 100 | 10 | 0.025 | 0.1 |
| 10 | 100 | 10 | 100 | 10 | 0.1 | 0.1 |
| 10 | 250 | 10 | 100 | 10 | 0.25 | 0.1 |

17 AA standard (+iSTD 0.1) mixture: 0.1 µmol/mL

Break open an ampoule of the 0.1 µmol/mL 17 AA standard solution

Accurately pipet 0.9 mL of the AA standard mixture into an LC vial

Into the same LC vial, pipet accurately 100 µL of the iSTD mixture (1 µmol/mL)

Mix well by vortexing

Aliquot NLT 100 µL into an LC vial with an LC vial insert

Store at 2-8° C. until HPLC analysis (step 3.6)

HPLC Conditions

| | |
|---|---|
| Instrument | Agilent 1260 LC with UV and Fluorescence detector |
| Column | AdvanceBio AAA LC, 2.7 µm, 4.6 × 100 mm Agilent 655950-802 |

-continued

| | |
|---|---|
| Gulard column | AdvanceBio AAA guard column, 2.7 µm, 4.6 × 5 mm Agilent 820750-931 |
| Mobile phase aqueous | 10 mM $Na_2HPO_4$ 10 mM $Na_2B_4O_7$ (pH 8.2) |

-continued

| | | | |
|---|---|---|---|
| Mobile phase organic | 45/45/10 ACN/MeOH/water | | |
| Flow rate | 1.5 mL/min | | |
| Gradient | Minute | % Aqueous | % Organic |
| | 0.0 | 98 | 2 |
| | 0.35 | 98 | 2 |
| | 13.4 | 43 | 57 |
| | 13.5 | 0 | 100 |
| | 15.7 | 0 | 100 |
| | 15.8 | 98 | 2 |
| | 18 | 98 | 2 |
| Column temperature | 40° C. | | |
| Injection | 1 μL | | |
| Needle wash | Flush port for 7s | | |

| Online derivatization (Use Injector Program) | Function | Parameter |
|---|---|---|
| | Draw | Draw 2.5 μL from location "1" with default speed using default offset (borate buffer) |
| | Draw | Draw 1 μL from sample with default speed using default offset |
| | Mix | Mix 3.5 μL from seat with default speed for 5 times |
| | Wait | Wait 0.2 min |
| | Draw | Draw 0.5 μL from location "2" with default speed using default offset (OPA) |
| | Mix | Mix 4 μL from seat with default speed for 10 times |
| | Draw | Draw 0.4 μL from location "3" with default speed using default offset (FMOC) |
| | Mix | Mix 4.4 μL from seat with default speed for 10 times |
| | Draw | Draw 32 μL from location "4" with default speed using default offset (Injection diluent) |
| | Mix | Mix 20 μL from seat with default speed for 8 times |
| | Inject | Inject |
| | Wait | Wait 0.1 min |
| | Valve | Switch valve to "Bypass" |

| UV | Response time: 1 s<br>Autobalance: prerun<br>Slit: 4 nm | | | |
|---|---|---|---|---|
| | Wavelength | Bandwidth | Reference | Bandwith |
| | 338 nm | 10 nm | 390 nm | 20 nm |
| | Switch between the last eluting OPA-derivatized AA (Lysine) and before the 1st eluting FMOC-derivatized AA (Hydroxyproline): ~11 min | | | |
| | 262 nm | 16 nm | 324 nm | 8 nm |

| FLR | Response time: 1 s<br>PMT gain: 10 (adjust if needed) | |
|---|---|---|
| | Excitation | Emission |
| | 340 nm | 450 nm |
| | Switch between the last eluting OPA-derivatized AA (Lysine) and before the 1st eluting FMOC-derivatized AA (Hydroxyproline): ~11 min | |
| | 260 nm | 325 |

HPLC Analysis (Example Sequence for Sample Analysis)

| Vial # | Replicates | Sample description |
|---|---|---|
| P1-A1 | 5 | Blank: 0.1N HCl |
| P1-A2 | 3* | 0.025 μmol/mL 17AA (+iSTD): initial |
| P1-A3 | 3* | 0.1 μmol/mL 17AA (+iSTD): initial |
| P1-A4 | 3* | 0.25 μmol/mL 17AA (+iSTD): initial |
| P1-A1 | 2 | Blank: 0.1N HCl |
| P1-A5 | 1 | 0.1 μmol/mL 5AA (+iSTD): RT and check standard |
| P1-A1 | 2 | Blank: 0.1N HCl |
| P1-B1 | 1 | Conjugate sample A: acid hydrolyzed |
| P1-B2 | 1 | Conjugate sample B: acid hydrolyzed |
| . . . | 1 | . . . |
| Bracket with 0.1 μmol/mL STD (+iSTD) injection between every 10 sample injections | | |
| P1-A1 | 2 | Blank: 0.1N HCl |
| P1-A2 | 1 | 0.025 μmol/mL STD (+iSTD): end |
| P1-A3 | 1 | 0.1 μmol/mL STD (+iSTD): end |
| P1-A4 | 1 | 0.25 μmol/mL STD (+iSTD): end |
| 5 | 1 | Water 100 μL (needle cleaning) |
| | | Column flushing with organic mobile phase |

*For information only analysis, run only one injection as initial standard and end standard.

System Suitability Criteria

Analyze retention time and peak area for each AA of interest used in quantitation (D/S/G/R) and internal standards (Norvaline and Sarcosine) in standard injections (both UV and FLR).

| Parameter | Criteria |
|---|---|
| Blanks | No significant interference in UV and FLR |
| % RSD (Retention time), initial 3 | NMT 5% |
| % RSD (Area), initial 3 | NMT 20% |
| % RSD (Relative Area), initial 3 | NMT 20% |
| % RSD (Retention time), all | NMT 5% |
| % RSD (Area), all | NMT 20% |
| % RSD (Relative Area), all | NMT 20% |
| Resolution: | Baseline separation |
| Glycine from other AAs | |
| Norvaline (iSTD) from other AAs | |
| Sarcosine (iSTD) vs. Proline | |
| Linearity | RSQ NLT 0.99 |
| Check standard | Quantitated result: within 80%~120% of theoretical |

Data Analysis—Analyze Samples Only when System Suitability Passes

Integration Guidelines

Only integrate the AA of interest

Start from "automatic integration"

Manually adjust the integration as necessary

Identification of AA of Interest

RT of AA of interest and internal standards in the 17AA (+iSTD) standard mixture should match the RT of the 5AA (+iSTD) standard mixture RT of the AA in each sample should match the RT of the standard (UV/FLR)

Relative area $(D,S,G,R)$=Area $(D,S,G,R)$/Area (Norvaline)

Relative area $(P)$=Area $(P)$/Area (Sarcosine)

Standard calibration curve

Calculate concentrations of standard solutions using the reported value on certificate of analysis or actual weights adjusted by dilution factor during the standard preparation.

Plot the average area or average relative area vs. concentration for each AA of interest from the standard injections: 0.025, 0.1, and 0.25 μmol/mL. Perform linear regression.

$$Conc = m*Area\ or\ Relative\ Area + b$$

Where, m is the slope of the linear fitted curve and b is the Y-intercept of the linear fitted curve.

The RSQ should be no less than 0.99.

If the linearity fails, prepare fresh derivatization reagents/standard solutions, and troubleshoot system malfunction and repeat the test.

Sample Analysis

Quantitation can be done by both UV and FLR

Quantitation is done using relative area (area ratio relative to the internal standard)

Calculate concentration of AA: G, R, D, S in each sample using the linear fitted standard curve:

$$Conc,AA\ (\mu mol/mL) = (m*Area\ or\ Relative\ Area + b)$$

Calculate concentration of the total GRGDSP (SEQ ID NO: 60) by averaging the concentration of each AA:

Concentration, total GRGDSP (SEQ ID NO: 60) (μmol/mL)=(Conc, G/2+Conc, R+Conc, D+Conc, S+Conc, P)/5

μmol (Total GRGDSP) (SEQ ID NO: 60)/g (conjugate)=Conc, total GRGDSP (SEQ ID NO: 60) (μmol/mL)×0.25 mL/1.0 mL×20 mL/Weight (g)

μmol (conjugated GRGDSP (SEQ ID NO: 60))/g (conjugate)=μmol (Total GRGDSP (SEQ ID NO: 60))/g (conjugate)−μmol (Residual free GRGDSP (SEQ ID NO: 60))/g (conjugate)

Example 26: Exemplary Assay to Determine Residual Free Peptide in a CBP-Polymer Composition This assay uses liquid chromatography-mass spectroscopy (LC-MS) to determine the amount of residual, unconjugated peptide in a composition containing a peptide-polymer conjugate, e.g., typically after one or more purification steps have been performed to remove a substantial portion, e.g., greater than 95%, 98%, 99% or more, of unconjugated peptide. In brief, a sample of the conjugate in saline solution is added to a molecular weight cut-off (MWCO) tube that has a MWCO higher than the molecular weight of the peptide, the tube is centrifuged to separate the residual peptide from the conjugate, and the amount of peptide is quantitated by LC-MS using as a standard a reference composition containing a known concentration of the same peptide.

Example 27: Exemplary Quantitative Amine Assay to Determine Amine-Conjugation Density in an Afibrotic Polymer Modified with a Compound of Formula (I)

This assay determines the amount of an amine-containing compound (e.g., a compound of Formula I, e.g., Compound 101 in Table 4) in a polymer chemically modified with the amine compound. A sample of the chemically-modified polymer is subjected to acid hydrolysis, which cleaves off the conjugated amine and the weight % of total amine in the hydrolyzed sample is quantitated by reverse-phase, liquid chromatorgraphy with ultraviolet detection (LC-UV) using the unconjugated amine compound as a standard. The identity of the LC peak can be further confirmed by mass spectrometry. The weight % of total amine can be used as the % conjugation of the amine-compound in the chemically-modified polymer. A more precise result can be obtained by determining the amount of any residual unconjugated amine compound in an unhydrolyzed sample of the chemically-modified polymer using any suitable method (e.g., as described below) and subtracting that amount from the total peptide amount.

The assay is further described below as applied to determining % conjugation density in an alginate chemically modified with Compound 101 (i.e., CM-LMW-Alg-101); however, the skilled artisan can readily modify the assay to determine the conjugation density of any Formula I compound used to chemically-modify a polysaccharide (e.g., an alginate) or another polymer that does not contain amines. Also, the skilled person can readily substitute any equipment, material or chemical specified below with a different equipment, material or chemical that can perform or provide substantially the same function or role in the assay.

Definitions

| Abbreviation | Definition |
|---|---|
| LC-UV-MS | Liquid Chromatography-Ultra-Violet-Mass Spectrometry |
| VLVG | Pronova Ultrapure VLVG sodium alginate |
| SLG100 | Pronova Ultrapure Sterile Alginate |
| TIC | Total Ion Chromatogram |
| RT | Retention Time |
| ACN | Acetonitrile |
| SST | System Suitability |
| RSD | Relative Standard Deviation |
| TBD | To Be Determined |
| NMT | No More Than |
| m/z | Mass charge ratio |

Equipment and Materials

Equipment

- Agilent 1260 LC system (DAD: 13 μL/10 mm flow cell)
- Agilent SQ MS detector (G1956B)
- ChemStation software
- Hot/stir plate with heating blocks, IKA RCT BS001
- Analytical balance, Mettler Toledo XPE105
- Centrifuge, Beckman Coulter Allegra 25R
- Vortex mixer, VWR 97043-562

Materials

- XBridge C18, 2.5 μm, 4.6×50 mm, Waters 186006037
- SG-SM0001 reference material (>98.0% purity)
- 2N HCl (ACS grade), BDH 7203-1
- Ammonia solution 28%-30% (ACS grade), MilliPore Sigma 1.05423.1000
- Acetronitrile (LCMS grade), Fisher Chemical A955-4
- Water (LCMS grade), Fisher Chemical W6-4
- 0.9% saline, ROBio SAL-090
- Microwave reaction vials with PTFE lined caps, Chemglass CG-4920-02
- Vivaspin 20 3 kDa MWCO concentrator, GE Healthcare 28-9323-58
- 50 mL Centrifuge tubes, VWR 10160-140
- Crimper, Chemglass CG-4930-20
- Decapper, VWR 10806-372
- Graduated cylinders, class A
- Volumetric transfer pipets (to deliver) class A
- Volumetric flasks, class A
- Gastight syringe 1 mL, Hamilton 81316

Transfer pipette (200 μL variable volume), Eppendorf 3123000055

Transfer pipette (1000 μL variable volume), Eppendorf 3123000063

Transfer pipette (10 mL variable volume), Eppendorf 3123000080

Disposable transfer pipet, VWR 16001-180

Stir bar, VWR 58948-078

LC vial and cap, VWR 46610-724

Assortment of lab glassware

Procedure

Reagent Preparation

NOTE: the volumes can be scaled proportionally to make a smaller or larger batch 0.1% ammonia in water (aqueous mobile phase)

Using a 1-L graduated cylinder, measure and transfer 1 L of LCMS grade water to a mobile phase bottle.

Using a 1-mL volumetric transfer pipet or Hamilton syringe, measure 1.0 mL of the concentrated ammonia and transfer to the same mobile phase bottle.

Mix well by inverting and shaking manually.

Expiration/storage condition −1 month at ambient 0.1% Ammonia in ACN (Organic Mobile Phase)

Using a 1-L graduated cylinder, measure and transfer 1 L of LCMS grade ACN to a mobile phase bottle.

Using a 1-mL volumetric transfer pipet or Hamilton syringe, measure 1.0 mL of the concentrated ammonia and transfer to the same mobile phase bottle.

Mix well by inverting and shaking manually.

Expiration/storage condition −1 month at ambient

Acid Hydrolysis of Solid Conjugate Sample

Weigh 50±5 mg of the lyophilized conjugate solid, into a microwave reaction vial, make sure the conjugate stays on the bottom of the vial Add 10.0 mL of 2N HCl using a 10-mL transfer pipet or volumetric pipet Add one stir bar Seal the PTFE lined cap with a crimper Place each sample vial in the matching heat block on a hot/stir plate Heat at 120° C., stir at 400 rpm, for 120 minutes Remove from heat and let cool to ambient temperature Transfer the entire solution from the reaction vial to a 25-mL volumetric flask with a disposable transfer pipet Pipet 5 mL of LCMS grade water into the empty reaction vial, rinse the inner wall thoroughly with the same disposable transfer pipet, and transfer the rinseate completely to the same 25-mL volumetric flask Repeat the above step twice Bring to mark of the volumetric flask with LCMS grade water Transfer completely to a 50-mL centrifuge tube Centrifuge at 3000 rpm for 10 minutes Take supernatant for HPLC analysis Store at 2-8° C.

Acid Hydrolysis of Conjugate in Saline Sample

Weigh 1000±50 mg of the conjugate solution in saline into a microwave reaction vial Add 10.0 mL of 2N HCl using a 10-mL transfer pipet or volumetric pipet Add one stir bar Seal the PTFE lined cap with a crimper Place each sample vial in the matching heat block on a hot/stir plate Heat at 120° C., stir at 400 rpm, for 120 minutes Remove from heat and let cool to ambient temperature Transfer the entire solution from the reaction vial to a 25-mL volumetric flask with a disposable transfer pipet Pipet 5 mL of LCMS grade water into the empty reaction vial, rinse the inner wall thoroughly with the same disposable transfer pipet, and transfer the rinseate completely to the same 25-mL volumetric flask Repeat the above step twice Bring to mark of the volumetric flask with LCMS grade water Transfer completely to a 50-mL centrifuge tube Centrifuge at 3000 rpm for 10 minutes Take supernatant for HPLC analysis Store at 2-8° C.

Sample Preparation for Residual Free Amine in Solid Conjugate

Weigh 50±5 mg of the lyophilized conjugate solid, into a scintillation vial

Pipet 5.0 mL of saline into the scintillation vial

Dissolve completely by shaking and vortexing for 10 minutes

Transfer completely to a MWCO tube

Centrifuge at 5000 rpm for 60 minutes (Position the flat side of membrane in parallel to the rotor arm)

Remove the top portion of the MWCO tube and discard

Transfer the sample in the bottom portion completely to a 5 mL volumetric flask

Bring to mark with water or saline and invert to mix well

Transfer to a scintillation vial for storage at 2-8° C.

Transfer an aliquot for HPLC analysis

Sample Preparation for Residual Free Amine in Conjugate in Saline

Weigh 1000±50 mg of the conjugate (or blend with unmodified alginate) in saline, into a MWCO tube Pipet 4.0 mL of saline into the MWCO tube Invert and vortex the tube 5 times or until the solution is mixed well to fully extract free amine Centrifuge at 5000 rpm for 90 minutes Remove the top portion of the MWCO tube and discard Transfer the sample in the bottom portion completely to a 5 mL volumetric flask Bring to mark with water and invert to mix well Transfer to a scintillation vial for storage at 2-8° C.

Transfer an aliquot for HPLC analysis

Standard Preparation

Standard Solution: 1 mg/mL

Weigh 50.00±5.00 mg of SG-SM0001 standard into a scintillation vial

Add ~10 mL of LCMS-grade water, dissolve the solid completely by shaking and vortexing Transfer completely to a 50-mL volumetric flask by rinsing the scintillation vial twice with LCMS-grade water, using a disposable transfer pipet Bring to volume with LCMS-grade water, mix well Store at 2-8° C.

Standard Solution: 0.01 mg/mL

Pipet 100 μL of the 1 mg/mL solution to a 10-mL volumetric flask

Bring to volume with LCMS-grade water

Mix well by inverting

Store at 2-8° C.

HPLC Condition PCP

| | |
|---|---|
| Instrument | Agilent 1260 LC with DAD and SQ MS (optional) |
| Column | XBridge C18, 2.5 μm, 4.6 × 50 mm |
| Mobile phase aqueous | 0.1% ammonia |

-continued

| | |
|---|---|
| Mobile phase organic | 0.1% ammonia in ACN |
| Flow rate | 1.0 mL/min |

| Gradient | Minute | % Aqueous | % Organic |
|---|---|---|---|
| | 0.0 | 98 | 2 |
| | 6.0 | 86 | 14 |
| | 12.0 | 20 | 80 |
| | 12.1 | 98 | 2 |
| | 15.0 | 98 | 2 |
| Column temperature | 30° C. | | |
| Injection | 10 μL | | |
| UV | Detection: 220 nm, bw 10 nm; Reference: 360 nm, bw 100 nm; Response time: 1 s Autobalance: prerun Slit: 4 nm | | |
| MS (optional) | API-ES (scan: positive and negative) Drying gas: 12 L/min; Nebulizer pressure: 55 psig; Drying gas temperature: 350° C.; Capillary Voltage: 3000 V; Scan range 90-1000; Fragmentor 70 V; Gain 1.00; Threshold 150; Step size 0.10 | | |

HPLC Analysis

Example Sequence for Sample Analysis

| Vial # | Replicates | Sample description |
|---|---|---|
| 1 | 2 | Blank: water |
| 2 | 5* | 0.01 mg/mL standard: initial |
| 3 | 1 | Conjugate sample A: residual free amine |
| 4 | 1 | Conjugate sample B: residual free amine |
| . . . | 1 | . . . |
| Bracket with standard injection between every 10 sample injections | | |
| 1 | 1 | Blank: water |
| 2 | 1 | 0.01 mg/mL standard: end |
| 11 | 5* | 1.0 mg/mL standard: initial |
| 12 | 1 | Conjugate sample A: acid hydrolyzed |
| 13 | 1 | Conjugate sample B: acid hydrolyzed |
| . . . | 1 | . . . |
| Bracket with standard injection between every 10 sample injections | | |
| 11 | 1 | 1.0 mg/mL standard: end |
| 1 | 1 | Flush column with 50:50 $H_2O$:ACN |

*For information only analysis, run only one injection as initial standard and end standard.

System Suitability Criteria

| Parameter | Criteria |
|---|---|
| Blanks | No significant interference in UV and TIC (optional) |
| % RSD (Retention time), initial 5 SG-SM0001 | NMT 2% |
| % RSD (area), initial 5 SG-SM0001 | NMT 10% |
| % RSD (Retention time), initial 5 and all bracketing SG-SM0001 | NMT 2% |

-continued

| Parameter | Criteria |
|---|---|
| % RSD (area), initial 5 and all bracketing SG-SM0001 | NMT 10% |
| m/z: amine peak (optional) | 392.1 ± 0.5 |

Data Analysis—Analyze Samples Only when System Suitability Passes

Integration Guidelines

Only integrate the amine peak

Start from "automatic integration"

Manually adjust the integration as necessary

Identification of Amine (optional) m/z of the amine peak in each sample should be within 392.1±0.5.

RT of the amine peak in UV in each sample matches the RT of the standard.

Concentration,Standard (mg/mL)=Weight (mg)/50 mL/dilution factor,

Where dilution factor=1 for 1.0 mg/mL standard;

Where dilution factor=100 for 0.01 mg/mL standard

Concentration,free amine (mg/mL)=Area,non-hydrolyzed sample/Area,0.01 standard×Concentration, 0.01 standard % Residual free amine=Concentration,free amine (mg/mL)×5 mL/weight,non-hydrolyzed conjugate (mg)×100

Concentration,total amine (mg/mL)=Area,hydrolyzed sample/Area,1.0 standard×Concentration,1.0 standard % Total amine=Concentration,total amine (mg/mL)×25 mL/weight,hydrolyzed conjugate (mg)×100

EQUIVALENTS AND SCOPE

This application refers to various issued patents, published patent applications, journal articles, and other publications, all of which are incorporated herein by reference in their entirety. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present disclosure, as defined in the following claims.

The invention claimed is:

1. A hydrogel capsule comprising:

(a) a cell-containing compartment which comprises a plurality of engineered retinal pigment epithelial (RPE) cells encapsulated in a first polymer composition which comprises an alginate covalently modified with a cell-binding peptide (CBP) via a linker, wherein the linker is joined to the amine-terminus of the CBP; and (b) a barrier compartment surrounding the cell-containing compartment and comprising a second polymer composition which comprises an alginate covalently modified with a compound of Formula (I):

(I)

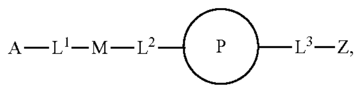

or a pharmaceutically acceptable salt thereof, wherein:

A is $N(R^C)$—, —$N(R^C)C(O)$—, —$C(O)N(R^C)$—, —$N(R^C)C(O)(C_1$-$C_6$-alkylene)-, —$N(R^C)C(O)(C_1$-$C_6$-alkenylene)-, wherein alkylene is optionally substituted by one or more $R^1$;

$L^1$ is alkyl optionally substituted by one or more $R^2$;

$L^2$ is a bond;

$L^3$ is a bond or alkyl optionally substituted by one or more $R^2$;

M is alkyl, heteroalkyl, or aryl, each of which is optionally substituted by one or more $R^3$;

P is triazolyl, optionally substituted by one or more $R^4$;

Z is hydrogen, alkyl, alkenyl, alkynyl, heteroalkyl, —$OR^A$, —$C(O)R^A$, —$C(O)OR^A$, —$C(O)N(R^C)(R^D)$, —$N(R^C)$ C $(O)R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^C$, $R^D$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring, optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})$ $(R^{D1})$, —$N(R^{C1})C(O)R^{B1}$, —$C(O)N(R^{C1})$, $SR^{E1}$, $S(O)_xR^{E1}$, —$OS(O)_xR^{E1}$, —$N(R^{C1})S(O)_xR^{E1}$, —$S(O)_xN(R^{C1})(R^{D1})$, —$P(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4;

wherein the compound of Formula (I) is covalently bound to the alginate through the A moiety within the barrier compartment;

wherein the cell-containing compartment is substantially free of any compound of Formula (I) and the barrier compartment is substantially free of cells and substantially free of the CBP;

wherein the engineered RPE cells comprise an exogenous nucleotide sequence encoding a therapeutic polypeptide, and wherein the CBP peptide comprises RGD (SEQ ID NO: 43) or RGDSP (SEQ ID NO: 59) and the linker consists essentially of one glycine residue, two glycine residues, three glycine residues, one beta-alanine residue, two beta-alanine residues or three beta-alanine residues.

2. The hydrogel capsule of claim 1, wherein the CBP is RGD (SEQ ID NO: 43) or RGDSP (SEQ ID NO: 59) and the linker consists essentially of one glycine residue joined to the amine terminus of the CBP.

3. The hydrogel capsule of claim 1, wherein the compound of Formula (I) is

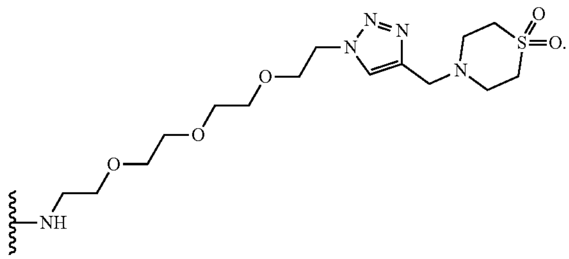 [SMILES: *NCCOCCOCCOCCn1cc(CN2CCS(=O)(=O)CC2)nn1]
.

4. The hydrogel capsule of claim 1, wherein the therapeutic polypeptide is selected from the group consisting of a Factor VII polypeptide and a FIX polypeptide.

5. The hydrogel capsule of claim 1, wherein the engineered RPE cells are derived from ARPE-19 cells.

6. The hydrogel capsule of claim 1, wherein:

the second polymer composition in the barrier compartment further comprises an unmodified alginate with a molecular weight of 150 kDa-250 kDa and a guluronic acid (G): mannuronic acid (M) ratio of greater than or equal to 1.5, the alginate in the covalently modified alginate in the barrier compartment has a molecular weight of less than 75 kDa, a G: M ratio of greater than or equal to 1.5 and the compound is

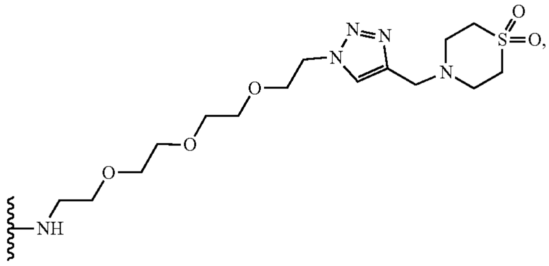 [SMILES: *NCCOCCOCCOCCn1cc(CN2CCS(=O)(=O)CC2)nn1]
, and the conjugation density of

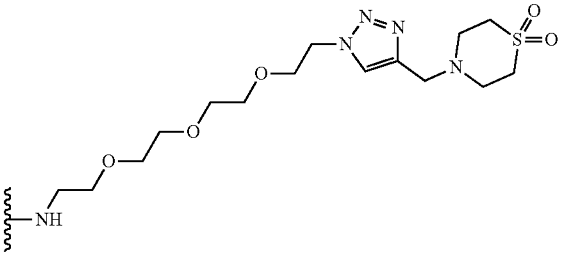 [SMILES: *NCCOCCOCCOCCn1cc(CN2CCS(=O)(=O)CC2)nn1]

in the covalently modified alginate, as determined by combustion analysis for percent nitrogen, is at least 2.0% nitrogen and less than 9.0% nitrogen.

7. A hydrogel capsule comprising:

(a) a cell-containing compartment which comprises a plurality of cells encapsulated in a first polymer composition comprising a first RGD-polymer, wherein the first RGD-polymer comprises an alginate covalently modified with an RGD peptide via a linker, and (b) a barrier compartment surrounding the cell-containing compartment and comprising a second polymer composition which comprises a mixture of an unmodified alginate and an alginate covalently modified with at least one compound selected from

| Compound No. | Structure |
|---|---|
| 100 | 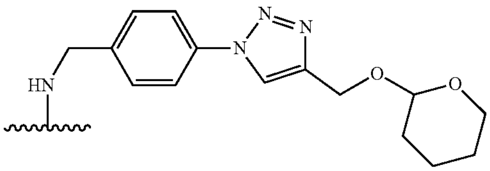 [SMILES: *NCc1ccc(-n2cc(COC3CCCCO3)nn2)cc1] |

-continued
| Compound No. | Structure |
| --- | --- |
| 101 | 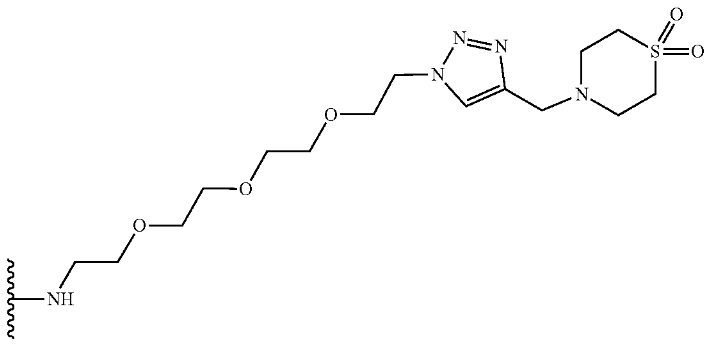 [SMILES: *NCCOCCOCCOCCn1cc(CN2CCS(=O)(=O)CC2)nn1] |
| 102 | 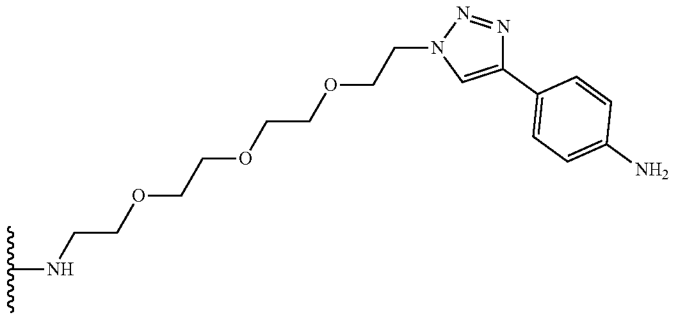 [SMILES: *NCCOCCOCCOCCn1cc(-c2ccc(N)cc2)nn1] |
| 103 | 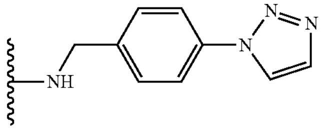 [SMILES: *NCc1ccc(-n2ccnn2)cc1] |
| 104 | 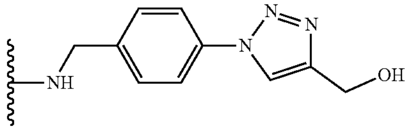 [SMILES: *NCc1ccc(-n2cc(CO)nn2)cc1] |
| 105 | 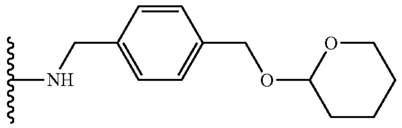 [SMILES: *NCc1ccc(COC2CCCCO2)cc1] |
| 106 | 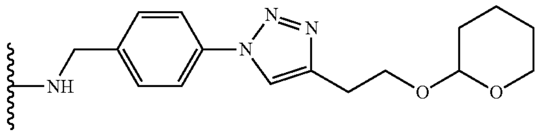 [SMILES: *NCc1ccc(-n2cc(CCOC3CCCCO3)nn2)cc1] |
| 107 | 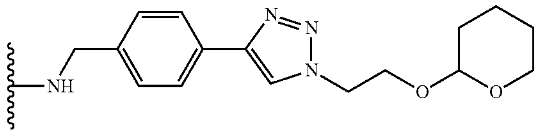 [SMILES: *NCc1ccc(-c2cn(CCOC3CCCCO3)nn2)cc1] |
| 108 | 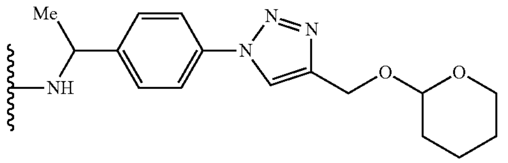 [SMILES: *NC(C)c1ccc(-n2cc(COC3CCCCO3)nn2)cc1] |

-continued
| Compound No. | Structure |
|---|---|
| 109 | 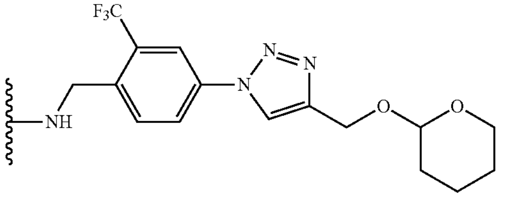 [SMILES: *NCc1ccc(-n2cc(COC3CCCCO3)nn2)cc1C(F)(F)F] |
| 110 | 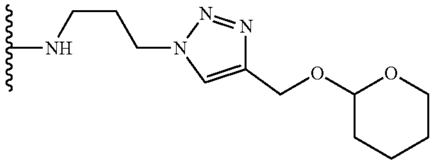 [SMILES: *NCCCn1cc(COC2CCCCO2)nn1] |
| 111 | 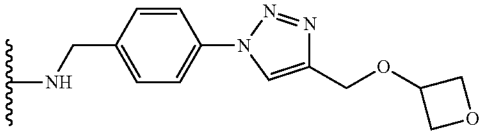 |
| 112 | 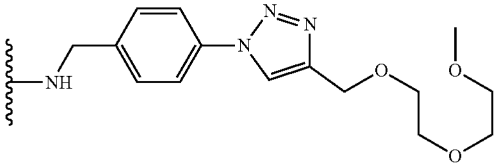 [SMILES: *NCc1ccc(-n2cc(COCCOCCOC)nn2)cc1] |
| 113 | 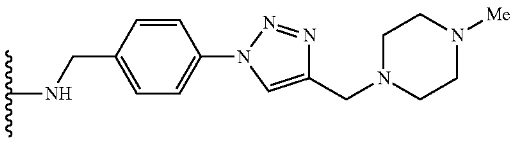 [SMILES: *NCc1ccc(-n2cc(CN3CCN(C)CC3)nn2)cc1] |
| 114 | 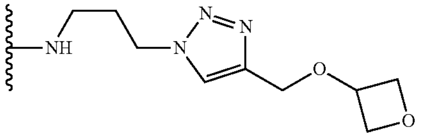 [SMILES: *NCCCn1cc(COC2COC2)nn1] |
| 115 | 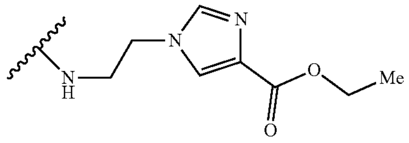 [SMILES: *NCCn1cnc(C(=O)OCC)c1] |
| 116 | 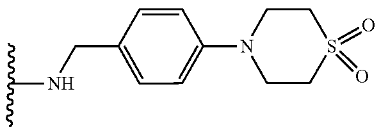 [SMILES: *NCc1ccc(N2CCS(=O)(=O)CC2)cc1] |
| 117 | 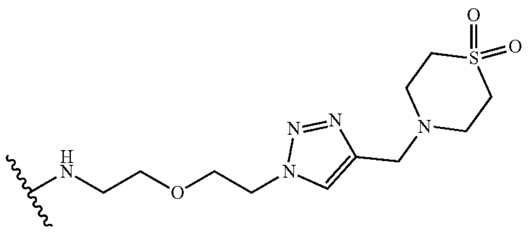 [SMILES: *NCCOCCn1cc(CN2CCS(=O)(=O)CC2)nn1] |

-continued

| Compound No. | Structure |
| --- | --- |
| 118 | 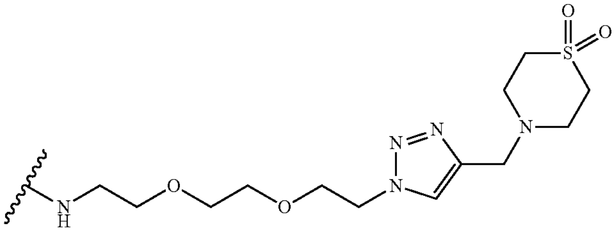 [SMILES: *NCCOCCOCCn1cc(CN2CCS(=O)(=O)CC2)nn1] |
| 119 | 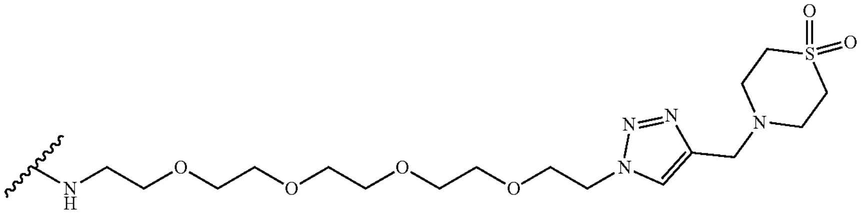 [SMILES: *NCCOCCOCCOCCOCCn1cc(CN2CCS(=O)(=O)CC2)nn1] |
| 120 | 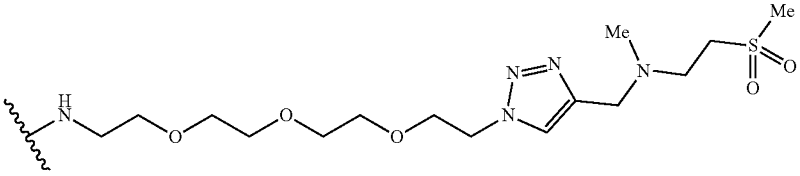 [SMILES: *NCCOCCOCCOCCn1cc(CN(C)CCS(C)(=O)=O)nn1] |

wherein the first RGD-polymer comprises RGD (SEQ ID NO: 43) or RGDSP (SEQ ID NO: 59) and the linker comprises one glycine residue, two glycine residues, three glycine residues, one beta-alanine residue, two beta-alanine residues or three beta-alanine residues;

wherein the plurality of cells are engineered ARPE-19 cells; and, wherein the engineered ARPE-19 cells comprise a coding sequence for a therapeutic polypeptide.

8. The hydrogel capsule of claim 1, wherein the exogenous nucleotide sequence is a codon-optimized FIX-padua coding sequence selected from the group consisting of SEQ ID NO: 19, 20 and 21.

9. The hydrogel capsule of claim 1, wherein the compound of Formula (I) is a compound selected from:

| Compound No. | Structure |
| --- | --- |
| 100 | 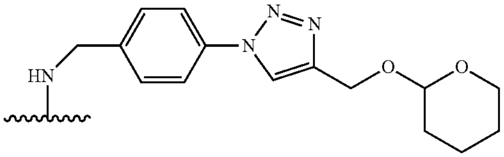 [SMILES: *NCc1ccc(-n2cc(COC3CCCCO3)nn2)cc1] |
| 101 | 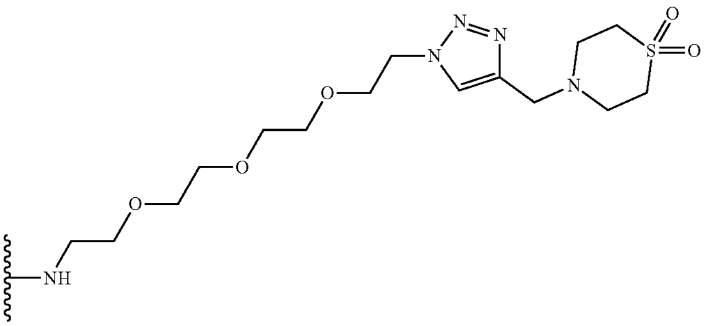 [SMILES: *NCCOCCOCCOCCn1cc(CN2CCS(=O)(=O)CC2)nn1] |

-continued
| Compound No. | Structure |
|---|---|
| 102 | 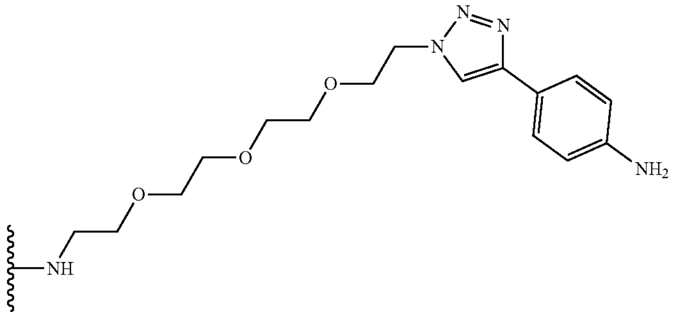 [SMILES: *NCCOCCOCCOCCn1cc(-c2ccc(N)cc2)nn1] |
| 103 | 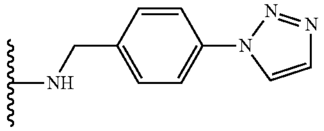 [SMILES: *NCc1ccc(-n2ccnn2)cc1] |
| 104 | 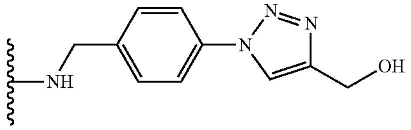 [SMILES: *NCc1ccc(-n2cc(CO)nn2)cc1] |
| 105 | 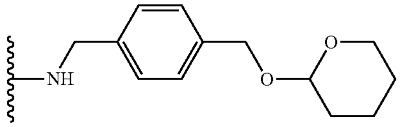 [SMILES: *NCc1ccc(COC2CCCCO2)cc1] |
| 106 | 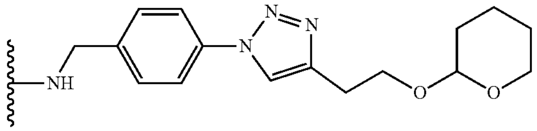 [SMILES: *NCc1ccc(-n2cc(CCOC3CCCCO3)nn2)cc1] |
| 107 | 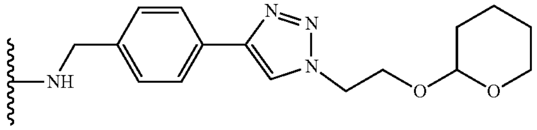 [SMILES: *NCc1ccc(-c2cn(CCOC3CCCCO3)nn2)cc1] |
| 108 | 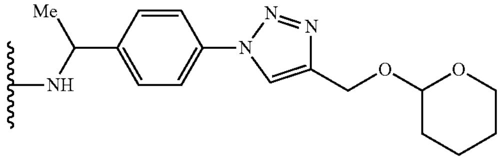 [SMILES: *NC(C)c1ccc(-n2cc(COC3CCCCO3)nn2)cc1] |
| 109 | 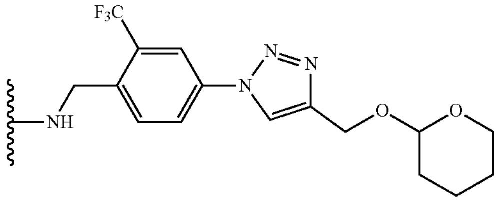 [SMILES: *NCc1ccc(-n2cc(COC3CCCCO3)nn2)cc1C(F)(F)F] |
| 110 | 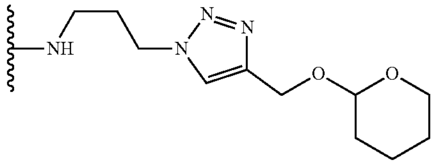 [SMILES: *NCCCn1cc(COC2CCCCO2)nn1] |

-continued
| Compound No. | Structure |
|---|---|
| 111 | 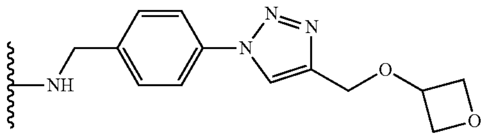 [SMILES: *NCc1ccc(-n2cc(COC3COC3)nn2)cc1] |
| 112 | 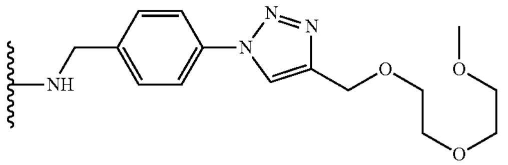 [SMILES: *NCc1ccc(-n2cc(COCCOCCOC)nn2)cc1] |
| 113 | 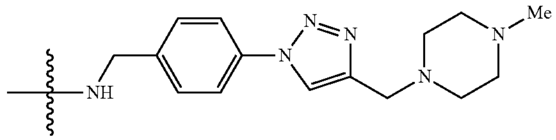 [SMILES: *NCc1ccc(-n2cc(CN3CCN(C)CC3)nn2)cc1] |
| 114 | 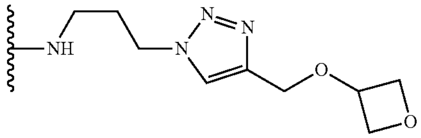 [SMILES: *NCCCn1cc(COC2COC2)nn1] |
| 115 | 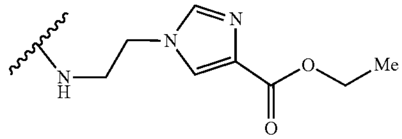 [SMILES: *NCCn1cnc(C(=O)OCC)c1] |
| 116 | 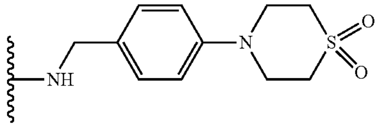 [SMILES: *NCc1ccc(N2CCS(=O)(=O)CC2)cc1] |
| 117 | 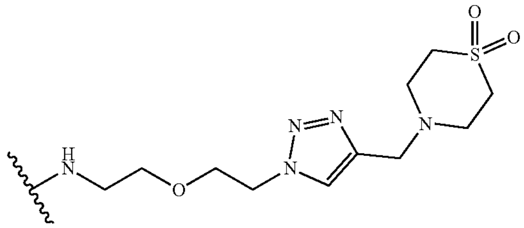 [SMILES: *NCCOCCn1cc(CN2CCS(=O)(=O)CC2)nn1] |
| 118 | 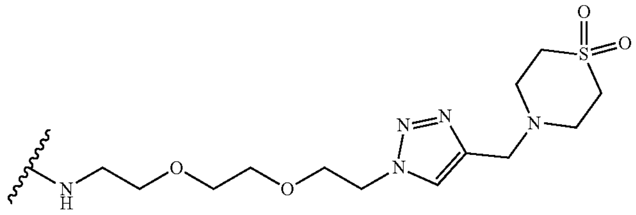 [SMILES: *NCCOCCOCCn1cc(CN2CCS(=O)(=O)CC2)nn1] |

-continued
| Compound No. | Structure |
| --- | --- |
| 119 | 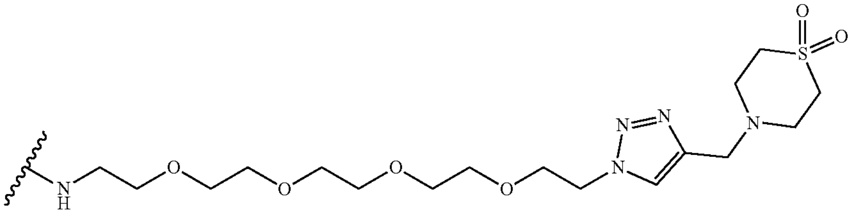 [SMILES: *NCCOCCOCCOCCOCCn1cc(CN2CCS(=O)(=O)CC2)nn1] |
| 120 | 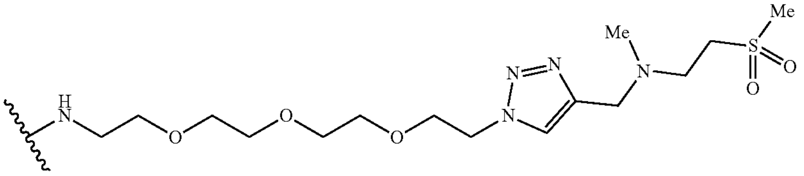 [SMILES: *NCCOCCOCCOCCn1cc(CN(C)CCS(C)(=O)=O)nn1] |
| 121 | 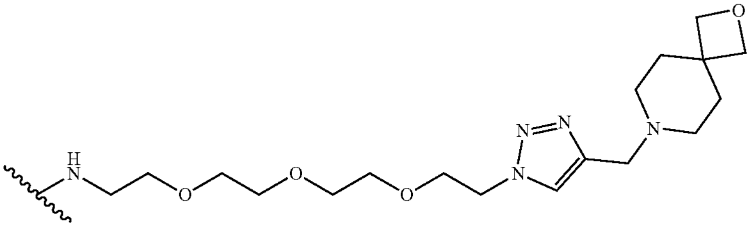 [SMILES: *NCCOCCOCCOCCn1cc(CN2CCC3(CC2)COC3)nn1] |
10. The hydrogel capsule of claim 9, wherein the compound of Formula (I) is selected from the group consisting of
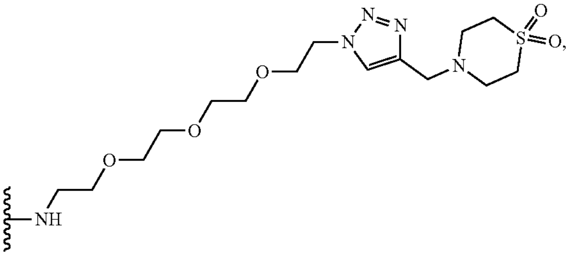
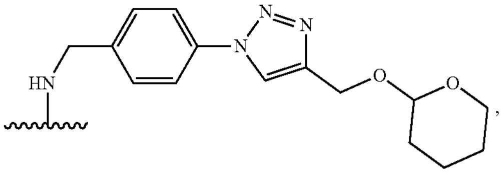
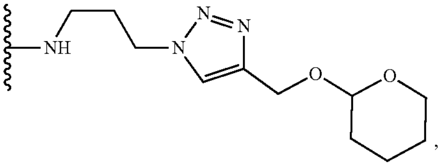
-continued
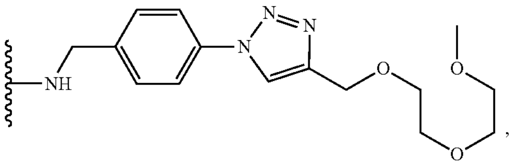
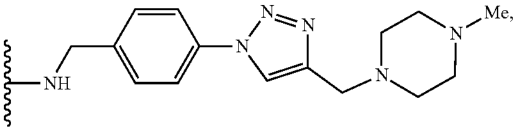
and
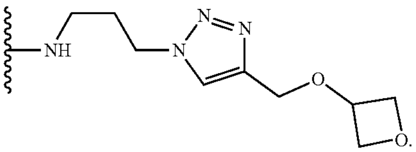
* * * * *